US007494992B2

(12) United States Patent
Chubb et al.

(10) Patent No.: US 7,494,992 B2
(45) Date of Patent: Feb. 24, 2009

(54) ANTIPARASITIC TERPENE ALKALOIDS

(75) Inventors: Nathan A. Chubb, Deal (GB); Douglas J. Critcher, Deal (GB); James J. Eshelby, Broadstairs (GB); Graham Lunn, Canterbury (GB); Andrew J. Rudge, Sandwich (GB); Nigel D. Walshe, Deal (GB); Paul H Wiedenau, Deal (GB); David H. Williams, Canterbury (GB)

(73) Assignee: Pfizer Inc., New York, NY (US)

( * ) Notice: Subject to any disclaimer, the term of this patent is extended or adjusted under 35 U.S.C. 154(b) by 703 days.

(21) Appl. No.: 10/777,713

(22) Filed: Feb. 12, 2004

(65) Prior Publication Data
US 2007/0185101 A1    Aug. 9, 2007

(30) Foreign Application Priority Data
Feb. 14, 2003  (GB)  ............................. 0303439.4

(51) Int. Cl.
*C07D 491/04*   (2006.01)
*A61K 31/5365*  (2006.01)

(52) U.S. Cl. ............. 514/229.8; 544/63; 504/223

(58) Field of Classification Search .......... 544/63; 514/229.8; 504/223
See application file for complete search history.

(56) References Cited
FOREIGN PATENT DOCUMENTS

GB    2240100    1/1990

WO    WO 95/19363    1/1995

OTHER PUBLICATIONS

The Merck Manual of Medical Information—Home Edition, Section 17. Infections, Chapter 184 on the web site http:llwww.merck.comlmrkshared/mmanual_homelsec171184.jsp, downloaded on Nov. 26, 2003.*
Stephen M. Berg et al "*Journal of Pharmaceutical Sciences*", vol. 66, No. 1, Jan. 1977.

* cited by examiner

*Primary Examiner*—Kahsay T Habte
(74) *Attorney, Agent, or Firm*—Gregg C. Benson; A. Dean Olson

(57) ABSTRACT

The present invention relates to novel terpene alkaloids and their use as antiparasitic agents. The present invention also relates to an antiparasitic agent which comprises a terpene alkaloid compound of this invention as an effective ingredient in an antiparasitic formulation.

More particularly, the present invention relates to derivatives of the terpene alkaloid (1S,2R,4aS,5R,8R,8aR)-2-(acetyloxy)-8a-hydroxy-3,8-dimethyl-5-(1-methylethenyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate. Pharmaceutical compositions comprising the same are also disclosed.

31 Claims, No Drawings

ANTIPARASITIC TERPENE ALKALOIDS

CROSS-REFERENCE TO RELATED APPLICATIONS

This application claims the benefit of provisional British Patent Application No. 0303439.4 filed on 14 Feb. 2003.

TECHNICAL FIELD

The present invention relates to novel terpene alkaloids and their use as antiparasitic agents. The present invention also relates to an antiparasitic treatment which comprises a terpene alkaloid compound of this invention as an effective ingredient in an antiparasitic formulation.

More particularly, the present invention relates to derivatives of the terpene alkaloid (1S,2R,4aS,5R,8R,8aR)-2-(acetyloxy)-8a-hydroxy-3,8-dimethyl-5-(1-methylethenyl)-1, 2,4a,5,6,7,8,8a-octahydronaphthalen-1-yl(2S,3aR,9bR)-6-chloro-9b-hydroxy-5-methyl-1,2,3,3a,5,9b-hexahydropyrrolo[2,3-c][2,1]benzoxazine-2-carboxylate. Processes for producing these compounds and pharmaceutical compositions comprising the same are also disclosed.

A further aspect of the invention is a novel binding assay which is used to assess the potential antiparasitic activity of these compounds by measuring how tightly they bind to membranes purified from parasite homogenates. The affinity is calculated according to how readily the compounds of the present invention displace a radiolabeled, reduced analogue of (1S,2R,4aS,5R,8R,8aR)-2-(acetyloxy)-8a-hydroxy-3,8-dimethyl-5-(1-methylethenyl)-1,2,4a,5,6,7,8,8a-octahydronaphthalen-1-yl(2S,3aR,9bR)-6-chloro-9b-hydroxy-5-methyl-1,2,3,3a,5,9b-hexahydropyrrolo[2,3-c][2,1]benzoxazine-2-carboxylate from these membranes.

Certain terpene alkaloids, including (1S,2R,4aS,5R,8R,8aR)-2-(acetyloxy)-8a-hydroxy-3,8-dimethyl-5-(1-methylethenyl)-1,2,4a,5,6,7,8,8a-octahydronaphthalen-1-yl(2S,3aR,9bR)-6-chloro-9b-hydroxy-5-methyl-1,2,3,3a,5,9b-hexahydropyrrolo[2,3-c][2,1]benzoxazine-2-carboxylate which can be isolated from the fermentation broths of certain microorganisms, are known to possess anthelmintic, ectoparasiticidal and insecticidal activity with utility in animal and human health, agriculture and horticulture (See WO 95/19363 and UK 2240100 respectively).

However, when administered to infected animals, their in vivo potencies were found to be too low as to preclude commercial development.

Surprisingly, we have found certain terpene alkaloid derivatives possess good in vivo activity and thus are effective as antiparasitic agents in animals. The present invention thus provides compounds that are effective as antiparasitic agents for use in animals and humans.

The compounds of the present invention may be formed by synthetic modification of (1S,2R,4aS,5R,8R,8aR)-2-(acetyloxy)-8a-hydroxy-3,8-dimethyl-5-(1-methylethenyl)-1, 2,4a,5,6,7,8,8a-octahydronaphthalen-1-yl(2S,3aR,9bR)-6-chloro-9b-hydroxy-5-methyl-1,2,3,3a,5,9b-hexahydropyrrolo[2,3-c][2,1]benzoxazine-2-carboxylate. The compounds of the invention show activity against insects, pests, acari, free living nematodes and endo- and ecto-parasites afflicting animals.

The present invention provides a compound of formula (I):

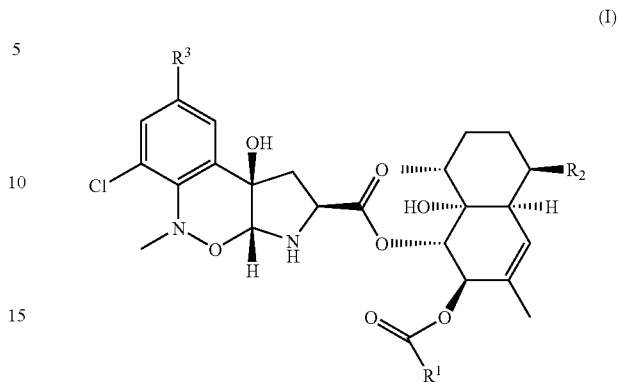

(I)

or a pharmaceutically or veterinarily acceptable salt or solvate thereof, wherein $R^1$ is H, $C_1$-$C_6$ alkyl, $C_2$-$C_6$ haloalkyl, $C_3$-$C_8$ cycloalkyl, $C_2$-$C_6$ alkenyl, $C_2$-$C_6$ alkynyl, aryl or —$OR^4$, said $C_1$-$C_6$ alkyl, $C_3$-$C_8$ cycloalkyl and aryl being optionally substituted by one or more substitutents selected from $COOR^{13}$, —$OCOR^{12}$, —$OCOOR^{13}$ and —$OCONR^{12}R^{12}$ and said $C_2$-$C_6$ alkenyl and $C_2$-$C_6$ alkynyl being optionally substituted by one or more halo;

$R^2$ is $C_1$-$C_6$ alkyl, $C_2$-$C_6$ alkenyl, or a 5- or 6-membered aromatic or non-aromatic heterocycle containing one or more atoms selected from N, O and S, said $C_1$-$C_6$ alkyl being optionally substituted by one or more substitutents selected from —$NR^5R^6$, —$CONR^5R^6$, —$OR^{12}$, —$OCOR^{12}$, —$OCOOR^{12}$, —$OCONR^{12}R^{14}$, =$NOR^7$ and halo, said $C_2$-$C_6$ alkenyl being optionally substituted by one or more substitutents selected from halo and —$COOR^{13}$ and said 5- or 6-membered aromatic heterocycle containing one or more atoms selected from N, O and S being optionally substituted by one or more substitutents selected from $C_1$-$C_6$ alkyl and aryl;

$R^3$ is H, halo, aryl, $C_2$-$C_6$ alkenyl, $C_2$-$C_7$ alkanoyl, or a 5- or 6-membered aromatic heterocycle containing one or more atoms selected from N, O and S;

$R^4$ is $C_1$-$C_2$ alkyl, $C_2$-$C_6$ alkenyl or $C_2$-$C_6$ alkynyl, each optionally substituted by one or more halo, or —$OC(O)$$OR^a$ where $R^a$ is $C_1$-$C_6$ alkyl;

$R^5$ and $R^6$ either, when taken together with the nitrogen atom to which they are attached, represent a saturated, partially unsaturated or aromatic, mono-, bi- or tricyclic heterocycle of up to 16 atoms optionally containing 1 or more additional heteroatoms selected from O, N and S, said heterocycle being optionally fused to a benzene or pyridyl ring and optionally substituted (including the optional benzene or pyridyl ring) by one or more $R^8$ and optionally substituted (including the optional benzene or pyridyl ring) on any aromatic ring thereof by —$NR^{15}R^{16}$, with the proviso that the heterocycle may not contain an —NH— group;

or $R^5$ and $R^6$ are each independently selected from H, $C_1$-$C_6$ alkyl, $C_3$-$C_8$ cycloalkyl, —CO—($C_3$-$C_8$)cycloalkyl, —$COR^{10}$, $C_2$-$C_7$ alkanoyl, aryl, —$OR^{13}$, —$COOR^{13}$, —$CONR^{12}R^{12}$ or —$SO_2R^{13}$, said $C_2$-$C_7$ alkanoyl being optionally substituted by $OR^{13}$ or halo, said $C_1$-$C_6$ alkyl and $C_3$-$C_8$ cycloalkyl being optionally substituted by one or more $R^8$ and said $C_3$-$C_8$ cycloalkyl being optionally fused to a saturated or unsaturated ring of from 5 to 6 atoms, optionally containing one or more O, N or S atoms, said fused ring being optionally substituted by one or more $C_1$-$C_6$ alkyl with the proviso that when $R^5$ is H or —$CH_3$, $R^6$ is not $C_1$-$C_6$ alkyl;

$R^7$ is $C_1$-$C_6$ alkyl, $C_2$-$C_6$ alkenyl, $C_2$-$C_6$ alkynyl or aryl, said alkyl being optionally substituted by aryl;

$R^8$ is $C_1$-$C_6$ alkyl, $C_3$-$C_8$ cycloalkyl, $R^9$, $R^{10}$, —$OR^9$, —$OR^{10}$, $COR^9$, $COR^{10}$, —O—($C_1$-$C_6$ alkyl)-$R^{10}$, $C_2$-$C_6$ alkenyl, —$OR^{13}$, —$SR^9$, —$SR^{10}$, —$SO_2R^{10}$, —$OCOR^{12}$, —$OCOOR^{12}$, —$OCONR^{12}R^{13}$, —$CONR^{12}R^{13}$, —$CONR^{12}R^{13}$, —$NR^{12}COR^{12}$, —$NR^{12}COOR^2$, —$NR^{12}CONR^{12}R^{12}$, —$COOR^{13}$, —$COR^{12}$, oxo or halo, said $C_3$-$C_8$ cycloalkyl being optionally substituted by aryl, said $C_1$-$C_6$ alkyl being optionally substituted by one or more substitutents selected from $C_3$-$C_8$ cycloalkyl, $R^9$, $R^{10}$, —$OR^{10}$, —$OR^{13}$, —$SR^9$, —$SR^{11}$, —$OCOR^{12}$, —$OCOOR^{12}$, —$OCONR^{12}R^{12}$, —$NR^{12}COR^{12}$, —$NR^{12}COOR^{12}$, —$NR^{12}CONR^{12}R^{12}$, —$COR^{12}$ or halo, and said $C_2$-$C_6$ alkenyl being optionally substituted by one or more substitutents selected from halo or aryl;

$R^9$ is (a) a 5- or 6-membered aromatic heterocycle containing one or more atom(s) selected from N, O and S and optionally fused to a benzene ring, said aromatic heterocycle being optionally substituted (including on the optional benzene ring) by one or more substitutents selected from $C_1$-$C_6$ alkyl, $C_1$-$C_6$ haloalkyl, $C_3$-$C_8$ cycloalkyl, —$OR^{13}$, —$NR^{12}R^{12}$, —$CO_2R^{13}$, cyano and halo, or (b) a 4- to 8-membered saturated heterocycle containing one or more atoms selected from O and S and optionally fused to a benzene ring, said saturated heterocycle being optionally substituted (including on the optional benzene ring) by one or more substitutents selected from $C_1$-$C_6$ alkyl and $C_3$-$C_8$ cycloalkyl;

$R^{10}$ is aryl optionally substituted by one or more substitutents selected from $C_1$-$C_6$ alkyl, $C_1$-$C_6$ haloalkyl, —$OR^{13}$, —$NR^{12}R^{12}$, —$CO_2R^{13}$, cyano or halo and optionally fused to a saturated or unsaturated ring of 5 or 6 atoms, optionally containing one or more O, N or S atoms, said fused ring being optionally substituted by one or more $C_1$-$C_6$ alkyl;

$R^{11}$ is H, $C_1$-$C_6$ alkyl or $C_3$-$C_8$ cycloalkyl;

each $R^{12}$ is independently H, $C_1$-$C_6$ alkyl, $C_1$-$C_6$ haloalkyl, $C_3$-$C_8$ cycloalkyl or aryl, said $C_1$-$C_6$ alkyl being optionally substituted by aryl;

each $R^{13}$ is independently $C_1$-$C_6$ alkyl, $C_1$-$C_6$ haloalkyl, $C_3$-$C_8$ cycloalkyl or aryl, said $C_1$-$C_6$ alkyl being optionally substituted by aryl;

$R^{14}$ is $C_1$-$C_6$ alkyl, $C_3$-$C_8$ cycloalkyl or aryl, said $C_1$-$C_6$ alkyl each optionally substituted by aryl or —NHaryl;

$R^{15}$ and $R^{16}$ are either each independently selected from H, $C_1$-$C_6$ alkyl and $C_3$-$C_8$ cycloalkyl or, when taken together with the nitrogen atom to which they are attached, represent a 3- to 8-membered ring optionally containing one or more additional heteroatoms selected from O and S; and 'aryl' means phenyl or naphthyl;

with the proviso that when $R^3$ is H and $R^1$ is methyl, $R^2$ is not isopropenyl.

A preferred group of compounds of formula (I) is that wherein:

$R^1$ is $C_1$-$C_6$ alkyl, $C_1$-$C_4$ alkenyl, $C_1$-$C_4$ alkynyl, $OC_1$-$C_6$ alkyl, $OC_1$-$C_4$ alkenyl or $OC_1$-$C_4$ alkynyl; and $R^2$ is a thiazole ring optionally substituted with $C_1$ to $C_4$ alkyl; a piperazine ring optionally substituted with $C_1$ to $C_4$ alkyl; an isopropenyl group optionally substituted by halo; or an isopropyl group optionally substituted by one or more halo; $NR^7R^8$ wherein $R^7$ and $R^8$ may be taken together to represent a ring of up to 7 atoms optionally containing oxygen or may be independently selected from H or $C_1$ to $C_4$ cycloalkyl; =$NOR^{17}$ wherein $R^{17}$ may be selected from $C_1$ to $C_6$, $C_1$ to $C_4$ alkynyl or $C_1$ to $C_4$ alkenyl;

A more preferred group of compounds of formula (I) is that in which:

$R^1$ is —$CH_3$, —O-allyl or —O-propargyl;

$R^2$ is 2-ethylthiazol-4-yl, isopropyl, piperazinyl, 1,2-difluoropropen-2-yl, 1-oxoprop-2-yl methyl oxime, 1-oxoprop-2-yl propargyl oxime, 1-oxoprop-2-yl allyl oxime, 1-N-morpholinoprop-2-yl, 1-fluoroprop-2-yl, 1,1-difluoroprop-2-yl;

$R^3$, $R^4$ and $R^5$ are H;

Particularly preferred individual compounds of the invention include compounds of formula (I) where $R^3$, $R^4$, and $R^5$ all are H, and $R^1$ and $R^2$ are as indicated below:

| R1 = | R2 = |
|---|---|
| $CH_3$ | 2-Ethylthiazol-4-yl, isopropyl |
| $CH_3$ | 1,2-difluoropropen-2-yl |
| $CH_3$ | 1-oxoprop-2-yl methyl oxime |
| $CH_3$ | 1-oxoprop-2-yl propargyl oxime |
| $CH_3$ | 1-oxoprop-2-yl allyl oxime |
| $CH_3$ | isopropyl |
| $CH_3$ | 1-N-morpholinoprop-2-yl |
| $CH_3$ | 1-fluoroprop-2-yl |
| $CH_3$ | 1,1-difluoroprop-2-yl |
| $CH_3$ | piperazin-1-yl (optionally 4-substituted with $C_1$-$C_6$ alkyl, phenyl, benzyl each of which groups may optionally be halo-substituted by up to 3 halo atoms |
| Opropargyl | isopropenyl |
| Opropargyl | isopropyl |
| Oallyl | isopropyl |

In the above definition, halo means fluoro, chloro, bromo or iodo.

The compounds of formula (I) may contain one or more chiral centres and therefore can exist as stereoisomers, i.e. as enantiomers or diastereoisomers, as well as mixtures thereof. The invention includes both the individual stereoisomers of the compounds of formula (I) together with mixtures thereof. Separation of diastereoisomers may be achieved by conventional techniques, e.g. by fractional crystallisation or chromatography (including HPLC) of a diastereoisomeric mixture of a compound of formula (I) or a suitable salt or derivative thereof. An individual enantiomer of a compound of formula (I) may be prepared from a corresponding optically pure intermediate or by resolution, either by HPLC of the racemate using a suitable chiral support or, where appropriate, by fractional crystallisation of the diastereoisomeric, salts formed by reaction of the racemate with a suitable optically active acid.

Also included in the invention are radiolabelled derivatives of compounds of formula (I) which are suitable for biological studies.

The pharmaceutically, veterinarily and agriculturally acceptable salts of the compounds of formula (I) are, for example, non-toxic acid addition salts formed with inorganic acids such as hydrochloric, hydrobromic, sulphuric and phosphoric acid, with organo-carboxylic acids, or with organo-sulphonic acids. For a review of suitable salts, see J. Pharm. Sci., 1977, 66, 1.

In a further aspect, the present invention provides processes for the preparation of a compound of formula (I), or a pharmaceutically, veterinarily or agriculturally acceptable salt thereof, or a pharmaceutically, veterinarily or agriculturally acceptable solvate (including hydrate) of either entity, as illustrated below.

It will be appreciated by persons skilled in the art that, within certain of the processes described, the order of the synthetic steps employed may be varied and will depend inter alia on factors such as the nature of other functional groups present in a particular substrate, the availability of key intermediates, and the protecting group strategy (if any) to be adopted. Clearly, such factors will also influence the choice of reagent for use in the said synthetic steps. It will also be appreciated that various standard substitutent or functional group interconversions and transformations within certain compounds of formula (I) will provide other compounds of formula (I).

Regarding the use of the compounds of the invention in humans, there is provided:

a pharmaceutical parasiticidal composition comprising a compound of formula (I), or a pharmaceutically acceptable salt thereof, or a pharmaceutically acceptable solvate of either entity, together with a pharmaceutically acceptable diluent or carrier, which may be adapted for topical administration;

a compound of formula (I), or a pharmaceutically acceptable salt thereof, or a pharmaceutically acceptable solvate of either entity, or a pharmaceutical composition containing any of the foregoing, for use as a medicament;

the use of a compound of formula (I), or a pharmaceutically acceptable salt thereof, or a pharmaceutically acceptable solvate of either entity, or a pharmaceutical composition containing any of the foregoing, for the manufacture of a medicament for the treatment of a parasitic infestation;

and a method of treating a parasitic infestation in a human being which comprises treating said human being with an effective amount of a compound of formula (I) or a pharmaceutically acceptable salt thereof, or a pharmaceutically acceptable solvate of either entity, or a pharmaceutical composition containing any of the foregoing.

With respect to their use in non-human animals, the compounds of the present invention may be administered alone or in a formulation appropriate to the specific use envisaged, the particular species of host animal being treated and the parasite involved. The methods by which the compounds may be administered include oral administration by capsule, bolus, tablet or drench, topical administration as a pour-on, spot-on, dip, spray, mousse, shampoo or powder formulation or, alternatively, they can be administered by injection (e.g. subcutaneously, intramuscularly or intravenously), or as an implant.

Such formulations are prepared in a conventional manner in accordance with standard veterinary practice. Thus capsules, boluses or tablets may be prepared by mixing the active ingredient with a suitable finely divided diluent or carrier additionally containing a disintegrating agent and/or binder such as starch, lactose, talc or magnesium stearate, etc. Oral drenches are prepared by dissolving or suspending the active ingredient in a suitable medium. Pour-on or spot-on formulations may be prepared by dissolving the active ingredient in an acceptable liquid carrier vehicle such as butyl digol, liquid paraffin or a non-volatile ester, optionally with the addition of a volatile component such as propan-2-ol. Alternatively, pour-on, spot-on or spray formulations can be prepared by encapsulation, to leave a residue of active agent on the surface of the animal. Injectable formulations may be prepared in the form of a sterile solution which may contain other substances, for example enough salts or glucose to make the solution isotonic with blood. Acceptable liquid carriers include vegetable oils such as sesame oil, glycerides such as triacetin, esters such as benzyl benzoate, isopropyl myristate and fatty acid derivatives of propylene glycol, as well as organic solvents such as pyrrolidin-2-one and glycerol formal. The formulations are prepared by dissolving or suspending the active ingredient in the liquid carrier such that the final formulation contains from 0.01 to 10% by weight of the active ingredient.

These formulations will vary with regard to the weight of active compound contained therein, depending on the species of host animal to be treated, the severity and type of infection and the body weight of the host. For parenteral, topical and oral administration, typical dose ranges of the active ingredient are 0.01 to 100 mg per kg of body weight of the animal. Preferably the range is 0.1 to 10 mg per kg.

As an alternative the compounds may be administered with the animal feedstuff and for this purpose a concentrated feed additive or premix may be prepared for mixing with, the normal animal feed.

The compounds of the invention are highly active antiparasitic, agents having particular utility as anthelmintics, ectoparasiticides, insecticides and acaricides.

Thus the compounds are effective in treating a variety of conditions caused by endoparasites including, in particular, helminthiasis which is most frequently caused by a group of parasitic worms described as nematodes and which can cause severe economic losses in swine, sheep, horses and cattle as well as affecting domestic animals and poultry. The compounds are also effective against other nematodes which affect various species of animals including, for example, *Dirofilaria* in dogs and various parasites which can infect humans including gastrointestinal parasites such as *Ancylostoma, Necator, Ascaris, Strongyloides, Trichinella, Calpillaria, Trichuris, Enterobius* and parasites which are found in the blood or other tissues and organs such as filiarial worms and the extra intestinal stages of *Strongyloides* and *Trichinella*.

The compounds are also of value in treating ectoparasite infections including in particular arthropod ectoparasites of animals and birds such as ticks, mites, lice, fleas, blowfly, biting insects and migrating dipterous larvae which can affect cattle and horses.

The compounds are also insecticides active against household pests such as cockroach, clothes moth, carpet beetle and the housefly as well as being useful against insect pests of stored grain and of agricultural plants such as spider mites, aphids, caterpillars and migratory orthopterans such as locusts.

Therefore, according to a further aspect of the invention, there is provided a veterinary or agricultural formulation comprising a compound of formula (I), or a veterinarily or agriculturally acceptable salt thereof, or a veterinarily or agriculturally acceptable solvate of either entity, together with a veterinarily or agriculturally acceptable diluent or carrier. Preferably, the formulation is adapted for topical administration.

The invention further provides a compound of formula (I), or a veterinarily or agriculturally acceptable salt thereof, or a veterinarily or agriculturally acceptable solvate of either entity, or a veterinarily or agriculturally acceptable formulation containing any of the foregoing, for use as a parasiticide.

It also provides a method of treating a parasitic infestation at a locus, which comprises treatment of the locus with an effective amount of a compound of formula (I), or a veterinarily or agriculturally acceptable salt thereof, or a veterinarily or agriculturally acceptable solvate of either entity, or a veterinarily or agriculturally acceptable formulation containing any of the foregoing.

Preferably, the locus is the intestine, skin or fur of an animal.

It is to be appreciated that reference to treatment includes prophylaxis as well as the alleviation and/or cure of established symptoms of a parasitic infection. Treatment thus also includes palliative care.

Compound Evaluation

The in vitro assay for measurement of compounds which displace $^3$H-dihydro-(1S,2R,4aS,5R,8R,8aR)-2-(acetyloxy)-8a-hydroxy-3,8-dimethyl-5-(1-methylethenyl)-1,2,4a,5,6,7,8,8a-octahydronaphthalen-1-yl(2S,3aR,9bR)-6-chloro-9b-hydroxy-5-methyl-1,2,3,3a,5,9b-hexahydropyrrolo[2,3-c][2,1]benzoxazine-2-carboxylate from fly head $P_2$ membranes represents another aspect of the invention and was performed as follows.

Novel antiparasitic compounds can be identified rapidly using a radiometric assay that measures the displacement of $^3$H-dihydro-(1S,2R,4aS,5R,8R,8aR)-2-(acetyloxy)-8a-hydroxy-3,8-dimethyl-5-(1-methylethenyl)-1,2,4a,5,6,7,8,8a-octahydronaphthalen-1-yl(2S,3aR,9bR)-6-chloro-9b-hydroxy-5-methyl-1,2,3,3a,5,9b-hexahydropyrrolo[2,3-c][2,1]benzoxazine-2-carboxylate from fly head $P_2$ membranes. This assay can be used to measure Ki values and thereby identify structure activity relationships. It can also be used as a high throughput screen (testing synthetic small molecules or natural products generated by microorganism fermentation) to identify novel chemical entities with antiparasitic activity.

To prepare fly head $P_2$ membranes, *Lucilia sericata* pupae (or any other insect pest) are hatched in an insectory and snap frozen in liquid nitrogen. The flies are shaken in a sieve and tray unit to separate the bodies from the heads/wings/legs. A smaller diameter sieve then separates the heads from wings and legs. The sieve diameters are dependent on the size of the flies being harvested. The fly heads are then used to prepare the $P_2$ membrane.

The fly head membrane is prepared in buffer consisting of 50 mM HEPES pH7.4, containing a cocktail of protease inhibitors (Boehringer Mannheim Complete®). All steps are carried out on ice or at 4° C. The fly heads are homogenised in 5-10 volumes of buffer at 30 000 rpm using a Polytron homogeniser. The homogenate is then spun in a centrifuge at 1000×g for 10 minutes and the supernatant filtered through gauze. The filtered supernatant is then spun at 20 000×g for 1 hour and the $P_2$ membrane pellet resuspended in buffer and stored in aliquots at −80° C.

To measure binding of $^3$H-dihydro-(1S,2R,4aS,5R,8R,8aR)-2-(acetyloxy)-8a-hydroxy-3,8-dimethyl-5-(1-methylethenyl)-1,2,4a,5,6,7,8,8a-octahydronaphthalen-1-yl(2S,3aR,9bR)-6-chloro-9b-hydroxy-5-methyl-1,2,3,3a,5,9b-hexahydropyrrolo[2,3-c][2,1]benzoxazine-2-carboxylate to the fly head $P_2$ membranes, 400 μl of protein at a concentration of 0.5 mg/ml, is added to a deep well plate, containing $^3$H-dihydro-CJ-12662 giving a final concentration of 1 nM of the radioactive ligand. Control wells also contain either buffer or 5×10$^{-6}$M (1S,2R,4aS,5R,8R,8aR)-2-(acetyloxy)-8a-hydroxy-3,8-dimethyl-5-(1-methylethenyl)-1,2,4a,5,6,7,8,8a-octahydronaphthalen-1-yl(2S,3aR,9bR)-6-chloro-9b-hydroxy-5-methyl-1,2,3,3a,5,9b-hexahydropyrrolo[2,3-c][2,1]benzoxazine-2-carboxylate (final concentration). Other wells contain the compound of interest serially diluted in 5 fold dilutions from 5×10$^{-6}$M. For a high throughput screen, compounds are added at one concentration only to allow rapid screening of large numbers of compounds. The assay plate is incubated at 30° C. for 90 minutes. The plate is then harvested onto glass fibre filters (pre-soaked in 0.5% Triton X-100) on a filtration manifold and rapidly washed under vacuum with 5×1 ml washes of 50 mM HEPES containing 0.25% Triton X-100. After drying, the radioactivity bound to the filters is measured using melted solid scintillant in a scintillation counter. Serially diluted wells are plotted as binding (counts per minute) vs. log$_{10}$ (competitor concentration) and Ki values (Kd=7 nM) calculated and compared to (1S,2R,4aS,5R,8R,8aR)-2-(acetyloxy)-8a-hydroxy-3,8-dimethyl-5-(1-methylethenyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate. In a high throughput screen, compounds showing ≧70% inhibition of $^3$H-dihydro-(1S,2R,4aS,5R,8R,8aR)-2-(acetyloxy)-8a-hydroxy-3,8-dimethyl-5-(1-methylethenyl)-1,2,4a,5,6,7,8,8a-octahydronaphthalen-1-yl(2S,3aR,9bR)-6-chloro-9b-hydroxy-5-methyl-1,2,3,3a,5,9b-hexahydropyrrolo[2,3-c][2,1]benzoxazine-2-carboxylate binding are active.

Instruments Used to Acquire Characterising Data

Nuclear magnetic resonance (NMR) spectral data were obtained using Varian Inova 300, Varian Inova 400, Varian Unityplus 400, Bruker AC 300 MHz, Bruker AM 250 MHz, or Varian T60 MHz spectrometers, the observed chemical shifts (δ) being consistent with the proposed structures. Mass spectral (MS) data were obtained on a Finnigan Masslab Navigator, a Fisons Instruments Trio 1000, or a Hewlett Packard GCMS system model 5971 spectrometer. The calculated and observed ions quoted refer to the isotopic composition of lowest mass. HPLC means high performance liquid chromatography. Room temperature means 20 to 25° C.

Salt Preparations

Wherever applicable the hydrochloride salt can be prepared by dissolving the product in a mixture of methanol:ether (1:5) and adding hydrogen chloride (1 M solution in diethyl ether, 2 eq.). The mixture is concentrated in vacuo to give the hydrochloride salt.

Similarly, other salts such as trifluoroacetic acid salts and acetic acid salts can be prepared by dissolving the product in a suitable solvent such as ethyl acetate or methanol and adding the corresponding acid (2 eq). The reaction mixture can then be concentrated in vacuo to give the desired salt.

Stereochemistry

All stereoisomers of $R^2$ are within the scope of this invention, except where specifically described. The $R^2$ substitutent may include single diastereomers as well as mixtures of stereoisomers.

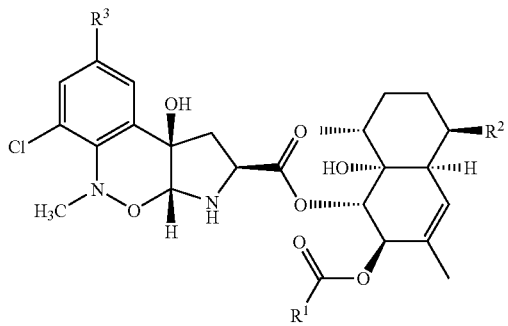

Generic Procedures

Generic Process A

Methanol (3 ml) was added to the corresponding amine (0.39 mmol, 1.5 equiv.), which was placed in a Stem® Reaction Block. In those cases where the amine was an ammonium salt, triethylamine (55 □l, 0.4 mmol) was added. A solution of 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl}3-(1,1-dimethylethyl) (2S,3aR,9bR)-6-chloro-9b-({[(1,1-dimethylethyl)oxy]carbonyl}oxy)-5-methyl-1, 2,5,9b-tetrahydropyrrolo[2,3-c][2,1]benzoxazine-2,3(3aH)-dicarboxylate (Preparation 160, 200 mg, 0.26 mmol) in methanol (2 ml, analytical grade) was added, and the reaction mixtures were stoppered with a rubber septum and stirred for 5 hours at ambient temperature. Borohydride on Amberlite® IRA400 (200 mg, 0.5 mmol) was added and the mixture stirred at room temperature for 18 h. The reaction mixture was then filtered through a filter cartridge (Isolute™, 6 ml), the residue washed with methanol (2 ml), and the filtrate concentrated under a stream of nitrogen. To the resulting crude product was added hydrogen chloride (4 N solution in dioxane, 2 ml), the mixture was agitated on an orbital shaker for 10 min, transferred to a hot plate (50° C.) and concentrated under a stream of nitrogen for 40 min. Triethylamine (20% v/v in dichloromethane, 2 ml) was added and the mixture was concentrated under a stream of nitrogen, followed by addition and evaporation of triethylamine (20% v/v in dichloromethane, 2 ml). The crude reaction product was then dissolved in a acetonitrile:dimethylsulfoxide (4:1, 1 ml) and purified by automated preparative liquid chromatography (Gilson system, 10×150 mm Phenomenex Magellen C18 .5□ column) using a 0.1% aqueous trifluoroacetic acid:acetonitrile gradient (95:5 to 5:95). Evaporation of the eluant in a Genevac system gave the final product.

Generic Process B

To the corresponding amine (0.33 mmol, 1.5 equiv.) was added a solution of 2-{(1S,2R,4aS,5R,8R,8aR)-2-(acetyloxy)-8a-hydroxy-3,8-dimethyl-5-[1-methyl-2-oxoethyl]-1, 2,4a,5,6,7,8,8a-octahydronaphthalen-1-yl}3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2, 3-c][2,1]benzoxazine-2,3(3aH)-dicarboxylate (Preparation 160, 170 mg, 0.22 mmol) in dichloromethane (2 ml). In those cases where the amine was an ammonium salt, triethylamine (5.5□l, 0.4 mmol) was added. Sodium triacetoxyborohydride (93 mg, 0.44 mmol) was added to the reaction, and the mixture was stirred in a Stem® reaction block for 18 h. The mixture was then diluted with dichloromethane (4 ml) and water (2 ml) and stirred vigorously for 20 min. The layers were separated by means of a filter cartridge with a hydrophobic frit (Whatman 12 ml 1 PS filter media), and the organic filtrate concentrated under a stream of nitrogen. To the resulting crude product was added hydrogen chloride (4 N solution in dioxane, 2 ml), the mixture was agitated on an orbital shaker for 10 min, transferred to a hot plate (50° C.) and concentrated under a stream of nitrogen for 40 min. Triethylamine (20% v/v in dichloromethane, 2 ml) was added and the mixture concentrated under a stream of nitrogen, followed by addition and evaporation of further triethylamine (20% v/v in dichloromethane, 2 ml). The crude reaction product was then dissolved in a acetonitrile:dimethylsulfoxide mixture (4:1, 1 ml), and purified by automated preparative liquid chromatography (Gilson system, 10×150 mm Phenomenex Magellen C18 5□ column) using a 0.1% aqueous trifluoroacetic acid:acetonitrile gradient (95:5 to 5:95). Evaporation of the eluant in a Genevac system gave the final product.

Generic Process C

A solution of (1S,2R,4aS,5R,8R,8aR)-2-(acetyloxy)-8a-hydroxy-3,8-dimethyl-5-[1-methyl-2-oxoethyl]-1,2,4a,5,6, 7,8,8a-octahydronaphthalen-1-yl(2S,3aR,9bR)-6-chloro-9b-hydroxy-5-methyl-1,2,3,3a,5,9b-hexahydropyrrolo[2,3-c] [2,1]benzoxazine-2-carboxylate (Preparation 141, 21 mg, 0.0375 mmol), the amine (0.1 mmol), tetramethylammonium triacetoxyborohydride (26 mg, 0.1 mmol), triethylamine (20□l, 0.15 mmol) in 1-methyl-2-pyrrolidinone (0.9 ml) was shaken at ambient temperature for 18 h. The reaction mixture was then directly injected onto the HPLC column for purification using a 0.1% aqueous trifluoroacetic acid:acetonitrile gradient (95:5 to 5:95). The purified product was obtained after evaporation of the solvents in a Genevac system.

Autopurification was carried out using a Gilson HPLC system using a Phenomenex Magellen® 150 mm×10 mm .5□ ODS column at ambient temperature. Elution was by gradient formed from 0.1% aqueous trifluoroacetic acid:acetonitrile (95:5 to 5:95) over 12 min. The products were detected by UV at 215 nm. All fractions from autopurification were analysed by loop injection into a Micromass "Platform LC"® single-quadrupole mass spectrometer with APCI probe.

Generic Process D

To a solution of 2-{(1S,2R,4aS,5R,8R,8aR)-2-(acetyloxy)-8a-hydroxy-3,8-dimethyl-5-[1-methyl-2-oxoethyl]-1, 2,4a,5,6,7,8,8a-octahydronaphthalen-1-yl}3-(1,1-dimethylethyl) (2S,3aR,9bR)-6-chloro-9b-({[(1,1-dimethylethyl) oxy]carbonyl}oxy)-5-methyl-1,2,5,9b-tetrahydropyrrolo[2, 3-c][2,1]benzoxazine-2,3(3aH)-dicarboxylate (Preparation 160, 200 mg, 0.26 mmol) in methanol (5 ml) was added the corresponding primary amine (0.52 mmol, 2 equiv.). Triethylamine (80 □l, 0.58 mmol) was added in those cases where the amine was an ammonium salt. The reaction mixture was stirred for 18 hours at ambient temperature in a Stem® reaction block. Then borohydride on Amberlite® IRA400 (Aldrich, 2.5 mmol/g resin, 150 mg, 0.38 mmol) was added and the stirring continued for 2.5 days. The reaction mixture was filtered using a disposable filter cartridge (6 ml) and the residue rinsed with methanol. 4-Benzyloxybenzaldehyde, polymer-bound (Aldrich, 2.8 mmol/g resin, 180 mg, 0.5 mmol) was added to scavenge excess amine and the reaction mixture then stirred for 18 h at room temperature. The reaction solution was filtered using disposable filter cartridges (6 ml), the residue rinsed with methanol and the filtrate concentrated under a stream of nitrogen. The crude product was dissolved in dichloromethane (20 ml). Of this reaction mixture (5 ml) was added to anhydrous pyridine (8. □l, 0.10 mmol) and the corresponding acid chloride (0.1 mmol, 1.5 equiv.) added and the reaction stirred at room temperature for 3 hours. The solvents were evaporated under a stream of nitrogen. To the resulting crude product was added hydrogen chloride (4 N solution in dioxane, 2 ml), the mixture was stirred at room temperature for 45 min, transferred to a hot plate (50° C.) and concentrated under a stream of nitrogen. Triethylamine (20% v/v in dichloromethane, 2 ml) was added and the mixture was concentrated under a stream of nitrogen. The crude reaction product was then dissolved in acetonitrile:dimethylsulfoxide (8:1, 1 ml), filtered using a Whatman HPLC filter and purified by automated preparative liquid chromatography (Gilson system, 10×150 mm Phenomenex Magellen C18 .5□ column), using a 0.1% aqueous trifluoroacetic acid:acetonitrile gradient ranging from 95:5 to 5:95. Evaporation of the eluant in a Genevac system gave the final product.

Generic Process E

To the solution of 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl}3-(1,1-dimethylethyl)(2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate (Preparation 160, 100 mg, 0.13 mmol) in methanol (2 ml) was added the corresponding amine (0.52 mmol, 4 equiv.), and the mixture stirred at room temperature for 18 h. Borohydride on Amberlite® IRA400 (Aldrich, 2.5 mmol/g resin, 77 mg, 0.19 mmol) was added and the mixture agitated with an orbital shaker at room temperature for 18 h. Then benzyloxybenzaldehyde, polymer-bound (Aldrich, 2.8 mmol/g resin, 460 mg, 1.29 mmol) was added to scavenge excess amine and the reaction mixture was shaken for 18 h. The reaction mixture was filtered, the residue was washed with methanol and the filtrate concentrated to dryness under a stream of nitrogen. A solution of the crude product (0.064 mmol) in dichloromethane was placed into a 48-well-plate (Flexchem Synthesis Block), and polymer-bound N-methylmorpholine (3.0 mmol/g resin, 32 mg, 0.096 mmol) was added by means of a dispensing plate. The corresponding acid chloride (0.16 mmol, 2.5 eq.) was added and the reaction mixture shaken at room temperature for 18 h. Polymer-bound tris(2-aminoethyl)amine, (4.8 mmol/g resin, 41 mg, 0.2 mmol) was then added with a dispensing plate and the mixtures shaken at room temperature for 18 h. The reaction mixture was then filtered into another 48-well-block and the filtrates concentrated under a stream of nitrogen. The crude residue was dissolved in hydrogen chloride, (1 M solution in acetic acid, 0.5 ml), shaken at room temperature for 1 hour and then concentrated to dryness under a stream of nitrogen. The crude reaction product was then dissolved in a acetonitrile (1 ml) and purified by automated preparative liquid chromatography (Gilson system, 10×150 mm Phenomenex Magellen C18 .5□ column), using a 0.1% aqueous trifluoroacetic acid:acetonitrile gradient (95:5 to 5:95). Evaporation of the eluant in a Genevac system gave the product.

Generic Process G

To a solution of (2R)-2-[(1R,4R,4aS,5R,6R)-5-({[(2S,3aR,9bR)-6-chloro-3-{[(1,1-dimethylethyl)oxy]carbonyl}-9b-({[(1,1-dimethylethyl)oxy]carbonyl}oxy)-5-methyl-1,2,3,3a,5,9b-hexahydropyrrolo[2,3-c][2,1]benzoxazin-2-yl]carbonyl}oxy)-6-(acetyloxy)-4a-hydroxy-4,7-dimethyl-1,2,3,4,4a,5,6,8a-octahydronaphthalen-1-yl]propanoic acid (Preparation 181, 200 mg, 0.25 mmol) in dichloromethane (2 ml) was added 1-hydroxybenzotriazole (Aldrich, 58 mg, 0.38 mmol) and 1-(3-dimethylaminopropyl)-3-ethylcarbodiimide hydrochloride salt (96 mg, 0.5 mmol), and the mixture was stirred at room temperature for 0.5 hours. The reaction mixture was added to a solution of the corresponding amine (0.38 mmol) in dichloromethane (2 ml) and stirred at room temperature for 36 hours. The reaction mixture was diluted with dichloromethane (2 ml) and water (7 ml) and stirred vigorously for 45 min. The layers were separated by means of a filter cartridge with a hydrophobic frit (Whatman 12 ml 1 PS filter media), and the organic filtrate concentrated under a stream of nitrogen followed by drying in vacuo. To a solution of the crude product in dioxane (1 ml) was added a hydrogen chloride (4M solution in dioxane solution, 2 ml) and the reaction mixture was stirred at room temperature for 25 min. The reaction mixture was concentrated under a stream of nitrogen for 40 min (hotplate 50° C.), then, a solution of triethylamine in dichloromethane (25% v/v, 2 ml) was added and the mixture again concentrated under reduced pressure. The crude reaction product was purified by automated preparative liquid chromatography (Gilson system, 10×150 mm Phenomenex Magellen C18 .5□ column), using a 0.1% aqueous trifluoroacetic acid:acetonitrile gradient (95:5 to 5:95). Evaporation of the eluant in a Genevac system gave the product.

The Examples given in the following Table 1 were prepared by the methods referred to above and the Table includes physical characterising data for each compound synthesised. The synthesis of a number of representative compounds are also described in more detail after Table 2. Table 2 indicates the precursor compounds used in the synthesis of the compounds of the invention.

TABLE 1

Table of Examples

| Ex No. | Compound Name | Data* |
|---|---|---|
| 1 | (1S,2R,4aS,5S,8R,8aR)-2-(acetyloxy)-8a-hydroxy-3,8-dimethyl-5-(1-methylethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=563.3 C29H39ClN2O7+H requires 563.25. NMR(CDCl3, selected data): 0.6(d, 3H), 0.9-1.1(m, 7H), 1.9(septet, 1H), 2.1(s, 3H), 3.35(s, 3H), 5.2(s, 1H), 7.2(d, 1H). |

TABLE 1-continued

Table of Examples

| Ex No. | Compound Name | Data* |
|---|---|---|
| 2 | (1S,2R,4aS,5R,8R,8aR)-8a-hydroxy-3,8-dimethyl-5-(1-methylethenyl)-2-[(2-methylpropanoyl)oxy]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(TSP): M/Z[MH+]=589.6 C31H41ClN2O7+H requires 589.3. NMR(CDCl3, selected data): 0.6(d, 3H), 1.18(dd, 6H), 1.9(septet, 1H), 1.8(s, 3H), 3.4(s, 3H), 4.75(s, 1H), 5.0(s, 1H), 5.1(s, 1H), 5.25-5.3(s, 2H), 5.4(s, 1H), 7.2(d, 1H). |
| 3 | (1S,2R,4aS,5R,8R,8aR)-2-(hexanoyloxy)-8a-hydroxy-3,8-dimethyl-5-(1-methylethenyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(TSP): M/Z[MH+]=617.3 C33H45ClN2O7+H requires 617.3. NMR(CDCl3, selected data): 0.55(d, 3H), 0.9(m, 3H), 1.85(s, 3H), 2.3(m, 3H), 3.35(s, 3H), 5.2(s, 1H), 7.2(d, 1H). |
| 4 | (1S,2R,4aS,5R,8R,8aR)-2-(acetyloxy)-5-[2-(acetyloxy)-1-methylethyl]-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(TSP): M/Z[MH+]=621.2, C31H41ClN2O9+H requires 621.3. NMR(CDCl3, selected data): 0.8(d, 3H), 1.0(d, 3H), 2.0(s, 3H), 2.1(s, 3H), 2.3(m, 3H), 3.35(s, 3H), 5.25(s, 1H), 7.2(d, 1H). |
| 5 | (1S,2R,4aS,5R,8R,8aR)-2-(acetyloxy)-8a-hydroxy-3,8-dimethyl-5-{1-methyl-2-[(2-methylpropanoyl)oxy]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(TSP): M/Z[MH+]=649.2, C33H45ClN2O9+H requires 649.3. NMR(CDCl3, selected data): 0.6(d, 3H), 1.1(d, 3H), 1.6(s, 3H), 2.1(s, 3H), 2.1(s, 3H), 2.3(m, 3H), 3.35(s, 3H), 5.25(s, 1H), 7.0(m, 1H), 7.2(d, 1H), 7.4(d, 1H). |
| 6 | (1S,2R,4aS,5R,8R,8aR)-2-[(cyclopropylcarbonyl)oxy]-8a-hydroxy-3,8-dimethyl-5-(1-methylethenyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=587.3, C31H39ClN2O7+H requires 587.3. NMR(CDCl3, selected data): 0.7(d, 3H), 0.85-0.95(m, 2H), 1.0-1.1(m, 2H), 3.35(s, 3H), 5.3(s, 1H), 7.2(d, 1H). |
| 7 | (1S,2R,4aS,5S,8R,8aR)-8a-hydroxy-3,8-dimethyl-5-(1-methylethyl)-2-{[(prop-2-ynyloxy)carbonyl]oxy}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(TSP): M/Z[MH+]=603.0, C31H39ClN2O8+H requires 603.2. NMR(CDCl3, selected data): 0.8(d, 3H), 1.0(m, 6H), 1.75-1.8(m, 6H), 2.0(1H, septet), 3.1(s, 1H), 3.35(s, 3H), 4.8(s, 2H), 5.25(s, 1H), 72(d, 1H). |
| 8 | (1S,2R,4aS,5S,8R,8aR)-8a-hydroxy-3,8-dimethyl-5-(1-methylethyl)-2-({[(2,2,2-trichloroethyl)oxy]carbonyl}oxy)-1,2,4a,5,6,7,8,8a-octahydronaphthalen-1-yl (2S,3aR,9bR)-6-chloro-9b-hydroxy-5-methyl-1,2,3,3a,5,9 b-hexahydropyrrolo[2,3-c][2,1]benzoxazine-2-carboxylate | MS(TSP): M/Z[MH+]=694.9, C30H38Cl4N2O8+H requires 695.1. NMR(CDCl3, selected data): 0.6(d, 3H), 1.0(m, 6H), 1.95(1H, septet), 3.4(s, 3H), 4.7(d, 1H), 4.85(d, 1H), 5.4(s, 1H), 7.2(d, 1H). |
| 9 | (1S,2R,4aS,5S,8R,8aR)-8a-hydroxy-3,8-dimethyl-2-({[(1-methylethyl)oxy]carbonyl}oxy)-5-(1-methylethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(TSP): M/Z[MH+]=605.9, C31H41ClN2O8+H requires 605.3. NMR(CDCl3, selected data): 0.6(m, 3H), 1.0(m, 6H), 1.8(s, 3H), 1.95(1H, septet), 3.4(s, 3H), 4.7(s, 1H), 4.8(s, 1H), 5.4(s, 1H), 7.2(d, 1H). |
| 10 | (1S,2R,4aS,5S,8R,8aR)-8a-hydroxy-3,8-dimethyl-5-(1-methylethyl)-2-{[(prop-2-enyloxy)carbonyl]oxy}-1,2,4a,5,6,7,8,8a-octahydronaphthalen-1-yl (2S,3aR,9bR)-6-chloro- | MS(TSP): M/Z[MH+]=605.5, C31H41ClN2O8+H requires 605.3. NMR(CDCl3, selected data): |

TABLE 1-continued

Table of Examples

| Ex No. | Compound Name | Data* |
|---|---|---|
|  | 9b-hydroxy-5-methyl-1,2,3,3a,5,9b-hexahydropyrrolo[2,3-c][2,1]benzoxazine-2-carboxylate | 0.65(d, 3H), 1.0(d, 6H), 1.95(1H, septet), 3.4(s, 3H), 4.65(m, 2H), 5.25-5.35(m, 4H), 5.9(m, 1H), 7.25(d, 1H). |
| 11 | (1S,2R,4aS,5S,8R,8aR)-1-({[(2S,3aR,9bR)-6-chloro-9b-hydroxy-5-methyl-1,2,3,3a,5,9b-hexahydropyrrolo[2,3-c][2,1]benzoxazin-2-yl]carbonyl}oxy)-8a-hydroxy-3,8-dimethyl-5-(1-methylethenyl)-1,2,4a,5,6,7,8,8a-octahydronaphthalen-2-yl methyl butanedioate | MS(ES): M/Z[MH+]=633.2, C32H41ClN2O9+H requires 633.3. NMR(CDCl3, selected data): 0.6(d, 3H), 3.4(s, 3H), 3.65-3.7(m, 5H), 4.75(s, 1H), 5.0(s, 1H), 5.3-5.35(m, 2H), 7.25(d, 1H). |
| 12 | (1S,2R,4aS,5S,8R,8aR)-8a-hydroxy-3,8-dimethyl-5-(1-methylethenyl)-2-(pent-4-enoyloxy)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=601.2, C32H41ClN2O7+H requires 601.3. NMR(CDCl3, selected data): 0.45(d, 3H), 1.8(s, 3H), 3.4(s, 3H), 4.7(s, 1H), 5.0-5.1(m, 4H), 5.2(s, 1H), 5.35(s, 1H), 5.4 5.8(s, 1H), 7.2(d, 1H). |
| 13 | (1S,2R,4aS,5R,8R,8aR)-2-(acetyloxy)-8a-hydroxy-3,8-dimethyl-5-{1-methyl-2-[({[2-(naphthalen-1-ylamino)ethyl]amino}carbonyl)oxy]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=791.2, C42H51ClN4O9+H requires 791.3. NMR(CDCl3, selected data): 0.8(d, 3H), 1.0(d, 3H), 2.1(s, 3H), 3.2(s, 3H), 3.2-3.5(m, 4H), 5.3(s, 1H), 6.5(m, 1H), 6.9-7.5(m, 7H), 7.7-7.8(m, 2H). |
| 14 | (1S,2R,4aS,5R,8R,8aR)-2-{[(acetyloxy)acetyl]oxy}-8a-hydroxy-3,8-dimethyl-5-(1-methylethenyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=619.1, C31H39ClN2O9+H requires 619.2. NMR(CDCl3, selected data): 0.6(d, 3H), 1.65(s, 3H), 1.85(s, 3H), 2.15(s, 3H), 3.4(s, 3H), 4.6(dd, 2H), 5.25(s, 1H), 7.2(m, 1H). |
| 15 | (1S,2R,4aS,5R,8R,8aR)-2-(formyloxy)-8a-hydroxy-3,8-dimethyl-5-(1-methylethenyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=547.1, C28H35ClN2O7+H requires 547.2. NMR(CDCl3, selected data): 0.45(d, 3H), 1.65(s, 3H), 1.85(s, 3H), 3.35(s, 3H), 5.25(s, 1H), 7.2(d, 1H), 8.1(s, 1H). |
| 16 | (1S,2R,4aS,5R,8R,8aR)-8a-hydroxy-3,8-dimethyl-5-(1-methylethenyl)-2-[(3,3,3-trifluoropropanoyl)oxy]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=629.1, C30H36ClF3N2O7+H requires 629.2. NMR(CDCl3, selected data): 0.5(d, 3H), 1.65(s, 3H), 1.9(s, 3H), 3.2(dd, 2H), 3.35(s, 3H), 5.25(s, 1H), 7.2(d, 1H). |
| 17 | (1S,2R,4aS,5S,8R,8aR)-2-(acetyloxy)-5-[4-(ethyloxy)-1-methyl-4-oxobut-2-enyl]-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=647.3, C33H43ClN2O9+H requires 647.3. NMR(CDCl3, selected data): 0.85(d, 3H), 1.1(t, 3H), 1.15(d, 3H), 1.7(s, 3H), 2.1(s, 3H), 3.3(s, 3H), 3.9(m, 2H), 5.3(s, 1H), 5.85(d, 1H), 6.9(dd, 1H), 7.25(d, 1H). |
| 18 | (1S,2R,4aS,5R,8R,8aR)-2-(acetyloxy)-5-(2,2-difluoro-1-methylethenyl)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(TSP): M/Z[MH+]=597.2, C29H35ClF2N2O7+H requires 597.2. NMR(CDCl3, selected data): 0.8(d, 3H), 1.7(s, 3H), 2.1(s, 3H), 2.2(s, 3H), 3.3(s, 3H), 5.1(s, 1H), 5.2(s, 1H), 5.3(s, 1H), 5.5(s, 1H), 7.25(m, 1H). |

TABLE 1-continued

Table of Examples

| Ex No. | Compound Name | Data* |
|---|---|---|
| 19 | (1S,2R,4aS,5R,8R,8aR)-2-(acetyloxy)-5-[2-fluoro-1-methylethyl]-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(TSP): M/Z[MH+]=581.1, C29H38ClFN2O7+H requires 581.2. NMR(CDCl3, selected data): 0.8(d, 3H), 1.1(d, 3H), 1.6(s, 3H), 2.1(s, 3H), 2.2(s, 3H), 3.3(s, 3H), 4.3-4.7(m, 2H), 5.4(s, 1H), 7.25(m, 1H). |
| 20 | (1S,2R,4aS,5S,8R,8aR)-2-(acetyloxy)-8a-hydroxy-3,8-dimethyl-5-[(1-methyl-2-morpholin-4-yl)ethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=648.3, C33H46ClN3O8+H requires 648.3. NMR(CDCl3, selected data): 0.8(d, 3H), 1.05(d, 3H), 1.7(s, 3H), 2.1(s, 3H), 2.4-2.6(m, 5H), 3.4(s, 3H), 3.6-3.8(m, 4H), 5.3(s, 1H), 7.25(m, 1H). |
| 21 | (1S,2R,4aS,5R,8R,8aR)-2-(acetyloxy)-5-(2-ethyl-1,3-thiazol-4-yl)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(TSP): M/Z[MH+]=631.7, C31H38ClN3O7S+H requires 632.2. NMR(CDCl3, selected data): 0.8(d, 3H), 1.3(s, 3H), 1.4(t, 3H), 2.1(s, 3H), 3.0(q, 2H), 3.35(s, 3H), 5.2(s, 1H), 7.25(m, 1H), 7.7(m, 1H). |
| 22 | (1S,2R,4aS,5R,8R,8aR)-2-(acetyloxy)-5-[2,2-difluoro-1-methylethyl]-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(TSP): M/Z[MH+]=600.3, C29H37ClF2N2O7+H requires 600.2. NMR(CDCl3, selected data): 0.6(d, 3H), 1.1(d, 3H), 2.05(s, 3H), 2.1(s, 3H), 3.35(s, 3H), 5.25-5.3(m, 2H), 5.95(t, 1H), 7.2(d, 1H). |
| 23 | (1S,2R,4aS,5R,8R,8aR)-2-(acetyloxy)-5-[2,2-difluoro-1-methylethyl]-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(TSP): M/Z[MH+]=599.9, C29H37ClF2N2O7+H requires 600.2. NMR(CDCl3, selected data): 0.9(d, 3H), 1.1(d, 3H), 2.1(s, 3H), 3.3(s, 3H), 5.4(s, 1H), 5.9(t, 1H), 7.2(m, 1H). |
| 24 | (1S,2R,4aS,5R,8R,8aR)-2-(acetyloxy)-5-(2,2-dichloro-1-methylethenyl)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(TSP): M/Z[MH+]=629.2, C29H35Cl3N2O7+H requires 629.2. NMR(CDCl3, selected data): 0.8(d, 3H), 1.25(s, 3H), 1.95(s, 3H), 2.1(s, 3H), 3.3(s, 3H), 5.1(s, (1H), 5.2(s, 1H), 5.3(s, 1H), 5.4(s, 1H), 7.2(d, 1H). |
| 25 | (1S,2R,4aS,5S,8R,8aR)-2-(acetyloxy)-8a-hydroxy-3,8-dimethyl-5-{1-methyl-2-[(phenylmethyl)amino]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=668.308, C36H46ClN3O7+H requires 668.310. NMR(CDCl3, selected data): 0.8(d, 3H), 1.1(d, 3H), 1.65(s, 3H), 2.05(s, 3H), 3.25(s, 3H), 4.05(s, 2H), 5.2(s, 1H), 7.2(d, 1H), 7.3-7.5(m, 5H). |
| 26 | (1S,2R,4aS,5S,8R,8aR)-2-(acetyloxy)-5-(2-{[(2-chlorophenyl)methyl]amino}-1-methylethyl)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=702.269, C36H45Cl2N3O7+H requires 702.271. NMR(CDCl3, selected data): 0.8(d, 3H), 1.15(d, 3H), 1.7(s, 3H), 2.1(s, 3H), 3.3(s, 3H), 4.3(s, 2H), 5.2(s, 1H), 7.1-7.6(m, 6H). |
| 27 | (1S,2R,4aS,5S,8R,8aR)-2-(acetyloxy)-5-{2-[(furan-2-ylmethyl)amino]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=658.288, C34H44ClN3O8+H requires 658.289. NMR(CDCl3, selected data): 0.7(m, 3H), 1.15(d, 3H), 1.75(s, 3H), 2.1(s, 3H), 3.15(s, 3H), 4.3(m, 2H), 5.3(s, |

TABLE 1-continued

Table of Examples

| Ex No. | Compound Name | Data* |
|---|---|---|
| | | 1H), 6.4(m, 1H), 6.5(m, 1H), 7.2(m, 1H), 7.5(m, 1H). |
| 28 | (1S,2R,4aS,5S,8R,8aR)-2-(acetyloxy)-8a-hydroxy-3,8-dimethyl-5-(1-methyl-2-{[(2-methylphenyl)methyl]amino}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=682.323, C37H48ClN3O7+H requires 682.326. NMR(CDCl3, selected data): 0.8(d, 3H), 1.1(d, 3H), 1.7(s, 3H), 2.1(s, 3H), 2.4(s, 3H), 3.3(s, 3H), 4.1(m, 2H), 5.2(s, 1H), 7.1-7.3(m, 5H), 7.45(m, 1H). |
| 29 | (1S,2R,4aS,5S,8R,8aR)-2-(acetyloxy)-8a-hydroxy-3,8-dimethyl-5-(1-methyl-2-{[(1S)-1-phenylethyl]amino}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(AP): M/Z[MH+]=682.3252, C37H48ClN3O7+H requires 682.3259. NMR(CDCl3, selected data): 0.8(d, 3H), 1.1(d, 3H), 1.6(s, 3H), 1.7(d, 3H), 2.1(s, 3H), 3.3(s, 3H), 5.2(s, 1H), 6.8-7.6(m, 8H). |
| 30 | (1S,2R,4aS,5S,8R,8aR)-2-(acetyloxy)-5-(2-{[(3-chlorophenyl)methyl]amino}-1-methylethyl)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=702.270, C36H45Cl2N3O7+H requires 702.271. NMR(CDCl3, selected data): 0.7(d, 3H), 1.1(d, 3H), 1.7(s, 3H), 2.1(s, 3H), 2.4(s, 3H), 3.3(s, 3H), 3.9-4.1(m, 3H), 5.2(s, 1H), 6.95(m, 1H), 7.1-7.25(m, 2H), 7.3-7.4(m, 3H), 7.45(m, 1H). |
| 31 | (1S,2R,4aS,5S,8R,8aR)-2-(acetyloxy)-8a-hydroxy-3,8-dimethyl-5-[1-methyl-2-({[2-(methyloxy)phenyl]methyl}amino)ethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=698.323, C37H48ClN3O8+H requires 698.321. NMR(CDCl3, selected data): 0.8(d, 3H), 1.1(d, 3H), 1.7(s, 3H), 2.1(s, 3H), 3.3(s, 3H), 3.85(s, 3H), 4.05-4.3(m, 2H), 5.2(s, 1H), 6.85-7.0(m, 5H), 7.2(d, 1H), 7.4(m, 1H). |
| 32 | (1S,2R,4aS,5S,8R,8aR)-2-(acetyloxy)-8a-hydroxy-3,8-dimethyl-5-[1-methyl-2-(4-pyridin-2-ylpiperazin-1-yl)ethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=724.350, C38H50ClN5O7+H requires 724.348. NMR(CDCl3, selected data): 0.7(d, 3H), 1.1(d, 3H), 1.7(s, 3H), 2.1(s, 3H), 2.2-2.4(m, 4H), 3.3(s, 3H), 3.4-3.6(m, 4H), 5.2(s, 1H), 6.6-6.7(m, 2H), 7.0(t, 1H), 7.2(d, 1H), 7.35(d, 1H), 7.5(m, 1H), 8.2(m, 1H). |
| 33 | (1S,2R,4aS,5S,8R,8aR)-2-(acetyloxy)-5-(2-{bis[2-(methyloxy)ethyl]amino}-1-methylethyl)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=694.347, C35H52ClN3O9+H requires 694.347. NMR(CDCl3, selected data): 0.65(d, 3H), 1.0(d, 3H), 1.7(s, 3H), 2.1(s, 3H), 2.4-2.8(m, 8H), 3.3-3.4(m, 9H), 3.4-3.5(m, 4H), 5.2-5.3(s, 2H), 7.2(d, 1H). |
| 34 | (1S,2R,4aS,5S,8R,8aR)-2-(acetyloxy)-8a-hydroxy-3,8-dimethyl-5-{1-methyl-2-[(2-thien-2-ylethyl)amino]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=688.280, C35H46ClN3O7S+H requires 688.282. NMR(CDCl3, selected data): 0.75(d, 3H), 1.15(d, 3H), 1.65(s, 3H), 2.1(s, 3H), 2.6-2.85(m, 4H), 3.2-3.3(m, 5H), 5.2(s, 1H), 6.8-7.0(m, 3H), 7.1-7.3(m, 3H). |
| 35 | (1S,2R,4aS,5S,8R,8aR)-2-(acetyloxy)-8a-hydroxy-3,8-dimethyl-5-[1-methyl-2-({[4-(trifluoromethyl)phenyl]methyl}amino)ethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c] | MS(ES): M/Z[MH+]=736.296, C37H45ClF3N3O7+H requires 736.298. NMR(CDCl3, selected data): 0.8(m, 3H), 1.1(d, 3H), 1.7(s, 3H), 2.1(s, 3H), 3.3(s, |

TABLE 1-continued

Table of Examples

| Ex No. | Compound Name | Data* |
|---|---|---|
| | c][2,1]benzoxazine-2-carboxylate | 3H), 3.8-4.2(m, 3H), 5.25(s, 1H), 6.9(t, 1H), 7.1(d, 1H), 7.2(d, 1H), 7.5-7.7(m, 4H). |
| 36 | (1S,2R,4aS,5S,8R,8aR)-2-(acetyloxy)-8a-hydroxy-3,8-dimethyl-5-{1-methyl-2-[methyl(2-{[2-(methyloxy)phenyl]oxy}ethyl)amino]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=742.346, C39H52ClN3O9+H requires 742.347. NMR(CDCl3, selected data): 0.8(m, 3H), 1.2(d, 3H), 1.7(s, 3H), 2.1(s, 3H), 3.0-3.2(m, 3H), 3.3(s, 3H), 3.4-3.9(m, 4H), 3.85(s, 3H), 5.2(s, 1H), 6.8-7.0(m, 4H), 7.0(m, 1H), 7.2(d, 1H), 7.35(d, 1H). |
| 37 | (1S,2R,4aS,5S,8R,8aR)-2-(acetyloxy)-8a-hydroxy-3,8-dimethyl-5-(1-methyl-2-{(1-methylethyl)[2-(phenylsulfonyl)ethyl]amino}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=788.333, C40H54ClN3O9S+H requires 788.335. NMR(CDCl3, selected data): 0.9(d, 3H), 1.15(d, 3H), 1.35(d, 3H), 1.45(d, 3H), 1.7(s, 3H), 2.1(s, 3H), 3.3(s, 3H), 3.4-3.9(m, 4H), 3.85(s, 3H), 5.2(s, 1H), 7.0(t, 1H), 7.2(d, 1H), 7.3(d, 1H), 7.55-7.65(m, 2H), 7.7(m, 1H), 7.9(m, 2H). |
| 38 | (1S,2R,4aS,5S,8R,8aR)-2-(acetyloxy)-5-{2-[(2,3-dihydro-1,4-benzodioxin-2-ylmethyl)(methyl)amino]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=740.332, C39H50ClN3O9+H requires 740.331. NMR(CDCl3, selected data): 0.8(d, 3H), 1.2(m, 3H), 1.7(s, 3H), 2.1(s, 3H), 3.0(s, 3H), 3.3(s, 3H), 4.05-4.3(m, 4H), 5.2(s, 1H), 6.8-7.05(m, 5H), 7.2-7.35(m, 2H). |
| 39 | (1S,2R,4aS,5S,8R,8aR)-2-(acetyloxy)-8a-hydroxy-3,8-dimethyl-5-[1-methyl-2-(4-{[2-(methyloxy)phenyl]methyl}piperazin-1-yl)ethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=767.379, C41H55ClN4O8+H requires 767.379. NMR(CDCl3, selected data): 0.8(d, 3H), 1.15(d, 3H), 1.7(s, 3H), 2.1(s, 3H), 3.3(s, 3H), 3.85(s, 3H), 4.3(s, 2H), 5.2(s, 1H), 6.9-7.1(m, 4H), 7.2-7.5(m, 3H). |
| 40 | (1S,2R,4aS,5S,8R,8aR)-2-(acetyloxy)-5-{2-[4-(1,1-dimethylethyl)piperidin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=702.3900, C38H56ClN3O7+H requires 702.3885. NMR(CDCl3, selected data): 0.8-0.95(m, 12H), 0.9-1.1(m, 3H), 1.65-1.75(m, 3H), 2.1-2.15(m, 3H), 2.2-2.5(m, 8H), 3.3-3.35(s, 3H), 5.2(s, 1H), 7.05(m, 1H), 7.2(m, 1H). |
| 41 | (1S,2R,4aS,5S,8R,8aR)-2-(acetyloxy)-8a-hydroxy-3,8-dimethyl-5-(1-methyl-2-{4-[(phenylmethyl)oxy]piperidin-1-yl}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=752.3678, C41H54ClN3O8+H requires 752.3678. NMR(CDCl3, selected data): 0.8(d, 3H), 1.1(d, 3H), 1.7(s, 3H), 2.1(s, 3H), 3.25-3.4(m, 7H), 4.55(s, 2H), 5.2(s, 1H), 7.0(m, 1H), 7.2-7.4(m, 7H). |
| 42 | (1S,2R,4aS,5S,8R,8aR)-2-(acetyloxy)-5-{2-[7,8-bis(methyloxy)-3,4-dihydroisoquinolin-2(1H)-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=754.3463, C40H52ClN3O9+H requires 754.3470. NMR(CDCl3, selected data): 0.8(d, 3H), 1.1(d, 3H), 1.7(s, 3H), 2.1(s, 3H), 3.0-3.35(m, 8H), 3.3(s, 3H), 3.8(s, 3H), 3.9(s, 3H), 4.55(s, 2H), 5.2(s, 1H), 6.8-6.9(m, 2H), 7.0(m, 1H), 7.2(m, 1H), 7.35(m, 1H). |

TABLE 1-continued

Table of Examples

| Ex No. | Compound Name | Data* |
|---|---|---|
| 43 | (1S,2R,4aS,5S,8R,8aR)-2-(acetyloxy)-8a-hydroxy-3,8-dimethyl-5-[1-methyl-2-(methyl{[4-(methyloxy)phenyl]methyl}amino)ethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=712.3382, C38H50ClN3O8+H requires 712.3365. NMR(CDCl3, selected data): 0.85(m, 3H), 1.7(s, 3H), 2.1(s, 3H), 2.6-2.9(m, 9H), 3.3(s, 3H), 3.85(s, 3H), 4.15(m, 2H), 5.2(s, 1H), 6.9-7.1(m, 3H), 7.2(m, 1H), 7.2-7.25(m, 2H). |
| 44 | (1S,2R,4aS,5S,8R,8aR)-2-(acetyloxy)-5-(2-{4-[(ethyloxy)carbonyl]-1,4-diazepan-1-yl}-1-methylethyl)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=733.3554, C37H53ClN4O9+H requires 733.3579. NMR(CDCl3, selected data): 0.8(d, 3H), 1.2(d, 3H), 1.3(t, 3H), 1.7(s, 3H), 2.1(s, 3H), 2.9-3.2(m, 14H), 3.3(s, 3H), 4.1-4.3(m, 4H), 5.2(s, 1H), 7.0(m, 3H), 7.2-7.35(m, 2H). |
| 45 | (1S,2R,4aS,5S,8R,8aR)-2-(acetyloxy)-8a-hydroxy-3,8-dimethyl-5-{1-methyl-2-[4-(phenylmethyl)-1,4-diazepan-1-yl]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=751.3840, C41H55ClN4O7+H requires 751.3838. NMR(CDCl3, selected data): 0.8(d, 3H), 1.15(d, 3H), 1.7(s, 3H), 2.1(s, 3H), 2.9-4.0(m, 12H), 3.3(s, 3H), 4.3(s, 2H), 5.2(s, 1H), 6.95(m, 1H), 7.2(d, 1H), 7.4-7.5(m, 6H). |
| 46 | (1S,2R,4aS,5S,8R,8aR)-5-{2-[acetyl(ethyl)amino]-1-methylethyl}-2-(acetyloxy)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=649.0, C33H46ClN3O8+H requires 648.3052. NMR(CDCl3, selected data): 0.75-0.8(m, 3H), 0.95-1.0(m, 3H), 1.2-1.3(m, 3H), 1.65-1.75(m, 3H), 2.1(s, 3H), 2.15(s, 3H), 3.3(s, 3H), 5.2(s, 1H), 7.2(d, 1H). |
| 47 | (1S,2R,4aS,5S,8R,8aR)-5-{2-[acetyl(cyclopropyl)amino]-1-methylethyl}-2-(acetyloxy)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=660.2, C34H46ClN3O8+H requires 660.3052. NMR(CDCl3, selected data): 0.7-0.8(m, 5H), 0.9-1.0(m, 6H), 1.7(s, 3H), 2.1(s, 3H), 2.2(s, 3H), 3.3(s, 3H), 5.2(s, 1H), 7.0(dd, 1H), 7.2(d, 1H), 7.35(d, 1H). |
| 48 | (1S,2R,4aS,5S,8R,8aR)-2-(acetyloxy)-5-(2-{cyclopropyl[(methyloxy)carbonyl]amino}-1-methylethyl)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(TSP): M/Z[MH+]=676.7, C34H46ClN3O9+H requires 676.3001. NMR(CDCl3, selected data): 0.6-0.7(m, 5H), 0.7-0.9(m, 3H), 1.0(d, 3H), 1.7(s, 3H), 2.1(s, 3H), 2.2(s, 3H), 3.35(s, 3H), 3.7(s, 3H), 5.25(s, 1H), 7.0(dd, 1H), 7.2(d, 1H), 7.4(d, 1H). |
| 49 | (1S,2R,4aS,5S,8R,8aR)-2-(acetyloxy)-5-(2-{ethyl[(methyloxy)carbonyl]amino}-1-methylethyl)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(TSP): M/Z[MH+]=664.4, C33H46ClN3O9+H requires 664.3001. NMR(CDCl3, selected data): 0.8(t, 3H), 1.0(m, 3H), 1.2(m, 3H), 1.7(s, 3H), 2.1(s, 3H), 3.35(s, 3H), 3.65(s, 3H), 5.2-5.25(m, 2H), 7.0(m, 1H), 7.2(m, 1H), 7.4(d, 1H). |
| 50 | (1S,2R,4aS,5S,8R,8aR)-2-(acetyloxy)-5-(2-{[(2,5-dichlorophenyl)methyl]amino}-1-methylethyl)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b- | MS(AP+): M/Z[MH+]=736, C36H44Cl3N3O7+H requires 736.2323. NMR(CDCl3, selected data): 0.8(d, 3H), 1.1(d, 3H), 1.7(s, |

TABLE 1-continued

Table of Examples

| Ex No. | Compound Name | Data* |
|---|---|---|
| | hexahydropyrrolo[2,3-c][2,1]benzoxazine-2-carboxylate | 3H), 2.1(s, 3H), 3.3(s, 3H), 4.3(s, 2H), 5.2(s, 2H), 6.95(dd, 1H), 7.2(d, 1H), 7.3-7.4(m, 3H), 7.6(s, 1H). |
| 51 | (1S,2R,4aS,5S,8R,8aR)-2-(acetyloxy)-5-(2-{[(3,5-dichlorophenyl)methyl]amino}-1-methylethyl)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(AP+): M/Z[MH+]=736, C36H44Cl3N3O7+H requires 736.2323. NMR(CDCl3, selected data): 0.7(m, 3H), 1.1(m, 3H), 1.7(s, 3H), 2.1(s, 3H), 3.3(s, 3H), 3.9-4.1(m, 2H), 5.3(s, 1H), 6.9(m, 1H), 7.1-7.4(m, 5H). |
| 52 | (1S,2R,4aS,5S,8R,8aR)-2-(acetyloxy)-5-(2-{cyclopropyl[(ethylamino)carbonyl]amino}-1-methylethyl)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=689.4, C35H49ClN4O8+H requires 689.3317. NMR(CDCl3, selected data): 0.7-0.8(m, 5H), 0.8-0.9(m, 3H), 0.95(d, 3H), 1.1(t, 3H), 1.7(s, 3H), 2.1(s, 3H), 3.3(s, 3H), 3.65-3.8(m, 2H), 5.2(s, 1H), 6.95(dd, 1H), 7.2(d, 1H), 7.3(d, 1H). |
| 53 | (1S,2R,4aS,5S,8R,8aR)-2-(acetyloxy)-8a-hydroxy-3,8-dimethyl-5-{1-methyl-2-[methyl(phenylmethyl)amino]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=682, C37H48ClN3O7+H requires 682.3259. NMR(CDCl3, selected data): 0.8(d, 3H), 0.85-1.1(m, 3H), 1.6(s, 3H), 2.1(s, 3H), 2.65-2.75(m, 3H), 3.1-3.15(m, 3H), 4.2-4.6(m, 3H), 5.2(s, 1H), 6.9-7.4(m, 3H), 7.45-7.6(m, 5H). |
| 54 | (1S,2R,4aS,5S,8R,8aR)-2-(acetyloxy)-8a-hydroxy-3,8-dimethyl-5-{1-methyl-2-[4-(phenylmethyl)piperazin-1-yl]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=737, C40H53ClN4O7+H requires 737.3681. NMR(CDCl3, selected data): 0.8(d, 3H), 1.2(d, 3H), 1.65(s, 3H), 2.1(s, 3H), 3.0-3.4(m, 6H), 3.3(s, 3H), 3.5-3.7(m, 6H), 4.2(s, 2H), 5.2(s, 1H), 7.0(m, 1H), 7.2(m, 1H), 7.4-7.5(m, 6H). |
| 55 | (1S,2R,4aS,5S,8R,8aR)-2-(acetyloxy)-8a-hydroxy-3,8-dimethyl-5-[1-methyl-2-(3-methylpiperidin-1-yl)ethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=660, C35H50ClN3O7+H requires 660.3416. NMR(CDCl3, selected data): 0.8(d, 3H), 1.0-1.05(m, 3H), 1.2(d, 3H), 1.7(s, 3H), 2.1(s, 3H), 2.7-2.9(m, 12H), 3.3(s, 3H), 5.2(s, 2H), 7.0(m, 1H), 7.2(m, 1H), 7.35(d, 1H). |
| 56 | (1S,2R,4aS,5S,8R,8aR)-2-(acetyloxy)-8a-hydroxy-3,8-dimethyl-5-[1-methyl-2-(4-pyrimidin-2-ylpiperazin-1-yl)ethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=725.2, C37H49ClN6O7+H requires 725.3430. NMR(CDCl3, selected data): 0.8(d, 3H), 1.1(d, 3H), 1.6(s, 3H), 2.1(s, 3H), 2.3-2.65(m, 8H), 3.35(s, 3H), 4.75-4.9(m, 4H), 5.2(m, 2H), 6.5(m, 1H), 7.0(dd, 1H), 7.2(m, 1H), 7.4(d, 1H), 8.3-8.35(m, 2H). |
| 57 | (1S,2R,4aS,5S,8R,8aR)-2-(acetyloxy)-8a-hydroxy-3,8-dimethyl-5-(1-methyl-2-{methyl[2-(phenyloxy)ethyl]amino}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=712, C38H50ClN3O8+H requires 712.3365. NMR(CDCl3, selected data): 0.8(d, 3H), 1.2(d,3H), 1.6(s, 3H), 2.1(s, 3H), 2.9-3.05(m, 4H), 3.3(s, 3H), 4.4-4.5(m, 2H), 5.2(m, 1H), |

TABLE 1-continued

Table of Examples

| Ex No. | Compound Name | Data* |
|---|---|---|
| | | 6.85-7.0(m, 3H), 7.0(dd, 1H), 7.2(m, 1H), 7.25-7.35(m, 3H). |
| 58 | (1S,2R,4aS,5S,8R,8aR)-2-(acetyloxy)-8a-hydroxy-3,8-dimethyl-5-[1-methyl-2-thiomorpholin-4-ylethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=664, $C_{33}H_{46}ClN_3O_7S$+H requires 663.2745. NMR(CDCl3, selected data): 0.85(d, 3H), 1.2(d, 3H), 1.7(s, 3H), 2.1(s, 3H), 2.9-3.2(m, 11H), 3.3(s, 3H), 5.2(m, 1H), 7.0(dd, 1H), 7.2-7.3(m, 2H). |
| 59 | (1S,2R,4aS,5S,8R,8aR)-2-(acetyloxy)-5-{2-[cyclohexyl(methyl)amino]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=674, $C_{36}H_{52}ClN_3O_7$+H requires 674.3572. NMR(CDCl3, selected data): 0.85(d, 3H), 1.15-1.25(m, 6H), 1.3-1.5(m, 6H), 1.7(s, 3H), 1.9-2.0(m, 2H), 2.1(s, 3H), 2.7-2.85(m, 3H), 3.3(s, 3H), 5.2(m, 1H), 7.0(m, 1H), 7.2(m, 1H), 7.35(dd, 1H). |
| 60 | (1S,2R,4aS,5S,8R,8aR)-2-(acetyloxy)-8a-hydroxy-3,8-dimethyl-5-{1-methyl-2-[methyl(pyridin-2-ylmethyl)amino]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=683, $C_{36}H_{47}ClN_4O_7$+H requires 683.3212. NMR(CDCl3, selected data): 0.8(d, 3H), 1.1(d, 3H), 1.65(s, 3H), 2.1(s, 3H), 2.95(s, 3H), 3.3(s, 3H), 4.45(m, 2H), 5.2(m, 1H), 7.0(m, 1H), 7.2(m, 1H), 7.35(m, 1H), 7.5(m, 1H), 7.65(m, 1H), 7.85(m, 1H), 8.65(m, 1H). |
| 61 | (1S,2R,4aS,5S,8R,8aR)-2-(acetyloxy)-5-[2-(3,6-dihydropyridin-1(2H)-yl)-1-methylethyl]-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=644, $C_{34}H_{46}ClN_3O_7$+H requires 644.3103. NMR(CDCl3, selected data): 0.85(d, 3H), 1.15(d, 3H), 1.7(s, 3H), 2.1(s, 3H), 3.3(s, 3H), 4.45(m, 2H), 5.1-5.2(m, 2H), 5.7(m, 1H), 6.0(m, 1H), 7.0(m, 1H), 7.35(m, 1H). |
| 62 | (1S,2R,4aS,5S,8R,8aR)-2-(acetyloxy)-8a-hydroxy-3,8-dimethyl-5-(1-methyl-2-{[phenyl(pyridin-3-yl)methyl]amino}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=745, $C_{41}H_{49}ClN_4O_7$+H requires 745.3. NMR(CDCl3, selected data): 0.8(d, 3H), 1.05(d, 3H), 1.6(s, 3H), 2.1(s, 3H), 3.3(s, 3H), 4.45(m, 2H), 5.0-5.15(m, 3H), 6.9-7.6(m, 9H), 8.1(m, 1H), 8.6(m, 1H), 8.8(m, 1H). |
| 63 | (1S,2R,4aS,5S,8R,8aR)-2-(acetyloxy)-8a-hydroxy-3,8-dimethyl-5-{1-methyl-2-[4-(2-phenylethyl)piperazin-1-yl]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=751.3, $C_{41}H_{55}ClN_4O_7$+H requires 751.3838. NMR(CDCl3, selected data): 0.8(d, 3H), 1.15(d, 3H), 1.7(s, 3H), 2.1(s, 3H), 3.25-3.35(m, 4H), 3.55-3.65(m, 6H), 5.2(m, 1H), 7.0(m, 1H), 7.2-7.4(m, 7H). |
| 64 | (1S,2R,4aS,5S,8R,8aR)-2-(acetyloxy)-5-{2-[4-(1,3-benzodioxol-5-ylmethyl)piperazin-1-yl]-1-methylethyl}-8a-hydroxy-3,8-dimethyl-1,2,4a,5,6,7,8,8a-octahydronaphthalen-1-yl | MS(ES): M/Z[MH+]=781, $C_{41}H_{53}ClN_4O_9$+H requires 781.3579. NMR(CDCl3, selected data): |

TABLE 1-continued

Table of Examples

| Ex No. | Compound Name | Data* |
|---|---|---|
| | (2S,3aR,9bR)-6-chloro-9b-hydroxy-5-methyl-1,2,3,3a,5,9b-hexahydropyrrolo[2,3-c][2,1]benzoxazine-2-carboxylate | 0.8(d, 3H), 1.15(d, 3H), 1.7(s, 3H), 2.1(s, 3H), 3.3(s, 3H), 3.5-3.75(m, 9H), 5.2(m, 1H), 6.0(s, 2H), 6.8-6.85(m, 2H), 6.9(s, 1H), 7.0(m, 1H), 7.2-7.3(m, 2H). |
| 65 | (1S,2R,4aS,5S,8R,8aR)-2-(acetyloxy)-8a-hydroxy-3,8-dimethyl-5-(1-methyl-2-{4-[3-(methyloxy)phenyl]piperazin-1-yl}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=753, C40H53ClN4O8+H requires 753.3630. NMR(CDCl3, selected data): 0.8(d, 3H), 1.15(d, 3H), 1.7(s, 3H), 2.1(s, 3H), 3.3(s, 3H), 3.25-3.8(m, 9H), 3.8(s, 3H), 5.2(m, 1H), 6.45(m, 1H), 6.3-6.4(m, 2H), 7.0(m, 1H), 7.2-7.35(m, 3H). |
| 66 | (1S,2R,4aS,5S,8R,8aR)-2-(acetyloxy)-5-[2-(4-{[(4-chlorophenyl)methyl]oxy}piperidin-1-yl)-1-methylethyl]-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=786, C41H53Cl2N3O8+H requires 786.3288. NMR(CDCl3, selected data): 0.8(d, 3H), 1.1(d, 3H), 1.65(s, 3H), 2.1(s, 3H), 2.55-2.75(m, 8H), 2.9-3.2(m, 4H), 3.3(s, 3H), 4.5(s, 2H), 5.2(s, 1H), 7.0(m, 1H), 7.2-7.4(m, 6H). |
| 67 | (1S,2R,4aS,5S,8R,8aR)-2-(acetyloxy)-8a-hydroxy-3,8-dimethyl-5-(1-methyl-2-{4-[2-(methyloxy)phenyl]piperazin-1-yl}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=752, C40H53ClN4O8+H requires 753.3630. NMR(CDCl3, selected data): 0.8(d, 3H), 1.2(d, 3H), 1.7(s, 3H), 2.1(s, 3H), 3.0-3.6(m, 11H), 3.3(s, 3H), 5.2(s, 1H), 6.9(m, 1H), 6.95-7.05(m, 3H), 7.1(m, 1H), 7.2-7.3(m, 2H). |
| 68 | (1S,2R,4aS,5S,8R,8aR)-2-(acetyloxy)-5-{2-[4-(furan-2-ylmethyl)piperidin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=727, C39H52ClN3O8+H requires 726.3521. NMR(CDCl3, selected data): 0.8(d, 3H), 1.2(d, 3H), 1.7(s, 3H), 2.1(s, 3H), 3.3(s, 3H), 3.5-3.7(m, 9H), 4.2(m, 2H), 5.2(m, 1H), 6.45(m, 1H), 6.6(m, 1H), 7.0(m, 1H), 7.2-7.3(m, 2H), 7.5(m, 1H). |
| 69 | (1S,2R,4aS,5S,8R,8aR)-2-(acetyloxy)-8a-hydroxy-3,8-dimethyl-5-(1-methyl-2-{4-[(3-methylphenyl)methyl]piperazin-1-yl}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=751, C41H55ClN4O7+H requires 751.3838. NMR(CDCl3, selected data): 0.8(d, 3H), 1.15(d, 3H), 1.65(s, 3H), 2.1(s, 3H), 2.35(s, 3H), 3.3(s, 3H), 3.5-3.75(m, 8H), 4.15(m, 2H), 5.2(s, 1H), 7.0(m, 1H), 7.15-7.35(m, 6H). |
| 70 | (1S,2R,4aS,5S,8R,8aR)-2-(acetyloxy)-5-{2-[(2,2-dimethylpropanoyl)(ethyl)amino]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=690, C36H52ClN3O8+H requires 690.3521. NMR(CDCl3, selected data): 0.85(d, 3H), 0.95(d, 3H), 1.25(t, 3H), 1.3(s, 9H), 1.7(s, 3H), 2.1(s, 3H), 3.3(s, 3H), 5.2(s, 1H), 7.0(dd, 1H), 7.2(m, 1H), 7.4(d, |
| 71 | (1S,2R,4aS,5S,8R,8aR)-2-(acetyloxy)-8a-hydroxy-3,8-dimethyl-5-{1-methyl-2-[methyl(propanoyl)amino]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=648, C33H46ClN3O8+H requires 648.3052. NMR(CDCl3, selected data): 0.8(d, 3H), 1.0(d, 3H), 1.2(m, 3H), 1.7(s, 3H), 2.1(s, 3H), 3.1(s, 3H), 3.3(s, 3H), |

TABLE 1-continued

Table of Examples

| Ex No. | Compound Name | Data* |
|---|---|---|
| | | 5.2(s, 1H), 7.0(m, 1H), 7.2(m, 1H), 7.4(d, 1H). |
| 72 | (1S,2R,4aS,5S,8R,8aR)-2-(acetyloxy)-8a-hydroxy-3,8-dimethyl-5-{1-methyl-2-[(1-methylethyl)(propanoyl)amino]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=676, C35H50ClN3O8+H requires 676.3365. NMR(CDCl3, selected data): 0.8(d, 3H), 0.9(d, 3H), 1.2(t, 3H), 1.3(m, 6H), 1.7(s, 3H), 2.1(s, 3H), 3.1(s, 3H), 3.3(s, 3H), 4.15(m, 2H), 5.2(s, 1H), 7.0(m, 1H), 7.2(m, 1H), 7.4(d, 1H). |
| 73 | (1S,2R,4aS,5S,8R,8aR)-2-(acetyloxy)-5-{2-[(2,2-dimethylpropanoyl)(1-methylethyl)amino]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=704, C37H54ClN3O8+H requires 704.3678. NMR(CDCl3, selected data): 0.8-0.9(m, 6H), 1.2-1.25(m, 6H), 1.3(s, 9H), 1.7(s, 3H), 2.1(s, 3H), 3.3(s, 3H), 5.2(s, 1H), 6.95(m, 1H), 7.2(m, 1H), 7.35(d, 1H). |
| 74 | (1S,2R,4aS,5S,8R,8aR)-2-(acetyloxy)-8a-hydroxy-3,8-dimethyl-5-(1-methyl-2-{(1-methylethyl)[(methyloxy)acetyl]amino}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=692, C35H50ClN3O9+H requires 692.3314. NMR(CDCl3, selected data): 0.8(m, 3H), 0.95(d, 3H), 1.2-1.3(m, 6H), 1.7(s, 3H), 2.1(s, 3H), 3.3(s, 3H), 3.4(s, 3H), 4.15(m, 2H), 5.2(s, 1H), 7.0(m, 1H), 7.2(m, 1H), 7.35(d, 1H). |
| 75 | (1S,2R,4aS,5S,8R,8aR)-2-(acetyloxy)-5-{2-[[(2-chlorophenyl)methyl](propanoyl)amino]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=758, C39H49Cl2N3O8+H requires 758.2975. NMR(CDCl3, selected data): 0.8(m, 3H), 1.0(d, 3H), 1.15(t, 3H), 1.7(s, 3H), 2.1(s, 3H), 3.3(s, 3H), 4.65(m, 2H), 5.2(s, 1H), 6.95-7.1(m, 2H), 7.2-7.45(m, 5H). |
| 76 | (1S,2R,4aS,5S,8R,8aR)-2-(acetyloxy)-5-(2-{[(2-chlorophenyl)methyl][(methyloxy)acetyl]amino}-1-methylethyl)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=774, C39H49Cl2N3O9+H requires 774.2924. NMR(CDCl3, selected data): 0.8(m, 3H), 1.0(m, 3H), 1.7(s, 3H), 2.1(s, 3H), 3.3(s, 3H), 3.4(s, 3H), 4.0-4.2(m, 3H), 4.65(m, 2H), 5.2(s, 1H), 7.0(m, 1H), 7.1(m, 1H), 7.2-7.5(m, 5H). |
| 77 | (1S,2R,4aS,5S,8R,8aR)-5-(2-{acetyl[(2-methylphenyl)methyl]amino}-1-methylethyl)-2-(acetyloxy)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=724, C39H50ClN3O8+H requires 724.3365. NMR(CDCl3, selected data): 0.75-0.8(m, 3H), 1.0(d, 3H), 1.7(s, 3H), 2.1(s, 3H), 2.3-2.35(m, 3H), 3.3(s, 3H), 5.25(s, 1H), 6.95-7.1(m, 2H), 7.2-7.4(m, 5H). |
| 78 | (1S,2R,4aS,5S,8R,8aR)-2-(acetyloxy)-8a-hydroxy-3,8-dimethyl-5-{1-methyl-2-[[(2-methylphenyl)methyl](propanoyl)amino]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=738, C40H52ClN3O8+H requires 738.3521. NMR(CDCl3, selected data): 0.8(d, 3H), 1.05(d, 3H), 1.1(t, 3H), 1.7(s, 3H), 2.1(s, 3H), 2.3(s, 3H), 3.3(s, 3H), 4.5(m, 2H), 5.25(s, 1H), 6.9-7.1(m, 2H), 7.15-7.3(m, 4H), 7.35(m, 1H). |
| 79 | (1S,2R,4aS,5S,8R,8aR)-2-(acetyloxy)-8a-hydroxy-3,8-dimethyl-5-(1-methyl-2-{[(methyloxy)acetyl][(2-methylphenyl)methyl]amino}ethyl)- | MS(ES): M/Z[MH+]=754, C40H52ClN3O9+H requires 754.3470. NMR(CDCl3, selected data): |

TABLE 1-continued

Table of Examples

| Ex No. | Compound Name | Data* |
|---|---|---|
| | 1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | 0.8(d, 3H), 1.0(d, 3H), 1.7(s, 3H), 2.1(s, 3H), 2.3(s, 3H), 3.3-3.35(m, 6H), 4.1(m, 2H), 4.55(m, 2H), 5.25(s, 1H), 6.9-7.1(m, 2H), 7.1-7.3(m, 4H), 7.4(m, 1H). |
| 80 | (1S,2R,4aS,5S,8R,8aR)-2-(acetyloxy)-5-[2-(4-{[(4-fluorophenyl)methyl]oxy}piperidin-1-yl)-1-methylethyl]-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=770, C41H53ClFN3O8+H requires 770.3583. NMR(CDCl3, selected data): 0.8(d, 3H), 1.2(d, 3H), 1.7(s, 3H), 1.9-2.1(m, 5H), 2.1(s, 3H), 2.9-3.1(m, 4H), 3.3(s, 3H), 4.5(s, 2H), 5.2(s, 1H), 6.95-7.1(m, 3H), 7.2-7.3(m, 4H). |
| 81 | (1S,2R,4aS,5S,8R,8aR)-2-(acetyloxy)-5-(2-{4-[(4-chlorophenyl)methyl]piperazin-1-yl}-1-methylethyl)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=771, C41H53Cl2N3O7+H requires 770.3339. NMR(CDCl3, selected data): 0.8(d, 3H), 1.2(d, 3H), 1.7(s, 3H), 1.9-2.1(m, 5H), 2.1(s, 3H), 3.3(s, 3H), 3.45-3.75(m, 8H), 4.1(s, 2H), 5.2(s, 1H), 7.0(dd, 1H), 7.2-7.35(m, 2H), 7.35-7.45(m, 4H). |
| 82 | (1S,2R,4aS,5S,8R,8aR)-2-(acetyloxy)-5-[2-(3,4-dihydroisoquinolin-2(1H)-yl)-1-methylethyl]-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=694, C38H48ClN3O7+H requires 694.3. NMR(CDCl3, selected data): 0.8(d, 3H), 1.2(d, 3H), 1.7(s, 3H), 2.1(m, 3H), 3.0-3.5(m, 5H), 5.2(s, 1H), 7.0(dd, 1H), 7.2-7.1-7.35(m, 7H). |
| 83 | (1S,2R,4aS,5S,8R,8aR)-2-(acetyloxy)-5-{2-[(2R,6S)-2,6-dimethylmorpholin-4-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=676, C35H50ClN3O8+H requires 676.3365. NMR(CDCl3, selected data): 0.8(d, 3H), 1.2(d, 3H), 1.2-1.3(m, 6H), 1.7(s, 3H), 2.1(s, 3H), 3.1-3.3(m, 6H), 3.3(s, 3H), 5.2(s, 1H), 7.0(dd, 1H), 7.2-7.35(m, 2H). |
| 84 | (1S,2R,4aS,5S,8R,8aR)-2-(acetyloxy)-8a-hydroxy-3,8-dimethyl-5-{1-methyl-2-[methyl(3,3,3-trifluoropropanoyl)amino]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=702.2, C33H43ClF3N3O8+H requires 702.2769. NMR(CDCl3, selected data): 0.85(m, 3H), 0.95(m, 3H), 1.7(s, 3H), 2.1(s, 3H), 3.1(s, 3H), 3.4(s,3H), 5.2(s, 1H), 7.0(m, 1H), 7.2-7.4(m, 2H). |
| 85 | (1S,2R,4aS,5S,8R,8aR)-2-(acetyloxy)-8a-hydroxy-3,8-dimethyl-5-{1-methyl-2-[[(2-methylphenyl)methyl](3,3,3-trifluoropropanoyl)amino]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=792.2, C40H49ClF3N3O8+H requires 792.3239. NMR(CDCl3, selected data): 0.8(m, 3H), 1.05(m, 3H), 1.7(s, 3H), 2.1(s, 3H), 2.3(s, 3H), 3.35(s, 3H), 4.5(m, 2H), 5.2(s, 1H), 6.9-7.4(m, 7H). |
| 86 | (1S,2R,4aS,5S,8R,8aR)-2-(acetyloxy)-8a-hydroxy-3,8-dimethyl-5-(1-methyl-2-{4-[(4-methylphenyl)methyl]piperazin-1-yl}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=751.2, C41H55ClN4O7+H requires 751.3838. NMR(CDCl3, selected data): 0.8(m, 3H), 1.1(m, 3H), 1.65(s, 3H), 2.1(s, 3H), 2.3(s, 3H), 3.3(s, 3H), 3.4-3.6(m, 8H), 4.0-4.15(m, 3H), 5.2(s, 1H), 6.9(dd, 1H), 7.1-7.3(m, 6H). |
| 87 | (1S,2R,4aS,5S,8R,8aR)-2-(acetyloxy)-8a-hydroxy-3,8-dimethyl-5-(1-methyl-2-{4-[6- | MS(ES): M/Z[MH+]=755, C38H51ClN6O8+H |

TABLE 1-continued

Table of Examples

| Ex No. | Compound Name | Data* |
|---|---|---|
| | (methyloxy)pyridazin-3-yl]piperazin-1-yl}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | requires 755.3535. NMR(CDCl3, selected data): 0.8(m, 3H), 1.1(m, 3H), 1.7(s, 3H), 2.1(s, 3H), 2.4-3.2(m, 12H), 3.3(s, 3H), 4.0(s, 3H), 5.2(s, 1H), 6.95-7.05(m, 2H), 7.15(m, 1H), 7.2-7.3(m, 2H). |
| 88 | (1S,2R,4aS,5S,8R,8aR)-2-(acetyloxy)-5-{2-[4-(6-chloropyrazin-2-yl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=759, C37H48Cl2N6O7+H requires 759.3040. NMR(CDCl3, selected data): 0.8(d, 3H), 1.15(d, 3H), 1.7(s, 3H), 2.1(s, 3H), 2.4-3.2(m, 12H), 3.3(s, 3H), 5.2(s, 1H), 7.0(m, 1H), 7.2(m, 1H), 7.3(d, 1H), 7.95(s, 1H), 8.05(s, 1H). |
| 89 | (1S,2R,4aS,5S,8R,8aR)-2-(acetyloxy)-5-{2-[4-(6-chloropyridin-2-yl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=758.2, C38H49Cl2N5O7+H requires 758.3087. NMR(CDCl3, selected data): 0.75(d, 3H), 1.1(d, 3H), 1.6(s, 3H), 1.95(s, 3H), 2.4-2.8(m, 10H), 3.1(s, 3H), 5.1(s, 1H), 6.45(d, 1H), 6.55(d, 1H), 6.95(dd, 1H), 7.1(d, 1H), 7.15(d, 1H), 7.35(dd, 1H). |
| 90 | (1S,2R,4aS,5S,8R,8aR)-2-(acetyloxy)-8a-hydroxy-3,8-dimethyl-5-[1-methyl-2-(4-phenylpiperazin-1-yl)ethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=723, C39H51ClN4O7+H requires 723.3525. NMR(CDCl3, selected data): 0.8(d, 3H), 1.1(d, 3H), 1.7(s, 3H), 2.1(s, 3H), 2.45-2.8(m, 8H), 3.15-3.25(m, 5H), 3.3(s, 3H), 5.1(s, 1H), 6.85(m, 1H), 6.9-6.95(m, 2H), 7.0(dd, 1H), 7.2-7.3(m, 3H), 7.35(dd, 1H). |
| 91 | (1S,2R,4aS,5S,8R,8aR)-2-(acetyloxy)-5-{2-[4-(cyclohexylmethyl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=743.3, C40H59ClN4O7+H requires 743.4151. NMR(CDCl3, selected data): 0.8(d, 3H), 1.1(d, 3H), 1.7(s, 3H), 1.7-1.85(m, 8H), 2.1(s, 3H), 3.3(s, 3H), 3.6-3.8(m, 8H), 5.2(s, 1H), 7.0(dd, 1H), 7.2-7.3(m, 2H). |
| 92 | (1S,2R,4aS,5S,8R,8aR)-2-(acetyloxy)-8a-hydroxy-3,8-dimethyl-5-{1-methyl-2-[4-(1,3-thiazol-2-yl)piperazin-1-yl]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=730.2, C36H48ClN5O7S+H requires 730.3041. NMR(CDCl3, selected data): 0.8(d, 3H), 1.1(d, 3H), 1.7(s, 3H), 2.15(s, 3H), 3.0-3.1(m, 2H), 3.3(s, 3H), 3.3-3.5(m, 4H), 3.85-4.05(m, 4H), 5.2(s, 1H), 6.7(s, 1H), 7.0(dd, 1H), 7.2-7.25(m, 2H), 7.3(m, 1H). |
| 93 | (1S,2R,4aS,5S,8R,8aR)-2-(acetyloxy)-5-{2-[4-(3-chloropyridin-2-yl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=758, C38H49Cl2N5O7+H requires 758.3087. NMR(CDCl3, selected data): 0.85(d, 3H), 1.15(d, 3H), 1.7(s, 3H), 2.15(s, 3H), 3.0-3.2(m, 4H), 3.35(s, 3H), 3.35-4.05(m, 6H), 5.2(s, 1H), 6.9(m, 1H), 7.0(dd, 1H), 7.2(m, 1H), 7.3(d, 1H), 7.6(m, 1H), 8.2(m, 1H). |

TABLE 1-continued

Table of Examples

| Ex No. | Compound Name | Data* |
|---|---|---|
| 94 | (1S,2R,4aS,5R,8R,8aR)-2-(acetyloxy)-8a-hydroxy-3,8-dimethyl-5-{1-methyl-2-oxo-2-[(phenylmethyl)amino]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=682, $C_{36}H_{44}ClN_3O_8$+H requires 682.2895. NMR(CDCl3, selected data): 0.9(m, 3H), 1.3(m, 3H), 1.7(s, 3H), 2.1(s, 3H), 3.3(s, 3H), 4.2(m, 2H), 5.3(s, 1H), 7.0(dd, 1H), 7.1-7.3(m, 4H), 7.5(m, 1H), 7.7(m, 1H), 7.9(m, 1H). |
| 95 | (1S,2R,4aS,5R,8R,8aR)-2-(acetyloxy)-5-{2-[[(2-chlorophenyl)methyl](methyl)amino]-1-methyl-2-oxoethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=730, $C_{37}H_{45}Cl_2N_3O_8$+H requires 730.2662. NMR(CDCl3, selected data): 0.9(m, 3H), 1.3(m, 3H), 1.75(s, 3H), 2.1(s, 3H), 3.1(s, 3H), 3.3(s, 3H), 5.15-5.2(m, 2H), 6.8(dd, 1H), 7.0-7.5(m, 5H), 7.75(m, 1H). |
| 96 | (1S,2R,4aS,5S,8R,8aR)-8a-hydroxy-3,8-dimethyl-5-(1-methylethyl)-2-{[(phenylamino)carbonyl]oxy}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(APCI): M/Z[MH+]=640.2, $C_{34}H_{42}ClN_3O_7$+H requires 640.2790. NMR(CDCl3, selected data): 0.8(m, 3H), 1.0(m, 6H), 1.75(s,3H), 3.3(s, 3H), 5.2(s, 1H), 6.6(s, 1H), 7.0(dd, 1H), 7.1(dd, 1H), 7.2(m, 1H), 7.3-7.4(m, 5H). |
| 97 | (1S,2R,4aS,5S,8R,8aR)-2-(acetyloxy)-5-[2-(cycloheptylamino)-1-methylethyl]-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(APCI): M/Z[MH+]=674, $C_{36}H_{52}ClN_3O_7$+H requires 674.3572. NMR(CDCl3, selected data): 0.9(m, 3H), 1.1(m, 3H), 1.6-1.9(m, 16H), 2.1(s, 3H), 3.3(s, 3H), 5.1-5.2(m, 2H), 7.0(dd, 1H), 7.2-7.4(m, 2H). |
| 98 | (1S,2R,4aS,5S,8R,8aR)-2-(acetyloxy)-5-{2-[4-(2-chloropyrimidin-4-yl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=759.1, $C_{37}H_{48}Cl_2N_6O_7$+H requires 759.3040. NMR(DMSO, selected data): 0.8(d, 3H), 1.1(d, 3H), 1.6(s, 3H), 2.1(s, 3H), 2.5(m, 2H), 2.95-3.1(m, 2H), 3.15(s, 3H), 3.2-3.8(m, 6H), 5.1(s, 1H), 7.0(d, 1H), 7.1(dd, 1H), 7.3(d, 1H), 7.35(d, 1H), 8.2(d, 1H). |
| 99 | (1S,2R,4aS,5S,8R,8aR)-2-(acetyloxy)-5-{2-[4-(5-chloropyridin-2-yl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=758.2, $C_{38}H_{49}Cl_2N_5O_7$+H requires 758.3087. NMR(CDCl3, selected data): 0.85(d, 3H), 1.15(m, 3H), 1.7(s, 3H), 2.1(s, 3H), 3.4(s, 3H), 3.5-3.6(m, 4H), 5.15-5.2(m, 2H), 6.65(d, 1H), 7.05(dd, 1H), 7.2(d, 1H), 7.3(d, 1H), 7.5(m, 1H), 8.15(m, 1H). |
| 100 | (1S,2R,4aS,5S,8R,8aR)-2-(acetyloxy)-5-{2-[4-(5-chloropyrazin-2-yl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=759.1, $C_{37}H_{48}Cl_2N_6O_7$+H requires 759.3040. NMR(CDCl3, selected data): 0.85(d, 3H), 1.25(m, 3H), 1.7(s, 3H), 2.1(s, 3H), 2.3-2.8(m, 9H), 3.3(s, 3H), 5.2(s, 1H), 7.0(dd, 1H), 7.2(d, 1H), 7.3(d, 1H), 7.95(s, 1H), 8.05(s, 1H). |
| 101 | (1S,2R,4aS,5S,8R,8aR)-2-(acetyloxy)-5-{2-[4-(4-chlorophenyl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro- | MS(ES): M/Z[MH+]=757.1, $C_{39}H_{50}Cl_2N_4O_7$+H requires 757.3135. NMR(CDCl3, selected |

TABLE 1-continued

Table of Examples

| Ex No. | Compound Name | Data* |
|---|---|---|
| | 9b-hydroxy-5-methyl-1,2,3,3a,5,9b-hexahydropyrrolo[2,3-c][2,1]benzoxazine-2-carboxylate | data): 0.8(d, 3H), 1.05(d, 3H), 1.7(s, 3H), 2.1(s, 3H), 2.45-2.8(m, 7H), 3.1-3.25(m, 4H), 3.3(s, 3H), 5.2(s, 1H), 6.8-6.85(m, 2H), 7.0(dd, 1H), 7.2-7.3(m, 3H), 7.4(d, 1H). |
| 102 | (1S,2R,4aS,5S,8R,8aR)-2-(acetyloxy)-8a-hydroxy-3,8-dimethyl-5-{1-methyl-2-[4-(4-methylphenyl)piperazin-1-yl]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=737.2, C40H53ClN4O7+H requires 737.3681. NMR(CDCl3, selected data): 0.8(d, 3H), 1.25(d, 3H), 1.7(s, 3H), 2.1(s, 3H), 2.3(s, 3H), 3.0-3.2(m, 4H), 3.3(s, 3H), 5.2(s, 1H), 6.85-6.9(m, 2H), 7.0(dd, 1H), 7.1-7.15(m, 2H), 7.2-7.35(d, 2H). |
| 103 | (1S,2R,4aS,5S,8R,8aR)-2-(acetyloxy)-5-{2-[4-(2-chlorophenyl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=757.1, C39H50Cl2N4O7+H requires 757.3. NMR(CDCl3, selected data): 0.8(d, 3H), 1.25(d, 3H), 1.7(s, 3H), 2.1(s, 3H), 3.0-3.5(m, 11H), 5.2(s, 1H), 6.95-7.1(m, 3H), 7.15-7.4(m, 4H). |
| 104 | (1S,2R,4aS,5S,8R,8aR)-2-(acetyloxy)-8a-hydroxy-3,8-dimethyl-5-(1-methyl-2-{4-[3-(trifluoromethyl)phenyl]piperazin-1-yl]ethyl)-1,2,4a,5,6,7,8,8a-octahydronaphthalen-1-yl (2S,3aR,9bR)-6-chloro-9b-hydro xy-5-methyl-1,2,3,3a,5,9b-hexahydropyrrolo[2,3-c][2,1]benzoxazine-2-carboxylate | MS(ES): M/Z[MH+]=792, C40H50ClF3N4O7+H requires 791.3398. NMR(CDCl3, selected data): 0.85(d, 3H), 1.25(d, 3H), 1.7(s, 3H), 2.1(s, 3H), 3.3(s, 3H), 3.5-3.8(m, 4H), 5.2(s, 1H), 7.0-7.15(m, 3H), 7.2-7.35(m, 3H), 7.3(dd, 1H). |
| 105 | (1S,2R,4aS,5S,8R,8aR)-2-(acetyloxy)-8a-hydroxy-3,8-dimethyl-5-(1-methyl-2-{4-[4-(methyloxy)phenyl]piperazin-1-yl}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=753.2, C40H53ClN4O8+H requires 753.3630. NMR(CDCl3, selected data): 0.8(d, 3H), 1.25(d, 3H), 1.7(s, 3H), 2.1(s, 3H), 3.0-3.15(m, 4H), 3.3(s, 3H), 3.4-3.6(m, 4H), 3.8(s, 3H), 5.2(s, 1H), 6.8-7.0(m, 5H), 7.2-7.35(m, 3H). |
| 106 | (1S,2R,4aS,5S,8R,8aR)-2-(acetyloxy)-8a-hydroxy-3,8-dimethyl-5-(1-methyl-2-{4-[2-(trifluoromethyl)phenyl]piperazin-1-yl}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=791.2, C40H50ClF3N4O7+H requires 791.3398. NMR(CDCl3, selected data): 0.8(d, 3H), 1.25(d, 3H), 1.7(s, 3H), 2.1(s, 3H), 2.9-3.1(m, 4H), 3.3(s, 3H), 5.2(s, 1H), 7.0-7.15(m, 3H), 7.2-7.35(m, 3H), 7.4(m, 1H). |
| 107 | (1S,2R,4aS,5S,8R,8aR)-2-(acetyloxy)-8a-hydroxy-3,8-dimethyl-5-(1-methyl-2-{4-[4-(trifluoromethyl)pyrimidin-2-yl]piperazin-1-yl}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=793.1, C38H48ClF3N6O7+H requires 793.3303. NMR(CDCl3, selected data): 0.6(d, 3H), 1.1(d, 3H), 1.7(s, 3H), 2.1(s, 3H), 2.5-2.8(m, 10H), 3.35(s, 3H), 3.6-3.8(m, 2H), 3.8-4.0(m, 4H), 5.2(s, 1H), 6.7(m, 1H), 7.0(dd, 1H), 7.2(m, 1H), 7.35(d, 1H), 8.5(m, 1H). |
| 108 | (1S,2R,4aS,5S,8R,8aR)-2-(acetyloxy)-5-{2-[4-(2-fluorophenyl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=741.2, C39H50ClFN4O7+H requires 741.3430. NMR(CDCl3, selected data): 0.8(d, 3H), 1.2(d, 3H), 1.7(s, 3H), 2.1(s, 3H), 3.0-3.2(m, 4H), 3.3(s, 3H), |

TABLE 1-continued

Table of Examples

| Ex No. | Compound Name | Data* |
|---|---|---|
| | | 3.3-3.55(m, 4H), 3.6-3.8(m, 2H), 5.2(s, 1H), 6.9-7.15(m, 5H), 7.2(d, 1H), 7.3(m, 1H). |
| 109 | (1S,2R,4aS,5S,8R,8aR)-2-(acetyloxy)-8a-hydroxy-3,8-dimethyl-5-{1-methyl-2-[4-(6-methylpyridin-2-yl)piperazin-1-yl]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=738.3, C39H52ClN5O7+H requires 738.3634. NMR(CDCl3, selected data): 0.8(d, 3H), 1.2(d, 3H), 1.7(s, 3H), 2.1(s, 3H), 2.65(s, 3H), 3.0-3.2(m, 2H), 3.3(s, 3H), 3.3-3.6(m, 4H), 4.0-4.2(m, 5H), 5.2(s, 1H), 6.8-6.85(m, 3H), 7.0(dd, 1H), 7.2(d, 1H), 7.9(m, 1H). |
| 110 | (1S,2R,4aS,5S,8R,8aR)-2-(acetyloxy)-5-{2-[4-(4-fluorophenyl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=741.3, C39H50ClFN4O7+H requires 741.3430. NMR(CDCl3, selected data): 0.8(d, 3H), 1.2(d, 3H), 1.7(s, 3H), 2.1(s, 3H), 2.65(s, 3H), 3.3(s, 3H), 3.3-4.0(m, 8H), 5.2(s, 1H), 6.85-6.95(m, 2H), 6.95-7.05(m, 3H), 7.2-7.35(m, 2H). |
| 111 | (1S,2R,4aS,5S,8R,8aR)-2-(acetyloxy)-8a-hydroxy-3,8-dimethyl-5-{1-methyl-2-[4-(1,3-thiazol-2-ylcarbonyl)piperazin-1-yl]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=758.2, C37H48ClN5O8S+H requires 758.2990. NMR(CDCl3, selected data): 0.8(d, 3H), 1.25(d, 3H), 1.7(s, 3H), 2.1(s, 3H), 3.1-3.2(m, 2H), 3.3(s, 3H), 3.4-4.2(m, 9H), 5.2(s, 1H), 7.0(dd, 1H), 7.2-7.35(m, 2H), 7.6(s, 1H), 7.9(s, 1H). |
| 112 | (1S,2R,4aS,5S,8R,8aR)-2-(acetyloxy)-8a-hydroxy-3,8-dimethyl-5-(1-methyl-2-{4-[(3-phenylpropyl)oxy]piperidin-1-yl}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=780.2, C43H58ClN3O8+H requires 780.3991. NMR(CDCl3, selected data): 0.8(d, 3H), 1.25(d, 3H), 1.7(s, 3H), 2.1(s, 3H), 2.4-3.1(m, 10H), 3.3(s, 3H), 3.3-3.5(m, 8H), 5.2(s, 1H), 7.0(dd, 1H), 7.1-7.3(m, 7H). |
| 113 | (1S,2R,4aS,5S,8R,8aR)-2-(acetyloxy)-8a-hydroxy-3,8-dimethyl-5-(1-methyl-2-{4-[5-(trifluoromethyl)pyridin-2-yl]piperazin-1-yl}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=792.2, C39H49ClF3N5O7+H requires 792.3351. NMR(CDCl3, selected data): 0.85(d, 3H), 1.25(d, 3H), 1.7(s, 3H), 2.1(s, 3H), 2.3-2.8(m, 8H), 3.3(s, 3H), 3.6-3.75(m, 5H), 5.2(s, 1H), 6.7(d, 1H), 7.0(dd, 1H), 7.2-7.35(m, 2H), 7.75(m, 1H), 8.45(s, 1H). |
| 114 | (1S,2R,4aS,5S,8R,8aR)-2-(acetyloxy)-8a-hydroxy-3,8-dimethyl-5-{1-methyl-2-[4-(phenylmethyl)piperidin-1-yl]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=736.3, C41H54ClN3O7+H requires 736.3729. NMR(CDCl3, selected data): 0.8(d, 3H), 1.2(d, 3H), 1.7(s, 3H), 2.1(s, 3H), 2.4-3.1(m, 15H), 3.3(s, 3H), 3.7(m, 2H), 5.2(s, 1H), 7.0(dd, 1H), 7.1-7.15(m, 2H), 7.2-7.35(m, 5H). |
| 115 | (1S,2R,4aS,5S,8R,8aR)-2-(acetyloxy)-8a-hydroxy-3,8-dimethyl-5-(1-methyl-2-{4-[3-(trifluoromethyl)pyridin-2-yl]piperazin-1-yl}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=792.2, C39H49ClF3N5O7+H requires 792.3351. NMR(CDCl3, selected data): 0.8(d, 3H), 1.2(d, 3H), 1.7(s, 3H), 2.1(s, 3H), 2.4-3.2(m, 8H), 3.3(s, 3H), |

TABLE 1-continued

Table of Examples

| Ex No. | Compound Name | Data* |
|---|---|---|
| | | 3.5-3.65(m, 4H), 5.2(s, 1H), 7.0(dd, 1H), 7.1(m, 1H), 7.2-7.35(m, 2H), 7.9(d, 1H), 8.5(m, 1H). |
| 116 | (1S,2R,4aS,5S,8R,8aR)-2-(acetyloxy)-8a-hydroxy-3,8-dimethyl-5-(1-methyl-2-{4-[3-(trifluoromethyl)phenyl]piperidin-1-yl}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=790.2, C41H51ClF3N3O7+H requires 790.3446. NMR(CDCl3, selected data): 0.8(d, 3H), 1.2(d, 3H), 1.65(s, 3H), 2.1(s, 3H), 2.2-2.6(m, 9H), 3.3(s, 3H), 3.5-3.65(m, 4H), 5.15(s, 1H), 7.0(dd, 1H), 7.2(m, 1H), 7.25(d, 1H), 7.35-7.55(m, 4H). |
| 117 | (1S,2R,4aS,5S,8R,8aR)-2-(acetyloxy)-8a-hydroxy-3,8-dimethyl-5-[1-methyl-2-(4-{[3-(trifluoromethyl)phenyl]methyl}piperazin-1-yl)ethyl]-1,2,4a,5,6,7,8,8a-octahydronaphthalen-1-yl(2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=805.2, C41H52ClF3N4O7+H requires 805.3555. NMR(CDCl3, selected data): 0.8(d, 3H), 1.2(d, 3H), 1.65(s, 3H), 2.1(s, 3H), 3.2-3.3(m, 4H), 3.3(s, 3H), 3.9(m, 2H), 5.2(s, 1H), 7.0(dd, 1H), 7.2-7.3(m, 2H), 7.4-7.7(m, 4H). |
| 118 | (1S,2R,4aS,5S,8R,8aR)-2-(acetyloxy)-5-(2-{4-[({3-[(ethyloxy)carbonyl]phenyl}methyl)oxy]piperidin-1-yl}-1-methylethyl)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=824.2, C44H58ClN3O10+H requires 824.3889. NMR(CDCl3, selected data): 0.75(d, 3H), 1.15(d, 3H), 1.35(t, 3H), 1.75(s, 3H), 2.1(s, 3H), 2.85-3.15(m, 9H), 3.3(s, 3H), 4.3(m, 2H), 4.5(m, 2H), 5.15(s, 1H), 6.95(dd, 1H), 7.15(d, 1H), 7.25(m, 1H), 7.3-7.4(m, 2H), 7.95-8.05(m, 2H). |
| 119 | (1S,2R,4aS,5S,8R,8aR)-2-(acetyloxy)-5-{2-[4-(1,3-benzoxazol-2-yl)piperidin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=763.2, C41H51ClN4O8+H requires 763.3474. NMR(CDCl3, selected data): 0.85(d, 3H), 1.2(m, 3H), 1.75(s, 3H), 2.1(s, 3H), 2.9-3.3(m, 11H), 3.3(s, 3H), 5.2(s, 1H), 7.0(dd, 1H), 7.2-7.3(m, 2H), 7.3-7.4(m, 2H), 7.5(m, 1H), 7.7(m, 1H). |
| 120 | (1S,2R,4aS,5S,8R,8aR)-2-(acetyloxy)-5-[2-(4-{[3,5-bis(trifluoromethyl)phenyl]methyl}piperazin-1-yl)-1-methylethyl]-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=873.1, C42H51ClF6N4O7+H requires 873.3429. NMR(CDCl3, selected data): 0.8(d, 3H), 1.2(m, 3H), 1.7(s, 3H), 2.1(s, 3H), 2.9-3.1(m, 6H), 3.3(s, 3H), 4.8(m, 2H), 5.2(s, 1H), 7.0(dd, 1H), 7.2-7.3(m, 2H), 7.8-7.9(m, 3H). |
| 121 | (1S,2R,4aS,5S,8R,8aR)-2-(acetyloxy)-8a-hydroxy-3,8-dimethyl-5-(1-methyl-2-{4-[2-(methyloxy)phenyl]piperidin-1-yl}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=752.2, C41H54ClN3O8+H requires 752.3678. NMR(CDCl3, selected data): 0.8(m, 3H), 1.25(m, 3H), 1.7(s, 3H), 2.1(s, 3H), 2.9-3.6(m, 11H), 3.3(s, 3H), 3.8(s, 3H), 5.2(s, 1H), 6.85-7.15(m, 5H), 7.2-7.3(m, 2H). |
| 122 | (1S,2R,4aS,5S,8R,8aR)-2-(acetyloxy)-5-(2-{4-[(4-fluorophenyl)methyl]piperazin-1-yl}-1-methylethyl)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=755.3, C40H52ClN4O7+H requires 755.3. NMR(CDCl3, selected data): 0.8(d, 3H), 1.2(d, 3H), 1.7(s, 3H), 2.1(s, 3H), 3.3(s, 3H), 3.4-3.7(m, 8H), 4.1(m, |

TABLE 1-continued

Table of Examples

| Ex No. | Compound Name | Data* |
|---|---|---|
| | | 2H), 5.2(s, 1H), 7.0-7.45(m, 7H). |
| 123 | (1S,2R,4aS,5S,8R,8aR)-2-(acetyloxy)-5-{2-[4-(4-cyanophenyl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=755.3, C40H52ClFN4O7+H requires 755.3587. NMR(CDCl3, selected data): 0.8(d, 3H), 1.2(d, 3H), 1.7(s, 3H), 2.1(s, 3H), 3.3(s, 3H), 3.4-3.7(m, 8H), 5.2(s, 1H), 7.0(dd, 1H), 7.1-7.15(m, 2H), 7.2-7.3(m, 2H), 7.4-7.5(m, 2H). |
| 124 | (1S,2R,4aS,5S,8R,8aR)-2-(acetyloxy)-5-{2-[4-(2,3-dihydro-1,4-benzodioxin-2-ylcarbonyl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=809.3, C42H53ClN4O10+H requires 809.3528. NMR(CDCl3, selected data): 0.8(d, 3H), 1.2(d, 3H), 1.7(s, 3H), 2.1(s, 3H), 2.9-3.9(m, 12H), 3.3(s, 3H), 5.2(s, 1H), 6.8-6.95(m, 4H), 7.0(dd, 1H), 7.2-7.35(m, 2H). |
| 125 | (1S,2R,4aS,5S,8R,8aR)-2-(acetyloxy)-5-{2-[4-(4-bromophenyl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=803.2, C39H50BrClN4O7+H requires 801.2630. NMR(CDCl3, selected data): 0.85(d, 3H), 1.2(d, 3H), 1.7(s, 3H), 2.1(s, 3H), 2.6-3.2(m, 12H), 3.3(s, 3H), 5.2(s, 1H), 6.8(m, 2H), 7.0(dd, 1H), 7.2-7.35(m, 2H), 7.4(m, 2H). |
| 126 | (1S,2R,4aS,5S,8R,8aR)-2-(acetyloxy)-8a-hydroxy-3,8-dimethyl-5-(1-methyl-2-{4-[4-(trifluoromethyl)phenyl]piperazin-1-yl}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=791.2, C40H50ClF3N4O7+H requires 791.3398. NMR(CDCl3, selected data): 0.8(d, 3H), 1.2(d, 3H), 1.7(s, 3H), 2.1(s, 3H), 2.6-3.3(s, 3H), 3.4-3.9(m, 6H), 5.2(s, 1H), 6.9-7.05(m, 3H), 7.15-7.35(m, 2H), 7.5(m, 2H). |
| 127 | (1S,2R,4aS,5S,8R,8aR)-2-(acetyloxy)-5-{2-[4-(2,4-difluorophenyl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=759.2, C39H49ClF2N4O7+H requires 759.3336. NMR(CDCl3, selected data): 0.8(d, 3H), 1.2(d, 3H), 1.7(s, 3H), 2.1(s, 3H), 2.9-3.3(m, 7H), 3.3(s, 3H), 3.35-3.45(m, 4H), 5.2(s, 1H), 6.85-7.05(m, 4H), 7.2(d, 1H), 7.3(m, 1H). |
| 128 | (1S,2R,4aS,5S,8R,8aR)-2-(acetyloxy)-8a-hydroxy-3,8-dimethyl-5-{1-methyl-2-[4-(pyridin-4-ylmethyl)piperazin-1-yl]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=738.3, C39H52ClN5O7+H requires 738.3634. NMR(CDCl3, selected data): 0.8(d, 3H), 1.2(d, 3H), 1.7(s, 3H), 2.1(s, 3H), 2.85-2.95(m, 2H), 3.3(s, 3H), 3.4-4.2(m, 10H), 5.2(s, 1H), 7.0(dd, 1H), 7.2(m, 1H), 7.3(m, 1H), 7.5(m, 2H), 8.7(m, 2H). |
| 129 | (1S,2R,4aS,5S,8R,8aR)-2-(acetyloxy)-5-(2-{4-[5-chloro-2-(methyloxy)phenyl]piperazin-1-yl}-1-methylethyl)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=787.2, C40H52Cl2N4O8+H requires 787.3240. NMR(CDCl3, selected data): 0.8(d, 3H), 1.2(d, 3H), 1.7(s, 3H), 2.1(s, 3H), 3.0-3.6(m, 10H), 3.3(s, 3H), 3.85(s, 3H), 5.2(s, 1H), 6.8(d, 1H), 6.85(s, 1H), 6.95-7.05(m, 2H), 7.2-7.3(m, 2H). |

TABLE 1-continued

Table of Examples

| Ex No. | Compound Name | Data* |
|---|---|---|
| 130 | (1S,2R,4aS,5S,8R,8aR)-2-(acetyloxy)-5-{2-[4-(3,5-dichlorophenyl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=, C39H49Cl3N4O7+H requires 791.2745. NMR(CDCl3, selected data): 0.8(d, 3H), 1.2(d, 3H), 1.7(s, 3H), 2.1(s, 3H), 3.0-3.6(m, 10H), 3.3(s, 3H), 3.45-3.7(m, 4H), 5.2(s, 1H), 6.7-6.8(m, 2H), 6.9-7.0(m, 2H), 7.2-7.3(m, 2H). |
| 131 | (1S,2R,4aS,5S,8R,8aR)-2-(acetyloxy)-8a-hydroxy-3,8-dimethyl-5-(1-methyl-2-{4-[(2E)-3-phenylprop-2-enyl]piperazin-1-yl}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=763.3, C42H55ClN4O7+H requires 763.3838. NMR(CDCl3, selected data): 0.8(d, 3H), 1.2(d, 3H), 1.7(s, 3H), 2.1(s, 3H), 3.3(s, 3H), 3.55-3.75(m, 8H), 5.2(s, 1H), 6.2(m, 1H), 6.8(d, 1H), 7.0(dd, 1H), 7.2(d, 1H), 7.25(m, 1H), 7.3-7.45(m, 5H). |
| 132 | (1S,2R,4aS,5S,8R,8aR)-2-(acetyloxy)-5-{2-[4-(diphenylmethyl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=813.3, C46H57ClN4O7+H requires 813.3994. NMR(CDCl3, selected data): 0.8(d, 3H), 1.2(d, 3H), 1.7(s, 3H), 2.1(s, 3H), 2.9-3.8(m, 6H), 3.3(s, 3H), 4.5(s, 1H), 5.2(s, 1H), 7.0(dd, 1H), 7.15-7.4(m, 8H), 7.45-7.55(m, 4H). |
| 133 | (1S,2R,4aS,5S,8R,8aR)-2-(acetyloxy)-5-{2-[4-(2,3-dimethylphenyl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=751.3, C41H55ClN4O7+H requires 751.3838. NMR(CDCl3, selected data): 0.8(d, 3H), 1.2(d, 3H), 1.7(s, 3H), 2.1(s, 3H), 2.2(s, 3H), 2.3(s, 3H), 3.0-3.2(m, 10H), 3.3(s, 3H), 4.5(s, 1H), 5.2(s, 1H), 6.9-7.05(m, 4H), 7.25-7.35(m, 2H). |
| 134 | (1S,2R,4aS,5S,8R,8aR)-2-(acetyloxy)-5-[2-(4-cyclopentylpiperazin-1-yl)-1-methylethyl]-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=715.3, C38H55ClN4O7+H requires 715.3838. NMR(CDCl3, selected data): 0.8(d, 3H), 1.2(d, 3H), 1.6-1.7(m, 4H), 1.7(s, 3H), 1.8-2.0(m, 5H), 2.1(s, 3H), 3.3(s, 3H), 3.6-3.8(m, 8H), 5.2(s, 1H), 7.0(dd, 1H), 7.2-7.3(m, 2H). |
| 135 | (1S,2R,4aS,5S,8R,8aR)-2-(acetyloxy)-5-{2-[4-(2-ethylphenyl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=751.3, C41H55ClN4O7+H requires 751.3838. NMR(CDCl3, selected data): 0.8(d, 3H), 1.2-1.3(m, 6H), 1.7(s, 3H), 2.1(s, 3H), 2.8-3.2(m, 11H), 3.3(s, 3H), 5.2(s, 1H), 7.0(dd, 1H), 7.1-7.3(m, 7H). |
| 136 | (1S,2R,4aS,5S,8R,8aR)-2-(acetyloxy)-5-(2-{4-[4-chloro-3-(trifluoromethyl)phenyl]piperazin-1-yl}-1-methylethyl)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=825.2, C40H49Cl2F3N4O7+H requires 825.3009. NMR(CDCl3, selected data): 0.8(d, 3H), 1.25(d, 3H), 1.7(s, 3H), 2.1(s, 3H), 3.3(s, 3H), 3.5-3.7(m, 4H), 5.2(s, 1H), 6.8-7.0(m, 2H), 7.1-7.3(m, 3H), 7.4(d, 1H). |
| 137 | (1S,2R,4aS,5S,8R,8aR)-2-(acetyloxy)-8a-hydroxy-3,8-dimethyl-5-{1-methyl-2-[4-(thien-2-ylcarbonyl)piperazin-1-yl]ethyl}-1,2,4a,5,6,7,8,8a-octahydronaphthalen-1-yl | MS(ES): M/Z[MH+]=757.2, C38H49ClN4O8S+H requires 757.3038. NMR(CDCl3, selected |

TABLE 1-continued

Table of Examples

| Ex No. | Compound Name | Data* |
|---|---|---|
| | (2S,3aR,9bR)-6-chloro-9b-hydroxy-5-methyl-1,2,3,3a,5,9b-hexahydropyrrolo[2,3-c][2,1]benzoxazine-2-carboxylate | data): 0.8(d, 3H), 1.2(d, 3H), 1.7(s, 3H), 2.1(s, 3H), 2.9-3.1(m, 4H), 3.3(s, 3H), 5.2(s, 1H), 7.0(dd, 1H), 7.1(m, 1H), 7.2-7.3(m, 2H), 7.35(m, 1H), 7.55(m, 1H). |
| 138 | (1S,2R,4aS,5S,8R,8aR)-2-(acetyloxy)-5-[2-(4-{[(butylamino)carbonyl]oxy}piperidin-1-yl)-1-methylethyl]-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=761.3, C39H57ClN4O9+H requires 761.3892. NMR(CDCl3, selected data): 0.8(d, 3H), 0.95(t, 3H), 1.2(d, 3H), 1.7(s, 3H), 2.1(s, 3H), 3.15-3.3(m, 4H), 3.3(s, 3H), 5.2(s, 1H), 7.0(dd, 1H), 7.2(m, 1H), 7.3(m, 1H). |
| 139 | (1S,2R,4aS,5S,8R,8aR)-2-(acetyloxy)-5-{2-[4-(2,4-dimethylphenyl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=751.3, C41H55ClN4O7+H requires 751.3838. NMR(CDCl3, selected data): 0.8(d, 3H), 1.2(d, 3H), 1.7(s, 3H), 2.1(s, 3H), 2.25(s, 3H), 2.3(s, 3H), 2.5-2.7(m, 8H), 3.0-3.2(m, 4H), 3.3(s, 3H), 3.7-3.85(m, 2H), 5.2(s, 1H), 6.9-7.1(m, 4H), 7.2-7.3(m, 2H). |
| 140 | (1S,2R,4aS,5S,8R,8aR)-2-(acetyloxy)-5-{2-[4-(2,5-dimethylphenyl)piperazin-1-yl]-1 methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=751.4, C41H55ClN4O7+H requires 751.3838. NMR(CDCl3, selected data): 0.8(d, 3H), 1.2(d, 3H), 1.7(s, 3H), 2.0(s, 3H), 2.15(s, 3H), 2.3(s, 3H), 2.8-3.4(m, 11H), 5.2(s, 1H), 6.75-6.85(m, 2H), 6.9-7.1(m, 2H), 7.15(m, 1H), 7.25(m, 1H). |
| 141 | (1S,2R,4aS,5S,8R,8aR)-2-(acetyloxy)-5-[2-(4-cyclopropylpiperazin-1-yl)-1-methylethyl]-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=687.3, C36H51ClN4O7+H requires 687.3524. NMR(CDCl3, selected data): 0.8(d, 3H), 0.9-1.0(m, 2H), 1.1-1.25(m, 6H), 1.7(s, 3H), 2.1(s, 3H), 3.3(s, 3H), 3.6-3.8(m, 8H), 5.2(s, 1H), 7.0(dd, 1H), 7.2-7.3(m, 2H). |
| 142 | (1S,2R,4aS,5S,8R,8aR)-2-(acetyloxy)-5-{2-[4-(cyclopentylcarbonyl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=743.3, C39H55ClN4O8+H requires 743.3787. NMR(CDCl3, selected data): 0.8(d, 3H), 1.2(d, 3H), 1.7(s, 3H), 2.1(s, 3H), 2.75-2.9(m, 6H), 3.0-3.2(m, 2H), 3.3(s, 3H), 3.5-4.2(m, 11H), 5.2(s, 1H), 7.0(dd, 1H), 7.2-7.3(m, 2H). |
| 143 | (1S,2R,4aS,5S,8R,8aR)-2-(acetyloxy)-8a-hydroxy-3,8-dimethyl-5-(1-methyl-2-{4-[6-(methyloxy)pyridin-2-yl]piperazin-1-yl}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=754.3, C39H52ClN5O8+H requires 754.3583. NMR(CDCl3, selected data): 0.8(d, 3H), 1.2(d, 3H), 1.7(s, 3H), 2.1(s, 3H), 3.3(s, 3H), 3.4-3.9(m, 10H), 3.85(m, 3H), 5.2(s, 1H), 6.15-6.25(m, 2H), 7.0(dd, 1H), 7.2-7.3(m, 2H), 7.5(m, 1H). |
| 144 | (1S,2R,4aS,5S,8R,8aR)-2-(acetyloxy)-5-{2-[4-(3,5-dimethylphenyl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl- | MS(ES): M/Z[MH+]=751.3, C41H55ClN4O7+H requires 751.3838. NMR(CDCl3, selected data): 0.8(d, 3H), 1.2(d, |

TABLE 1-continued

Table of Examples

| Ex No. | Compound Name | Data* |
|---|---|---|
| | 1,2,3,3a,5,9b-hexahydropyrrolo[2,3-c][2,1]benzoxazine-2-carboxylate | 3H), 1.7(s, 3H), 2.1(s, 3H), 2.3(s, 6H), 3.3(s, 3H), 3.3-3.9(m, 8H), 5.2(s, 1H), 6.8(s, 2H), 6.9(s, 1H), 7.0(dd, 1H), 7.2-7.3(m, 2H). |
| 145 | (1S,2R,4aS,5S,8R,8aR)-2-(acetyloxy)-5-{2-[4-(3,6-dimethylpyrazin-2-yl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=753.3, C39H53ClN6O7+H requires 753.3743. NMR(CDCl3, selected data): 0.8(d, 3H), 1.2(d, 3H), 1.7(s, 3H), 2.1(s, 3H), 2.5(s, 3H), 2.55(s, 3H), 2.9-3.1(m, 4H), 3.3(s, 3H), 3.5-3.9(m, 6H), 5.2(s, 1H), 7.0(dd, 1H), 7.2-7.3(m, 2H), 8.05(s, 1H). |
| 146 | (1S,2R,4aS,5S,8R,8aR)-2-(acetyloxy)-5-{2-[4-(2,6-dimethylphenyl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=751.3, C41H55ClN4O7+H requires 751.3838. NMR(CDCl3, selected data): 0.8(d, 3H), 1.25(d, 3H), 1.7(s, 3H), 2.1(s, 3H), 2.3-2.4(m, 6H), 2.8-3.1(m, 10H), 3.3(s, 3H), 5.2(s, 1H), 6.9-7.1(m, 4H), 7.2-7.3(m, 2H). |
| 147 | (1S,2R,4aS,5S,8R,8aR)-2-(acetyloxy)-8a-hydroxy-3,8-dimethyl-5-[(1S)-1-methyl-2-pyridin-3-ylethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=640.3, C34H42ClN3O7+H requires 640.2790. NMR(CDCl3, selected data): 0.8(d, 3H), 0.9(d, 3H), 1.7(s, 3H), 2.1(s, 3H), 3.3(s, 3H), 5.2(s, 1H), 7.0(dd, 1H), 7.2-7.35(m, 2H), 7.8(dd, 1H), 8.2(d, 1H), 8.7(d, 1H), 8.75(s, 1H). |
| 148 | (1S,2R,4aS,5S,8R,8aR)-2-(acetyloxy)-8a-hydroxy-3,8-dimethyl-5-[1-methyl-2-(3-oxa-9-azabicyclo[3.3.1]non-9-yl)ethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=688, C36H50ClN3O8+H requires 688.3. HPLC: 3.99 mins. |
| 149 | (1S,2R,4aS,5S,8R,8aR)-2-(acetyloxy)-8a-hydroxy-3,8-dimethyl-5-{1-methyl-2-[4-(4-methylpentanoyl)piperazin-1-yl]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=745, C39H57ClN4O8+H requires 745.4. HPLC: 4.24 mins. |
| 150 | (1S,2R,4aS,5S,8R,8aR)-2-(acetyloxy)-8a-hydroxy-3,8-dimethyl-5-[1-methyl-2-(4-oxo-1,3,4,6,7,11b-hexahydro-2H-pyrazino[2,1-a]isoquinolin-2-yl)ethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=763, C41H51ClN4O8+H requires 763.3. HPLC: 6.46 mins. |
| 151 | (1S,2R,4aS,5S,8R,8aR)-2-(acetyloxy)-5-{2-[3-[(ethyloxy)carbonyl]octahydroisoquinolin-2(1H)-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=772, C41H58ClN3O9+H requires 772.4. HPLC: 5.64 mins. |
| 152 | (1S,2R,4aS,5S,8R,8aR)-2-(acetyloxy)-5-(2-{4-[3,5-bis(methyloxy)phenyl]piperazin-1-yl}-1-methylethyl)-8a-hydroxy-3,8-dimethyl-1,2,4a,5,6,7,8,8a-octahydronaphthalen-1-yl | MS(ES): M/Z[MH+]=783.1, C41H55ClN4O9+H requires 783.3736. NMR(CDCl3, selected |

TABLE 1-continued

Table of Examples

| Ex No. | Compound Name | Data* |
|---|---|---|
| | (2S,3aR,9bR)-6-chloro-9b-hydroxy-5-methyl-1,2,3,3a,5,9b-hexahydropyrrolo[2,3-c][2,1]benzoxazine-2-carboxylate | data): 0.8(d, 3H), 1.25(d, 3H), 1.7(s, 3H), 2.1(s, 3H), 2.9-3.3(m, 6H), 3.3(s, 3H), 3.35-3.75(m, 4H), 3.8(s, 6H), 5.25(s, 1H), 6.1(s, 2H), 6.15(s, 1H), 7.0(dd, 1H), 7.2(d, 1H), 7.3(d, 1H). |
| 153 | (1S,2R,4aS,5S,8R,8aR)-2-(acetyloxy)-5-{2-[4-(2-cyanophenyl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=722.1, C40H50ClN5O7+H requires 722.3572. NMR(CDCl3, selected data): 0.8(d, 3H), 1.25(d, 3H), 1.7(s, 3H), 2.1(s, 3H), 2.3-3.25(m, 15H), 3.3(s, 3H), 5.25(s, 1H), 7.0(dd, 1H), 7.15-7.4(m, 7H). |
| 154 | (1S,2R,4aS,5S,8R,8aR)-2-(acetyloxy)-8a-hydroxy-3,8-dimethyl-5-[1-methyl-2-(4-phenylpiperidin-1-yl)ethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=748.1, C40H52ClN3O7+H requires 748.3477. NMR(CDCl3, selected data): 0.8(d, 3H), 1.2(d, 3H), 1.7(s, 3H), 2.1(s, 3H), 3.0-3.2(m, 4H), 3.3(s, 3H), 3.5-3.65(m, 4H), 3.7-3.9(m, 2H), 5.3(s, 1H), 7.0(dd, 1H), 7.15-7.3(m, 4H), 7.55-7.65(m, 2H). |
| 155 | (1S,2R,4aS,5S,8R,8aR)-2-(acetyloxy)-5-{2-[4-(3,4-dimethylphenyl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=751.1, C41H55ClN4O7+H requires 751.3838. NMR(CDCl3, selected data): 0.8(d, 3H), 1.2(d, 3H), 1.7(s, 3H), 2.1(s, 3H), 2.2(s, 3H), 2.25(s, 3H), 3.0-3.2(m, 4H), 3.3(s, 3H), 3.4-4.0(m, 6H), 5.2(s, 1H), 6.75(d, 1H), 6.8(s, 1H), 7.0(dd, 1H), 7.1(d, 1H), 7.2(d, 1H), 7.3(d, 1H). |
| 156 | (1S,2R,4aS,5S,8R,8aR)-2-(acetyloxy)-5-{2-[cyclopropyl(propanoyl)amino]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=674.3, C35H48ClN3O8+H requires 674.3208. NMR(CDCl3, selected data): 0.8(d, 3H), 0.95(d, 3H), 1.1(t, 3H), 1.7(s, 3H), 2.1(s, 3H), 3.3(s, 3H), 5.2(s, 1H), 7.0(dd, 1H), 7.2(d, 1H), 7.35(d, 1H). |
| 157 | (1S,2R,4aS,5S,8R,8aR)-2-(acetyloxy)-5-{2-[(cyclopropylcarbonyl)(phenyl)amino]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=722.3, C39H48ClN3O8+H requires 722.3208. NMR(CDCl3, selected data): 0.5-0.7(m, 2H), 0.8(d, 3H), 0.95(d, 3H), 1.7(s, 3H), 2.1(s, 3H), 3.3(s, 3H), 5.2(s, 1H), 7.0(dd, 1H), 7.2-7.5(m, 7H). |
| 158 | (1S,2R,4aS,5S,8R,8aR)-2-(acetyloxy)-5-{2-[(cyclohexylmethyl)(cyclopropylcarbonyl)amino]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=742.3, C40H56ClN3O8+H requires 742.3834. NMR(CDCl3, selected data): 0.7-0.8(m, 2H), 0.85(d, 3H), 0.9-1.1(m, 8H), 1.7(s, 3H), 2.1(s, 3H), 2.4-2.7(m, 7H), 3.3(s, 3H), 5.2(s, 1H), 6.9(dd, 1H), 7.2-7.3(m, 2H). |
| 159 | (1S,2R,4aS,5S,8R,8aR)-2-(acetyloxy)-5-{2-[(cyclohexylmethyl)(propanoyl)amino]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2- | MS(ES): M/Z[MH+]=730.3, C39H56ClN3O8+H requires 730.3834. NMR(CDCl3, selected data): 0.85(d, 3H), 0.95(d, 3H), 1.6-1.9(m, 9H), 2.1(s, |

TABLE 1-continued

Table of Examples

| Ex No. | Compound Name | Data* |
|---|---|---|
| | c][2,1]benzoxazine-2-carboxylate | 3H), 3.3(s, 3H), 5.2(s, 1H), 6.9(dd, 1H), 7.2-7.3(m, 2H). |
| 160 | (1S,2R,4aS,5S,8R,8aR)-2-(acetyloxy)-5-{2-[(cyclopropylcarbonyl)(methyl)amino]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=660.3, C34H46ClN3O8+H requires 660.3052. NMR(CDCl3, selected data): 0.7-0.85(m, 2H), 0.85(d, 3H), 0.9-1.1(m, 6H), 1.7(s, 3H), 2.1(s, 3H), 3.2(s, 3H), 3.3(s, 3H), 5.2(s, 1H), 7.0(dd, 1H), 7.2-7.3(m, 2H). |
| 161 | (1S,2R,4aS,5S,8R,8aR)-2-(acetyloxy)-8a-hydroxy-3,8-dimethyl-5-{1-methyl-2-[methyl(phenylcarbonyl)amino]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=696.2, C37H46ClN3O8+H requires 696.3052. NMR(CDCl3, selected, data): 0.8(m, 3H), 1.1(m, 3H), 1.7(s, 3H), 2.1(s,3H), 3.0(s, 3H), 3.3(s, 3H), 5.1-5.2(m, 2H), 7.0(dd, 1H), 7.2-7.4(m, 7H). |
| 162 | (1S,2R,4aS,5S,8R,8aR)-2-(acetyloxy)-8a-hydroxy-3,8-dimethyl-5-(1-methyl-2-{methyl[(phenyloxy)acetyl]amino}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=726.2, C38H48ClN3O9+H requires 726.3157. NMR(CDCl3, selected data): 0.8-0.95(m, 3H), 1.4-1.5(m, 7H), 1.7(s, 3H), 2.1(s, 3H), 2.85(s, 3H), 3.3(s, 3H), 5.2(m, 1H), 6.85-7.0(m, 4H), 7.15-7.4(m, 4H). |
| 163 | (1S,2R,4aS,5S,8R,8aR)-2-(acetyloxy)-5-{2-[4-(4-amino-5-cyano-6-methylpyrimidin-2-yl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=779.2, C39H51ClN8O7+H requires 779.3647. NMR(CDCl3, selected data): 0.8(d, 3H), 1.1(d, 2H), 1.6(s, 3H), 2.1(s, 3H), 2.3(s, 3H), 3.2(s, 3H), 3.65-4.0(m, 10H), 5.1(s, 1H), 7.05(dd, 1H), 7.2(m, 1H), 7.4(d, 1H). |
| 164 | (1S,2R,4aS,5S,8R,8aR)-2-(acetyloxy)-5-{2-[(2S,5R)-2,5-dimethyl-4-prop-2-enylpiperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=715, C38H55ClN4O7+H requires 715.4. HPLC: 4.05 mins. |
| 165 | (1S,2R,4aS,5S,8R,8aR)-2-(acetyloxy)-5-[2-(8-azabicyclo[3.2.1]oct-8-yl)-1-methylethyl]-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=672, C36H50ClN3O7+H requires 672.3. HPLC: 4.05 mins. |
| 166 | (1S,2R,4aS,5S,8R,8aR)-2-(acetyloxy)-5-{2-[(3S,8aR)-3-(phenylmethyl)hexahydropyrrolo[1,2-a]pyrazin-2(1H)-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=777, C43H57ClN4O7+H requires 777.4. HPLC: 4.37 mins. |
| 167 | (1S,2R,4aS,5S,8R,8aR)-2-(acetyloxy)-5-[2-(3-{[(3,4-difluorophenyl)methyl]oxy}piperidin-1-yl)-1-methylethyl]-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate. | MS(ES): M/Z[MH+]=788, C41H52ClF2N3O8+H requires 788.3. HPLC: 4.43 mins. |
| 168 | (1S,2R,4aS,5S,8R,8aR)-2-(acetyloxy)-8a-hydroxy-3,8-dimethyl-5-{1-methyl-2-[(3R)-3-(methyloxy)piperidin-1-yl]ethyl}-1,2,4a,5,6,7,8,8a-octahydronaphthalen-1-yl | MS(ES): M/Z[MH+]=676, C35H50ClN3O8+H requires 676.3. HPLC: 7.16 mins. |

TABLE 1-continued

Table of Examples

| Ex No. | Compound Name | Data* |
|---|---|---|
| | (2S,3aR,9bR)-6-chloro-9b-hydroxy-5-methyl-1,2,3,3a,5,9b-hexahydropyrrolo[2,3-c][2,1]benzoxazine-2-carboxylate | |
| 169 | (1S,2R,4aS,5S,8R,8aR)-2-(acetyloxy)-8a-hydroxy-3,8-dimethyl-5-{1-methyl-2-[1-methyl-6,7-bis(methyloxy)-3,4-dihydroisoquinolin-2(1H)-yl]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=768, C41H54ClN3O9+H requires 768.3. HPLC: 4.11 mins. |
| 170 | (1S,2R,4aS,5S,8R,8aR)-2-(acetyloxy)-8a-hydroxy-3,8-dimethyl-5-[1-methyl-2-(2-methyl-4-piperidin-1-yl-5,8-dihydropyrido[3,4-d]pyrimidin-7(6H)-yl)ethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=793, C42H57ClN6O7+H requires 793.4. HPLC: 4.3 mins. |
| 171 | (1S,2R,4aS,5S,8R,8aR)-2-(acetyloxy)-5-{2-[4-(4-chlorophenyl)-6,7-dihydrothieno[3,2-c]pyridin-5(4H)-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=793, C42H49Cl2N3O7S+H requires 810. |
| 172 | (1S,2R,4aS,5S,8R,8aR)-2-(acetyloxy)-8a-hydroxy-3,8-dimethyl-5-[1-methyl-2-(3-{[4-(methyloxy)phenyl]sulfanyl}-8-azabicyclo[3.2.1]oct-8-yl)ethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=810, C43H56ClN3O8S+H requires 810.4. HPLC: 4.49 mins. |
| 173 | (1S,2R,4aS,5S,8R,8aR)-2-(acetyloxy)-8a-hydroxy-3,8-dimethyl-5-{1-methyl-2-[4-(4-methylpiperazin-1-yl)piperidin-1-yl]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=744, C39H58ClN5O7+H requires 744.4. HPLC: 1.71 mins. |
| 174 | (1S,2R,4aS,5S,8R,8aR)-2-(acetyloxy)-5-(2-{3-[(3-chloropyridin-2-yl)oxy]piperidin-1-yl}-1-methylethyl)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=773, C39H50Cl2N4O8+H requires 773.3. HPLC: 4.37 mins. |
| 175 | (1S,2R,4aS,5S,8R,8aR)-2-(acetyloxy)-8a-hydroxy-3,8-dimethyl-5-{1-methyl-2-[4-(3-methylquinoxalin-2-yl)piperazin-1-yl]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=789, C42H53ClN6O7+H requires 789.4. HPLC: 4.3 mins. |
| 176 | (1S,2R,4aS,5S,8R,8aR)-2-(acetyloxy)-8a-hydroxy-5-{2-[7-(hydroxymethyl)-3-azabicyclo[3.3.1]non-3-yl]-1-methylethyl}-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=716, C38H54ClN3O8+H requires 716.4. HPLC: 3.99 mins. |
| 177 | (1S,2R,4aS,5S,8R,8aR)-2-(acetyloxy)-5-[2-(3,11-diazatricyclo[7.3.1.0~2,7~]trideca-2,4,6-trien-11-yl)-1-methylethyl]-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=735, C40H51ClN4O7+H requires 735.4. HPLC: 4.05 mins. |
| 178 | (1S,2R,4aS,5S,8R,8aR)-2-(acetyloxy)-5-[2-(4,10-diazatricyclo[6.3.1.0~2,7~]dodeca-2,4,6-trien-10-yl)-1-methylethyl]-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=721, C39H49ClN4O7+H requires 721.3. HPLC: 3.67 mins. |

TABLE 1-continued

Table of Examples

| Ex No. | Compound Name | Data* |
|---|---|---|
| 179 | — | MS(ES): M/Z[MH+]=748, C42H54ClN3O7+H requires 748.4. HPLC: 4.56 mins. |
| 180 | (1S,2R,4aS,5S,8R,8aR)-5-{2-[(4aR,9aS)-2,3,4,4a,9,9a-hexahydro-1H-indeno[2,1-b]pyridin-1-yl]-1-methylethyl}-2-(acetyloxy)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=734, C41H52ClN3O7+H requires 734.4. HPLC: 4.37 mins. |
| 181 | (1S,2R,4aS,5S,8R,8aR)-2-(acetyloxy)-5-[2-(3-cyclohexyl-3-methylpiperidin-1-yl)-1-methylethyl]-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=742, C41H60ClN3O7+H requires 742.4. HPLC: 4.68 mins. |
| 182 | (1S,2R,4aS,5S,8R,8aR)-2-(acetyloxy)-8a-hydroxy-5-[2-(4-{2-[(2-hydroxyethyl)oxy]ethyl}piperazin-1-yl)-1-methylethyl]-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=742, C41H60ClN3O7+H requires 742.4. HPLC: 4.68 mins. |
| 183 | (1S,2R,4aS,5S,8R,8aR)-2-(acetyloxy)-8a-hydroxy-3,8-dimethyl-5-[1-methyl-2-(3-methyl-3-pyridin-2-ylpiperidin-1-yl)ethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=737, C40H53ClN4O7+H requires 737.4. HPLC: 4.37 mins. |
| 184 | (1S,2R,4aS,5S,8R,8aR)-2-(acetyloxy)-5-{2-[4-(3,5-dichloropyridin-4-yl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=793, C38H48Cl3N5O7+H requires 792.3. HPLC: 4.37 mins. |
| 185 | (1S,2R,4aS,5S,8R,8aR)-2-(acetyloxy)-8a-hydroxy-3,8-dimethyl-5-{1-methyl-2-[(3S)-3-methyl-3-phenylpiperidin-1-yl]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=736, C41H54ClN3O7+H requires 736.4. |
| 186 | (1S,2R,4aS,5S,8R,8aR)-2-(acetyloxy)-5-(2-{3-[(4-fluorophenyl)sulfanyl]-8-azabicyclo[3.2.1]oct-8-yl}-1-methylethyl)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=798, C42H53ClFN3O7S+H requires 798.3. HPLC: 4.49 mins. |
| 187 | (1S,2R,4aS,5S,8R,8aR)-2-(acetyloxy)-8a-hydroxy-3,8-dimethyl-5-(1-methyl-2-{4-[(pyridin-2-ylsulfanyl)methyl]piperidin-1-yl}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=769, C40H53ClN4O7S+H requires 769.3. HPLC: 4.3 mins. |
| 188 | (1S,2R,4aS,5S,8R,8aR)-2-(acetyloxy)-8a-hydroxy-3,8-dimethyl-5-(1-methyl-2-{3-[(pyridin-2-ylsulfanyl)methyl]piperidin-1-yl}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=769, C40H53ClN4O7S+H requires 769.3. HPLC: 4.3 mins. |
| 189 | (1S,2R,4aS,5S,8R,8aR)-2-(acetyloxy)-8a-hydroxy-3,8-dimethyl-5-[1-methyl-2-(2-{[methyl(methyloxy)amino]carbonyl}piperidin-1-yl)ethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=733, C37H53ClN4O9+H requires 733.4. HPLC: 4.05 mins. |

TABLE 1-continued

Table of Examples

| Ex No. | Compound Name | Data* |
|---|---|---|
| 190 | (1S,2R,4aS,5S,8R,8aR)-2-(acetyloxy)-5-(2-{4-[(3,4-dichlorophenyl)methyl]piperazin-1-yl}-1-methylethyl)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=806, C40H51Cl3N4O7+H requires 805.3. HPLC: 4.62 mins. |
| 191 | (1S,2R,4aS,5S,8R,8aR)-2-(acetyloxy)-8a-hydroxy-3,8-dimethyl-5-{1-methyl-2-[2-(2-piperidin-1-ylethyl)piperidin-1-yl]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=757, C41H61ClN4O7+H requires 757.4. HPLC: 1.71 mins. |
| 192 | (1S,2R,4aS,5S,8R,8aR)-2-(acetyloxy)-8a-hydroxy-3,8-dimethyl-5-{1-methyl-2-[(1-methylethyl)(2-{[2-(methyloxy)phenyl]oxy}ethyl)amino]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=770, C41H56ClN3O9+H requires 770.4. HPLC: 4.3 mins. |
| 193 | (1S,2R,4aS,5S,8R,8aR)-2-(acetyloxy)-8a-hydroxy-3,8-dimethyl-5-{1-methyl-2-[methyl(2-phenylcyclopropyl)amino]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=708, C39H50ClN3O7+H requires 708.3. HPLC: 4.43 mins. |
| 194 | (1S,2R,4aS,5S,8R,8aR)-2-(acetyloxy)-8a-hydroxy-3,8-dimethyl-5-(1-methyl-2-{methyl[3-(1,2,4,5-tetrahydro-3H-3-benzazepin-3-yl)propyl]amino}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=779, C43H59ClN4O7+H requires 779.4. HPLC: 3.73 mins. |
| 195 | (1S,2R,4aS,5S,8R,8aR)-2-(acetyloxy)-5-{2-[{2-[(2,6-dichlorophenyl)oxy]ethyl}(methyl)amino]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=781, C38H48Cl3N3O8+H requires 780.3. HPLC: 4.43 mins. |
| 196 | (1S,2R,4aS,5S,8R,8aR)-2-(acetyloxy)-5-{2-[[(4-chlorophenyl)methyl](ethyl)amino]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=730, C38H49Cl2N3O7+H requires 730.3. HPLC: 4.3 mins. |
| 197 | (1S,2R,4aS,5S,8R,8aR)-2-(acetyloxy)-8a-hydroxy-3,8-dimethyl-5-(1-methyl-2-{methyl[(3-methylthien-2-yl)methyl]amino}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=702, C36H48ClN3O7S+H requires 702.3. HPLC: 4.24 mins. |
| 198 | (1S,2R,4aS,5S,8R,8aR)-2-(acetyloxy)-5-{2-[4-(3-chloro-4-methylphenyl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=771, C40H52Cl2N4O7+H requires 771.3. HPLC: 4.56 mins. |
| 199 | (1S,2R,4aS,5S,8R,8aR)-2-(acetyloxy)-5-{2-[(diphenylmethyl)(methyl)amino]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=758, C43H52ClN3O7+H requires 758.4. |
| 200 | (1S,2R,4aS,5S,8R,8aR)-2-(acetyloxy)-8a-hydroxy-3,8-dimethyl-5-(1-methyl-2-{4-[5-methyl-2-(methyloxy)phenyl]piperazin-1- | MS(ES): M/Z[MH+]=767, C41H55ClN4O8+H requires 767.3. HPLC: 4.43 mins. |

TABLE 1-continued

Table of Examples

| Ex No. | Compound Name | Data* |
|---|---|---|
| | yl}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | |
| 201 | (1S,2R,4aS,5S,8R,8aR)-2-(acetyloxy)-5-(2-{4-[2-(ethyloxy)phenyl]piperazin-1-yl}-1-methylethyl)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=767, C41H55ClN4O8+H requires 767.3. HPLC: 4.43 mins. |
| 202 | (1S,2R,4aS,5S,8R,8aR)-2-(acetyloxy)-8a-hydroxy-3,8-dimethyl-5-(1-methyl-2-{(2S,4R)-4-methyl-2-[(methyloxy)carbonyl]piperidin-1-yl}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=718, C37H52ClN3O9+H requires 718.3. |
| 203 | (1S,2R,4aS,5S,8R,8aR)-2-(acetyloxy)-8a-hydroxy-5-{2-[(2S)-2-(2-hydroxyethyl)piperidin-1-yl]-1-methylethyl}-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=690, C36H52ClN3O8+H requires 690.4. |
| 204 | (1S,2R,4aS,5S,8R,8aR)-2-(acetyloxy)-8a-hydroxy-3,8-dimethyl-5-{1-methyl-2-[(3S)-3-(methyloxy)piperidin-1-yl]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=676, C35H50ClN3O8+H requires 676.3. |
| 205 | (1S,2R,4aS,5S,8R,8aR)-2-(acetyloxy)-8a-hydroxy-3,8-dimethyl-5-(1-methyl-2-{2-[(methyloxy)carbonyl]octahydro-1H-indol-1-yl}ethyl)-1,2,4a,5,6,7,8,8a-octahydronaphthalen-1-yl (2S,3aS,9bS)-6-chloro-9b-hydroxy-5-methyl-1,2,3,3a,5,9b-hexahydropyrrolo[2,3-c][2,1]benzoxazine-2-carboxylate | MS(ES): M/Z[MH+]=744, C39H54ClN3O9+H requires 744.4. |
| 206 | (1S,2R,4aS,5S,8R,8aR)-2-(acetyloxy)-8a-hydroxy-3,8-dimethyl-5-{1-methyl-2-[(2S)-4-methyl-2-[(methyloxy)carbonyl]-3,6-dihydropyridin-1(2H)-yl]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=716, C37H50ClN3O9+H requires 716.3. |
| 207 | (1S,2R,4aS,5S,8R,8aR)-2-(acetyloxy)-8a-hydroxy-5-[2-(3-hydroxy-8-azabicyclo[3.2.1]oct-8-yl)-1-methylethyl]-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=688, C36H50ClN3O8+H requires 688.3. |
| 208 | (1S,2R,4aS,5S,8R,8aR)-2-(acetyloxy)-8a-hydroxy-3,8-dimethyl-5-[1-methyl-2-(3-methyl-3-phenylpiperidin-1-yl)ethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=736, C41H54ClN3O7+H requires 736.4. |
| 209 | (1S,2R,4aS,5S,8R,8aR)-2-(acetyloxy)-8a-hydroxy-3,8-dimethyl-5-(1-methyl-2-{(phenylmethyl)[2-(phenyloxy)ethyl]amino}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=788, C44H54ClN3O8+H requires 788.4. |
| 210 | (1S,2R,4aS,5S,8R,8aR)-2-(acetyloxy)-8a-hydroxy-3,8-dimethyl-5-((1R)-1-methyl-2-{4-[4-(trifluoromethyl)-2-pyrimidinyl]-1-piperazinyl}ethyl)-1,2,4a,5,6,7,8,8a-octahydro-1-naphthalenyl (2S,3aR,9bR)-6-chloro-9b-hydroxy- | MS(ES): M/Z(M+H) 793.4; C38H48ClF3O7N6+H requires 793.1. H-NMR(CDCl3, selected data): 0.85(d, 3H), 3.30(s, 3H), |

TABLE 1-continued

Table of Examples

| Ex No. | Compound Name | Data* |
|---|---|---|
| | 5-methyl-1,2,3,3a,5,9b-hexahydropyrrolo[2,3-c][2,1]benzoxazine-2-carboxylate-TFA salt | 4.30(m, 1H), 5.20(s, 1H), 5.25(s, 1H), 5.40(m, 1H), 5.50(m, 1H), 6.90(d, 1H), 7.05(t, 1H), 7.25(d, 1H), 7.45(d, 1H), 8.55(d, 1H) |
| 211 | (1S,2R,4aS,5S,8R,8aR)-2-(acetyloxy)-8a-hydroxy-3,8-dimethyl-5-((1R)-1-methyl-2-{4-[5-(trifluoromethyl)-2-pyridinyl]-1-piperazinyl}ethyl)-1,2,4a,5,6,7,8,8a-octahydro-1-naphthalenyl (2S,3aR,9bR)-6-chloro-9b-hydroxy-5-methyl-1,2,3,3a,5,9b-hexahydropyrrolo[2,3-c][2,1]benzoxazine-2-carboxylate-TFA salt | MS(ES): M/Z(M+H) 792.5; C39H49ClF3O7N5+H requires 792. 1H-NMR(CDCl3, selected data): 0.90(d, 3H), 3.30(s, 3H), 4.30(m, 1H), 5.20(s, 1H), 5.25(s, 1H), 5.40(m, 1H), 5.50(m, 1H), 6.65(d, 1H), 7.05(t, 1H), 7.25(d, 1H), 7.50(d, 1H), 7.75(d, 1H), 8.45(s, 1H). |
| 212 | (1S,2R,5S,8R,8aR)-2-(acetyloxy)-5-((1R)-2-{4-[bis(4-fluorophenyl)methyl]piperazin-1-yl}-1-methylethyl)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ESI): M/Z[MH+]=849.2, C46H55ClF2N4O7+H requires 849.3806. NMR(CDCl3, selected data): 0.8(d, 3H), 1.2(d, 3H), 1.7(s, 3H), 2.1(s, 3H), 2.7-3.20(m, 12H), 3.3(s, 3H), 4.1(m, 1H), 4.4(s, 1H), 5.1(s, 1H), 5.2(s, 1H), 5.3(s, 1H), 5.5(s, 1H), 7.00-7.5(m, 11H). |
| 213 | (1S,2R,5S,8R,8aR)-2-(acetyloxy)-5-{(1R)-2-[4-(5-chloropyrimidin-2-yl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ESI): M/Z[MH+]=759.1, C37H48Cl2N6O7+H requires 759.3040. NMR(CDCl3, selected data): 0.8(d, 3H), 1.2(d, 3H), 1.7(s, 3H), 2.1(s, 3H), 2.4-3.1(m, 8H), 3.3(s, 3H), 4.1(m, 1H), 4.7-4.9(m, 2H), 5.1(s, 1H), 5.2(s, 1H), 5.3(s, 1H), 5.5(s, 1H), 7.0-7.3(m, 3H), 8.3(s, 2H). |
| 214 | (1S,2R,4aS,5S,8R,8aR)-2-(acetyloxy)-5-{(1R)-2-[4-(5-bromopyrimidin-2-yl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ESI): M/Z[MH+]=805.3, C37H48BrClN6O7+H requires 803.2535. NMR(CDCl3, selected data): 0.8(d, 3H), 1.1(d, 3H), 1.7(s, 3H), 2.1(s, 3H), 2.3-2.6(m, 8H), 3.3(s, 3H), 3.6-3.8(m, 5H), 4.1(m, 1H), 5.1-5.2(m, 2H), 5.3(s, 1H), 5.6(s, 1H), 7.0-7.4(m, 3H), 8.3(s, 2H). |
| 215 | (1S,2R,4aS,5S,8R,8aR)-2-(acetyloxy)-5-{(1R)-2-[4-(6-chloro-1,3-benzothiazol-2-yl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ESI): M/Z[MH+]=814.3, C40H49Cl2N5O7S+H requires 814.2808: NMR(CDCl3, selected data): 0.8(m, 3H), 1.1(m, 3H), 1.7(s, 3H), 2.1(s, 3H), 2.3-2.8(m, 8H), 3.3(s, 3H), 3.5-3.8(m, 4H), 4.1(m, 1H), 5.1-5.4(m, 4H), 5.6(s, 1H), 7.0-7.6(m, 6H). |
| 216 | (1S,2R,4aS,5S,8R,8aR)-2-(acetyloxy)-5-((1R)-2-{4-[(3,4-dichlorophenyl)methyl]piperazin-1-yl}-1-methylethyl)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | NMR(CDCl3, selected data): 0.8(m, 3H), 1.1(m, 3H), 1.5(s, 5H), 1.7(s, 3H), 2.1(s, 3H), 2.4-2.8(m, 8H), 3.35(s, 3H), 3.6(s, 1H), 4.1(m, 1H), 5.1-5.6(m, 4H), 6.7-7.4(m, 6H). |
| 217 | (1S,2R,4aS,5S,8R,8aR)-2-(acetyloxy)-8a-hydroxy-3,8-dimethyl-5-((1R)-1-methyl-2-{4-[5-(trifluoromethyl)pyrimidin-2-yl]piperazin-1-yl}ethyl)-1,2,4a,5,6,7,8,8a-octahydronaphthalen-1-yl(2S,3aR,9bR)-6-chloro-9b-hydroxy-5-methyl- | MS(ESI): M/Z[MH+]=793.4, C38H48ClF3N6O7+H requires 793.3303. NMR(CDCl3, selected data): 0.8(m, 3H), 1.2(m, 3H), 1.7(s, |

TABLE 1-continued

Table of Examples

| Ex No. | Compound Name | Data* |
|---|---|---|
|  | 1,2,3,3a,5,9b-hexahydropyrrolo[2,3-c][2,1]benzoxazine-2-carboxylate | 3H), 2.5(m, 2H), 2.6(s 3H), 2.8(s, 1H), 3.1(m, 2H), 3.3(s, 3H), 4.1(m, 1H), 5.1(m, 2H), 5.3(s, 1H), 5.5(s, 1H), 7.0-7.1(m, 1H), 7.2-7.4(m, 3H), 8.6(s, 2H). |
| 218 | (1S,2R,4aS,5S,8R,8aR)-2-(acetyloxy)-5-((1R)-2-{4-[(4-chlorophenyl)oxy]piperidin-1-yl}-1-methylethyl)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | MS(ES): M/Z[MH+]=770, C40H51Cl2N3O8+H requires 772.3131. NMR(CDCl3, selected data): 0.8(m, 3H), 1.1(m, 3H), 1.3(m, 4H), 1.7(s, 3H), 2.1(s, 3H), 2.2(s, 1H), 3.1(s, 1H), 3.3(s, 3H), 3.6(s, 1H), 4.1(m, 1H), 4.25(s, 1H), 5.1(m, 2H), 5.3(s, 1H), 5.6(s, 1H), 6.8(d, 2H), 7.0(dd, 1H), 7.2-7.3(m, 3H), 7.35(d, 1H). |

*NMR data given for acetate or trifluoroacetate salts

Table of Precursors

| Ex No. | Name of Terpene Alkaloid Precursor | Preparation Number of TA Precursor |
|---|---|---|
| 1 | (1S,2R,4aS,5R,8R,8aR)-2-(acetyloxy)-8a-hydroxy-3,8-dimethyl-5-(1-methylethenyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | 1 |
| 2 | (1S,2R,4aS,5R,8R,8aR)-2,8a-dihydroxy-3,8-dimethyl-5-(1-methylethenyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | 139 |
| 3 | (1S,2R,4aS,5R,8R,8aR)-2,8a-dihydroxy-3,8-dimethyl-5-(1-methylethenyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | 139 |
| 4 | (1S,2R,4aS,5S,8R,8aR)-2-(acetyloxy)-8a-hydroxy-5-[2-hydroxy-1-methylethyl]-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | 140 |
| 5 | (1S,2R,4aS,5S,8R,8aR)-2-(acetyloxy)-8a-hydroxy-5-[2-hydroxy-1-methylethyl]-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | 140 |
| 6 | (1S,2R,4aS,5R,8R,8aR)-2,8a-dihydroxy-3,8-dimethyl-5-(1-methylethenyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | 139 |
| 7 | (1S,4aS,5S,8aR)-2,8a-dihydroxy-3,8-dimethyl-5-(1-methylethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | 144 |
| 8 | (1S,4aS,5S,8aR)-2,8a-dihydroxy-3,8-dimethyl-5-(1-methylethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | 144 |
| 9 | (1S,4aS,5S,8aR)-2,8a-dihydroxy-3,8-dimethyl-5-(1-methylethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | 144 |
| 10 | (1S,4aS,5S,8aR)-2,8a-dihydroxy-3,8-dimethyl-5-(1-methylethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | 144 |
| 11 | (1S,2R,4aS,5R,8R,8aR)-2,8a-dihydroxy-3,8-dimethyl-5-(1-methylethenyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | 139 |
| 12 | (1S,2R,4aS,5R,8R,8aR)-2,8a-dihydroxy-3,8-dimethyl-5-(1-methylethenyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | 139 |
| 13 | (1S,2R,4aS,5S,8R,8aR)-2-(acetyloxy)-8a-hydroxy-5-{2-[(1H-imidazol-1-ylcarbonyl)oxy]-1-methylethyl}-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | 143 |
| 14 | (1S,2R,4aS,5R,8R,8aR)-2,8a-dihydroxy-3,8-dimethyl-5-(1-methylethenyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | 139 |

-continued

| Ex No. | Name of Terpene Alkaloid Precursor | Preparation Number of TA Precursor |
|---|---|---|
| 15 | (1S,2R,4aS,5R,8R,8aR)-2,8a-dihydroxy-3,8-dimethyl-5-(1-methylethenyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | 139 |
| 16 | (1S,2R,4aS,5R,8R,8aR)-2,8a-dihydroxy-3,8-dimethyl-5-(1-methylethenyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | 139 |
| 17 | (1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | 141 |
| 18 | 2[(1R,2R,4aS,5R,8S,8aS)-2-(acetyloxy)-5-(2,2-difluoro-1-methylvinyl)-8a-hydroxy-3,8-dimethyl-1,2,4a,5,6,7,8,8a-octahydro-1-naphthalenyl] 3-(tert-butyl) (2S,3aR,9bR)-9b-[(tert-butoxycarbonyl)oxy]-6-chloro-5-methyl-1,2,5,9b-tetrahydropyrrolo[2,3-c][2,1]benzoxazine-2,3(3aH)-dicarboxylate | 156 |
| 19 | 2-{(1S,2R,4aS,5S,8R,8aR)-2-(acetyloxy)-8a-hydroxy-5-[2-hydroxy-1-methylethyl]-3,8-dimethyl-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 157 |
| 20 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 21 | (1S,2R,4aS,5R,8R,8aR)-5-(2-ethyl-1,3-thiazol-4-yl)-1,8a-dihydroxy-3,8-dimethyl-1,2,4a,5,6,7,8,8a-octahydronaphthalen-2-yl acetate | 166 |
| 21 | (2S,3aR,9bR)-6-chloro-3-{[(1,1-dimethylethyl)oxy]carbonyl}-9b-({[(1,1-dimethylethyl)oxy]carbonyl}oxy)-5-methyl-1,2,3,3a,5,9b-hexahydropyrrolo[2,3-c][2,1]benzoxazine-2-carboxylic acid | 153 |
| 22 | 2-{(1S,2R,4aS,5R,8R,8aR)-2-(acetyloxy)-5-[2,2-difluoro-1-methylethyl]-8a-hydroxy-3,8-dimethyl-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 167 |
| 23 | 2-{(1S,2R,4aS,5R,8R,8aR)-2-(acetyloxy)-5-[2,2-difluoro-1-methylethyl]-8a-hydroxy-3,8-dimethyl-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 168 |
| 24 | 2-[(1S,2R,4aS,5R,8R,8aR)-2-(acetyloxy)-5-(2,2-dichloro-1-methylethenyl)-8a-hydroxy-3,8-dimethyl-1,2,4a,5,6,7,8,8a-octahydronaphthalen-1-yl] 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 172 |
| 25 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 26 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 27 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 28 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 29 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 30 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 31 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 32 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 33 | (1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | 141 |
| 34 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 35 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b- | 160 |

-continued

| Ex No. | Name of Terpene Alkaloid Precursor | Preparation Number of TA Precursor |
|---|---|---|
| | ({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | |
| 36 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 37 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 38 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 39 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 40 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 41 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 42 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 43 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 44 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 45 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 46 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 47 | 2-[(1S,2R,4aS,5S,8R,8aR)-5-{2-[acetyl(cyclopropyl)amino]-1-methylethyl}-2-(acetyloxy)-8a-hydroxy-3,8-dimethyl-1,2,4a,5,6,7,8,8a-octahydronaphthalen-1-yl] 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 177 |
| 48 | 2-[(1S,2R,4aS,5S,8R,8aR)-2-(acetyloxy)-5-(2-{cyclopropyl[(methyloxy)carbonyl]amino}-1-methylethyl)-8a-hydroxy-3,8-dimethyl-1,2,4a,5,6,7,8,8a-octahydronaphthalen-1-yl] 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 179 |
| 49 | 2-[(1S,2R,4aS,5S,8R,8aR)-2-(acetyloxy)-5-(2-{ethyl[(methyloxy)carbonyl]amino}-1-methylethyl)-8a-hydroxy-3,8-dimethyl-1,2,4a,5,6,7,8,8a-octahydronaphthalen-1-yl] 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 178 |
| 50 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 51 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 52 | 2-[(1S,2R,4aS,5S,8R,8aR)-2-(acetyloxy)-5-(2-{cyclopropyl[(ethylamino)carbonyl]amino}-1-methylethyl)-8a-hydroxy-3,8-dimethyl-1,2,4a,5,6,7,8,8a-octahydronaphthalen-1-yl] 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 180 |
| 53 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 54 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 55 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 56 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3- | 160 |

-continued

| Ex No. | Name of Terpene Alkaloid Precursor | Preparation Number of TA Precursor |
|---|---|---|
|  | (1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate |  |
| 57 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 58 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 59 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 60 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 61 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 62 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 63 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 64 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 65 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 66 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 67 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 68 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 69 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 70 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 71 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 72 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 73 | 2-{(1S,2R,4aS,5R,8R,8aR)-2-(acetyloxy)-8a-hydroxy-3,8-dimethy-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 74 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 75 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 76 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 77 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5- | 160 |

-continued

| Ex No. | Name of Terpene Alkaloid Precursor | Preparation Number of TA Precursor |
|---|---|---|
| 78 | methyl-1,2,5,9b-tetrahydropyrrolo[2,3-c][2,1]benzoxazine-2,3(3aH)-dicarboxylate 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 79 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 80 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 81 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 82 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 83 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 84 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 85 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 86 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 87 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 88 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 89 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 90 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 91 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 92 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 93 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 94 | (2R)-2-[(1R,4R,4aS,5R,6R)-5-({[(2S,3aR,9bR)-6-chloro-3-{[(1,1-dimethylethyl)oxy]carbonyl}-9b-({[(1,1-dimethylethyl)oxy]carbonyl}oxy)-5-methyl-1,2,3,3a,5,9b-hexahydropyrrolo[2,3-c][2,1]benzoxazin-2-yl] carbonyl}oxy)-6-(acetyloxy)-4a-hydroxy-4,7-dimethyl-1,2,3,4,4a,5,6,8a-octahydronaphthalen-1-yl]propanoic acid | 181 |
| 95 | (2R)-2-[(1R,4R,4aS,5R,6R)-5-({[(2S,3aR,9bR)-6-chloro-3-{[(1,1-dimethylethyl)oxy]carbonyl}-9b-({[(1,1-dimethylethyl)oxy]carbonyl}oxy)-5-methyl-1,2,3,3a,5,9b-hexahydropyrrolo[2,3-c][2,1]benzoxazin-2-yl] carbonyl}oxy)-6-(acetyloxy)-4a-hydroxy-4,7-dimethyl-1,2,3,4,4a,5,6,8a-octahydronaphthalen-1-yl]propanoic acid | 181 |
| 96 | (1S,2R,4aR,8R,8aR)-8a-hydroxy-2-[(1H-imidazol-1-ylcarbonyl)oxy]-3,8-dimethyl-5-(1-methylethenyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | 142 |
| 97 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 98 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b- | 160 |

-continued

| Ex No. | Name of Terpene Alkaloid Precursor | Preparation Number of TA Precursor |
|---|---|---|
|  | ({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate |  |
| 99 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 100 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 101 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 102 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 103 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 104 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 105 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 106 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 107 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 108 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 109 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 110 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 111 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 112 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 113 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 114 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 115 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 116 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 117 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 118 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 119 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |

-continued

| Ex No. | Name of Terpene Alkaloid Precursor | Preparation Number of TA Precursor |
|---|---|---|
| 120 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 121 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 122 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 123 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 124 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 125 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 126 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 127 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 128 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 129 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 130 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 131 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 132 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 133 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 134 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 135 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 136 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 137 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 138 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 139 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 140 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 141 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3- | 160 |

-continued

| Ex No. | Name of Terpene Alkaloid Precursor | Preparation Number of TA Precursor |
|---|---|---|
| 142 | (1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 143 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 144 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 145 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 146 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 147 | 2-[(1S,2R,4aS,5R,8R,8aR)-2-(acetyloxy)-8a-hydroxy-3,8-dimethyl-5-(1-methylethenyl)-1,2,4a,5,6,7,8,8a-octahydronaphthalen-1-yl] 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 152 |
| 148 | (1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | 141 |
| 149 | (1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | 141 |
| 150 | (1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | 141 |
| 151 | (1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | 141 |
| 152 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 153 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 154 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 155 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 156 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 157 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 158 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 159 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 160 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 161 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 162 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 163 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3- | 160 |

| Ex No. | Name of Terpene Alkaloid Precursor | Preparation Number of TA Precursor |
|---|---|---|
| 164 | (1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate (1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | 141 |
| 165 | (1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | 141 |
| 166 | (1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | 141 |
| 167 | (1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | 141 |
| 168 | (1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | 141 |
| 169 | (1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | 141 |
| 170 | (1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | 141 |
| 171 | (1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | 141 |
| 172 | (1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | 141 |
| 173 | (1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | 141 |
| 174 | (1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | 141 |
| 175 | (1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | 141 |
| 176 | (1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | 141 |
| 177 | (1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | 141 |
| 178 | (1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | 141 |
| 179 | (1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | 141 |
| 180 | (1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | 141 |
| 181 | (1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | 141 |
| 182 | (1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | 141 |
| 183 | (1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | 141 |
| 184 | (1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | 141 |
| 185 | (1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | 141 |
| 186 | (1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | 141 |
| 187 | (1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | 141 |

-continued

| Ex No. | Name of Terpene Alkaloid Precursor | Preparation Number of TA Precursor |
|---|---|---|
| 188 | (1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | 141 |
| 189 | (1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | 141 |
| 190 | (1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | 141 |
| 191 | (1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | 141 |
| 192 | (1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | 141 |
| 193 | (1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | 141 |
| 194 | (1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | 141 |
| 195 | (1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | 141 |
| 196 | (1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | 141 |
| 197 | (1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | 141 |
| 198 | (1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | 141 |
| 199 | (1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | 141 |
| 200 | (1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | |
| 201 | (1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | 141 |
| 202 | (1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | 141 |
| 203 | (1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | 141 |
| 204 | (1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | 141 |
| 205 | (1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | 141 |
| 206 | (1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | 141 |
| 207 | (1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | 141 |
| 208 | (1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | 141 |
| 209 | (1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | 141 |
| 210 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 159 |
| 211 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 159 |
| 212 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl } 3-(1,1-dimethylethyl) (2S,3aR,9bR)-6-chloro-9b- | 160 |

| Ex No. | Name of Terpene Alkaloid Precursor | Preparation Number of TA Precursor |
|---|---|---|
| | ({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | |
| 213 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 214 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 215 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 216 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl } 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 217 | 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl} 3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate | 160 |
| 218 | (1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate | 141 |

The synthesis of a number of representative compounds are now described in more detail and the remaining compounds may be prepared in an analogous manner.

EXAMPLE 1

(1S,2R,4aS,5S,8R,8aR)-2-(acetyloxy)-8a-hydroxy-3,8-dimethyl-5-(1-methylethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate To a solution of (1S,2R,4aS,5R,8R,8aR)-2-(acetyloxy)-8a-hydroxy-3,8-dimethyl-5-(1-methylethenyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate (Preparation 1,200 mg) in isopropanol (20 ml) was added platinum on carbon (10% w/w, 20 mg) and the resulting mixture was hydrogenated at room temperature with stirring under 1 atmosphere pressure of hydrogen for 18 hours. The mixture was filtered through celite and concentrated in vacuo to give a white solid. The solid was purified by preparative HPLC (1 inch diameter Ultrasphere C18 column, 2 injections; 70:30 acetonitrile:water) to give the product as a white solid (89 mg).

EXAMPLE 2

(1S,2R,4aS,5R,8R,8aR)-8a-hydroxy-3,8-dimethyl-5-(1-methylethenyl)-2-[(2-methylpropanoyl)oxy]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate To a solution of (1S,2R,4aS,5R,8R,8aR)-2,8a-dihydroxy-3,8-dimethyl-5-(1-methylethenyl)-1,2,4a,5,6,7,8,8a-octahydronaphthalen-1-yl (2S,3aR,9bR)-6-chloro-9b -hydroxy-5-methyl-1,2,3,3a,5,9b-hexahydropyrrolo[2,3-c][2,1]benzoxazine-2-carboxylate (Preparation 139, 25 mg, 0.05 mmol) and 4-dimethylaminopyridine (6 mg, 0.05 mmol) in dichloromethane (2 ml) was added isobutyric anhydride (17 mg, 0.11 mmol) and the resulting mixture stood at room temperature for 18 h. The crude product was purified by column chromatography on a Sepak® silica (1.5 g) cartridge eluting with hexane:dichlcromethane (1:1, 2 ml) then hexane:ethyl acetate (4:1 then 2:1 then 1:1, 3 ml each). The pure fractions were combined and concentrated in vacuo, to give the title compound (11 mg, 37%).

EXAMPLE 3

(1S,2R,4aS,5R,8R,8aR)-2-(hexanoyloxy)-8a-hydroxy-3,8-dimethyl-5-(1-methylethenyl)-1,2,4a,5,6,7,8,8a-octahydronaphthalen-1-yl (2S,3aR,9bR)-6-chloro-9b -hydroxy-5-methyl-1,2,3,3a,5,9b-hexahydropyrrolo[2,3-c][2,1]benzoxazine-2-carboxylate To a solution of (1S,2R,4aS,5R,8R,8aR)-2,8a-dihydroxy-3,8-dimethyl-5-(1-methylethenyl)-1,2,4a,5,6,7,8,8a-octahydronaphthalen-1-yl (2S,3aR,9bR)-6-chloro-9b -hydroxy-5-methyl-1,2,3,3a,5,9b-hexahydropyrrolo[2,3-c][2,1]benzoxazine-2-carboxylate (Preparation 139, 51 mg, 0.10 mmol) and 4-dimethylaminopyridine (14 mg, 0.11 mmol) in dichloromethane (5 ml) was added hexanoic anhydride (43 mg, 0.2 mmol) and the resulting mixture stood at room temperature over a weekend. The crude product was purified by column chromatography over silica (10 g) eluting with hexane:ethyl acetate (2:1). The pure fractions were combined and concentrated in vacuo to give the title compound (43 mg, 97%).

EXAMPLE 4

(1S,2R,4aS,5R,8R,8aR)-2-(acetyloxy)-5-[2-(acetyloxy)-1-methylethyl]-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexa hydropyrrolo[2,3-c][2,1]benzoxazine-2-carboxylate To ((1S,2R,4aS,5S,8R,8aR)-2-(acetyloxy)-8a-hydroxy-5-[2-hydroxy-1-methylethyl]-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate (Preparation 140, 63.8 mg, 0.11 mmol) in dichloromethane (1.1 ml) was added acetic anhydride (22 mg, 2.0 □l, 0.22 mmol) and 4-dimethylaminopyridine (14.3 mg, 0.12 mmol) and the reaction mixture stirred at room temperature for 18 hours. The reaction mixture was diluted with dichloromethane (20 ml) and washed with aqueous citric acid solution, dried (MgSO$_4$) and concentrated in vacuo to give a gum. The crude product was purified by chromatography on silica eluting with hexane:ethyl acetate (60:40). The pure fractions were combined and concentrated in vacuo, to give the title product as a white solid (42 mg, 61%).

EXAMPLE 5

(1S,2R,4aS,5R,8R,8aR)-2-(acetyloxy)-8a-hydroxy-3, 8-dimethyl-5-{1-methyl-2-[(2-methylpropanoyl)oxy] ethyl}-1,2,4a,5,6,7,8,8a-octahydronaphthalen-1-yl (2S,3aR,9bR)-6-chloro-9b-hydroxy-5-methyl-1,2,3, 3a,5,9b-hexahydropyrrolo[2,3-c][2,1]benzoxazine-2-carboxylate To a solution of (1S,2R,4aS,5S,8R,8aR)-2-(acetyloxy)-8a-hydroxy-5-[2-hydroxy-1-methylethyl]-3,8-dimethyl-1,2,4a, 5,6,7,8,8a-octahydronaphthalen-1-yl(2S,3aR,9bR)-6-chloro-9b-hydroxy-5-methyl-1,2,3,3a,5,9b-hexahydropyrrolo[2,3-c][2,1]benzoxazine-2-carboxylate (Preparation 140, 100 mg, 0.17 mmol) and 4-dimethylaminopyridine (21 mg, 0.35 mmol) in dichloromethane (5 ml) at <0° C. was added isobutyric anhydride (0.06 ml, 0.35 mmol) and the resulting mixture allowed to warm to room temperature over 30 minutes. After 3 hours the reaction mixture was treated with water (5 ml) and extracted with dichloromethane (2×5 ml). The combined organic layers were washed with saturated aqueous sodium chloride solution and concentrated in vacuo. The crude product was purified by column chromatography on silica eluting with hexane:ethyl acetate (1:1 to 1:2). The pure fractions were combined and concentrated in vacuo to give the title compound (48 mg, 43%).

EXAMPLE 6

(1S,2R,4aS,5R,8R,8aR)-2-[(cyclopropylcarbonyl) oxy]-8a-hydroxy-3,8-dimethyl-5-(1-methylethenyl)-1,2,4a,5,6,7,8,8a-octahydronaphthalen-1-yl(2S,3aR, 9bR)-6-chloro-9b-hydroxy-5-methyl-1,2,3,3a,5,9b-hexahydropyrrolo[2,3-c][2,1]benzoxazine-2-carboxylate To a solution of (1S,2R,4aS,5R,8R,8aR)-2,8a-dihydroxy-3,8-dimethyl-5-(1-methylethenyl)-1,2,4a,5,6,7,8,8a-octahydronaphthalen-1-yl (2S,3aR,9bR)-6-chloro-9b -hydroxy-5-methyl-1,2,3,3a,5,9b-hexahydropyrrolo[2,3-c][2,1] benzoxazine-2-carboxylate (Preparation 139, 100 mg, 0.19 mmol) and 4-dimethylaminopyridine (30 mg, 0.25 mmol) in tetrahydrofuran (10 ml) was added cyclopropanecarboxylic acid (400 mg, 4.7 mmol) and 1-(3-dimethylaminopropyl)-3-ethylcarbodiimide hydrochloride (90 mg, 0.58 mmol) and the resulting mixture stirred at room temperature for 18 h. The reaction mixture was passed through a Sepak® cartridge (silica, 1.5 g) to remove insoluble material and the solvent removed in vacuo. The crude product was purified to give the title compound (20 mg, 18%).

EXAMPLE 7

(1S,2R,4aS,5S,8R,8aR)-8a-hydroxy-3,8-dimethyl-5-(1-methylethyl)-2-{[(prop-2-ynyloxy)carbonyl]oxy}-1,2,4a,5,6,7,8,8a-octahydronaphthalen-1-yl (2S,3aR, 9bR)-6-chloro-9b-hydroxy-5-methyl-1,2,3,3a,5,9b-hexahydropyrrolo[2,3-c][2,1]benzoxazine-2-carboxylate To (1S,4aS,5S,8aR)-2,8a-dihydroxy-3,8-dimethyl-5-(1-methylethyl)-1,2,4a,5,6,7,8,8a-octahydronaphthalen-1-yl (2S,3aR,9bR)-6-chloro-9b-hydroxy-5-methyl-1,2,3,3a,5, 9b-hexahydropyrrolo[2,3-c][2,1]benzoxazine-2-carboxylate (Preparation 144, 500 mg, 0.96 mmol) and 4-dimethylaminopyridine (350 mg, 2.9 mmol) in dichloromethane (25 ml) at 0° C. under nitrogen was added propargyl chloroformate (170 mg, 1.44 mmol) and the resulting mixture stirred at 0° C. for 30 minutes and at room temperature for 3 hours. The reaction mixture was diluted with dichloromethane (100 ml) and washed with citric acid solution (3×50 ml) and water (2×50 ml), dried (MgSO$_4$) and concentrated in vacuo to give a solid. The crude product was purified by flash chromatography on silica (40 g) eluting with hexane:ethyl acetate (3:2). The pure fractions were combined and concentrated in vacuo to give the title product (462 mg, 80%).

EXAMPLE 8

(1S,2R,4aS,5S,8R,8aR)-8a-hydroxy-3,8-dimethyl-5-(1-methylethyl)-2-({[(2,2,2-trichloroethyl)oxy] carbonyl}oxy)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1] benzoxazine-2-carboxylate The title compound was prepared by the method of Example 9 substituting isopropenyl chloroformate with 2,2, 2-trichloroethyl chloroformate (30.5 mg, 0.14 mmol) to give the title product (55 mg, 82%).

EXAMPLE 9

(1S,2R,4aS,5S,8R,8aR)-8a-hydroxy-3,8-dimethyl-2-({[(1-methylethenyl)oxy]carbonyl}oxy)-5-(1-methylethyl)-1,2,4a,5,6,7,8,8a-octahydronaphthalen-1-yl (2S,3aR,9bR)-6-chloro-9b-hydroxy-5-methyl-1,2,3, 3a,5,9b-hexahydropyrrolo[2,3-c][2,1]benzoxazine-2-carboxylate To (1S,4aS,5S,8aR)-2,8a-dihydroxy-3,8-dimethyl-5-(1-methylethyl)-1,2,4a,5,6,7,8,8a-octahydronaphthalen-1-yl (2S,3aR,9bR)-6-chloro-9b-hydroxy-5-methyl-1,2,3,3a,5, 9b-hexahydropyrrolo[2,3-c][2,1]benzoxazine-2-carboxylate (Preparation 144, 50 mg, 0.096 mmol) and 4-dimethylaminopyridine (35 mg, 0.29 mmol) in dichloromethane (5 ml) at 0° C. under nitrogen was added isopropenyl chloroformate (17.4 mg, 0.144 mmol) and the resulting mixture stirred at 0° C. for 30 minutes and at room temperature for 2 hours. The reaction mixture was diluted with dichloromethane (25 ml) and washed with citric acid solution (3×15 ml), dried (MgSO$_4$) and concentrated in vacuo. The crude product was purified by chromatography on silica (5 g) eluting with hexane:ethyl acetate (1:1). The pure fractions were combined and concentrated in vacuo to give the title product (56 mg, 96%).

EXAMPLE 10

((1S,2R,4aS,5S,8R,8aR)-8a-hydroxy-3,8-dimethyl-
5-(1-methylethyl)-2-{[(prop-2-enyloxy)carbonyl]
oxy}-1,2,4a,5,6,7,8,8a-octahydronaphthalen-1-yl
(2S,3aR,9bR)-6-chloro-9b-hydroxy-5-methyl-1,2,3,
3a,5,9b-hexahydropyrrolo[2,3-c][2,1]benzoxazine-2-
carboxylate Allyl chloroformate (17.4 mg) was added to a stirred, cooled (0° C.) solution of (1S,4aS,5S,8aR)-2,8a-dihydroxy-3,8-dimethyl-5-(1-methylethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate (Preparation 144, 50 mg) and 4-dimethylaminopyridine (35 mg) in dichloromethane (5 ml) under an atmosphere of nitrogen. After 30 minutes, the reaction was allowed to warm to room temperature over 15 hours. The reaction mixture was diluted with dichloromethane (25 ml), washed with aqueous citric acid (10% w/w, 3×15 ml) and dried (MgSO₄). After evaporation of solvent in vacuo, the residue was purified by flash column chromatography on silica (5 g) eluting with 1:1 ethyl acetate:hexane to give the product (44 mg, 76%).

EXAMPLE 11

(1S,2R,4aS,5S,8R,8aR)-1-({[(2S,3aR,9bR)-6-
chloro-9b-hydroxy-5-methyl-1,2,3,3a,5,9b-hexahy-
dropyrrolo[2,3-c][2,1]benzoxazin-2-yl]
carbonyl}oxy)-8a-hydroxy-3,8-dimethyl-5-(1-
methylethenyl)-1,2,4a,5,6,7,8,8a-
octahydronaphthalen-2-yl methyl butanedioate A mixture of (1S,2R,4aS,5R,8R,8aR)-2,8a-dihydroxy-3,8-dimethyl-5-(1-methylethenyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate (Preparation 139, 100 mg, 0.19 mmol), commercially available 4-(methyloxy)-4-oxobutanoic acid (50 mg, 0.38 mmol), 4-dimethylaminopyridine (60 mg, 0.5 mmol), 1-(3-dimethylaminopropyl)-3-ethylcarbodiimide hydrochloride (90 mg, 0.58 mmol) and dichloromethane (5 ml) was stirred for 18 h and the reaction mixture concentrated in vacuo. The crude product was purified by chromatography on a Biotage® 12M column eluting with dichloromethane:diethyl ether (4:1). The pure fractions were combined and the solvent removed in vacuo to give the title product (23 mg, 18%).

EXAMPLE 12

(1S,2R,4aS,5S,8R,8aR)-8a-hydroxy-3,8-dimethyl-5-
(1-methylethenyl)-2-(pent-4-enoyloxy)-1,2,4a,5,6,7,
8,8a-octahydronaphthalen-1-yl(2S,3aR,9bR)-6-
chloro-9b-hydroxy-5-methyl-1,2,3,3a,5,9b-
hexahydropyrrolo[2,3-c][2,1]benzoxazine-2-
carboxylate The title compound was prepared by the method of Example 11 substituting 4-(methyloxy)-4-oxobutanoic acid with commercially available pent-4-enoic acid (50 mg, 0.50 mmol) to give the title compound (64 mg, 56%).

EXAMPLE 13

(1S,2R,4aS,5R,8R,8aR)-2-(acetyloxy)-8a-hydroxy-3,
8-dimethyl-5-{1-methyl-2-[({[2-(naphthalen-1-
ylamino)ethyl]amino}carbonyl)oxy]ethyl}-1,2,4a,5,
6,7,8,8a-octahydronaphthalen-1-yl (2S,3aR,9bR)-6-
chloro-9b-hydroxy-5-methyl-1,2,3,3a,5,9b-
hexahydropyrrolo[2,3-c][2,1]benzoxazine-2-
carboxylate To (1S,2R,4aS,5S,8R,8aR)-2-(acetyloxy)-8a-hydroxy-5-{2-[(1H-imidazol-1-ylcarbonyl)oxy]-1-methylethyl}-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate (Preparation 143, 80 mg, 0.12 mmol) in pyridine (5 ml) was added 4-dimethylaminopyridine (16 mg, 0.13 mmol) followed by N-1-naphthyethylenediamine dihydrochloride salt (32 mg, 0.12 mmol). After stirring the reaction mixture for 48 h, the reaction mixture was concentrated in vacuo and purified by flash chromatography eluting with hexane ethyl acetate (2:1 and then 1:1) to give the pure title compound.

EXAMPLE 14

(1S,2R,4aS,5R,8R,8aR)-2-{[(acetyloxy)acetyl]oxy}-
8a-hydroxy-3,8-dimethyl-5-(1-methylethenyl)-1,2,
4a,5,6,7,8,8a-octahydronaphthalen-1-yl(2S,3aR,
9bR)-6-chloro-9b-hydroxy-5-methyl-1,2,3,3a,5,9b-
hexahydropyrrolo[2,3-C][2,1]benzoxazine-2-
carboxylate To (1S,2R,4aS,5R,8R,8aR)-2,8a-dihydroxy-3,8-dimethyl-5-(1-methylethenyl)-1, 2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate (Preparation 139, 210 mg, 0.4 mmol) and 4-dimethylaminopyridine (65 mg, 0.53 mmol) in dichloromethane (10 ml) was added (acetyloxy)acetic acid (60 mg, 0.51 mmol) and 1-(3-dimethylaminopropyl)-3-ethylcarbodiimide hydrochloride (90 mg, 0.58 mmol). The resultant mixture was stirred at room temperature and upon completion was concentrated in vacuo. The crude product was purified by chromatography on a Biotage® 12M column eluting with hexane:ethyl acetate (2:1). The pure fractions were combined and the solvent removed in vacuo to give the title product (150 mg, 61%).

EXAMPLE 15

(1S,2R,4aS,5R,8R,8aR)-2-(formyloxy)-8a-hydroxy-
3,8-dimethyl-5-(1-methylethenyl)-1,2,4a,5,6,7,8,8a-
octahydronaphthalen-1-yl(2S,3aR,9bR)-6-chloro-9b-
hydroxy-5-methyl-1,2,3,3a,5,9b-hexahydropyrrolo
[2,3-c][2,1]benzoxazine-2-carboxylate The title compound was prepared by the method of Example 14 substituting (acetyloxy)acetic acid with commercially available formic acid (2.0 □l, 0.53 mmol) to give the title compound (160 mg, 73%).

EXAMPLE 16

(1S,2R,4aS,5R,8R,8aR)-8a-hydroxy-3,8-dimethyl-5-(1-methylethenyl)-2-[(3,3,3-trifluoropropanoyl)oxy]-1,2,4a,5,6,7,8,8a-octahydronaphthalen-1-yl (2S,3aR, 9bR)-6-chloro-9b-hydroxy-5-methyl-1,2,3,3a,5,9b-hexahydropyrrolo[2,3-c][2,1]benzoxazine-2-carboxylate The title compound was prepared by the method of Example 14 substituting (acetyloxy)acetic acid with commercially available 3,3,3-trifluoropropionic acid to give the title compound (165 mg, 66%).

EXAMPLE 17

(1S,2R,4aS,5S,8R,8aR)-2-(acetyloxy)-5-[4-(ethyloxy)-1-methyl-4-oxobut-2-enyl]-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3, 3a,5,9b-hexahydropyrrolo[2,3-c][2,1]benzoxazine-2-carboxylate A solution of ((1S,2R,4aS,5R,8R,8aR)-2-(acetyloxy)-8a-hydroxy-3,8-dimethyl-5-[1-methyl-2-oxoethyl]-1,2,4a,5,6, 7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate (Preparation 141, 94 mg, 0.163 mmol) and carbethoxymethylene triphenylphosphorane (68 mg, 0.195 mmol) in anhydrous toluene (5 ml) was refluxed under nitrogen for 3 hours and then stirred at room temperature for 18 h before concentrating in vacuo. The residue was treated with sulfuric acid (10%) and extracted with two aliquots of ethyl acetate. The combined organic extracts were washed with saturated aqueous sodium hydrogen carbonate solution and saturated aqueous sodium chloride solution, dried (MgSO$_4$) and concentrated in vacuo. The crude product was taken up in acetonitrile (1 ml), filtered, and purified by preparative HPLC on a Dynamex®, 5 mm×21.6 mm column, eluting with acetonitrile:water (60:40). The pure fractions were concentrated in vacuo to give the title product (7 mg, 6%).

EXAMPLE 18

(1S,2R,4aS,5R,8R,8aR)-2-(acetyloxy)-5-(2,2-difluoro-1-methylethenyl)-8a -hydroxy-3,8-dimethyl-1, 2,4a,5,6,7,8,8a-octahydronaphthalen-1-yl (2S,3aR, 9bR)-6-chloro-9b-hydroxy-5-methyl-1,2,3,3a,5,9b-hexahydropyrrolo[2,3-c][2,1]benzoxazine-2-carboxylate A stirred solution of 2-[(1R,2R,4aS,5R,8S,8aS)-2-(acetyloxy)-5-(2,2-difluoro-1-methylvinyl)-8a-hydroxy-3,8-dimethyl-1,2,4a,5,6,7,8,8a-octahydro-1-naphthalenyl]3-(tert-butyl)(2S,3aR,9bR)-9b-[(tert-butoxycarbonyl)oxy]-6-chloro-5-methyl-1,2,5,9b-tetrahydropyrrolo[2,3-c][2,1]benzoxazine-2,3(3aH)-dicarboxylate (Preparation 156, 120 mg) in ethyl acetate (3 ml) was treated with concentrated hydrochloric acid (1 ml). After 50 minutes the homogenous mixture was diluted with ethyl acetate (50 ml) and washed with water (2×20 ml) followed by saturated, aqueous sodium chloride (20 ml). The combined organic extracts were dried (Na$_2$SO$_4$) and evaporated to give a white solid. The crude product was purified by flash column chromatography on silica gel eluting with ethyl acetate:hexane (1:1) to give a white solid (33 mg).

EXAMPLE 19

(1S,2R,4aS,5R,8R,8aR)-2-(acetyloxy)-5-[2-fluoro-1-methylethyl]-8a-hydroxy-3,8-dimethyl-1,2,4a,5,6,7, 8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate To 2-{(1S,2R,4aS,5S,8R,8aR)-2-(acetyloxy)-8a-hydroxy-5-[2-hydroxy 1-1 methylethyl]-3,8-dimethyl-1,2,4a,5,6,7,8, 8a-octahydronaphthalen-1-yl}3-(1,1-dimethylethyl)(2S, 3aR,9bR)-6-chloro-9b-({[(1,1-dimethylethyl)oxy]carbonyl}oxy)-5-methyl-1,2,5,9b-tetrahydropyrrolo[2,3-c] [2,1]benzoxazine-2,3(3aH)-dicarboxylate (Preparation 157, 200 mg, 0.26 mmol) in dichloromethane at −78° C. was added diethylaminosulfur trifluoride (45 mg, 3.4 □l, 0.28 mmol) over 10 minutes. The resulting mixture was allowed to warm to room temperature and then stirred for 18 h. The reaction mixture was cooled to −78° C. and diethylaminosulfur trifluoride (3.4 □l, 0.28 mmol) added. Again, the resulting mixture was allowed to warm to room temperature and stirred for 18 h. The reaction mixture was quenched with water and extracted with hexane:ether (1:2). The organic extract washed with saturated aqueous sodium chloride solution, dried (MgSO$_4$) and concentrated in vacuo to give the Boc-protected intermediate 2-{(1S,2R,4aS,5R,8R,8aR)-2-(acetyloxy)-5-[2-fluoro-1-methylethyl]-8a-hydroxy-3,8-dimethyl-1,2,4a, 5,6,7,8,8a-octahydronaphthalen-1-yl}3-(1,1-dimethylethyl) (2S,3aR,9bR)-6-chloro-9b-({[(1,1-dimethylethyl)oxy] carbonyl}oxy)-5-methyl-1,2,5,9b-tetrahydropyrrolo[2,3-c] [2,1]benzoxazine-2,3(3aH)-dicarboxylate as a white solid (172 mg, 86%).

To a solution of the Boc-protected intermediate 2-{(1S,2R, 4aS,5R,8R,8aR)-2-(acetyloxy)-5-[2-fluoro-1-methylethyl]-8a-hydroxy-3,8-dimethyl-1,2,4a,5,6,7,8,8a-octahydronaphthalen-1-yl}3-(1,1-dimethylethyl)(2S,3aR,9bR)-6-chloro-9b-({[(1,1-dimethylethyl)oxy]carbonyl}oxy)-5-methyl-1,2, 5,9b-tetrahydropyrrolo[2,3-c][2,1]benzoxazine-2,3(3aH)-dicarboxylate in ethyl acetate (5 ml) was added concentrated hydrochloric acid (12 N, 1.5 ml) and the resulting mixture was stirred for 1 hour. The reaction mixture was diluted with ethyl acetate (50 ml), washed with water (3×20 ml) and saturated aqueous sodium chloride solution (20 ml), dried (MgSO$_4$) and concentrated in vacuo to give a foam (125 mg, 83%). The crude product was purified by chromatography on silica eluting with hexane:ethyl acetate (2:1 then 1:1). The pure fractions were combined and concentrated in vacuo to give a white solid (50 mg, 33%). This product was further purified by preparative HPLC using a 1 inch "Microsorb" ODS column, eluting with water:acetonitrile (30:70) with a flow rate of 20 ml per minute. The pure fractions were eluted at 10 to 10.5 minutes and were combined and concentrated in vacuo to give the title product as a white solid (15 mg, 10%).

EXAMPLE 20

((1S,2R,4aS,5S,8R,8aR)-2-(acetyloxy)-8a-hydroxy-3,8-dimethyl-5-[(1-methyl-2-morpholin-4-ylethyl]-1, 2,4a,5,6,7,8,8a-octahydronaphthalen-1-yl (2S,3aR, 9bR)-6-chloro-9b-hydroxy-5-methyl-1,2,3,3a,5,9b-hexahydropyrrolo[2,3-c][2,1]benzoxazine-2-carboxylate A solution of 2-{(1S,2R,4aS,5R,8R,8aR)-2-(acetyloxy)-8a-hydroxy-3,8-dimethyl-5-[1-methyl-2-oxoethyl]-1,2,4a,5, 6,7,8,8a-octahydronaphthalen-1-yl}3-(1,1-dimethylethyl)

(2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate (Preparation 160, 200 mg, 0.26 mmol) and morpholine (33.6 mg, 0.39 mmol) in 1,2-dichloroethane (1.5 ml) was stirred for 20 min before adding sodium triacetoxyborohydride (0.11 mg, 0.28 mmol) and stirring for 15 h. The reaction mixture was poured into water (50 ml) and extracted with dichloromethane (3×30 ml). The combined organic extracts were washed with water (20 ml), dried ($Na_2SO_4$) and concentrated in vacuo. The crude residue was purified using a Biotage cartridge (8 g, silica), eluting with methanol:dichloromethane gradient (2:98 to 6:94) to give the Boc-protected intermediate as a white foam (203 mg).

The Boc-protected intermediate (203 mg) in ethyl acetate (1.5 ml) was treated with concentrated hydrochloric acid (0.5 ml). After 20 minutes the reaction mixture was diluted with ethyl acetate (50 ml), washed with aqueous sodium hydrogen carbonate (10% w/w, 50 ml) and then water (30 ml). The combined organic extracts were dried ($Na_2SO_4$) and evaporated to give the title compound (114 mg).

EXAMPLE 21

(1S,2R,4aS,5R,8R,8aR)-2-(acetyloxy)-5-(2-ethyl-1,3-thiazol-4-yl)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate To a solution of (1S,2R,4aS,5R,8R,8aR)-5-(2-ethyl-1,3-thiazol-4-yl)-1,8a-dihydroxy-3,8-dimethyl-1,2,4a,5,6,7,8,8a-octahydronaphthalen-2-yl acetate (Preparation 166, 94 mg), and (2S,9bR)-6-chloro-3-{[(1,1-dimethylethyl)oxy]carbonyl}-9b-({[(1,1-dimethylethyl)oxy]carbonyl}oxy)-5-methyl-1,2,3,3a,5,9b-hexahydropyrrolo[2,3-c][2,1]benzoxazine-2-carboxylic acid (Preparation 153, 90 mg) in dichloromethane-(4 ml) was added N-methylimidazole (0.05 ml) and 1-(2-mesitylenesulfonyl)-3-nitro-1H-1, 2,4-triazole. The reaction mixture was stirred at room temperature for 3 hours before evaporating in vacuo. The crude mixture was purifying by flash column chromatography on silica gel eluting with ethyl acetate:hexane (20:80 to, 50:50) to give the coupled intermediate as a gum (110 mg). A stirred solution of this intermediate 110 mg) in ethyl acetate (5 ml) was treated with concentrated hydrochloric acid (1 ml). After 40 minutes the homogenous mixture was diluted with ethyl acetate (50 ml), washed with dilute aqueous sodium chloride (50 ml), dried ($MgSO_4$) and evaporated. The crude product was purified by column chromatography on silica gel eluting with ethyl acetate:hexane (5:95 to 50:50) to give the title compound as a white solid (34 mg).

EXAMPLE 22

(1S,2R,4aS,5R,8R,8aR)-2-(acetyloxy)-5-[2,2-difluoro-1-methylethyl]-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydro pyrrolo[2,3-c][2,1]benzoxazine-2-carboxylate To a solution of 2-{(1S,2R,4aS,5R,8R,8aR)-2-(acetyloxy)-5-[2,2-difluoro-1-methylethyl]-8a-hydroxy-3,8-dimethyl-1,2,4a,5,6,7,8,8a-octahydronaphthalen-1-yl}3-(1,1-dimethylethyl)(2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate (Preparation 167, 35 mg, 0.044 mmol) in ethyl acetate (0.5 ml) was added concentrated hydrochloric acid (0.5 ml) and the resulting mixture stirred at room temperature for 20 minutes. The reaction mixture was poured into buffer solution (pH7, 15 ml) and extracted with ethyl acetate. The organic phase washed with water and saturated aqueous sodium chloride solution, dried ($Na_2SO_4$) and concentrated in vacuo. The crude product was purified by flash column chromatography gradient eluting with hexane:ethyl acetate (2:1 to 1:1). The pure fractions were combined and concentrated in vacuo to give the title product (15 mg, 57%).

EXAMPLE 23

(1S,2R,4aS,5R,8R,8aR)-2-(acetyloxy)-5-[2,2-difluoro-1-methylethyl]-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydro pyrrolo[2,3-c][2,1]benzoxazine-2-carboxylate To a solution of 2-{(1S,2R,4aS,5R,8R,8aR)-2-(acetyloxy)-5-[2,2-difluoro-1-methylethyl]-8a-hydroxy-3,8-dimethyl-1,2,4a,5,6,7,8,8a-octahydronaphthalen-1-yl}3-(1,1-dimethylethyl)(2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate (Preparation 168, 135 mg, 0.17 mmol) in ethyl acetate (1.5 ml) was added concentrated hydrochloric acid (1.5 ml) and the resulting mixture stirred at room temperature for 20 minutes. The reaction mixture was poured into buffer solution (pH7, 30 ml) and extracted with ethyl acetate. The organic phase washed with water and saturated aqueous sodium chloride solution, dried ($Na_2SO_4$) and concentrated in vacuo to give a yellowish oil (145 mg, 142%). The crude product was purified by flash column chromatography gradient eluting with hexane:ethyl acetate (2:1 to 1:1). The pure fractions were combined and concentrated in vacuo to give the title product (61 mg, 60%).

EXAMPLE 24

(1S,2R,4aS,5R,8R,8aR)-2-(acetyloxy)-5-(2,2-dichloro-1-methylethenyl)-8a -hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate 2-[(1S,2R,4aS,5R,8R,8aR)-2-(acetyloxy)-5-(2,2-dichloro-1-methylethenyl)-8a-hydroxy-3,8-dimethyl-1,2,4a,5,6,7,8,8a-octahydronaphthalen-1-yl]3-(1,1-dimethylethyl) (2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate (Preparation 172 0.10 g) was added to hydrogen chloride (1 M in acetic acid, 1 ml) and the resulting solution was stirred at room temperature. After 40 min, the crude mixture was diluted with diethyl ether (10 ml) and water (10 ml), the organic layer was separated and then washed with sodium hydrogen carbonate (5×10 ml), brine (10 ml) and dried ($MgSO_4$) and concentrated in vacuo. The crude product was purified by flash chromatography using a Bond ElutR cartridge eluting with a gradient of hexane:ethyl acetate (100:0 to then 50:50) to give the title compound.

EXAMPLE 32

(1S,2R,4aS,5S,8R,8aR)-2-(acetyloxy)-8a-hydroxy-3, 8-dimethyl-5-[1-methyl-2-(4-pyridin-2-ylpiperazin-1-yl)ethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate To 1-(2-pyridyl)piperazine (44.0 mg, 0.39 mmol) was added a solution of 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl}3-(1,1-dimethylethyl) (2S,3aR,9bR)-6-chloro-9b-({[(1,1-dimethylethyl)oxy]carbonyl}oxy)-5-methyl-1, 2,5,9b-tetrahydropyrrolo[2,3-c][2,1]benzoxazine-2,3(3aH)-dicarboxylate (Preparation 160, 200 mg, 0.257 mmol) in 1,2-dichloroethane. The resultant mixture was stirred at room temperature for 10 minutes before sodium triacetoxyborohydride (109 mg, 0.51 mmol) was added in one portion. The resultant reaction mixture was sealed and stirred for 60 hours. The reaction mixture was poured onto water (50 ml) and extracted with dichloromethane (3×30 ml). The combined extracts were washed with water (20 ml), dried ($Na_2SO_4$) and concentrated in vacuo. The crude bis-Boc protected product was purified by chromatography on a Biotage® cartridge (silica, 8 g) eluting with methanol:dichloromethane (2:98) for 11 minutes then a gradient of methanol:dichloromethane (2:98 to 6:94) over 40 minutes then methanol:dichloromethane (6:94). The pure fractions were collected to give the bis-Boc protected intermediate as a colourless glass (104.4 mg, 44%). Deprotection was effected by adding a solution of the intermediate in ethyl acetate (1.5 ml) to concentrated aqueous hydrochloric acid (0.5 ml). The resultant mixture was stirred for 20 minutes before pouring onto ethyl acetate (50 ml) and aqueous sodium hydrogen carbonate solution (2N, 40 ml). The aqueous layer was extracted with ethyl acetate-(20 ml) and the combined organic extracts washed with water (20 ml), dried ($Na_2SO_4$) and concentrated in vacuo. The crude product was purified by flash chromatography using a Biotage® silica (8 g) cartridge gradient eluting with methanol:dichloromethane (2:98 to 6:98). The pure fractions were collected to give the title compound (20.50 mg, 11%).

EXAMPLE 33

(1S,2R,4aS,5S,8R,8aR)-2-(acetyloxy)-5-(2-{bis[2-(methyloxy)ethyl]amino}-1-methylethyl)-8a-hydroxy-3,8-dimethyl-1,2,4a,5,6,7,8,8a-octahydronaphthalen-1-yl(2S,3aR,9bR)-6-chloro-9b-hydroxy-5-methyl-1,2,3,3a,5,9b-hexahydropyrrolo[2,3-c][2,1]benzoxazine-2-carboxylate The title compound was prepared by the method of Example 32 substituting 1-(2-pyridyl)piperazine with bis-(2-methoxyethyl)amine (51.3 mg, 0.39 mmol) to give the intermediate as a colourless glass (146.3 mg, 64%) and the title compound (51.70 mg, 29%).

EXAMPLE 47

(1S,2R,4aS,5S,8R,8aR)-5-{2-[acetyl(cyclopropyl)amino]-1-methylethyl}-2-(acetyloxy)-8a-hydroxy-3,8-dimethyl-1,2,4a,5,6,7,8,8a-octahydronaphthalen-1-yl(2S,3aR,9bR)-6-chloro-9b-hydroxy-5-methyl-1,2,3,3a,5,9b-hexahydropyrrolo[2,3-c][2,1]benzoxazine-2-carboxylate A solution of 2-[(1S,2R,4aS,5S,8R,8aR)-5-{2-[acetyl(cyclopropyl)amino]-1-methylethyl}-2-(acetyloxy)-8a-hydroxy-3,8-dimethyl-1,2,4a,5,6,7,8,8a-octahydronaphthalen-1-yl]3-(1,1-dimethylethyl)(2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate (Preparation 177, 91 mg, 0.10 mmol) in hydrochloric acid (4M solution in dioxane, 3 ml) was stirred under nitrogen for 1 hour. The reaction mixture was cooled to 0° C. and quenched with sodium hydrogen carbonate solution. The mixture was extracted with ethyl acetate and the combined organic fractions washed with sodium hydrogen carbonate solution, dried ($Na_2SO_4$) and concentrated in vacuo. The crude product was purified by column chromatography on silica (3 g) eluting with ethyl acetate:heptane (2:1). The pure fractions were recombined and concentrated in vacuo to give the title product as a yellow glassy solid (31 mg, 47%).

EXAMPLE 48

(1S,2R,4aS,5S,8R,8aR)-2-(acetyloxy)-5-(2-{cyclopropyl[(methyloxy)carbonyl]amino}-1-methylethyl)-8a-hydroxy-3,8-dimethyl-1,2,4a,5,6,7,8,8a-octahydronaphthalen-1-yl(2S,3aR,9bR)-6-chloro-9b-hydroxy-5-methyl-1,2,3,3a,5,9b-hexahydropyrrolo[2,3-c][2,1]benzoxazine-2-carboxylate A solution of 2-[(1S,2R,4aS,5S,8R,8aR)-2-(acetyloxy)-5-(2-{cyclopropyl[(methyloxy)carbonyl]amino}-1-methylethyl)-8a-hydroxy-3,8-dimethyl-1, 2,4a,5,6,7,8,8a-octahydronaphthalen-1-yl]3-(1,1-dimethylethyl)(2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate (Preparation 179, 108 mg, 0.12 mmol) in hydrogen chloride (4M solution in dioxane, 2 ml) was stirred under nitrogen for 1 hour. The reaction mixture was cooled to 0° C. and quenched with sodium hydrogen carbonate solution. The mixture was extracted with ethyl acetate and the combined organic fractions washed with sodium hydrogen carbonate solution, dried ($Na_2SO_4$) and concentrated in vacuo. The crude product was purified by column chromatography on silica (2 g) eluting with ethyl acetate:heptane (1:1). The pure fractions were recombined and concentrated in vacuo to give the title product as a yellow glassy solid (30 mg, 37%).

EXAMPLE 49

(1S,2R,4aS,5S,8R,8aR)-2-(acetyloxy)-5-(2-{ethyl[(methyloxy)carbonyl]amino}-1-methylethyl)-8a-hydroxy-3,8-dimethyl-1,2,4a,5,6,7,8,8a-octahydronaphthalen-1-yl(2S,3aR,9bR)-6-chloro-9b-hydroxy-5-methyl-1,2,3,3a,5,9b-hexahydropyrrolo[2,3-c][2,1]benzoxazine-2-carboxylate The title compound was prepared by the method of Example 48 substituting 2-[(1S,2R,4aS,5S,8R,8aR)-2-(acetyloxy)-5-(2-{cyclopropyl[(methyloxy)carbonyl]amino}-1-methylethyl)-8a-hydroxy-3,8-dimethyl-1,2,4a,5,6,7,8,8a-octahydronaphthalen-1-yl]3-(1,1-dimethylethyl)(2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate with 2-[(1S,2R,4aS,5S,8R,8aR)-2-(acetyloxy)-5-(2-{ethyl[(methyloxy)carbonyl]amino}-1-methylethyl)-8a-hydroxy-3,8-dimethyl-1,2,4a,5,6,7,8,8a-octahydronaphthalen-1-yl]3-(1,1-dimethylethyl)(2S,3aR,9bR)-6-chloro-9b-({[(1,1-dimethylethyl)oxy]carbonyl}oxy)-5-methyl-1,2,5,9b- tetrahydropyrrolo[2,3-c][2,1]benzoxazine-2,3(3aH)-dicarboxylate (Preparation 178, 89 mg, 0.10 mmol) to give the title compound as a pale yellow solid (21 mg, 31%).

EXAMPLE 52

(1S,2R,4aS,5S,8R,8aR)-2-(acetyloxy)-5-(2-{cyclopropyl[(ethylamino)carbonyl]amino}-1-methylethyl)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate The title compound was prepared by the method of Example 47 substituting 2-[(1S,2R,4aS,5S,8R,8aR)-5-{2-[acetyl(cyclopropyl)amino]-1-methylethyl}-2-(acetyloxy)-8a-hydroxy-3,8-dimethyl-1,2,4a,5,6,7,8,8a-octahydronaphthalen-1-yl]-3-(1,1-dimethylethyl)(2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate with 2-[(1S,2R,4aS,5S,8R,8aR)-2-(acetyloxy)-5-(2-{cyclopropyl[(ethylamino)carbonyl]amino}-1-methylethyl)-8a-hydroxy-3,8-dimethyl-1,2,4a,5,6,7,8,8a-octahydronaphthalen-1-yl]3-(1,1-dimethylethyl)(2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate (Preparation 180, 114 mg, 0.13 mmol) to give the title compound as an off white solid (25 mg, 28%).

EXAMPLE 96

(1S,2R,4aS,5S,8R,8aR)-8a-hydroxy-3,8-dimethyl-5-(1-methylethyl)-2-{[(phenylamino)carbonyl]oxy}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate To (1S,2R,4aR,8R,8aR)-8a-hydroxy-2-[(1H-imidazol-1-ylcarbonyl)oxy]-3,8-dimethyl-5-(1-methylethenyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate (Preparation 142, 510 mg, 0.83 mmol) in anhydrous pyridine (10 ml) was added aniline hydrochloride (500 mg, 3.8 mmol) and 4-dimethylaminopyridine (240 mg, 2.0 mmol). The reaction mixture was stirred at room temperature under nitrogen for 4 days before pouring into dichloromethane (100 ml) and washing with saturated aqueous citric acid solution (2×50 ml). The organic fraction was dried (Na$_2$SO$_4$) and concentrated in vacuo to give a yellowish solid (490 mg, 93%). The crude product was purified by flash column chromatography on silica gel eluting with a hexane:ethyl acetate gradient (1:1 to 1:5). The pure fractions were collected and concentrated in vacuo to give (1S,2R,4aS,5S,8R,8aR)-8a-hydroxy-3,8-dimethyl-5-(1-methylethenyl)-2-{[(phenylamino)carbonyl]oxy}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate (440 mg, 83%). To a solution of the (1S,2R,4aS,5S,8R,8aR)-8a-hydroxy-3,8-dimethyl-5-(1-methylethenyl)-2-{[(phenylamino)carbonyl]oxy}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate (100 mg, 0.157 mmol) in ethyl acetate (30 ml) was added platinum(IV) oxide (10 mg, 0.044 mmol) and the resulting mixture was hydrogenated at room temperature under 60 psi hydrogen for 10 hours. The reaction mixture was filtered and the filtrate concentrated in vacuo. The crude product, was purified by flash column chromatography on silica gel eluting with hexane ethyl acetate (1:1). The product was further purified to give the title product (19 mg, 19%).

EXAMPLE 101

(1S,2R,4aS,5S,8R,8aR)-2-(acetyloxy)-5-{2-[4-(4-chlorophenyl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate To a solution of 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl}3-(1,1-dimethylethyl)(2S,3aR,9bR)-6-chloro-9b-({[(1,1-dimethylethyl)oxy]carbonyl}oxy), 5-methyl-1,2,5,9b-tetrahydropyrrolo[2,3-c][2,1]benzoxazine-2,3(3aH)-dicarboxylate (Preparation 160, 620 mg, 0.80 mmol) in dichloromethane (8 ml) was added 1-(4-chlorophenyl)piperazine (Preparation 78, 254 mg, 1.08 mmol). After 10 min triethylamine (0.15 ml, 1.2 mmol) and sodium triacetoxyborohydride (110 mg, 0.52 mmol) were added and the reaction mixture stirred at room temperature under nitrogen for 16 h. The reaction mixture was diluted with dichloromethane (10 ml) and half-saturated aqueous sodium hydrogen carbonate solution (15 ml) and stirred for approximately 30 min. The aqueous layer re-extracted with dichloromethane (15 ml) and the combined organic layers were dried (Na$_2$SO$_4$) and concentrated in vacuo to give the Boc protected intermediate.

To the Boc protected intermediate was added hydrogen chloride (4N in dioxane, 6 ml). The reaction mixture was then stirred at room temperature for 45 min before addition of triethylamine (3 ml) accompanied by cooling in an ice bath. The reaction mixture was diluted with ethyl acetate (20 ml) and saturated aqueous sodium hydrogen carbonate solution (15 ml) and the layers separated. The aqueous layer was re-extracted with ethyl acetate (20 ml) and the combined organic layers washed with aqueous sodium hydrogen carbonate solution and brine, before being dried (Na$_2$SO$_4$) and concentrated in vacuo. The crude product was purified to give the title compound (273 mg, 0.361 mmol).

EXAMPLE 106

(1S,2R,4aS,5S,8R,8aR)-2-(acetyloxy)-8a-hydroxy-3,8-dimethyl-5-(1-methyl-2-{4-[2-(trifluoromethyl)phenyl]piperazin-1-yl}ethyl)-1,2,4a,5,6,7,8,8a-octahydronaphthalen-1-yl (2S,3aR,9bR)-6-chloro-9b-hydroxy-5-methyl-1, 2,3,3a,5,9b-hexahydropyrrolo[2,3-c][2,1]benzoxazine-2-carboxylate 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl}3-(1,1-dimethylethyl)-(2S,3aR,9bR)-6-chloro-9b-({[(1,1-dimethylethyl)oxy]carbonyl}oxy)-5-methyl-1, 2,5,9b-tetrahydropyrrolo[2,3-c][2,1]benzoxazine-2,3(3aH)-dicarboxylate (Preparation 160, 600 mg, 0.77 mmol), 1-[2-(trifluoromethyl)phenyl]piperazine (Preparation 130, 300 mg, 1 mmol) and triethylamine (0.3 ml, 2 mmol) were dissolved in dichloromethane (6 ml) and sodium triacetoxyborohydride; (240 mg, 1.1 mmol) added. The reaction mixture was stirred at room temperature for 16 h before addition of saturated aqueous sodium hydrogen carbonate solution (5 ml). After further vigorous stirring for 15 min, the reaction mixture was diluted with dichloromethane (40 ml) and water (20 ml). The organic layer was separated and the aqueous layer re-extracted with dichloromethane (20 ml). The combined organic layers were washed with water, dried ($Na_2SO_4$) and evaporated to dryness to give the Boc protected intermediate.

To a solution of the Boc protected intermediate in ethyl acetate (6 ml) was added concentrated hydrochloric acid (2 ml) and the reaction mixture was stirred at room temperature for 25 min. Saturated aqueous sodium hydrogen carbonate solution (30 ml) was then added to adjust the reaction mixture to pH 8. After stirring for a further 10 min, the reaction mixture was diluted with ethyl acetate (30 ml) and the organic layer separated. The aqueous layer was re-extracted with ethyl acetate (2×30 ml) and the combined organic layers washed with NaCl solution, dried ($Na_2SO_4$) and concentrated in vacuo. Purification gave the title compound (133 mg).

EXAMPLE 107

(1S,2R,4aS,5S,8R,8aR)-2-(acetyloxy)-8a-hydroxy-3,
8-dimethyl-5-(1-methyl-2-{4-[4-(trifluoromethyl)
pyrimidin-2-yl]piperazin-1-yl}ethyl)-1, 2,4a,5,6,7,8,
8a-octahydronaphthalen-1-yl (2S,3aR,9bR)-6-
chloro-9b-hydroxy-5-methyl-1,2,3,3a,5,9b-
hexahydropyrrolo[2,3-c][2,1]benzoxazine-2-
carboxylate To a solution of 1-[5-(trifluoromethyl)pyrid-2-yl]piperazine (6.4 g, 28.0 mmol) and 1-(5-(trifluoromethyl)-2-{(1S, 2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl}3-(1,1-dimethylethyl)(2S,3aR, 9bR)-6-chloro-9b-({[(1,1-dimethylethyl)oxy] carbonyl}oxy)-5-methyl-1,2,5,9b-tetrahydropyrrolo[2,3-c][2,1]benzoxazine-2,3(3aH)-dicarboxylate (Preparation 160, 15 g, 19 mmol) and 2-piperazin-1-yl-4-(trifluoromethyl)pyrimidine (4.5 g, 19 mmol) in dichloromethane (150 ml) was added sodium triacetoxyborohydride (6.0 g, 28 mmol) portionwise. The reaction mixture was stirred at room temperature for 40 h, before aqueous sodium hydrogen carbonate solution was added. After 15 min the layers were separated and the aqueous layer was re-extracted with dichloromethane (3×150 ml). The combined organic extracts were dried ($MgSO_4$) and concentrated in vacuo to give the Boc protected intermediate as a white foam.

To a cooled solution of the Boc protected intermediate (68 g, 62 mmol) in ethyl acetate (250 ml) was added concentrated hydrochloric acid (80 ml). The reaction mixture was stirred for 21 min before water (300 ml) was added and the layers separated. The aqueous layer was then extracted with dichloromethane (3×250 ml). The combined organic layers were washed with saturated aqueous sodium hydrogen carbonate, dried ($MgSO_4$) and concentrated in vacuo. The residue was dissolved in warm acetonitrile (150 ml) and a solid was precipitated. The solid washed with acetonitrile and dried in vacuo to give the title compound as a white solid (25.3 g, 51%).

EXAMPLE 113

(1S,2R,4aS,5S,8R,8aR)-2-(acetyloxy)-8a-hydroxy-3,
8-dimethyl-5-(1-methyl-2-{4-[5-(trifluoromethyl)
pyridin-2-yl]piperazin-1-yl}ethyl)-1,2,4a,5,6,7,8,8a-
octahydronaphthalen-1-yl (2S,3aR,9bR)-6-chloro-
9b-hydroxy-5-methyl-1, 2,3,3a,5,9b-
hexahydropyrrolo[2,3-c][2,1]benzoxazine-2-
carboxylate A solution of 1-[5-(trifluoromethyl)pyrid-2-yl]piperazine (6.4 g, 28.0 mmol) and 1-(5-(trifluoromethyl)-2-{(1S,2R, 4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl}3-(1,1-dimethylethyl)(2S,3aR,9bR)-6-chloro-9b-({ [(1,1-dimethylethyl)oxy]carbonyl}oxy)-5-methyl-1,2,5,9b-tetrahydropyrrolo[2,3-c][2,1]benzoxazine-2,3(3aH)-dicarboxylate (Preparation 160, 19.5 g, 25.1 mmol) in dichloromethane (200 ml) was stirred for 30 min at room temperature. Sodium triacetoxyborohydride (7.9 g, 37.5 mmol) was added portionwise over 3 min and the reaction mixture was stirred for 18 h at room temperature. Saturated sodium hydrogen carbonate solution (200 ml) was added portionwise and the reaction mixture was stirred for 20 min. The layers were separated and the aqueous phase was re-extracted with dichloromethane (2×200 ml). The combined organic layers were washed with water (200 ml), dried ($Na_2SO_4$) and concentrated in vacuo to give the Boc protected intermediate as a white foam (26.2 g). To a solution of the Boc protected intermediate (40 g) in ethyl acetate (210 ml) was added concentrated hydrochloric acid (70 ml) over 5 min and the reaction mixture was at room temperature for 30 min. Water (300 ml) was added and the product was extracted with dichloromethane (3×300 ml). The combined organic extracts were washed with sodium hydrogen carbonate solution and then dried ($MgSO_4$) and concentrated in vacuo to give the crude product as a yellow foam (19 g). The crude residue was dissolved in hot methanol (30 ml) and slowly cooled to room temperature, the solids were washed with cold methanol to give the product as a white solid (9.5 g), a second crop was obtained (5 g) as an off-white solid by reducing the volume of the filtrate.

EXAMPLE 125

(1S,2R,4aS,5S,8R,8aR)-2-(acetyloxy)-5-{2-[4-(4-
bromophenyl)piperazin-1-yl]-1-methylethyl}-8a-
hydroxy-3,8-dimethyl-1, 2,4a,5,6,7,8,8a-octahy-
dronaphthalen-1-yl (2S,3aR,9bR)-6-chloro-9b-
hydroxy-5-methyl-1,2,3,3a,5,9b-hexahydropyrrolo
[2,3-c][2,1]benzoxazine-2-carboxylate To a solution of 2-{(1S,2R,4aS,5R,8R,8aR)-2-(acetyloxy)-8a-hydroxy-3,8-dimethyl-5-[1-methyl-2-oxoethyl]-1, 2,4a,5,6,7,8,8a-octahydronaphthalen-1-yl}3-(1,1-dimethylethyl)(2S,3aR,9bR)-6-chloro-9b-({[(1,1-dimethylethyl)oxy] carbonyl}oxy)-5-methyl-1,2,5,9b-tetrahydropyrrolo[2,3-c] [2,1]benzoxazine-2,3(3aH)-dicarboxylate (Preparation 160, 170 mg, 0.22 mmol) in dichloromethane (2 ml) was added 1-(4-bromophenyl)-piperazine hydrochloride (91.0 mg, 0.33 mmol) and triethylamine (60 μl). The reaction mixture was stirred at room temperature for 1 h before addition of sodium triacetoxyborohydride (93 mg, 0.44 mmol). The reaction mixture was then stirred for a further 18 h. Dichloromethane (5 ml) and water (3 ml) were added, followed by vigorous stirring for 30 min, and the reaction mixture was filtered through a hydrophobic frit. The organic layer was separated and concentrated under a stream of nitrogen. To the residue was added hydrogen chloride (4N in dioxane, 2 ml) before vigorous shaking for 15 min and concentration under a stream of nitrogen for 40 min. A mixture of triethylamine and dichloromethane (1:5, 2 ml) was added and the resulting solution concentrated under a stream of nitrogen. The residue was dissolved in acetonitrile (900 µl) and filtered before purification to give the bis TFA salt of the title compound as an off white solid (55 mg).

EXAMPLE 126

(1S,2R,4aS,5S,8R,8aR)-2-(acetyloxy)-8a-hydroxy-3, 8-dimethyl-5-(1-methyl-2-{4-[4-(trifluoromethyl) phenyl]piperazin-1-yl}ethyl)-1,2,4a,5,6,7,8,8a-octahydronaphthalen-1-yl (2S,3aR,9bR)-6-chloro-9b-hydroxy-5-methyl-1, 2,3,3a,5,9b-hexahydropyrrolo [2,3-c][2,1]benzoxazine-2-carboxylate To a solution of 2-{(1S,2R,4aS,5R,8R,8aR)-2-(acetyloxy)-8a-hydroxy-3,8-dimethyl-5-[1-methyl-2-oxoethyl]-1, 2,4a,5,6,7,8,8a-octahydronaphthalen-1-yl}3-(1,1-dimethylethyl)(2S,3aR,9bR)-6-chloro-9b-({[(1,1-dimethylethyl)oxy] carbonyl}oxy)-5-methyl-1,2,5,9b-tetrahydropyrrolo[2,3-c] [2,1]benzoxazine-2,3(3aH)-dicarboxylate (Preparation 160, 170 mg, 0.22 mmol) in dichloromethane (2 ml) was added 1-(4-trifluoromethylphenyl)piperazine (75.5 mg, 0.33 mmol). The reaction mixture was stirred for 1 h at room temperature before addition of sodium triacetoxyborohydride (93 mg, 0.44 mmol). The reaction mixture was then stirred for a further 18 h. Dichloromethane (5 ml) and water (3 ml) were added, followed by vigorous stirring for 30 min, and the reaction mixture was filtered through a hydrophobic frit. The organic layer was separated and concentrated under a stream of nitrogen. To the residue was added hydrogen chloride (4N in dioxane, 2 ml) before vigorous shaking for 15 min and concentration under a stream of nitrogen for 40 min. A mixture of triethylamine and dichloromethane (1:5, 2 ml) was added and the resulting solution was concentrated under a stream of nitrogen. The residue was dissolved in acetonitrile (900 µl) and filtered before purification to give the bis TFA salt of the title compound as an off white solid (63 mg).

EXAMPLE 127

(1S,2R,4aS,5S,8R,8aR)-2-(acetyloxy)-5-{2-[4-(2,4-difluorophenyl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1, 2,3,3a,5,9b-hexahydropyrrolo [2,3-c][2,1]benzoxazine-2-carboxylate The title compound was prepared using method described in Example 126, substituting 1-(4-trifluoromethylphenyl) piperazine with 1-(2,4-difluorophenyl)piperazine (65 mg, 0.33 mmol) to give the desired compound (49 mg).

EXAMPLE 130

(1S,2R,4aS,5S,8R,8aR)-2-(acetyloxy)-5-{2-[4-(3, 5-dichlorophenyl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1, 2,3,3a,5,9b-hexahydropyrrolo[2, 3-c][2,1]benzoxazine-2-carboxylate The title compound was prepared using method described in Example 126, substituting 1-(4-trifluoromethylphenyl) piperazine with 1-(3,5-dichlorophenyl)piperazine (76 mg, 0.33 mmol) to give the desired compound (58 mg).

EXAMPLE 135

(1S,2R,4aS,5S,8R,8aR)-2-(acetyloxy)-5-{2-[4-(2-ethylphenyl)piperazin-1-yl]-1-methylethyl}-8a-hydroxy-3,8-dimethyl-1, 2,4a,5,6,7,8,8a-octahydronaphthalen-1-yl (2S,3aR,9bR)-6-chloro-9b-hydroxy-5-methyl-1,2,3,3a,5,9b-hexahydropyrrolo [2,3-c][2,1]benzoxazine-2-carboxylate The title compound was prepared using method described in Example 126, substituting 1-(4-trifluoromethylphenyl) piperazine with 1-(2-ethylphenyl)piperazine (62 mg, 0.33 mmol) to give the desired compound (51 mg).

EXAMPLE 147

(1S,2R,4aS,5S,8R,8aR)-2-(acetyloxy)-8a-hydroxy-3, 8-dimethyl-5-[(1S)-1-methyl-2-pyridin-3-ylethyl]-1, 2,4a,5,6,7,8,8a-octahydronaphthalen-1-yl(2S,3aR, 9bR)-6-chloro-9b-hydroxy-5-methyl-1,2,3,3a,5,9b-hexahydropyrrolo[2,3-c][2,1]benzoxazine-2-carboxylate-TFA salt To a solution of 2-[(1S,2R,4aS,5R,8R,8aR)-2-(acetyloxy)-8a-hydroxy-3,8-dimethyl-5-(1-methylethenyl)-1,2,4a,5,6,7, 8,8a-octahydronaphthalen-1-yl]3-(1,1-dimethylethyl) (2S, 3aR,9bR)-6-chloro-9b-({[(1,1-dimethylethyl)oxy] carbonyl}oxy)-5-methyl-1, 2,5,9b-tetrahydropyrrolo[2,3-c] [2,1]benzoxazine-2,3(3aH)-dicarboxylate (Preparation 152, 600 mg, 0.795 mmol) in tetrahydrofuran (9 ml) at 0° C. was added 9-BBN (0.5M solution in tetrahydrofuran, 4.3 ml, 2.12 mmol) over 20 minutes and the resulting mixture was allowed to warm to room temperature with stirring over 3 hours. Potassium carbonate (440 mg, 3.2 mmol) was added and the reaction mixture stirred for 15 minutes. A solution of (1,1'-bis(diphenylphosphino)ferrocene)palladium (II) chloride (130 mg, 0.16 mmol) and 3-iodopyridine (326 mg, 1.59 mmol) in anhydrous N,N-dimethylformamide (12 ml) was degassed and added to the reaction mixture to give a deep red solution. The reaction mixture was heated under nitrogen to 50° C. for 10 hours. After one hour the solution had become a pale orange colour and after ten hours it was a dark brown/red. The reaction was concentrated in vacuo and the residue dissolved in dichloromethane (400 ml), washed with water (2×200 ml), dried (Na$_2$SO$_4$) and concentrated in vacuo. The crude product was purified twice by chromatography on a Biotage® cartridge (silica, 90 g) eluting with ethyl acetate: hexane (1:9 to 1:1). The pure fractions were concentrated in vacuo to give the intermediate as an off-white foam (200 mg, 29%). The intermediate was treated with hydrogen chloride (4M solution in dioxane, 2 ml) and the resultant mixture shaken for 30 minutes before the mixture was concentrated by evaporation. The residue was treated with triethylamine (20% v/v in dichloromethane, 2 ml), concentrated in vacuo and the residue taken up in acetonitrile (0.9 ml) and filtered. The crude product was purified by HPLC on a Magellen 5 □C18, 150×21.2 mm column at 40° C. eluting with TFA (0.1% aqueous solution):acetonitrile (95:5 for 3 minutes flow rate 20 ml/min, then to 2:98 over 15 minutes flow rate 23 ml/min, then 2:98 for 4 minutes flow rate 25 ml/min). The pure fractions were combined and concentrated in vacuo to give the title product as the mono trifluoroacetic acid salt as a white solid (35 mg, 7%).

EXAMPLE 210

(1S,2R,4aS,5S,8R,8aR)-2-(acetyloxy)-8a-hydroxy-3, 8-dimethyl-5-((1R)-1-methyl-2-{4-[4-(trifluoromethyl)-2-pyrimidinyl]-1-piperazinyl}ethyl)-1,2,4a,5, 6,7,8,8a-octahydro-1-naphthalenyl (2S,3aR,9bR)-6-chloro-9b-hydroxy-5-methyl-1,2,3,3a,5,9b-hexahydropyrrolo[2,3-c][2,1]benzoxazine-2-carboxylate-TFA salt 2-[(1S,2R,4aS,5S,8R,8aR)-2-(acetyloxy)-8a-hydroxy-3, 8-dimethyl-5-((1R)-1-methyl-2-{4-[4-(trifluoromethyl)-2-pyrimidinyl]-1-piperazinyl}ethyl)-1,2,4a,5,6,7,8,8a-octahydro-1-naphthalenyl]3-tert-butyl (2S,3aR,9bR)-9b-[(tert-butoxycarbonyl)oxy]-6-chloro-5-methyl-1,2,5,9b-tetrahydropyrrolo[2,3-c][2,1]benzoxazine-2,3(3aH)-dicarboxylate, (Preparation 187, 587 mg, 0.59 mmol) in ethyl acetate (10 ml) at room temperature was added concentrated hydrochloric acid (2 ml). The mixture was stirred vigorously for 30 min and then poured cautiously onto saturated aqueous sodium bicarbonate (30 ml). The mixture was diluted with ethyl acetate (50 ml) and the two layers were separated. The organic layer washed with water (20 ml) and brine (20 ml) before being dried (MgSO4), filtered and evaporated in vacuo. The residue was purified by preparative HPLC using a Phenomenex LUNA 2 column (5 μm $C_{18}$ silica, 21.2×150 mm, temperature 40° C.), eluting with a gradient of acetonitrile:0.1% aqueous trifluoroacetic acid (30:70 for 14 mins, then 90:10 for 4 mins and then 30:70 for 2 mins), at a flow rate of 20 ml/min and UV detection at 220 nm. The TFA salt of the title compound was obtained as a pale yellow solid (211 mg, 39%).

EXAMPLE 211

(1S,2R,4aS,5S,8R,8aR)-2-(acetyloxy)-8a-hydroxy-3, 8-dimethyl-5-((1R)-1-methyl-2-{4-[5-(trifluoromethyl)-2-pyridinyl]-1-piperazinyl}ethyl)-1,2,4a,5,6,7, 8,8a-octahydro-1-naphthalenyl (2S,3aR,9bR)-6-chloro-9b-hydroxy-5-methyl-1,2,3,3a,5,9b-hexahydropyrrolo[2,3-c][2,1]benzoxazine-2-carboxylate-TFA salt To a solution of 2-[(1S,2R,4aS,5S,8R,8aR)-2-(acetyloxy)-8a-hydroxy-3,8-dimethyl-5-((1R)-1-methyl-2-{4-[5-(trifluoromethyl)-2-pyridinyl]-1-piperazinyl}ethyl)-1,2,4a,5,6, 7,8,8a-octahydro-1-naphthalenyl]3-tert-butyl (2S,3aR,9bR)-9b-[(tert-butoxycarbonyl)oxy]-6-chloro-5-methyl-1,2,5,9b-tetrahydropyrrolo[2,3-c][2,1]benzoxazine-2,3(3aH)-dicarboxylate, (Preparation 188, 660 mg, 0.65 mmol) in ethyl acetate (10 ml) at room temperature was added concentrated hydrochloric acid (2 ml). The mixture was stirred vigorously for 30 min and then poured cautiously onto saturated aqueous sodium bicarbonate (30 ml). The mixture was diluted with ethyl acetate (50 ml) and the two layers were separated. The organic layer washed with water (20 ml) and brine (20 ml) before being dried (MgSO$_4$), filtered and evaporated in vacuo. The residue was purified by preparative HPLC using a Phenomenex LUNA 2 column (5 μm $C_{18}$ silica, 21.2×150 mm, temperature 40° C.), eluting with a gradient of acetonitrile: 0.1% aqueous trifluoroacetic acid (30:70 for 14 mins, then 90:10 for 4 mins and then 30:70 for 2 mins), at a flow rate of 20 ml/min and UV detection at 220 nm. The TFA salt of the title compound was obtained as a pale yellow solid (220 mg, 36%).

EXAMPLE 212

(1S,2R,5S,8R,8aR)-2-(acetyloxy)-5-((1R)-2-{4-[bis (4-fluorophenyl)methyl]piperazin-1-yl}-1-methylethyl)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate To a solution of 2-{(1S,2R,4aS,5R,8R,8aR)-2-(acetyloxy)-8a-hydroxy-3,8-dimethyl-5-[1-methyl-2-oxoethyl]-1, 2,4a,5,6,7,8,8a-octahydronaphthalen-1-yl}3-(1,1-dimethylethyl)(2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate (Preparation 160, 170 mg, 0.22 mmol) in dichloromethane (2 ml) was added 1-(4,4'-difluorobenzhydryl)piperazine (94.6 mg, 0.33 mmol). The reaction mixture was stirred for 1 h at room temperature before addition of sodium triacetoxyborohydride (93 mg, 0.44 mmol). The reaction mixture was then stirred for a further 18 h. Dichloromethane (5 ml) and water (3 ml) were added, followed by vigorous stirring for 30 min, and the reaction mixture was filtered through a hydrophobic frit. The organic layer was separated and concentrated under a stream of nitrogen. To the residue was added hydrogen chloride (4N in dioxane, 2 ml) before vigorous shaking for 15 min and concentration under a stream of nitrogen for 40 min. A mixture of triethylamine and dichloromethane (1:5, 2 ml) was added and the resulting solution concentrated under a stream of nitrogen. The residue was dissolved in acetonitrile (900 μl) and filtered before purification to give the bis TFA salt of the title compound as an off white solid (45 mg).

EXAMPLE 213

(1S,2R,5S,8R,8aR)-2-(acetyloxy)-5-{(1R)-2-[4-(5-chloropyrimidin-2-yl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate To a solution of 2-{(1S,2R,4aS,5R,8R,8aR)-2-(acetyloxy)-8a-hydroxy-3,8-dimethyl-5-[1-methyl-2-oxoethyl]-1, 2,4a,5,6,7,8,8a-octahydronaphthalen-1-yl}3-(1,1-dimethylethyl)(2S,3aR,9bR)-6-chloro-9b-({[(1,1-dimethylethyl)oxy]carbonyl}oxy)-5-methyl-1,2,5,9b-tetrahydropyrrolo[2,3-c] [2,1]benzoxazine-2,3(3aH)-dicarboxylate, (Preparation 160, 550 mg, 0.71 mmol) and 5-chloro-2-piperazin-1-ylpyrimidine (Preparation 197, 200 mg, 1 mmol), in dichloromethane (8 ml) was added sodium triacetoxyborohydride (220 mg, 1 mmol). The reaction mixture was stirred at room temperature for 18 h before addition of saturated aqueous sodium hydrogen carbonate (5 ml). Vigorous stirring for 20 min was followed by separation of the layers using a filter cartridge fitted with a hydrophobic frit. The filtrate was evaporated under a stream of nitrogen to give the Boc-protected intermediate (800 mg, 0.83 mmol).

To a solution of the Boc protected intermediate, (800 mg) in ethyl acetate (7.5 ml) was added concentrated hydrochloric acid (2.5 ml). The reaction mixture was stirred at room temperature for 25 min before solid sodium hydrogen carbonate and saturated aqueous sodium hydrogen carbonate solution was added to adjust the reaction mixture to pH 5. The mixture was extracted with dichloromethane (2×20 ml) and the combined organic layers dried ($Na_2SO_4$) and concentrated in vacuo. The residue was purified to give the title compound (200 mg). The free base was obtained by dissolving in dichloromethane and shaking with aqueous sodium hydrogen carbonate solution. The layers were separated using a hydrophobic filter cartridge and concentrated to give the title compound

EXAMPLE 214

(1S,2R,4aS,5S,8R,8aR)-2-(acetyloxy)-5-{(1R)-2-[4-(5-bromopyrimidin-2-yl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate To a solution of 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl}3-(1,1-dimethylethyl)(2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate (Preparation 160, 150 mg, 0.19 mmol) in dichloromethane (2.5 ml) was added 5-bromo-2-piperazin-1-ylpyrimidine (61 mg, 0.25 mmol) and sodium triacetoxyborohydride (65 mg, 0.3 mmol). The reaction mixture was shaken for 22 h and saturated aqueous sodium hydrogen carbonate was added followed by further vigorous stirring for 30 min. The organic and aqueous layers were separated using a hydrophobic filter cartridge and the filtrate was concentrated under a stream of nitrogen to give the Boc protected intermediate.

To the Boc protected intermediate was added hydrogen chloride (4N in dioxane, 2.5 ml) and the resulting solution was shaken at room temperature for 25 min. The reaction mixture was concentrated under a stream of nitrogen and quenched with a mixture of triethylamine and dichloromethane (2:3, 2 ml). The mixture was again concentrated under a stream of nitrogen. The residue was diluted with dichloromethane (5 ml) and water (5 ml) and the layers separated using a hydrophobic frit. The filtrate was concentrated under a stream of nitrogen and purified to give the title compound. The free base was dissolved in dichloromethane, shaken with saturated aqueous sodium hydrogen carbonate and filtered through a hydrophobic frit to give the title compound (51 mg).

EXAMPLE 215

(1S,2R,4aS,5S,8R,8aR)-2-(acetyloxy)-5-{(1R)-2-[4-(6-chloro-1,3-benzothiazol-2-yl)piperazin-1-yl]-1-methylethyl}-8a-hydroxy-3,8-dimethyl-1, 2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate To a solution of 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl}3-(1,1-dimethylethyl)(2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate (Preparation 160, 150 mg, 0.19 mmol) in dichloromethane (2.5 ml) was added 6-chloro-2-piperazino-1,3-benzothiazole (63 mg, 0.25 mmol, commercially available, Maybridge) and sodium triacetoxyborohydride (65 mg, 0.3 mmol). The reaction mixture was shaken for 22 h and saturated aqueous sodium hydrogen carbonate was added followed by further vigorous stirring for 30 min. Separation of the layers was achieved by filtering the solution through a hydrophobic filter cartridge and the filtrates were concentrated under a stream of nitrogen to give the Boc protected intermediate.

To the Boc protected intermediate was added hydrogen chloride (4N in dioxane 2.5 ml). The reaction mixture was shaken at room temperature for 25 min before concentrating under a stream of nitrogen for 20 min and quenching with a mixture of triethylamine and dichloromethane (2:3, 2 ml). The mixture was again concentrated under a stream of nitrogen and the residue was dissolved in dichloromethane (5 ml) and water (5 ml). The layers were separated using a hydrophobic frit and the filtrate was concentrated under a stream of nitrogen and purified to give the title compound. The free base was obtained by dissolving in dichloromethane and shaking with saturated aqueous sodium hydrogen carbonate. This solution was, then filtered through a hydrophobic frit and the filtrate concentrated to give the title compound (58 mg).

EXAMPLE 216

(1S,2R,4aS,5S,8R,8aR)-2-(acetyloxy)-5-((1R)-2-{4-[(3,4-dichlorophenyl)methyl]piperazin-1-yl}-1-methylethyl)-8a-hydroxy-3,8-dimethyl-1, 2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate To a solution of 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl}3-(1,1-dimethylethyl)(2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate (Preparation 160, 150 mg, 0.19 mmol) and 1-(3,4-dichlorophenyl)piperazine hydrochloride salt (67 mg, 0.25 mmol) in dichloromethane (2.5 ml) was added triethylamine (50 μl) and sodium triacetoxyborohydride (65 mg, 0.3 mmol). The reaction mixture was stirred at room temperature for 20 h before saturated aqueous sodium hydrogen carbonate (3 ml) was added, followed by further vigorous stirring for 30 min. The reaction mixture was filtered through a hydrophobic filter cartridge and the filtrate evaporated under a stream of nitrogen to give Boc protected intermediate.

The Boc protected intermediate was dissolved in hydrogen chloride (4N dioxane, 2.5 ml) and stirred at room temperature for 25 min. The reaction mixture was concentrated under a stream of nitrogen (40° C., 25 min) and quenched with a mixture of triethylamine and dichloromethane (2:3, 2 ml). The mixture was again concentrated under a stream of nitrogen and the residues were partitioned between dichloromethane (5 ml) and saturated aqueous sodium hydrogen carbonate. The combined phases were filtered through a

EXAMPLE 217

(1S,2R,4aS,5S,8R,8aR)-2-(acetyloxy)-8a-hydroxy-3,
8-dimethyl-5-((1R)-1-methyl-2-{4-[5-(trifluorom-
ethyl)pyrimidin-2-yl]piperazin-1-yl}ethyl)-1,2,4a,5,
6,7,8,8a-octahydronaphthalen-1-yl (2S,3aR,9bR)-6-
chloro-9b-hydroxy-5-methyl-1,2,3,3a,5,9b-
hexahydropyrrolo[2,3-c][2,1]benzoxazine-2-
carboxylate To a solution of 2-{(1S,2R,4aS,5R,8R,8aR)-2-(acety-loxy)-8a-hydroxy-3,8-dimethyl-5-[1-methyl-2-oxoethyl]-1,2,4a,5,6,7,8,8a-octahydronaphthalen-1-yl}3-(1,1-dimethyl-ethyl)(2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate (Preparation 160, 170 mg, 219 μmol) and 2-piperazin-1-yl-5-(trifluoromethyl)pyrimidine TFA salt, (Preparation 198, 68 mg, 200 μmol) in dichloromethane (4 ml) was added sodium triacetoxyborohydride (93 mg, 440 mmol). The reaction mixture was stirred overnight and water added (5 ml). After further shaking, the layers were separated and the organic layer evaporated to dryness under a stream of nitrogen. The residue was dissolved in ethyl acetate (2 ml) and concentrated hydrochloric acid (1 ml) was added. After stirring for 20 min, saturated aqueous sodium hydrogen carbonate (20 ml) and ethyl acetate (20 ml) were added and the mixture was shaken. The organic layer was separated, dried (Na$_2$SO$_4$) and evaporated before purification to give the title compound (37 mg) as a TFA salt.

EXAMPLE 218

(1S,2R,4aS,5S,8R,8aR)-2-(acetyloxy)-5-((1R)-2-{4-
[(4-chlorophenyl)oxy]piperidin-1-yl}-1-methyl-
ethyl)-8a-hydroxy-3,8-dimethyl-1, 2,4a,5,6,7,8,8a-
octahydronaphthalen-1-yl (2S,3aR,9bR)-6-chloro-
9b-hydroxy-5-methyl-1,2,3,3a,5,9b-
hexahydropyrrolo[2,3-c][2,1]benzoxazine-2-
carboxylate To a solution of (1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate (Preparation 141, 60 mg, 0.11 mmol) and 4-[(4-chlorophenyl)oxy]piperidine (Preparation 200, 25 mg, 0.1 mmol) was added dichloromethane (2 ml) and sodium triacetoxyborohydride (35 mg, 0.16 mmol), followed by triethylamine (0.02 ml, 0.17 mmol). The reaction mixture was stirred at room temperature for 17 h, before diluting with dichloromethane (5 ml) and saturated aqueous sodium hydrogen carbonate (3 ml). The reaction mixture was shaken vigorously and the layers were separated using a hydrophobic filter cartridge. The filtrate was concentrated under a stream of nitrogen and purified to give the title compound (26 mg).

Preparation 4: 1-(cyclopentylcarbonyl)piperazine

Cyclopentane carboxylic acid (5.0 g, 44 mmol) was dissolved in chloroform (50 ml). Oxalyl chloride (4.6 ml, 52.5 mmol) was added dropwise under nitrogen and stirred at room temperature for 30 min. The reaction mixture was then heated under reflux for 1 h, before concentrating in vacuo to give cyclopentanecarbonyl chloride as a light yellow liquid.

Piperazine hexahydrate (8.55 g, 44.0 mmol) was dissolved in absolute ethanol (50 ml) and then refluxed for 10 min. Cyclopentanecarbonyl chloride (5.83 g, 44 mmol) was added dropwise at 65° C. and the reaction mixture was refluxed for 30 min and then stirred at room temperature for 18 h. The reaction mixture was cooled, filtered and the filtrate was concentrated in vacuo to give ~20 ml of solution. The concentrate was cooled and then filtered again. Ethanolic hydrogen chloride was added to the mother liquor, and the reaction mixture was concentrated to give a white solid, which was dissolved in water (15 ml). The solution was basified to pH 14 and the product was extracted with dichloromethane (7×50 ml). The extracts were dried, (Na$_2$SO$_4$) and concentrated to give the title compound as a yellowish residue, which was distilled to give the product (1.28 g, 7.0 mmol, 16%)

Preparation 10:
4-(8-azabicyclo[3.2.1]oct-3-ylsulfanyl)phenyl
methyl ether

To a stirred solution of 2,2,2-trichloroethyl 3-[(4-methoxyphenyl)sulfanyl]-8-azabicyclo[3.2.1]octane-8-carboxylate (Preparation 11, 52.7 g, 0.12 moles) in tetrahydrofuran under nitrogen was added zinc dust (20 g,) and potassium hydrogenphosphate (1 M, 125 ml). The reaction mixture was stirred for 2 h at room temperature before adding more zinc dust (30 g) followed by heating on a steam bath for 30 min. The reaction mixture was cooled to room temperature and diluted with water (1 l). Sodium carbonate was added to adjust the pH to 10. The reaction mixture was filtered and the filtrate was separated and then extracted with dichloromethane. The combined organic extracts were dried (Na$_2$SO$_4$) and concentrated in vacuo to give the title compound as a yellow oil (26.0 g, 84%). The oil was purified by column chromatography on silica gel (350 g) eluting with methanol:dichloromethane:0.88 ammonia solution (10:90:1) to give the product as an oil which crystallised on standing (13 g, 42%). The solid was further purified by stirring in ether and filtering to give a light yellow solid (9 g, 29%).

Preparation 11: 2,2,2-trichloroethyl 3-[(4-methoxyphenyl)sulfanyl]-8-azabicyclo[3.2.1]octane-8-carboxylate To a solution of methyl 4-[(8-methyl-8-azabicyclo[3.2.1]oct-3-yl)sulfanyl]phenyl ether (Preparation 12, 43.7 g, 0.16 moles) in benzene (400 ml) stirred under nitrogen was added potassium carbonate (24.3 g) and trichloroethylchloroformate (24.5 ml, 0.176 moles). The reactants were heated to reflux for 2 h before cooling, filtering and washing the collected solids with benzene. The mother liquor, was concentrated in vacuo to give the crude product as an oil. The crude product was stirred with ethyl acetate:hexane (5:95) to precipitate the title compound as a white solid (51.5 g, 76%).

Preparation 12: Methyl 4-[(8-methyl-8-azabicyclo
[3.2.1]oct-3-yl)sulfanyl]phenyl ether To a solution of methyl 8-methyl-8-azabicyclo[3.2.1]oct-3-yl sulfate (Preparation 13, 35 g, 0.16 mol) in tetrahydrofuran (300 ml) was added with cooling to 0° C. sodium hydride (60% dispersion in oil, 7 g, 0.17 mol). After complete addition, 4-methoxybenzene thiol (23.8 g, 0.16 mol) was added in tetrahydrofuran (300 ml). The reaction mixture was heated under reflux for 2 h and then cooled to 30° C. and water (250

--- hydrophobic filter cartridge and the filtrates were concentrated under a stream of nitrogen. Purification gave the title compound (44 mg).

ml) was added. The tetrahydrofuran was removed in vacuo, dichloromethane was added and the layers separated. The organic layer washed with water, sodium hydroxide (1 M solution), water, and saturated brine before drying (Na$_2$SO$_4$). The organic extracts were concentrated in vacuo to give the title compound (43.7 g, 100%).

Preparation 13: Methyl 8-methyl-8-azabicyclo[3.2.1]oct-3-yl sulfate

To a solution of 8-methyl-8-azabicyclo[3.2.1]octan-3-ol (299 g, 2.12 moles) in dichloromethane (3.5 l) was added triethylamine (445 ml, 3.2 moles) and the reaction mixture was cooled to −40° C. Methanesulfonyl chloride (293 g, 2.55 moles) was added dropwise over 90 min and the reaction mixture was then allowed to warm to room temperature. Water (1 l) was added and the organic extract washed with sodium-hydroxide (0.5M) water and saturated sodium chloride solution. The organic extracts were dried (Na$_2$SO$_4$) and concentrated in vacuo to give a yellow solid (262 g, 56%). The solid was recrystallised from hexane to give a first crop of the title compound as light yellow crystals (126.5 g, 27%), followed by a second crop (76.1 g, 16%).

Preparation 16: 2,5-dimethyl-3-piperazin-1-ylpyrazine

To a solution of 2,5-dimethyl-3-[4-(phenylmethyl)piperazin-1-yl]pyrazine (Preparation 17, 1.14 g, 4.04 mmol) in methanol (80 ml) was added ammonium formate (1.27 g, 20.2 mmol) followed by palladium (10% w/w on carbon, 0.17 g) under a nitrogen atmosphere. The reaction mixture was heated under reflux, after 2.5 h, more ammonium formate (0.64 g, 10.1 mmol) and palladium (0.06 g) were added. The reaction mixture was filtered through Celite® washed with methanol and concentrated in vacuo. The crude product was purified by flash chromatography using silica gel eluting with methanol:dichloromethane (8:92 and then 10:90) and then methanol:dichloromethane:0.88 ammonia solution (10:90:1). The title compound was obtained as a white solid (0.35 g, 45%).

Preparation 17: 2,5-dimethyl-3-[4-(phenylmethyl) piperazin-1-yl]pyrazine

3-Chloro-2,5-dimethylpyrazine (1.0 g, 7.0 mmol) and N-benzylpiperazine (3.7 ml, 21.0 mmol) were mixed under nitrogen and heated to 125° C. for 18 h. Saturated aqueous sodium hydrogen carbonate was added and the product was extracted with chloroform. The combined organic extracts were dried (Na$_2$SO$_4$) and concentrated in vacuo to give a yellow oil. The crude product was purified by flash chromatography using silica gel eluting with methanol:chloroform (2.5:97.5) to give the pure product as a yellow oil (1.14 g, 58%).

Preparation 18: 2-methyl-3-piperazin-1-ylquinoxaline

To a solution of 2-methyl-3-[4-(phenylmethyl)piperazin-1-yl]quinoxaline (Preparation 19, 1.68 g, 5.28 mmol) in methanol (106 ml) was added ammonium formate (1.66 g, 26.4 mmol) followed by palladium (10% w/w on carbon, 0.25 g) under a nitrogen atmosphere. After 12.5 h, more ammonium formate (0.83 g, 13.2 mmol) and palladium (0.12 g) were added. The reaction mixture was filtered through Celite® and evaporated to a yellow oil. The crude product was purified by flash chromatography using silica gel eluting with methanol:dichloromethane (5:95 and then 10:90). The title compound was obtained as a pale yellow oil which crystallised upon standing (0.46 g, 38%).

Preparation 19: 2-methyl-3-[4-(phenylmethyl)piperazin-1-yl]quinoxaline

2-Chloro-3-methylquinoxaline (1.0 g, 5.6 mmol) and N-benzylpiperazine (2.9 ml, 16.8 mmol) were mixed and heated to 125° C. for 18 h. Saturated aqueous sodium hydrogen carbonate was added and the product was extracted with chloroform. The combined organic extracts were dried (Na$_2$SO$_4$) and concentrated in vacuo to give a dark red oil. The crude product was purified by flash chromatography using silica gel eluting with methanol:dichloromethane (15:85) to give the pure product as a red oil which solidified upon standing (1.63 g, 94%).

Preparation 15: 3-chloro-2-pyridinyl 3-piperidinyl ether hydrochloride salt

To a stirred solution of racemic 3-hydroxypiperidine (1.12 g, 11.1 mmol) in tetrahydrofuran (20 ml) under nitrogen was added sodium hydride (60% dispersion in oil, 0.44 g, 11.1 mmol). The reaction mixture was stirred for 45 min before adding 2,3-chloropyridine (1.64 g, 11.1 mmol) and heating under reflux for 48 h. The reaction mixture was cooled to room temperature and quenched with water (5 ml) and extracted with ethyl acetate. The organic extracts were then washed with water, saturated aqueous ammonium chloride and brine before back washing with chloroform. The combined organic extracts were dried (MgSO$_4$) and concentrated in vacuo to give a crude orange oil (2.5 g). The crude product was chromatographed eluting with chloroform:methanol (15:1 to 8:1) to give a pale yellow oil (2.3 g). A solution of hydrogen chloride (4M in dioxane, 5 ml) was added to the pure product to give the hydrochloride salt upon concentration as a sticky yellow solid (2.27 g, 82%).

Preparation 21: (+)-3,11-diazatricyclo[7.3.1.0$^{2,7}$] trideca-2,4,6-triene hydrochloride salt Racemic 1,1-dimethylethyl 3,11-diazatricyclo[7.3.1.0$^{2,7}$] trideca-2,4,6-triene-11-carboxylate (Preparation 22, 0.47 g) was subjected to chiral preparative HPLC using a 5 cm×25 cm Chiracel AD column, eluting with heptane:isopropyl alcohol (95:5) at a flow rate of 120 ml/min over 20 min. The enantiomers were detected at 250 nm and were shown to have chiral purity of >98% enantiomeric excess, the first enantiomer to be eluted was designated enantiomer 1 and the second was designated enantiomer 2.

Enantiomer 2 of 1,1-dimethylethyl 3,11-diazatricyclo [7.3.1.0$^{2,7}$]trideca-2,4,6-triene-11-carboxylate was dissolved in ethyl acetate (5 ml) and treated with hydrochloric acid (3M, 2 ml) and then warmed to reflux for 18 h. The reaction mixture was cooled and filtered and the white precipitate washed with ethyl acetate and hexane. The hydrochloride salt of enantiomer 2 was obtained as a white powder 0.12 g, 82%).

Preparation 22: 1,1-dimethylethyl 3,11-diazatricyclo [7.3.1.0$^{2,7}$]trideca-2,4,6-triene-11-carboxylate A solution of 11-(phenylmethyl)-3,11-diazatricyclo [7.3.1.0$^{2,7}$]trideca-2,4,6-triene (Preparation 23, 0.74 g, 2.81 mmol), ammonium formate (6.0 g, 95 mmol) and palladium hydroxide (10 wt % on carbon, 0.21 g) in methanol (30 ml)

under nitrogen was heated under reflux for 1 h. The reaction mixture was filtered through a pad of Celite® and the pad washed with hot methanol. The combined organic layers were concentrated in vacuo, dichloromethane (100 ml) was added and the mixture was filtered and then concentrated to an oil. The oil was dissolved in dichloromethane and di-tert-butyl dicarbonate (0.65 g, 3.09 mmol) was added. The reaction mixture was concentrated in vacuo and purified by, flash chromatography eluting with ethyl acetate to give the title compound (0.23 g, 30%) and also 3,11-diazatricyclo[7.3.1.0$^{2,7}$]trideca-2,4,6-triene-11-carbaldehyde (0.36 g, 64%).

To 3,11-diazatricyclo[7.3.1.0$^{2,7}$]trideca-2,4,6-triene-11-carbaldehyde (0.36 g, 64%) was added sodium hydroxide (0.80 g, 20 mmol) in dioxane (7 ml) and water (3 ml) and the reaction mixture was heated under reflux for 9 h. More sodium hydroxide (0.40 g, 10 mmol) was added and the reaction mixture was refluxed for a further 9 h. The reaction mixture was cooled, diluted with saturated sodium hydrogen carbonate solution and extracted with dichloromethane. The organic extracts were dried and filtered and then di-tert-butyl dicarbonate (0.39 g, 1.83 mmol) was added and the reaction mixture was stirred for 2 h. The reaction mixture washed with brine, dried (Na$_2$SO$_4$) and concentrated to give an oil which was purified by flash chromatography eluting with ethyl acetate to give the title product (0.24 g).

Thus the title compound was obtained (0.47 g, 61%) by combination of the two components described.

Preparation 23: 11-(Phenylmethyl)-3,11-diazatricyclo[7.3.1.0$^{2,7}$]trideca-2,4,6-triene To a solution of 3-azatricyclo[7.2.1.0$^{2,7}$]dodeca-2,4,6-triene-10,11-diol (Preparation 24, 1.16 g, 6.07 mmol) in ethanol (40 ml) was added sodium periodate (1.35 g, 6.07 mmol) in water (20 ml) to produce a yellow slurry. After 15 min, water and ethyl acetate were added and the layers were separated, the aqueous layer washed with ethyl acetate (4×50 ml) and then dichloromethane. The combined organic extracts were dried (Na$_2$SO$_4$) to give an orange oil. The oil was diluted with dichloroethane (50 ml), benzylamine (0.65 g, 6.07 mmol) was added followed by sodium triacetoxyborohydride (4.12 g, 19.4 mmol). After 7 h, saturated sodium hydrogen carbonate solution (75 ml) and ethyl acetate (75 ml) were added and the reaction mixture was stirred for 20 min. The layers were separated and the aqueous layer was extracted with ethyl acetate (2×50 ml). The combined organic extracts were washed with water and brine, and then dried (Na$_2$SO$_4$) and concentrated in vacuo to give the crude product. Purification by flash chromatography produced the title compound as a light yellow oil (0.80 g, 50%).

Preparation 24: 3-azatricyclo[7.2.1.0$^{2,7}$]dodeca-2,4,6-triene-10,11-diol

A mixture of 3-azatricyclo[7.2.1.0$^{2,7}$]dodeca-2,4,6,10-tetraene (Preparation 25, 0.96 g, 6.11 mmol), trimethylamine N-oxide dihydrate (0.75 g, 6.73 mmol) and osmium tetroxide (2.5 wt % solution in 2-methyl-2-propanol, 2 ☐l) in dichloromethane (15 ml) were stirred for 18 h. A further portion of osmium tetroxide (2.5 wt % solution in 2-methyl-2-propanol, ca. 1 ☐l) was added and the reaction mixture was stirred for a further 18 h. The reaction mixture was subjected to chromatography eluting with hexane and then ethyl acetate to give the title compound as a solid (1.16 g, 100%).

Preparation 25: 3-azatricyclo[7.2.1.0$^{2,7}$]dodeca-2,4,6,10-tetraene

To a solution of 3-(cyclopent-3-en-1-ylmethyl)-1,2-dihydropyridin-2-yl trifluoromethanesulfonate (Preparation 26, 3.1 g, 10.1 mmol) in dimethylformamide (20 ml) stirred under nitrogen was added 1,3-bis(diphenylphosphino)propane (0.334 g, 0.8 mmol), triethylamine (1.52 g, 16.6 mmol) and palladium (II) acetate (0.072 g, 0.32 mmol). The reaction mixture was warmed to 100° C. and stirred for 18 h. Triethylamine (1 ml) was added and the reaction mixture was warmed to 110° C. for a further 6 h. The reaction mixture was cooled and poured into saturated brine solution (50%, 75 ml), and the product was extracted with ethyl acetate (4×30 ml). The combined organic extracts were washed with water (2 times), sodium hydrogen carbonate solution and brine before drying (Na$_2$SO$_4$) and concentrating in vacuo. The crude oil was purified by flash chromatography eluting with ethyl acetate:hexane (15:85) to give a colourless oil (1.07 g, 77%).

Preparation 26: 3-(cyclopent-3-en-1-ylmethyl)-1,2-dihydropyridin-2-yl trifluoromethanesulfonate To a solution of 3-(cyclopent-3-en-1-ylmethyl)pyridin-2(1H)-one (Preparation 27, 1.9 g, 10.8 mmol) in dichloromethane (50 ml) stirred at 0° C. was added trifluoromethanesulfonic anhydride (2.38 ml, 14.1 mmol) and then 2,6-lutidine (2.2 ml, 19 mmol). The reaction mixture was allowed to warm to room temperature and then stirred for 1 h. The reaction mixture was diluted with dichloromethane and washed with water (2 times), then saturated aqueous sodium hydrogen carbonate solution and then brine. The crude product was purified by flash chromatography eluting with ethyl acetate:hexane (10:90) to give the product as a colourless liquid-(3.1 g, 93%).

Preparation 27: 3-(cyclopent-3-en-1-ylmethyl)pyridin-2(1H)-one

To a cloudy dispersion containing 3-(cyclopent-3-en-ylmethyl)-2-(methyloxy)pyridine (Preparation 28, 2.1 g, 11.1 mmol) and sodium iodide (4.1 g, 27.8 mmol) in anhydrous acetonitrile (25 ml) was added chlorotrimethylsilane (3.0 g, 27.8 mmol). A white precipitate formed which was stirred for 30 min at room temperature and then for 1 h at 70° C. The reaction mixture was cooled to room temperature and water was added, followed by ethyl acetate (200 ml), the organic layer washed with water (4×) and then with sodium hydrogen carbonate solution and brine before drying (Na$_2$SO$_4$) to give the title compound as a yellow solid (1.93 g, 100%).

Preparation 28: 3-(Cyclopent-3-en-ylmethyl)-2-(methyloxy)pyridine

Cyclopent-3-en-yl[2-(methyloxy)pyridin-3-yl]methanone (Preparation 29, 10 g, 49.3 mmol), potassium hydroxide (85%, 16.8 g, 0.3 mol), and hydrazine (6.33 g, 198 mmol) in ethylene glycol (100 ml) were heated to 180° C. and stirred for 18 h. Water was added and the product was extracted with hexane:ethyl acetate (50:50). The combined organic extracts were washed with brine and concentrated in vacuo. The crude oil was purified by flash chromatography eluting with ethyl acetate:hexane (10:90) to give a colourless oil (4.75 g, 51%).

Preparation 29: Cyclopent-3-en-yl[2-(methyloxy) pyridin-3-yl]methanone

To 2-bromo-1,3,5-trimethylbenzene (16.9 g, 85 mmol) in tetrahydrofuran (340 ml) under a nitrogen atmosphere was added at −78° C. over 30 min tert-butyl lithium (1.7 M solution, 100 ml, 170 mmol). A yellow precipitate formed and was stirred for 1 h at −78° C. 2-(methyloxy)pyridine (8.45 g, 77.3 mmol) in tetrahydrofuran (10 ml) was added and the reaction mixture was warmed to 0° C. for 1 h and then to room temperature for 1 h. The reaction mixture was cooled to −70° C. and N-methyl-N-(methyloxy)cyclopent-3-ene-1-carboxamide (Preparation 30, 12.4 g, 80 mmol) was added in tetrahydrofuran (20 ml), the reaction mixture was allowed to gradually warm to room temperature over 18 h. Saturated aqueous sodium hydrogen carbonate (250 ml) was added and the mixture was stirred for 20 min, the product was extracted with diethyl ether (3×100 ml) the combined organic extracts were washed with water, then brine, and then dried ($Na_2SO_4$) and concentrated to give a yellow oil (26 g). The crude oil was purified by flash chromatography using silica gel eluting with diethyl, ether:hexane (10:90 and then 20:80). The title compound was obtained as a colourless oil (12.19 g, 75%).

Preparation 30: N-methyl-N-(methyloxy)cyclopent-3-ene-1-carboxamide

To a solution of cyclopent-3-ene-1-carboxylic acid (80.0 g, 0.71 mol) in dichloromethane (300 ml) was added 1,1'-carbonyldiimidazole (127.5 g, 0.78 mol) slowly and the reaction mixture was stirred at room temperature for 1 h. N,O-dimethylhydroxylamine (76.7 g, 0.78 mol) was added and stirred for 18 h at room temperature. The reaction mixture was poured into water (300 ml) and extracted with dichloromethane (100 ml). The organic extracts were washed with hydrochloric acid (1N, 2×200 ml) and then with brine before filtering through cotton wool, drying and concentrating. The product was purified by flash chromatography using silica gel eluting with dichloromethane to give the title compound (116.78 g, 95%).

Preparation 31: (−)-4,10-diazatricyclo[6.3.1.0$^{2,7}$]dodeca-2,4,6-triene hydrochloride salt Racemic 10-(phenylmethyl)-4,10-diazatricyclo[6.3.1.0$^{2,7}$]dodeca-2,4,6-triene (Preparation 32, 1.9 g) was subjected to chiral preparative HPLC using a 5 cm×25 cm Chiracel AD column, eluting with heptane:isopropyl alcohol (95:5) at a flow rate of 120 ml/min over 30 min. The enantiomers were detected at 250 nm and were shown to have chiral purity of >98% enantiomeric excess, the first enantiomer to be eluted was designated enantiomer 1 and the second was designated enantiomer 2. The eluants were concentrated to give enantiomer 1 (0.9 g) and enantiomer 2 (0.75 g).

Enantiomer 2 of 10-(phenylmethyl)-4,10-diazatricyclo [6.3.1.0$^{2,7}$]dodeca-2,4,6-triene (0.75 g) was dissolved in methanol (35 ml) and ammonium formate (4 g) was added followed by palladium hydroxide (10% wt on carbon, 0.20 g). The reaction mixture was heated under reflux for 2 h, cooled and filtered through a pad of Celite®, rinsing with methanol, the combined organic solutions were concentrated in vacuo. Dichloromethane was added and the resultant slurry was filtered and concentrated to give an oil (0.70 g). The oil was dissolved in methanol and hydrochloric acid (3 M, 6 ml) was added. The mixture was concentrated in vacuo to give a solid which was recrystallised by dissolving in methanol (20 ml) and adding diethyl ether until the reaction mixture went cloudy. The reaction mixture was stirred for 72 h before the solid was removed by filtration and washed with diethyl ether to give the pure hydrochloride salt of the title compound as a white solid (0.34 g).

Preparation 32: 10-(phenylmethyl)-4,10-diazatricyclo[6.3.1.0$^{2,7}$]dodeca-2,4,6-triene To a solution of 3-(phenylmethyl)-3-azabicyclo[3.2.1]octane-6,7-dicarbaldehye bis (O-methyloxime) (Preparation 33, 5.0 g, 15.2 mmol) in dichloroethane (150 ml) was added trifluoroacetic acid (17 ml) and the reaction mixture was stirred under nitrogen at room temperature for 20 min. The reaction mixture was heated under reflux for 2 h and then concentrated to give a brown oil. Ethyl acetate (100 ml) was added and the solution was treated with saturated sodium carbonate solution (70 ml) the layers were separated and the organic layer washed with brine and dried ($Na_2SO_4$) and concentrated to give an oil (4.0 g). The crude oil was purified by flash chromatography using silica gel eluting with ethyl acetate to give the title compound as an orange oil (1.93 g, 51%).

Preparation 33: 3-(phenylmethyl)-3-azabicyclo[3.2.1]octane-6,7-dicarbaldehye bis (O-methyloxime)

To a solution of 9-(phenylmethyl)-9-azatricyclo[5.3.1.0$^{2,6}$]undecane-3,4-diol (Preparation 34, 6.0 g, 21.9 mmol) in dioxane (100 ml) was added sodium periodate (5.0 g, 23.3 mmol) in water (50 ml). A thick slurry formed, water (50 ml) was added and the reaction mixture was stirred under nitrogen. Upon completion, the reaction mixture was diluted with water (150 ml) and saturated sodium carbonate (50 ml) and the product was extracted with ethyl acetate (2×150 ml). The combined organic extracts were washed with water, and then brine before drying ($Na_2SO_4$) and concentrating to give an orange oil (6.14 g). To the crude oil was added methanol (75 ml) and water (75 ml), followed by methoxylamine hydrochloride (7.34 g, 87.9 mmol) and sodium acetate (12.62 g, 153.8 mmol). The reaction mixture was shaken and then warmed on a steam bath for ca 15 min to give a clear solution, and was then stirred at room temperature for 18 h. Ethyl acetate (100 ml) and sodium carbonate solution (100 ml) were added and the layers were separated. The aqueous layer was extracted with ethyl acetate (3×50 ml) and the combined organic extracts were washed with brine and dried ($Na_2SO_4$) and concentrated to give the title compound as an oil (5.0 g, 69%).

Preparation 34: 9-(Phenylmethyl)-9-azatricyclo[5.3.1.0$^{2,6}$]undecane-3,4-diol A solution of 9-(phenylmethyl)-9-azatricyclo[5.3.1.0$^{2,6}$]undec-3-ene (Preparation 35, 6.7 g, 28.0 mmol), N-methylmorpholine N-oxide (3.45 g, 29.45 mmol) and osmium tetroxide (2.5 wt % in 2-methyl-2-propanol, 2 □l) in acetone (50 ml) was stirred for 18 h. Florisil and aqueous sodium hydrogensulfite (4 ml) were added and the reaction mixture was stirred for 30 min and filtered. Methanol (50 ml) was added and the reaction mixture was concentrated to give an oil which was purified by flash chromatography eluting with ethyl acetate:hexane (50:50) to give an oil (6.2 g, 80%) which crystallises upon standing.

Preparation 35: 9-(phenylmethyl)-9-azatricyclo [5.3.1.0²,⁶]undec-3-ene

To a stirred solution of tricyclo[5.2.1.0²,⁶]dec-3-ene-8,9-diol (Preparation 36, 6.24 g, 37.6 mmol) in dioxane (100 ml) was added sodium periodate (8.04 g, 37.6 mmol) in water (80 ml) and the reaction mixture was stirred vigorously for 45 min. The reaction mixture was extracted with ethyl acetate (4×100 ml) and the combined extracts were washed with brine, dried ($Na_2SO_4$) and concentrated in vacuo. The crude oil (6.1 g, 37.1 mmol) was diluted with dichloroethane (400 ml) and benzylamine (3.98 g, 37.1 mmol) was added. After 3 min, sodium triacetoxyborohydride (25.23 g, 119 mmol) was added and the reaction mixture was stirred at room temperature for 18 h. Saturated sodium carbonate solution (200 ml) was added, and after 30 min, the layers were separated and the aqueous layer was washed with dichloromethane (3×50 ml). The combined organic extracts were washed with brine, filtered and concentrated. The crude yellow oil was purified by flash chromatography eluting with ethyl acetate:dichloromethane (10:90) to give the title compound as a colourless oil (6.7 g, 75%)

Preparation 36: Tricyclo[5.2.1.0²,⁶]dec-3-ene-8,9-diol

A slurry of tricyclo[5.2.1.0²,⁶]deca-3,8-diene (26.5 g, 0.2 mol), trimethylamine N-oxide dihydrate (22.3 g, 0.2 mol) and osmium tetroxide (2.5 wt % solution in 2-methyl-2-propanol, 2 □l) in dichloromethane (200 ml) was stirred for 18 h. A further portion of osmium tetroxide (2.5 wt % solution in 2-methyl-2-propanol, ca. 2 □l) was added, water (25 ml) and acetone (50 ml) was added and the reaction mixture was stirred for a further 72 h. Pyridine (0.5 ml) and tetrabutylammonium acetate (0.5 g) were added. Florisil (10 g) and aqueous sodium hydrogensulfite solution was added and the reaction mixture was stirred for 20 min. The reaction mixture was filtered and the product was extracted with dichloromethane (3 times). The combined organic extracts were washed with water, brine and then concentrated to give an oil. The crude oil was purified by flash chromatography eluting with ethyl acetate:hexane (10:90) and then ethyl acetate, to give a waxy solid (6.5 g, 19%).

Preparation 39: 3-cyclohexyl-3-methylpiperidine hydrochloride salt

To a solution of 3-methyl-3-phenylpiperidine (500 mg, 2.85 mmol) in methanol (8 ml) was added concentrated hydrochloric acid (1 ml) and platinum (IV) oxide (500 mg). The reaction mixture was hydrogenated at 50 psi for 3 h before filtering through Celite® and concentrating. The crude residue was dissolved in dichloromethane and washed with sodium carbonate and concentrated to give a crude semi solid. The crude product was dissolved in diethyl ether (15 ml) and methanol (5 ml) and hydrogen chloride (1M in diethyl ether, 30 ml) was added to afford a white solid which was filtered to give the pure product (0.41 g, 66%).

Preparation 40: 3-methyl-3-(2-pyridinyl)piperidine

To a dried flask under nitrogen was added borane tetrahydrofuran complex (1 M solution, 8.79 ml, 8.79 mmol), and tetrahydrofuran (10 ml). The solution was cooled to 0° C. and a solution of 5-methyl-5-(2-pyridinyl)-2-piperidone (Preparation 41, 1 g, 5.26 mmol) in tetrahydrofuran (20 ml) was added. The reactants were warmed to room temperature and then heated at reflux for 6 h. Further borane tetrahydrofuran complex (1M solution, 8.79 ml, 8.79 mmol) was added and the reaction mixture was heated at reflux for 18 h. Thin layer chromatography still showed starting material was present so further borane tetrahydrofuran complex (1M solution, 8.79 ml, 8.79 mmol) was added and the reaction mixture was heated under reflux for 18 h. Upon completion hydrochloric acid (6M) was added to the reaction mixture and the mixture was stirred for 30 min. The reaction mixture was partially concentrated before adjusting to pH 11 with solid sodium hydroxide. The organic extracts were extracted with dichloromethane (5×20 ml) and dried ($Na_2SO_4$) to give a crude oil (0.45 g). The oil was purified by flash chromatography eluting with dichloromethane:methanol:0.88 ammonia solution (94:4:2) to give the title compound as an oil (0.20 g, 22%).

Preparation 41: 5-methyl-5-(2-pyridinyl)-2-piperidone

To methyl 4-cyano-4-(2-pyridinyl)pentanoate (Preparation 42, 2.5 g, 11.4 mmol) in ethanol (30 ml) was added Raney nickel (3 g) and the reaction mixture was hydrogenated for 78 h. The reaction mixture was filtered through Celite® washing with ethanol (3.20 ml). The combined organic extracts were concentrated in vacuo to give the crude desired product (2.2 g) which was purified by flash chromatography eluting with dichloromethane:methanol (96:7) to give the pure product as an oil (1.1 g, 5.1%).

Preparation 42: Methyl 4-cyano-4-(2-pyridinyl)pentanoate

To a dried flask under nitrogen was added 2-(2-pyridinyl)-propanenitrile (Preparation 43, 6.26 g, 47.4 mmol), t-butanol (30 ml), Triton B (6.66 g, 39.8 mmol) and methyl acrylate (6.12 g, 71.1 mmol). The reaction mixture was heated at reflux for 2.5 h. The solid was removed, and the filtrate concentrated in vacuo to give a yellow oil. Water (30 ml) was added and the product was extracted with diethyl ether. The organic extracts were dried ($Na_2SO_4$) and concentrated in vacuo to give a light yellow oil (4.32 g, 42%).

Preparation 43: 2-(2-pyridinyl)-propanenitrile

To a dried flask under nitrogen was added dimethyl sulphoxide (100 ml) and tosmic (20.95 g, 107.3 mmol). The reaction mixture was cooled to 0° C. before potassium t-butoxide (33.35° g, 297.1 mmol) was added. After 5 min, methanol (3.7 ml) was added followed by 1-(2-pyridinyl)ethanone (10 g, 32.5 mmol) and the reaction mixture was stirred at room temperature for 18 h. The reaction mixture was poured in brine:hexane:ethyl acetate (50:25:25). The organic extracts were dried ($Na_2SO_4$) and concentrated in vacuo to yield a crude oil. The oil was purified by flash chromatography eluting with ethyl acetate:hexane (3:7) to give the title compound as a brown solid (8.26 g, 76%).

Preparation 46: 2-[(4-piperidinylmethyl)sulfanyl]pyridine hydrochloride salts tert-Butyl 4-[(2-pyridinylsulfanyl)methyl]-1-piperidinecarboxylate (Preparation 47, 0.90 g, 2.9 mmol) in hydrogen chloride (4 M solution in dioxane, 7.5 ml) was stirred under nitrogen at room temperature. After 20 min a white solid precipitated out of solution. Diethyl ether was added and the reaction mixture was filtered and the solid washed with diethyl ether. The title compound was obtained as a solid (0.70 g, 98%).

Preparation 47 tert-butyl 4-[(2-pyridinylsulfanyl)methyl]-1-piperidinecarboxylate To a stirred solution of tert-butyl 4-(hydroxymethyl)-1-piperidinecarboxylate (Preparation 48, 1.0 g, 5 mmol) in benzene (40 ml) under nitrogen was added triphenyl phosphine (1.44 g, 5.5 mmol). Diethyl azodicarboxylate (0.86 ml, 5.5 mmol) in benzene (4 ml) was added dropwise and the reaction mixture was stirred for 5 min. 2-mercapto pyridine (0.61 g, 5.5 mmol) was added and the reaction mixture was stirred at room temperature for 2 h. The reaction mixture washed with sodium hydroxide (1M), water, and saturated brine. The organic extracts were dried ($Na_2SO_4$) and concentrated to an oil which was purified by flash chromatography on, silica gel eluting with dichloromethane:ethyl acetate (9:1). The title compound was obtained as an oil (0.7 g, 58%).

Preparation 48: tert-butyl 4-(hydroxymethyl)-1-piperidinecarboxylate

To a stirred solution of 1-tert-butyl 4-ethyl 1,4-piperidinedicarboxylate (Preparation 49, 12.8 g, 0.05 mol) in benzene (300 ml) under nitrogen was added slowly diisobutyl aluminium hydride (1 M solution, 100 ml, 0.1 mol). The reaction mixture was stirred at room temperature for 3 h before quenching by the addition of water (100 ml) followed by addition of hydrochloric acid (1 M) to adjust to pH 4. The organic layer was separated and the aqueous layer extracted with ethyl acetate. The combined organic extracts were dried ($Na_2SO_4$) and concentrated to give an oil. The crude oil was purified by flash chromatography on silica gel eluting with ethyl acetate:dichloromethane (6:4) to give the title compound as an oil (5.0 g, 46%).

Preparation 49: 1-tert-butyl 4-ethyl 1,4-piperidinedicarboxylate

To a solution of ethyl 4-piperidinecarboxylate (15.4 ml, 0.1 mol) in dichloromethane (100 ml) stirred under nitrogen and cooled to 0° C. was added di-tert-butyl dicarbonate (21.5 g, 0.1 mol). The reaction mixture was stirred at room temperature for 18 h before washing with water and then saturated brine. The organic extracts were dried ($Na_2SO_4$) and concentrated in vacuo to give the title compound as an oil (25 g, 97%).

Preparation 50: 2-[(3-piperidinylmethyl)sulfanyl]pyridine hydrochloride salt tert-Butyl 3-[(2-pyridinylsulfanyl)methyl]-1-piperidinecarboxylate (Preparation 51, 1.0 g, 3.2 mmol) in hydrogen chloride (4 M solution in dioxane, 8.1 ml) was stirred under nitrogen at room temperature. After 25 min a white solid precipitated out of solution. Diethyl ether was added and the reaction mixture was filtered and the solid washed with diethyl ether. The title compound was obtained as a solid (0.81 g, 100%).

Preparation 51: tert-butyl 3-[(2-pyridinylsulfanyl)methyl]-1-piperidinecarboxylate To a stirred solution of tert-butyl 3-(hydroxymethyl)-1-piperidinecarboxylate (Preparation 52, 1.0 g, 5 mmol) in benzene (40 ml) under nitrogen was added triphenyl phosphine (1.44 g, 5.5 mmol). Diethyl azodicarboxylate (0.86 ml, 5.5, mmol) in benzene (4 ml) was added dropwise and the reaction mixture was stirred for 5 min. 2-mercapto pyridine (0.61 g, 5.5 mmol) was added and the reaction mixture was stirred at room temperature for 2 h. The reaction mixture washed with sodium hydroxide (1M), water, and saturated brine. The organic extracts were dried ($Na_2SO_4$) and concentrated to an oil which was purified by flash chromatography on silica gel eluting with dichloromethane:ethyl acetate (9:1). The title compound was obtained as an oil (1.0 g, 65%).

Preparation 52: tert-butyl 3-(hydroxymethyl)-1-piperidinecarboxylate

To a stirred solution of 3-piperidinylmethanol (5.06 g, 44 mmol) in dichloromethane (100 ml) under nitrogen was added di-tert-butyl dicarbonate (9.6 g, 44 mmol) and the reaction mixture was stirred at room temperature for 18 h. The reaction mixture was washed with water and then saturated brine. The organic extracts were dried ($Na_2SO_4$) and concentrated in vacuo to give the title compound as an oil (9.0 g, 95%)

Preparation 56: N-methoxy-N-methyl-2-piperidinecarboxamide

To ethyl 2-piperidincarboxylate (18.3 g, 0.12 mol) was added N,O-dimethylhydroxylamine hydrochloride (34.1 g, 0.35 mol) in dichloromethane (200 ml) followed by dropwise addition of triethylaluminium (1M solution in hexane, 350 ml, 0.35 mol). The reaction mixture was stirred for 3 h before quenching with tartaric acid (1 M solution, 25 ml) with cooling to maintain a temperature of ~20° C. The reaction mixture was stirred for 18 h and then filtered through Celite®, the filtrate was concentrated in vacuo to give a white solid (6.2 g). The Celite® plug was stirred with methanol, filtered and the filtrate evaporated to dryness to give more solid (20 g). The solids were combined and purified by flash chromatography on silica gel eluting with dichloromethane and then dichloromethane:methanol (95:5) to give the pure product (15.8 g, 79%).

Preparation 67: 1-(3-chloro-4-methylphenyl)piperazine

To a mixture of 3-chloro-4-methylaniline (105.5 g, 0.745 mol) and diethanolamine (78.1 g, 0.745 mol) was added slowly with stirring and cooling, concentrated hydrochloric acid (c.a. 100 ml) to adjust the reaction mixture to pH 7. The reaction mixture was heated to remove water (66 ml), after standing for 18 h the mixture was heated to 240° C. for 6 h. Sodium hydroxide (5N, solution, 236 ml) was added and the product was extracted with chloroform (4×100 ml). The combined organic extracts were concentrated to give a red oil which was purified by distillation to give the title compound (107.0 g, 68%)

Preparation 87: Piperidin-4-yl butylcarbamate 1-(Phenylmethyl)piperidin-4-yl butylcarbamate (Preparation 109, 13.0 g) in ethanol (100 ml) containing palladium (5% on carbon) was hydrogenated at 60 psi to give the title compound as a green oil that solidified upon standing.

Preparation 89: 2-methyl-4-piperidin-1-yl-5,6,7,8-tetrahydropyrido[3,4-d]pyrimidine A solution of 2-methyl-7-(phenylmethyl)-4-piperidin-1-yl-5,6,7,8-tetrahydropyrido[3,4-d]pyrimidine (Preparation 88, 12 g) in ethanol (200 ml) was adjusted to pH 2 with concentrated hydrochloric acid, palladium (5% on carbon) was added and the reaction mixture was hydrogenated at 60 psi. The reaction mixture was filtered, and the filtrate concentrated in vacuo. Chloroform and sodium hydroxide (2 M solution) were added and the organic extracts were dried, and concentrated in vacuo. The crude residue was dissolved in petroleum ether (30-40) and cooled in ice, the title compound was collected as a solid.

Preparation 88: 2-methyl-7-(phenylmethyl)-4-piperidin-1-yl-5,6,7,8-tetrahydropyrido[3,4-d]pyrimidine 2-methyl-7-(phenylmethyl)-5,6,7,8-tetrahydropyrido[3,4-d]pyrimidin-4(4aH)-one (Preparation 85, 19 g) and phosphorous oxychloride (150 ml) was heated for 1.5 h. The reaction mixture was concentrated and poured onto ice. Sodium carbonate was added to adjust pH to 10, and the product was extracted with chloroform. The organic extracts were concentrated and then purified by passing through a thick pad of florisil (5 cm diameter) the product was eluted with chloroform. Evaporation gave a dark red oil which was dissolved in ethanol (100 ml) and piperidine (25 ml) was added. After 72 h, the reaction mixture was concentrated in vacuo then dissolved in chloroform and basified with sodium hydroxide (2 M solution). The reaction mixture was dried and concentrated before purifying by flash chromatography on florisil eluting the product with petroleum ether (30-40) to give the title compound (12.5 g)

Preparation 85: 2-Methyl-7-(phenylmethyl)-5,6,7,8-tetrahydropyrido[3,4-d]pyrimidin-4(4aH)-one Sodium metal (4.4 g, 0.19 mol) was dissolved in ethanol (300 ml) and acetamidine hydrochloride (9.3 g, 0.1 mol) was added. After 30 min, commercially available ethyl 3-oxo-1-(phenylmethyl)-piperidine-4-carboxylate hydrochloride (25 g, 0.084 mol) was added and the reaction mixture was refluxed for 18 h. The reaction mixture was filtered and the concentrated in vacuo to give the title compound (20 g).

Preparation 93:
1-(1,3-thiazol-2-ylcarbonyl)piperazine

Piperazine (2.33 g) was dissolved in glacial acetic acid (25 ml) and the reaction mixture was heated to 60° C. A suspension of 1,3-thiazole-2-carbonyl chloride (Preparation 107, 4.0 g, 27.1 mmol) in glacial acetic acid (10 ml) was added dropwise over 10 min and the reaction mixture was stirred at 60° C. for 30 min and then at room temperature for 18 h. The precipitated solid was filtered and dried, and the mother liquor was concentrated in vacuo. Water (50 ml) was added to the mother liquor and the solution was adjusted to pH 9 using sodium hydroxide solution (5M). The product was extracted with chloroform and the combined organic extracts were dried ($MgSO_4$) and concentrated in vacuo to give a yellow oil (1.85 g). The oil was dissolved in diethyl ether and hydrogen chloride (1 M solution in diethyl ether) was added, a white solid precipitated was filtered off and recrystallised from isopropanol to, give the title compound as a white solid (0.5 g)

Preparation 107: 1,3-thiazole-2-carbonyl chloride 1,3 thiazole-2-carboxylic acid (Preparation 92, 5.0 g, 39 mmol) was added to a solution containing sodium hydroxide (1.55 g), in water (26 ml). The solution was evaporated to dryness and the resultant solid was triturated with diethyl ether, filtered and dried in an oven at 60° C. for 6 h to give a brown solid (5.5 g). The solid was added to thionyl chloride (25 ml) and heated on a steam bath for 2 h. The excess thionyl chloride was removed in vacuo and the resultant oil was triturated with petroleum ether (40-60, 3×30 ml) to give the title compound as an oily solid upon filtration and evaporation (4.0 g, 70%).

Preparation 92: 1,3 thiazole-2-carboxylic acid

To a solution of 2-bromothiazole (16.4 g, 0.1 mol) in anhydrous diethyl ether (50 ml) at −70° C. was added slowly n-butyl lithium (1.6 M solution in hexane, 75 ml). The reaction mixture was stirred at −70° C. for 20 min and was then added portion-wise to powdered solid carbon dioxide (500 g). The reaction mixture was stirred for 18 h, and the resultant mixture was dissolved in water (70 ml) filtered and extracted with diethyl ether (3×75 ml). The aqueous layer was acidified by the addition of sulphuric acid (10 M solution) and cooled to 0° C. A solid crystallised out and was removed by filtration, washed with cold water, and dried at 50° C. for 6 h to give the title compound as a light brown solid (5.0 g).

Preparation 96: 4-{[(4-fluorophenyl)methyl]oxy}piperidine oxalate salt 1-acetyl-4-{[(4-fluorophenyl)methyl]oxy}piperidine (Preparation 97, 9 g, 36 mmol) in methanol (60 ml) and sodium hydroxide solution (5 M, 100 ml) were refluxed on a steam bath for 4 h. After cooling the solution was extracted with chloroform (3×100 ml) and the organic extracts were dried ($Na_2SO_4$) and concentrated to give an orange oil (8 g, 97%). A portion was dissolved in diethyl ether and treated with oxalic acid in ether to give a white solid which was recrystallised from ethanol to give needle crystals (3 g).

Preparation 97: 1-acetyl-4-{[(4-fluorophenyl)methyl]oxy}piperidine

1-Acetylpiperidin-4-ol (Preparation 193, 10 g, 70 mmol) in N,N-dimethylformamide (50 ml) was added dropwise to a stirred suspension of sodium hydride (50% wt dispersion in oil, 3.8 g, 80 mmol) in N,N-dimethylformamide (50 ml) at room temperature under nitrogen. After stirring the reaction mixture for 3 hours, 4-fluorobenzyl chloride (10.1 g, 70 mmol) in N,N-dimethylformamide (50 ml) was added dropwise and the reaction mixture was stirred for a further 4 h. The reaction mixture was filtered and the filtrate was evaporated to give an orange oil. Water was added and the mixture was extracted with petroleum ether (3×100 ml) and then with diethyl ether (3×100 ml). The combined organic extracts were washed with sodium hydroxide solution (1 M, 3×100 ml), before drying ($Na_2SO_4$) and concentrating to give the title compound as an oil (10.1 g, 99%).

Preparation 98: 4-{[(4-chlorophenyl)methyl]oxy}piperidine 1-acetyl-4-{[(4-chlorophenyl)methyl]oxy}piperidine (Preparation 99, 11 g, 41.1 mmol) in methanol (50 ml) and sodium hydroxide solution (5 M, 30 ml) were refluxed on a steam bath for 10 h. After cooling, methanol was removed and the remaining solution was extracted with petroleum ether (40-60, 3×30 ml). The organic extracts were dried ($Na_2SO_4$) and concentrated in vacuo to give an white solid (5.8 g, 62%). A portion was recrystallised from petroleum ether to give needle crystals (3 g).

Preparation 99: 1-acetyl-4-{[(4-chlorophenyl)methyl]oxy}piperidine

1-Acetylpiperidin-4-ol (Preparation 193, 10 g, 70 mmol) in N,N-dimethylformamide (50 ml) was added dropwise to a stirred suspension of sodium hydride (50% wt dispersion in oil, 4.8 g, 0.1 mol) in N,N-dimethylformamide (50 ml) at room temperature under nitrogen. After stirring the reaction mixture for 3 hours, 4-chlorobenzyl chloride (12.8 g, 80 mmol) in N,N-dimethylformamide (50 ml) was added dropwise and the reaction mixture was stirred for a further 4 h. The solution was filtered and the filtrate was evaporated to give an orange oil. Water was added and the mixture was extracted with petroleum ether (3×50 ml) and then with diethyl ether (3×50 ml). The combined organic extracts were dried ($Na_2SO_4$) and concentrated to give the title compound as an orange oil (15.8 g, 84%).

Preparation 100: ethyl 4-[(piperidin-4-yloxy)methyl]benzoate hydrochloride salt 4-[(Piperidin-4-yloxy)methyl]benzoic acid (Preparation 101, 7 g, 26 mmol) in ethanol (50 ml) and concentrated sulphuric acid (1 ml) were heated on a steam bath for 6 h. The solvent wasp removed in vacuo and the residue was dissolved in water, basified with sodium carbonate (5% w/v) and extracted with, diethyl ether (3×50 ml). The organic extracts were dried ($Na_2SO_4$) and concentrated to give the title compound as a pale yellow oil (4.4 g, 64%). A portion (1 g) was dissolved in diethyl ether and treated with hydrogen chloride (1 M solution in diethyl ether) to give a yellow solid which was recrystallised from ethanol and diethyl ether to give yellow platelets (0.5 g).

Preparation 101: 4-[(piperidin-4-yloxy)methyl]benzoic acid 1-acetyl-4-[(piperidin-4-yloxy)methyl]benzoic acid (Preparation 102, 20 g, 72 mmol), aqueous sodium hydroxide solution (5 M, 75 ml), and methanol (75 ml) were heated to 100° C. for 4 h, and then evaporated to give a thick suspension. The crystals were filtered off, dissolved in water and the pH adjusted to 1 with hydrochloric acid (2 M, 200 ml) at 0° C. The cloudy solution was evaporated to dryness and the white solid recrystallised from isopropyl alcohol to give the title compound (15.2 g, 90%).

Preparation 102: 1-acetyl-4-[(piperidin-4-yloxy)methyl]benzoic acid

1-Acetylpiperidin-4-ol (Preparation 196, 20 g, 0.14 mol) in N,N-dimethylformamide (50 ml) was added dropwise to a stirred suspension of sodium hydride (50% wt dispersion in oil, 19.2 g, 0.40 mol) in N,N-dimethylformamide (50 ml) at room temperature under nitrogen. After stirring the reaction mixture for 3 hours, 4-(bromomethyl)benzoic acid (30.1 g, 0.14 mol) in N,N-dimethylformamide (50 ml) was added dropwise to the solution at 0° C. and the reaction mixture was stirred for a further 4 h. The solution was diluted with water (200 ml) and then extracted with chloroform (3×150 ml). The aqueous layer was separated, cooled to 0° C. and the pH adjusted to 1 with concentrated hydrochloric acid. The white solid was filtered off and dried to give the title compound (27 g, 74%).

Preparation 103: 4-[(3-phenylpropyl)oxy]piperidine hydrochloride salt

A solution of 1-acetyl-4-[(3-phenylpropyl)oxy]piperidine (Preparation 104, 4 g) in sodium hydroxide (5 M solution, 20 ml) and methanol (20 ml) was heated on a steam bath for 6 hours during which time the methanol was allowed to evaporate off. After cooling the solution the product was extracted with chloroform (3×30 ml). The combined organic extracts were dried ($Na_2SO_4$) and concentrated to give a yellow oil (3.7 g, 88%). The product was dissolved in diethyl ether and treated with hydrogen chloride (1M solution in diethyl ether) to give a white solid which was filtered off and dried.

Preparation 104: 1-acetyl-4-[(3-phenylpropyl)oxy]piperidine

1-Acetylpiperidin-4-ol (Preparation 193, 8 g, 60 mmol) in N,N-dimethylformamide (50 ml) was added dropwise to a stirred suspension of sodium hydride (50% wt dispersion in oil, 3.68 g, 80 mmol) in N,N-dimethylformamide (50 ml) at room temperature under nitrogen. After stirring the reaction mixture for 4 hours, 1-bromo-3-phenylpropane (12.94 g, 65 mmol) in N,N-dimethylformamide (50 ml) was added dropwise to the solution at 0° C. and the reaction mixture was stirred for a further 4 h. The solution was diluted with isopropyl alcohol (20 ml) and water (100 ml) and then evaporated to give a semi solid. Water (100 ml) was added and the solution was extracted with petroleum ether (3×100 ml). The combined organic extracts were dried ($Na_2SO_4$) and concentrated in vacuo to give an orange oil (4.3 g, 27%).

Preparation 109: 1-(phenylmethyl)piperidin-4-yl butylcarbamate 1-(Phenylmethyl)piperidin-4-ol (10 g, 52.2 mmol) was stirred in dioxane (90 ml) at room temperature. N-butyl isocyanate (5.0 g, 52.2 mmol) in dioxane (10 ml) was added and the reaction mixture was heated under reflux for 24 h. Water (20 ml) was added and the reaction mixture was concentrated in vacuo to give a brown oil. The crude product was partitioned between diethyl ether and water and the organic extracts were dried ($MgSO_4$) to give the title compound as an oil (14 g, 92%).

Preparation 128: 1,1-dimethylethyl (3R)-3-hydroxypiperidine-1-carboxylate

To a solution of (3R)-piperidin-3-ol. (S) camphor sulphonic acid salt (Preparation 115, 5.03 g, 15.7 mmol) in dichloromethane (50 ml) and triethylamine (2.4 ml, 17.3 mmol) was added at 0° C. a solution of di-tert-butyl dicarbonate (3.8 g, 17.3 mmol) dropwise in dichloromethane (10 ml). The reaction mixture was stirred at room temperature for 3 d, before ethyl acetate and water were added. The organic extracts were washed with brine, dried ($MgSO_4$) and concentrated in vacuo to give the title compound as a colourless oil (3.29 g, 100%).

Preparation 115: (3R)-piperidin-3-ol. (S) camphor sulphonic acid salt (S)-camphor sulphonic acid (109.4 g, 0.47 mol) and racemic piperidin-3-ol (48.5 g, 0.47 mol) were dissolved in butanone (400 ml) and the reaction mixture was heated under reflux and then allowed to cool to room temperature. After stirring for several hours, the resultant precipitate was filtered off, washed with butanone and then dried in a vacuum oven at 55° C. The title compound was obtained as a white powder (52.27 g, 35%).

Preparation 127: 1,1-dimethylethyl (3S)-3-hydroxypiperidine-1-carboxylate

To a solution of (3S)-piperidin-3-ol. (R) camphor sulphonic acid salt (Preparation 116, 10.0 g, 31.4 mmol) in dichloromethane (80 ml) and triethylamine (5.0 ml, 35.3 mmol) was added at 0° C. di-tert-butyl dicarbonate (3.8 g, 17.3 mmol) in one portion. The reaction mixture was stirred at room temperature for 2 d, before concentrating in vacuo. The residue was partitioned between ethyl acetate and water, the organic extracts were washed with brine, dried (MgSO$_4$) and concentrated in vacuo to give the product as a pale yellow oil (6.25 g). The oil was purified by flash chromatography on silica gel eluting with diethyl ether:hexane (2:1 and then 1:0) to give the title compound as a colourless oil 5.2 g, 83%).

Preparation 116: (3S)-piperidin-3-ol. (R) camphor sulphonic acid salt (R)-camphor sulphonic acid (32.6 g, 0.14 mol) and piperidin-3-ol (14.8 g, 0.14 mol) were dissolved in butanone (150 ml) and the reaction mixture was heated under reflux and then allowed to cool to room temperature. After stirring for 6 h, the resultant precipitate was filtered off, washed with butanone and then dried in a vacuum oven. The title compound was obtained as a white solid (16.2 g, 36%).

Preparation 117: 1,1-dimethylethyl 3-hydroxypiperidine-1-carboxylate

To a solution of piperidin-3-ol hydrochloride salt (10.1 g, 0.1 mmol) in dichloromethane (30 ml) and triethylamine (13.3 ml, 95.4 mmol) was added a solution, of di-tert-butyl dicarbonate (19.8 g, 90.9 mmol) dropwise in dichloromethane. Upon completion the reaction mixture was added to diethyl ether (120 ml) washed with hydrochloric acid (1 M) and then with brine. The combined organic extracts were dried (MgSO$_4$) and concentrated in vacuo to give the title compound as a light yellow oil (17.7 g, 88%).

Preparation 126: (1S,2R,4aR,5R,8S,8aS)-1,8a-dihydroxy-5-isopropenyl-3,8-dimethyl-1,2,4a,5,6,7,8,8a-octahydro-2-naphthalenyl acetate and Preparation 118 Methyl (2S,3aR,9bR)-6-chloro-9b-hydroxy-5-methyl-1,2,3,3a,5,9b-hexahydropyrrolo[2,3-c][2,1]benzoxazine-2-carboxylate A solution of (1S,2R,4aS,5R,8R,8aR)-2-(acetyloxy)-8a-hydroxy-3,8-dimethyl-5-(1-methylethenyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate, (Preparation 1, 100 g) and triethylamine (10 ml) in methanol (1000 ml) was stirred at room temperature for 3 hours. The reaction mixture was evaporated and the residue was crystallised from ethyl acetate/hexane to give a pure sample of the terpene, (1S,2R,4aR,5R,8S,8aS)-1,8a-dihydroxy-5-isopropenyl-3,8-dimethyl-1,2,4a,5,6,7,8,8a-octahydro-2-naphthalenyl acetate (Preparation 126). The remaining solution was concentrated and purified by flash column chromatography on silica-gel eluting with ethyl acetate:dichloromethane:hexane (2:1:7) to give further terpene moiety (1S,2R,4aR,5R,8S,8aS)-1,8a-dihydroxy-5-isopropenyl-3,8-dimethyl-1,2,4a,5,6,7,8,8a-octahydro-2-naphthalenyl acetate as a white solid (Preparation 126, 43 g).

Further elution gave the alkaloid moiety, methyl (2S,3aR,9bR)-6-chloro-9b-hydroxy-5-methyl-1,2,3,3a,5,9b-hexahydropyrrolo[2,3-c][2,1]benzoxazine-2-carboxylate as a light yellow solid (Preparation 118, 50 g).

Preparation 125: ethyl decahydroisoquinoline-3-carboxylate 2-(1,1-dimethylethyl)3-ethyl octahydroisoquinoline-2,3(1H)-dicarboxylate (Preparation 124, 2.3 g, 7.4 mmol) was dissolved in ethyl acetate (220 ml) and then saturated with hydrogen chloride gas at 4° C. The reaction mixture was warmed to room temperature, stirred and then concentrated in vacuo to give the crude product which was triturated with diethyl ether. The resulting solid was filtered off and dried, in vacuo to give the title compound (1.24 g, 68%).

Preparation 124: 2-(1,1-dimethylethyl)3-ethyl octahydroisoquinoline-2,3(1H)-dicarboxylate 2-(1,1-dimethylethyl)3-ethyl 3,4-dihydroisoquinoline-2,3(1H)-dicarboxylate (Preparation 123, 3.1 g, 10.2 mmol) was dissolved in ethanol (250 ml) and rhodium (10% w/w on carbon, 0.3 g) was added. The reaction mixture was hydrogenated for 17 h at 50° C. and 50 psi. More rhodium (10% w/w on carbon, 0.3 g) was added and the mixture was hydrogenated for a further 17 h. Again this procedure, was repeated, with additional hydrogenation for 48 h. The catalyst was removed from the reaction mixture by filtration, upon concentration of the filtrate the crude-product was obtained (2.96 g). The crude product was purified firstly by flash chromatography on silica gel (70 g) eluting, with hexane:ethyl acetate (20:1 and then 10:1) and then by flash chromatography on silica gel eluting with hexane diethyl ether (5:1) to give the desired product (2.3 g, 73%).

Preparation 123: 2-(1,1-dimethylethyl)3-ethyl 3,4-dihydroisoquinoline-2,3(1H)-dicarboxylate To a solution of ethyl 1,2,3,4-tetrahydroisoquinoline-3-carboxylate (Preparation 122, 3.64 g, 17.7 mmol) in tetrahydrofuran (50 ml) was added a stirred solution of sodium hydrogen carbonate (2.97 g, 35.4 mmol) in water (60 ml). Di-tert-butyl dicarbonate (5.8 g, 26.6 mmol) was added slowly and the reaction mixture was stirred for 18 h before concentrating in vacuo. The residue was dissolved and partitioned between ethyl acetate (200 ml) and aqueous sodium hydrogen carbonate solution (5%, 200 ml). The aqueous layer washed with ethyl acetate (2×100 ml). The combined organic extracts were dried (Na$_2$SO$_4$) and concentrated in vacuo to give the crude product which was purified by flash chromatography on silica gel (70 g) eluting with hexane:ethyl acetate (20:1 and then 10:1) to give the title compound (4.4 g, 81%).

Preparation 122: ethyl 1,2,3,4-tetrahydroisoquinoline-3-carboxylate 1,2,3,4-Tetrahydroisoquinoline-3-carboxylic acid camphor sulphonic acid salt (Preparation 120, 6 g, 17.2 mmol) was dissolved in ethanol (140 ml) and saturated with hydrogen chloride (gas). The reaction mixture was heated under reflux for 18 h before concentrating in vacuo. The crude residue was dissolved in dichloromethane (150 ml) and washed with sodium hydrogen carbonate (150 ml). The organic layer was collected and washed again with sodium hydrogen carbonate (2×100 ml) before drying (Na$_2$SO$_4$) and concentrating in vacuo to give the title compound as a yellow oil (3.64 g, 100%).

Preparation 120:
1,2,3,4-tetrahydroisoquinoline-3-carboxylic acid

Phenylmethyl 1,2,3,4-tetrahydroisoquinoline-3-carboxylate camphor sulphonic acid salt (Preparation 121, 8.3 g, 18.9 mmol) was dissolved in ethanol (600 ml) and palladium on carbon (10%, 0.8 g) was added at room temperature under nitrogen. The reaction mixture was hydrogenated at room temperature at 30 psi for 3 h. The catalyst was removed by filtration and the filtrate was concentrated to give the title compound (6.6 g, 100%).

Preparation 121: Phenylmethyl
(3R)-1,2,3,4-tetrahydroisoquinoline-3-carboxylate

D-Phenylalanine (50 g, 0.3 mol) concentrated hydrochloric acid (386 ml), and formalin (37% wt, 113.7 ml) were heated at 95° C. with vigorous stirring for 4 h. The reaction mixture was cooled to room temperature and stirred for a further 2 h. The reaction mixture was filtered and the precipitate washed with cold water to give (3R)-1,2,3,4-tetrahydroisoquinoline-3-carboxylic acid as a white solid (25 g, 42%). Benzyl alcohol (64 g) and p-toluene sulphonic acid (26.9 g) were added and the reaction mixture was refluxed in benzene (400 ml) under Dean Stark conditions. The solvent was removed in vacuo, the crude residue was triturated with diethyl ether to give a solid which was then recrystallised from water and methanol to give the title compound as a white solid (28 g, 35%).

Preparation 139: (1S,2R,4aS,5R,8R,8aR)-2,8a-dihydroxy-3,8-dimethyl-5-(1-methylethenyl)-1,2,4a,5,6,7,8,8a-octahydronaphthalen-1-yl (2S,3aR,9bR)-6-chloro-9b -hydroxy-5-methyl-1,2,3,3a,5,9b-hexahydropyrrolo[2,3-c][2,1]benzoxazine-2-carboxylate To a stirred suspension of (1S,2R,4aS,5R,8R,8aR)-2-(acetyloxy)-8a-hydroxy-3,8-dimethyl-5-(1-methylethenyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate, (Preparation 1, 1 g) in methanol (25 ml) was added a solution of concentrated hydrochloric acid (2 ml) in methanol (25 ml). After 5 days the reaction mixture was diluted with dichloromethane (150 ml), washed with water (3×100 ml), filtered through cotton wool and evaporated to dryness to give a yellow, oily solid. This residue was partially dissolved in dichloromethane (25 ml) and hexane (50 ml) was slowly added. After 1 hour, the suspension was filtered to give the product as an off-white solid (900 mg).

Preparation 140 (1S,2R,4aS,5S,8R,8aR)-2-(acetyloxy)-8a-hydroxy-5-[2-hydroxy-1-methylethyl]-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate To a solution of (1S,2R,4aS,5R,8R,8aR)-2-(acetyloxy)-8a-hydroxy-3,8-dimethyl-5-(1-methylethenyl)-1,2,4a,5,6,7,8,8a-octahydronaphthalen-1-yl (2S,3aR,9bR)-6-chloro-9b -hydroxy-5-methyl-1,2,3,3a,5,9b-hexahydropyrrolo[2,3-c][2,1]benzoxazine-2-carboxylate (Preparation 1, 500 mg, 0.89 mmol) in tetrahydrofuran (8 ml) at −10° C. under nitrogen was added borane (1M solution in tetrahydrofuran, 2 ml, 2 mmol) and the resulting mixture stirred and allowed to come to room temperature. After 5 hours borane (1M solution in tetrahydrofuran, 1 ml, 1 mmol) was added and the reaction stirred at room temperature for 18 h. To the reaction mixture was added 4-methylmorpholine N-oxide (600 mg, 5.1 mmol) and the mixture heated to gentle reflux for 3 hours. The reaction mixture was concentrated in vacuo and the residue treated with water (30 ml) and extracted with ethyl acetate (2×30 ml). The combined organic extracts were washed with saturated aqueous sodium chloride solution, dried (MgSO$_4$) and the solvent removed in vacuo to give an orange glass. The crude product was purified by column chromatography on silica eluting with hexane:ethyl acetate (2:1 then 1:1) and then ethyl acetate. The pure fractions were combined and concentrated in vacuo to give a the title product as a yellow solid (132 mg, 26%).

Preparation 141: (1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl (2S,3aR,9bR)$_{76}$-chloro-9b-hydroxy-5-methyl-1,2,3,3a,5,9b-hexahydropyrrolo[2,3-c][2,1]benzoxazine-2-carboxylate To a stirred mixture of (1S,2R,4aS,5S,8R,8aR)-2-(acetyloxy)-8a-hydroxy-5-[2-hydroxy-1-methylethyl]-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate (Preparation 140, 230 mg, 0.40 mmol) and 4 Å molecular sieves in dichloromethane (18 ml) was added tetrapropylammonium perruthenate (23 mg, 0.065 mmol) and N-methylmorpholine-N-oxide (180 mg, 1.54 mmol) in nine portions. The resulting mixture was stirred for 36 hours before diluting with dichloromethane and washing with aqueous sodium hydrogen sulfite solution and then saturated aqueous sodium chloride solution. The organic extracts were dried and concentrated in vacuo. The crude product was purified by column chromatography on silica eluting with ethyl acetate:hexane (1:1) to give the title product (50 mg, 22%).

Preparation 142: (1S,2R,4aR,8R,8aR)-8a-hydroxy-2-[(1H-imidazol-1-ylcarbonyl)oxy]-3,8-dimethyl-5-(1-methylethenyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate To (1S,2R,4aS,5R,8R,8aR)-2,8a-dihydroxy-3,8-dimethyl-5-(1-methylethenyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate (Preparation 139, 50 mg, 0.10 mmol) in dichloromethane (1 ml) was added carbonyl diimidazole (17 mg, 0.10 mmol) at room temperature. Upon completion the reaction mixture was purified by flash chromatography eluting, with ethyl acetate:hexane (50:50 and then 100:0). The title compound was obtained as a white solid (36 mg).

Preparation 143: (1S,2R,4aS,5S,8R,8aR)-2-(acetyloxy)-8a-hydroxy-5-{2-[(1H-imidazol-1-ylcarbonyl)oxy]-1-methylethyl}-3,8-dimethyl-1,2,4a,5,6,7,8,8a-octahydronaphthalen-1-yl (2S,3aR,9bR)-6-chloro-9b-hydroxy-5-methyl-1, 2,3,3a,5,9b-hexahydropyrrolo[2,3-c][2,1]benzoxazine-2-carboxylate To (1S,2R,4aS,5S,8R,8aR)-2-(acetyloxy)-8a-hydroxy-5-[2-hydroxy-1-methylethyl]-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate(Preparation 140, 0.30 g, 0.52 mmol) in dichloromethane was added 1,1'-carbonyldiimidazole (0.92 g, 0.57 mmol) and the reaction mixture was stirred for 18 h. The reaction mixture was diluted with water and extracted with dichloromethane. The organic extracts were washed with brine, dried and then concentrated in vacuo. The crude product was purified by flash chromatography eluting with ethyl acetate:hexane (2:1) to give the title compound (0.16 g, 46%).

Preparation 144: (1S,4aS,5S,8aR)-2,8a-dihydroxy-3,8-dimethyl-5-(1-methylethyl)-1, 2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate To a stirred suspension of (1S,2R,4aS,5S,8R,8aR)-2-(acetyloxy)-8a-hydroxy-5-isopropyl-3,8-dimethyl-1,2,4a,5,6,7,8,8a-octahydro-1-naphthalenyl-(2S,3aR,9bR)-6-chloro-9b-hydroxy-5-methyl-1,2,3,3a,5,9b-hexahydropyrrolo[2,3-c][2,1]benzoxazine-2-carboxylate (Example 1, 887 mg) in methanol (25 ml) was added a solution of concentrated hydrochloric acid (1 ml) in methanol (25 ml). After 4 days the reaction mixture was diluted with dichloromethane (150 ml) and washed with water (3×100 ml). The combined aqueous layers were washed with dichloromethane (25 ml). All the organic phases were combined, dried and concentrated to yield a yellow solid (802 mg). Purification was achieved by flash column chromatography on silica gel eluting with 1:1 ethyl acetate:hexane to give the product (604 mg).

Preparation 145: 1,1-dimethylethyl 3-{[(3,4-difluorophenyl)methyl]oxy}piperidine-1-carboxylate To sodium hydride (60% w/w dispersion in oil, 0.62 g, 16.4 mmol) washed in pentane was added N,N-dimethylformamide (20 ml) and then 1,1-dimethylethyl 3-hydroxypiperidine-1-carboxylate (Preparation 117, 3.0 g, 14.9 mmol). The reaction mixture was stirred for 1 h, before adding 3,4-difluorobenzyl bromide (2.0 ml, 16.4 mmol) and stirring the reaction mixture for 18 h. The reaction mixture was concentrated in vacuo and the crude residue was dissolved in dichloromethane and washed with brine and dried (MgSO$_4$) before concentrating in vacuo. The crude residue was purified by flash chromatography to give the title compound (4.58 g, 94%).

Preparation 146: 3-{[(3,4-difluorophenyl)methyl]oxy}piperidine 1,1-dimethylethyl 3-{[(3,4-difluorophenyl)methyl]oxy}piperidine-1-carboxylate (Preparation 145, 3.38 g, 10.3 mmol) was dissolved in methanol (100 ml) and cooled 5 to 0° C., hydrogen chloride gas was bubbled into the reaction mixture for 3-5 min. The reaction mixture was concentrated in vacuo to give an oil, upon tituration with diethyl ether a white solid formed. The solid was separated by filtration to give the title compound (1.78 g, 65%) as the hydrochloride salt.

Preparation 152: 2-[(1S,2R,4aS,5R,8R,8aR)-2-(acetyloxy)-8a-hydroxy-3,8-dimethyl-5-(1-methylethenyl)-1,2,4a,5,6,7,8,8a-octahydronaphthalen-1-yl] 3-(1,1-dimethylethyl)(2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3 (3aH)-dicarboxylate A mixture of ((1S,2R,4aS,5R,8R,8aR)-2-(acetyloxy)-8a-hydroxy-3,8-dimethyl-5-(1-methylethenyl)-1,2,4a,5,6,7,8,8a-octahydronaphthalen-1-yl(2S,3aR,9bR)-6-chloro-9b-hydroxy-5-methyl-1,2,3,3a,5,9b-hexahydropyrrolo[2,3-c][2,1]benzoxazine-2-carboxylate, (Preparation 1, 200 mg), di-tert-butyl dicarbonate and 4-dimethylaminopyridine (10 mg) was heated at 65° C. for 1 hour, during which time effervescence was noted. The reaction mixture was evaporated and purified by flash column chromatography eluting with ether:hexane (45:55) to give the product (244 mg).

Preparation: 153: (2S,9bR)-6-chloro-3-{[(1,1-dimethylethyl)oxy]carbonyl}-9b-({[(1,1-dimethylethyl)oxy]carbonyl}oxy)-5-methyl-1,2,3,3a,5,9b-hexahydropyrrolo[2,3-c][2,1]benzoxazine-2-carboxylic acid A solution of (2S,3aR,9bR)-3-(tert-butoxycarbonyl)-9b-[(tert-butoxycarbonyl)oxy]-6-chloro-5-methyl-1,2,3,3a,5,9b-hexahydropyrrolo[2,3-c][2,1]benzoxazine-2-carboxylic acid (Preparation 150, 25.4 g) in ethyl acetate (200 ml) was treated with 10% palladium on charcoal (5 g) and stirred under 50 p.s.i. of hydrogen gas for 170 hours. The reaction mixture was filtered through celite, evaporated and purified by flash column chromatography eluting with ethyl acetate:hexane (1:4) to give the product as a white foam (17.5 g).

Preparation 150: (2S,3aR,9bR)-3-(tert-butoxycarbonyl)-9b-[(tert-butoxycarbonyl)oxy]-6-chloro-5-methyl-1,2,3,3a,5,9b-hexahydropyrrolo[2,3-c][2,1]benzoxazine-2-carboxylic acid A stirred mixture of 4-methoxybenzyl (2S,3aR,9bR)-6-chloro-9b-hydroxy-5-methyl-1,2,3,3a,5,9b-hexahydropyrrolo[2,3-c][2,1]benzoxazine-2-carboxylate (Preparation 155, 29 g), di-tert-butyl dicarbonate (100 g) and 4-dimethylaminopyridine (200 mg) was heated at 60° C. for 3 hours and then left at room temperature for 18 h. The reaction mixture was purified by flash chromatography using silica gel and eluting with a gradient of ethyl acetate:hexane (1:9 to 4:6) to give the product as a light yellow solid (25.4 g).

Preparation 155: 4-methoxybenzyl (2S,3aR,9bR)-6-chloro-9b-hydroxy-5-methyl-1,2,3,3a,5,9b-hexahydropyrrolo[2,3-c][2,1]benzoxazine-2-carboxylate A stirred solution of methyl (2S,3aR,9bR)-6-chloro-9b-hydroxy-5-methyl-1, 2,3,3a,5,9b-hexahydropyrrolo[2,3-c][2,1]benzoxazine-2-carboxylate (Preparation 118 25 g), para-methoxybenzyl alcohol (115 g) and titanium tetraethoxide (1.5 g) in toluene (300 ml) was heated at reflux for 1 hour. The reaction mixture was cooled, evaporated to a small volume and purified by flash column chromatography on silica gel eluting with a gradient of ethyl acetate:hexane (1:4 to 2:3) to give the product (29 g).

Preparation 157: 2-{(1S,2R,4aS,5S,8R,8aR)-2-(acetyloxy)-8a-hydroxy-5-[2-hydroxy-1-methylethyl]-3,8-dimethyl-1,2,4a,5,6,7,8,8a-octahydronaphthalen-1-yl}3-(1,1-dimethylethyl)(2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate and diastereomer Preparation 158 2-{(1S,2R,4aS,5S,8R,8aR)-2-(acetyloxy)-8a-hydroxy-5-[2-hydroxy-1-methylethyl]-3,8-dimethyl-1,2,4a,5,6,7,8,8a-octahydronaphthalen-1-yl}3-(1,1-dimethylethyl) (2S,3aR,9bR)-6-chloro-9b-({[(1,1-dimethylethyl)oxy]carbonyl}oxy)-5-methyl-1, 2,5,9b-tetrahydropyrrolo[2,3-c][2,1]benzoxazine-2,3(3aH)-dicarboxylate To a stirred, cooled (0° C.) solution of the product of 2-[(1S,2R,4aS,5R,8R,8aR)-2-(acetyloxy)-8a-hydroxy-3,8-dimethyl-5-(1-methylethenyl)-1,2,4a,5,6,7,8,8a-octahydronaphthalen-1-yl]3-(1,1-dimethylethyl)(2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate (Preparation 152, 6.15 g) in degassed tetrahydrofuran (100 ml) was added 9-borabicyclo[3.3.1]nonane (0.5M in tetrahydrofuran, 43.2 ml) dropwise over an hour. The reaction mixture was stirred for 3 hours at room temperature and quenched with a mixture of saturated aqueous sodium hydroxide (60 ml) and aqueous hydrogen peroxide (30%, 40 ml) which was added in portions with cooling. The reaction mixture was extracted with dichloromethane (3×400 ml) and the combined organic phases were washed with water (300 ml) and aqueous iron(II)sulfate (300 ml). The washed organic phases were dried ($Na_2SO_4$), evaporated and purified with Biotage® cartridges containing silica gel (2×80 g) using gradient elution ethyl acetate:hexane (1:4 to 2:3). The major hydroxy isomer 2-{(1S,2R,4aS,5S,8R,8aR)-2-(acetyloxy)-8a-hydroxy-5-[2-hydroxy-1-methylethyl]-3,8-dimethyl-1,2,4a,5,6,7,8,8a-octahydronaphthalen-1-yl}3-(1,1-dimethylethyl)(2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3 (3aH)-dicarboxylate, Preparation 158, 4.45 g) and the minor hydroxy isomer 2-{(1S,2R,4aS,5S,8R,8aR)-2-(acetyloxy)-8a-hydroxy-5-[2-hydroxy-1-methylethyl]-3,8-dimethyl-1,2,4a,5,6,7,8,8a-octahydronaphthalen-1-yl}3-(1,1-dimethylethyl)(2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate, (Preparation 157, 1.37 g) were both obtained as white foams.

Preparation 159: 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl}3-(1,1-dimethylethyl)(2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate To a solution of 2-{(1S,2R,4aS,5S,8R,8aR)-2-(acetyloxy)-8a-hydroxy-5-[2-hydroxy-1-methylethyl]-3,8-dimethyl-1,2,4a,5,6,7,8,8a-octahydronaphthalen-1-yl}3-(1,1-dimethylethyl)(2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate (Preparation 157, 780 mg, 1 mmol), dimethylsulfoxide (1.42 ml, 20 mmol) and triethylamine (1.39 ml, 10 mmol) in dichloromethane (10 ml) at 0° C. was added sulfur trioxide/pyridine complex (980 mg, 6 mmol) portion-wise over 10 minutes and the resulting mixture stirred for 3 hours at room temperature. The reaction mixture was diluted with water and dichloromethane and the organic layer washed with hydrochloric acid (0.5N solution in water, ×2) and aqueous sodium hydrogen carbonate solution, dried ($Na_2SO_4$) and concentrated in vacuo. The crude product was purified by column chromatography on silica eluting with hexane:ethyl acetate-(2:1). The pure fractions were combined and concentrated in vacuo to give the title product (695 mg, 89%) as a white solid.

Preparation 187: 2-[(1S,2R,4aS,5S,8R,8aR)-2-(acetyloxy)-8a-hydroxy-3,8-dimethyl-5-((1R)-1-methyl-{4-[4-(trifluoromethyl)-2-pyrimidinyl]-1-piperazinyl}ethyl)-1, 2,4a,5,6,7,8,8a-octahydro-1-naphthalenyl]3-tert-butyl (2S,3aR,9bR)-9b-[(tert-butoxycarbonyl)oxy]-6-chloro-5-methyl-1,2,5,9b-tetrahydropyrrolo[2,3-c][2,1]benzoxazine-2,3(3aH)-dicarboxylate To a solution of 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl}3-(1,1-dimethylethyl)(2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate (Preparation 159, 600 mg, 7.72 mmol) in dichloromethane (10 ml) was added 1[(4-trifluoromethyl)pyrimid-2-yl]piperazine (197 mg, 8.49 mmol) and triethylamine (0.16 ml, 1.16 mmol). After 30 min at room temperature sodium triacetoxyborohydride (213 mg, 1.00 mmol) was added and the reaction mixture was stirred at room temperature for 18 h. Saturated aqueous sodium hydrogen carbonate (10 ml) was added and stirred vigorously for 15 min, before adding water (10 ml) and dichloromethane (20 ml). The aqueous layer was separated and further washed with dichloromethane (2×10 ml), the combined organic extracts were dried ($MgSO_4$) and concentrated in vacuo to give a crude oil which was purified by flash chromatography (silica) eluting with ethyl acetate hexane (1:1) to give the title compound as a colourless oil (587 mg).

Preparation 188: 2-[(1S,2R,4aS,5S,8R,8aR)-2-(acetyloxy)-8a-hydroxy-3,8-dimethyl-5-((1R)-1-methyl-2-{4-[5-(trifluoromethyl)-2-pyridinyl]-1-piperazinyl}ethyl)-1,2,4a,5,6,7,8,8a-octahydro-1-naphthalenyl]3-tert-butyl (2S,3aR,9bR)-9b-[(tert-1-5 butoxycarbonyl)oxy]-6-chloro-5-methyl-1,2,5,9b-tetrahydropyrrolo[2,3-c][2,1]benzoxazine-2,3(3aH)-dicarboxylate To a solution of 2-{(1S,2R,4aS,5R,8R,8aR)-2-(acetyloxy)-8a-hydroxy-3,8-dimethyl -5-[1-methyl-2-oxoethyl]-1,2,4a,5,6,7,8,8a-octahydronaphthalen-1-yl}3-(1,1-dimethylethyl)(2S,3aR,9bR)-6-chloro-9b-({[(1,1-dimethylethyl)oxy]carbonyl}oxy) 5-methyl-1,2,5,9b-tetrahydropyrrolo[2,3-c][2,1]benzoxazine-2,3(3aH)-dicarboxylate (Preparation 159, 600 mg, 7.72 mmol) in dichloromethane (10 ml) was added 1-[5-(trifluoromethyl)pyrid-2-yl]piperazine (196 mg, 8.49 mmol) and triethylamine (0.16 ml, 1.16 mmol). After 30 min at room temperature sodium triacetoxyborohydride (213 mg, 1.00 mmol) was added and the reaction mixture was stirred at room temperature for 18 h. Saturated aqueous sodium hydrogen carbonate (10 ml) was added and stirred vigorously for 15 min, before adding water (10 ml) and dichloromethane (20 ml). The aqueous layer was separated and further washed with dichloromethane (2×10 ml), the combined organic extracts were dried (MgSO$_4$) and concentrated in vacuo to give a crude oil which was purified by flash chromatography (silica) eluting with ethyl acetate:hexane (1:1) to give the title compound as a colourless oil (660 mg).

Preparation 160: 2-{((1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl}3-(1,1-dimethylethyl)(2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate Dimethyl sulfoxide (6.02 g) and triethylamine (3.9 g) were added successively to a stirred, cooled (0° C.) solution of 2-{(1S,2R,4aS,5S,8R,8aR)-2-(acetyloxy)-8a-hydroxy-5-[2-hydroxy-1-methylethyl]-3,8-dimethyl-1,2,4a,5,6,7,8,8a-octahydronaphthalen-1-yl}3-(1,1-dimethylethyl)(2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate) (Preparation 158, 3 g) in dichloromethane (30 ml). Sulfur trioxide pyridine complex (3.9 g) was then added in 5 portions over 10 minutes. After 2 hours the reaction mixture was diluted with water, and, extracted with dichloromethane. The combined organic layers were washed with water and aqueous hydrochloric acid (1M), dried (Na$_2$SO$_4$), evaporated and purified by flash column chromatography on silica gel (30 g) eluting with ethyl acetate:hexane (1:1) to give the title compound (2.82 g) as a white foam.

Preparation 161: 2-[(1-methylethyl)oxy]ethyl (2S,3aR,9bR)-6-chloro-9b-hydroxy-5-methyl-1,2,3,3a,5,9b-hexahydropyrrolo[2,3-c][2,1]benzoxazine-2-carboxylate To methyl (2S,3aR,9bR)-6-chloro-9b-hydroxy-5-methyl-1,2,3,3a-,5,9b-hexahydropyrrolo[2,3-c][2,1]benzoxazine-2-carboxylate (Preparation 118, 0.20 g, 0.67 mmol) was added toluene (10 ml) titanium (IV) ethoxide (0.07 ml) and 2-isopropoxy ethanol. The reactants were stirred together and then heated under reflux for 1 h, before concentrating in vacuo. The crude residue was purified using a Sep Pak cartridge eluting with hexane and then hexane:ethyl acetate (50:50). Further purification by preparative HPLC was performed using a Magellan column 212×150 mm, flow rate 20 ml/min, eluting with a gradient of water:acetonitrile (55:45 to 90:10) over 8 min to yield the title compound (63.9 mg).

Preparation 163: 2-{(1S,2R,4aS,5S,8R,8aR)-2-(acetyloxy)-5-[2-(ethylamino) 1-methylethyl]-8a-hydroxy-3,8-dimethyl-1,2,4a,5,6,7,8,8a-octahydronaphthalen-1-yl}3-(1,1-dimethylethyl)(2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate To a solution of 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl}3-(1,1-dimethylethyl)(2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate](Preparation 160, 1.0 g, 1.28 mmol) in anhydrous dichloromethane (10 ml) was added ethylamine hydrochloride (0.15 g, 1.93 mmol) and triethylamine (0.27 ml, 1.93 mmol) and the reaction mixture was stirred at room temperature for 20 min. Sodium triacetoxyborohydride (0.38 g, 1.8 mmol) was added and the reaction mixture was stirred for 18 h. The reaction mixture was diluted with ethyl acetate and washed with sodium hydrogen carbonate. The organic extracts were separated, dried (Na$_2$SO$_4$) and concentrated in vacuo. The resultant residue was purified by flash chromatography using silica gel (20 g) eluting with ethyl acetate:methanol (100:0 and then 80:20) to give the title compound as a yellow foam (0.79 g, 77%).

Preparation 166 (1S,2R,4aS,5R,8R,8aR)-5-(2-ethyl-1,3-thiazol-4-yl)-1,8a-dihydroxy-3,8-dimethyl-1,2,4a,5,6,7,8,8a-octahydronaphthalen-2-yl acetate A solution of (3aS,4R,6aS,7R,10R,10aR)-7-(2-ethyl-1,3-thiazol-4-yl)-2,2,5,10-tetramethyl-4,6a,7,8,9,10-hexahydro-3aH-naphtho[1,8a-d][1,3]dioxol-4-yl acetate (Preparation 165, 345 mg) in methanolic para-toluenesulfonic acid (1% w/w, 10 ml) was stirred at room temperature for 12 days. The reaction mixture was partitioned between ethyl acetate and a mixture of dilute aqueous sodium chloride and saturated aqueous sodium hydrogen carbonate. The organic phase was dried (MgSO$_4$), evaporated and purified by flash column chromatography on silica gel using a gradient elution ethyl acetate:hexane (1:5 to 1:1) to give the product as a gum (94 mg).

Preparation 165: (3aS,4R,6aS,7R,10R,10aR)-7-(2-ethyl-1,3-thiazol-4-yl)-2,2,5,10-tetramethyl-4,6a,7,8,9,10-hexahydro-3aH-naphtho[1,8a-d][1,3]dioxol-4-yl acetate To a stirred solution of (3aS,4R,6aS,7R,10S,10aS)-7-(2-bromoacetyl)-2,2,5,10-tetramethyl-4,6a,7,8,9,10-hexahydro-3aH-naphtho[1,8a-d][1,3]dioxol-4-yl acetate (Preparation 164, 500 mg) in ethanol (5 ml) was added thiopropionamide (110 mg). The reaction mixture was stirred at room temperature for 24 hours and then partitioned between saturated aqueous sodium chloride and ethyl acetate. The organic phase was dried (MgSO$_4$), evaporated and purified by flash column chromatography on silica gel eluting with ethyl acetate:hexane (1:4) to give the product as a gum (345 mg).

Preparation 164 (3aS,4R,6aS,7R,10R,10aR)-7-(bromoacetyl)-2,2,5,10-tetramethyl-4, 6a,7,8,9,10-hexahydro-3aH-naphtho[1,8a-d][1,3]dioxol-4-yl acetate To a stirred, cooled (0° C.) solution of the product of (3aS,4R,6aS,7R,10S,10aS)-7-acetyl-2,2,5,10-tetramethyl-4,6a,7,8,9,10-hexahydro-3aH-naphtho[1,8a-d][1,3]dioxol-4-yl acetate (Preparation 148, 1.8 g) in diethyl ether (30 ml) was added triethylamine (1.8 ml) and trimethylsilyltrifluoromethanesulfonate (2.3 ml). After 30 minutes, N-bromosuccinimide (1.2 g) was added and the reaction mixture was allowed to warm to room temperature over three hours. The reaction mixture was partitioned between saturated aqueous sodium chloride and ethyl acetate. The organic phase was dried (MgSO$_4$), evaporated and purified by flash column chromatography on silica gel using a gradient elution ethyl acetate:hexane (1:9 to 2:8) to give the product as a gum (1.81 g).

Preparation 148 (3aS,4R,6aS,7R,10S,10aS)-7-acetyl-2,2,5,10-tetramethyl-4,6a,7,8,9,10-hexahydro-3aH-naphtho[1,8a-d][1,3]dioxol-4-yl acetate A solution of the product of (3aS,4R,6aS,7R,10S,10aS)-7-(1,2-dihydroxy-1-methylethyl)-2,2,5,10-tetramethyl-4,6a,7,8,9,10-hexahydro-3aH-naphtho[1,8a-d][1,3]dioxol-4-yl acetate (Preparation 147, 930 mg) in methanol (50 ml) was treated with sodium periodate (540 mg) and sonicated in an ultrasonic bath for 15 minutes. As the sodium periodate dissolved, a cloudy suspension formed. A further amount of sodium periodate (540 mg) was added and sonication was resumed for 15 min. After standing for 1 hour, the reaction mixture was diluted with water and solvent was evaporated. The residue was partitioned between water and dichloromethane and the organic phase was separated, washed with water and brine, dried ($Na_2SO_4$) and, concentrated in vacuo. The residual oil was purified by flash column chromatography on silica gel eluting with ethyl acetate:hexane (1:4) to give the product as a colourless oil (680 mg).

Preparation 147: (3aS,4R,6aS,7R,10S,10aS)-7-(1,2-dihydroxy-1-methylethyl)-2,2,5,10-tetramethyl-4,6a,7,8,9,10-hexahydro-3aH-naphtho[1,8a-d][1,3]dioxol-4-yl acetate A solution of N-methylmorpholine-N-oxide (350 mg) in a minimum volume of isopropyl alcohol was added dropwise over 1 hour to a stirred solution of (3aS,4R,6aR,7R,10S,10aS)-7-isopropenyl-2,2,5,10-tetramethyl-4,6a,7,8,9,10-hexahydro-3aH-naphtho[1,8a-d][1,3]dioxol-4-yl acetate (Preparation 149, 1 g) and osmium tetroxide (2% in tert-butanol, 1 ml) in acetone (10 ml). After 4 hours, further N-methylmorpholine-N-oxide (350 mg) was added and stirring was continued for 16 hours. The reaction mixture was concentrated in vacuo and purified by flash column chromatography on silica gel eluting with ethyl acetate:hexane (1:1) to give the product (950 mg).

Preparation 149: (3aS,4R,6aR,7R,10S,10aS)-7-isopropenyl-2,2,5,10-tetramethyl-4,6a,7,8,9,10-hexahydro-3aH-naphtho[1,8a-d][1,3]dioxol-4-yl acetate A stirred solution of (1S,2R,4aR,5R,8S,8aS)-1,8a-dihydroxy-5-isopropenyl-3,8-dimethyl-1,2,4a,5,6,7,8,8a-octahydro-2-naphthalenyl acetate (Preparation 126, 10 g) in 2,2-dimethoxypropane (200 ml) was treated with para-toluenesulfonic acid (700 mg). After 3 days, the solution was concentrated in vacuo and the residue purified by flash column chromatography on silica gel eluting with ethyl acetate:hexane (5:95) to give the product (10.55 g).

Preparation 156: 2-[(1R,2R,4aS,5R,8S,8aS)-2-(acetyloxy)-5-(2,2-difluoro-1-methylvinyl)-8a-hydroxy-3,8-dimethyl-1,2,4a,5,6,7,8,8a-octahydro-1-naphthalenyl]3-(tert-butyl) (2S,3aR,9bR)-9b-[(tert-butoxycarbonyl)oxy]-6-chloro-5-methyl-1,2,5,9b-tetrahydropyrrolo[2,3-c][2,1]benzoxazine-2,3(3aH)-dicarboxylate Diethylisopropylamine (0.15 ml) was added to a stirred solution of (2S,9bR)-6-chloro-3-{[(1,1-dimethylethyl)oxy]carbonyl}-9b-({[(1,1-dimethylethyl)oxy]carbonyl}oxy)-5-methyl-1,2,3,3a,5,9b-hexahydropyrrolo[2,3-c][2,1]benzoxazine-2-carboxylic acid (Preparation 153, 338 mg) and fluoro-N,N,N'-tetramethylformamidinium hexafluorophosphate (80%, 231 mg) in dichloromethane (2 ml). After 10 minutes, (1S,2R,4aS,5R,8S,8aS)-5-(2,2-difluoro-1-methylvinyl)-1,8a-dihydroxy-3,8-dimethyl-1,2,4a,5,6,7,8,8a-octahydro-2-naphthalenyl acetate (Preparation 154, 115 mg) and 4-dimethylaminopyridine (2 mg) were added and the reaction mixture was heated at reflux for 16 hours. The reaction mixture was diluted with dichloromethane (25 ml), washed with aqueous citric acid (10% w/w), dried ($Na_2SO_4$) and concentrated in vacuo. The solid residue was purified by flash column chromatography on silica gel eluting with ethyl acetate hexane (1:4) to give the product as a gum (120 mg, 1:1 mixture of epimers).

Preparation 154: (1S,2R,4aS,5R,8S,8aS)-5-(2,2-difluoro-1-methylvinyl)-1,8a-dihydroxy-3,8-dimethyl-1,2,4a,5,6,7,8,8a-octahydro-2-naphthalenyl acetate A solution of the product of (3aS,4R,6aS,7R,10S,10aS)-7-(2,2-difluoro-1-methylvinyl)-2,2,5,10-tetramethyl-4,6a,7,8,9,10-hexahydro-3aH-naphtho[1,8a-d][1,3]dioxol-4-yl acetate (Preparation 151, 400 mg) and para-toluenesulfonic acid in methanol (20 ml) was stirred at room temperature for 24 hours. The reaction mixture was quenched with excess aqueous sodium hydrogen carbonate, diluted with water and extracted with diethyl ether (2×). The combined organic phases were washed with concentrated aqueous sodium chloride, dried ($Na_2SO_4$) and evaporated. The solid residue was purified by flash column chromatography on silica gel eluting with ethyl acetate:hexane (5:95 and then 10:90) to give the product as a white solid (195 mg).

Preparation 151: (3aS,4R,16aS,7R,10S,10aS)-7-(2,2-difluoro-1-methylvinyl)-2,2,5,10-tetramethyl-4,6a,7,8,9,10-hexahydro-3aH-naphtho[1,8a-d][1,3]dioxol-4-yl acetate Dibromodifluoromethane (466 mg) was added dropwise to a stirred, cooled (0° C.) solution of hexamethylphosphorustriamide (85%, 850 mg) in freshly distilled triglyme (10 ml) forming a white slurry. After 10 minutes, a solution of (3aS,4R,6aS,7R,10S,10aS)-7-acetyl-2,2,5,10-tetramethyl-4,6a,7,8,9,10-hexahydro-3aH-naphtho[1,8a-d][1,3]dioxol-4-yl acetate (Preparation 148, 680 mg) in freshly distilled triglyme (10 ml) was added and the reaction mixture was stirred at room temperature for 16 hours. The reaction mixture was recooled to 0° C. and further hexamethylphosphorustriamide (850 mg) and dibromodifluoromethane (466 mg) were added. The reaction was allowed to warm to room temperature and stirred for 24 h. Further additions of hexamethylphosphorustriamide (1.7 g) and dibromodifluoromethane (1 g) were made at 0° C. and the reaction was stirred for 5 days. The reaction mixture was diluted with water and extracted with ether (2×). The combined organic phases were washed with water and then saturated aqueous sodium chloride, dried ($Na_2SO_4$) and concentrated. The gummy residue was purified by flash column chromatography on silica gel eluting with ethyl acetate:hexane (5:95) to give the product as an oil (400 mg).

Preparation 167: 2-{(1S,2R,4aS,5R,8R,8aR)-2-(acetyloxy)-5-[2,2-difluoro-1-methylethyl]-8a-hydroxy-3,8-dimethyl-1,2,4a,5,6,7,8,8a-octahydronaphthalen-1-yl}3-(1,1-dimethylethyl)(2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate To a solution of diethylaminosulfur trifluoride (4.1 □l, 0.31 mmol) in anhydrous dichloromethane (3 ml) at −78° C.

was added a solution of 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl}3-(1,1-dimethylethyl)(2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate (Preparation 160, 200 mg, 0.25 mmol) in anhydrous dichloromethane (2 ml) dropwise over 2 minutes. The resulting mixture was allowed to warm to room temperature and stirred for 18 h. The reaction mixture was diluted with dichloromethane (5 ml), washed with water (5 ml), dried (Na$_2$SO$_4$) and concentrated in vacuo to give the crude product (145 mg, 59%). This crude product was purified by column chromatography on silica gel eluting with hexane:ethyl acetate (10:1 to 3:1). The pure fractions were combined and concentrated in vacuo to give the title product (38 mg, 19%).

Preparation 168: 2-{(1S,2R,4aS,5R,8R,8aR)-2-(acetyloxy)-5-[2,2-difluoro-1-methylethyl]-8a-hydroxy-3,8-dimethyl-1,2,4a,5,6,7,8,8a-octahydronaphthalen-1-yl}3-(1,1-dimethylethyl)(2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate To a solution of diethylaminosulfur trifluoride (0.1 ml, 1.5 mmol) in anhydrous dichloromethane (4 ml) at −78° C. was added a solution of 2-{(1S,2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl}3-(1,1-dimethylethyl)(2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate (Preparation 159, 400 mg, 0.5 mmol) in anhydrous dichloromethane (6 ml) dropwise over 2 minutes. The resulting mixture was allowed to warm to room temperature over 1½ hours and stirred for a further 2½ hours. The reaction mixture was diluted with dichloromethane (10 ml), washed with water (10 ml), dried (Na$_2$SO$_4$) and concentrated in vacuo. The crude product was purified by flash chromatography on silica gel eluting with hexane:ethyl acetate (3:1 to 2:1). The pure fractions were combined and concentrated in vacuo to give the title product (145 mg, 36%).

Preparation 170: (3aS,4R,6aR,7R,10R,10aR)-7-(2,2-dichloro-1-methylethenyl)-2, 2,5,10-tetramethyl-4,6a,7,8,9,10-hexahydro-3aH-naphtho[1,8a-d][1,3]dioxol-4-yl acetate To dry lithium chloride (1.0 g) in tetrahydrofuran (45 ml) was added n-butyllithium (4.75 ml) at 0° C. under a nitrogen atmosphere. The mixture was stirred for 10 min and then cooled to −78° C. before adding diethylchloromethyl phosphonate (1.85 ml) in tetrahydrofuran (13 ml). After stirring for 10 min, carbon tetrachloride (1.15 ml) in tetrahydrofuran (13 ml) was added. After stirring for a further 10 min, a solution of 3aS,4R,6aS,7R,10S,10aS)-7-acetyl-2,2,5,10-tetramethyl-4,6a,7,8,9,10-hexahydro-3aH-naphtho[1,8a-d][1,3]dioxol-4-yl acetate (Preparation 148, 2 g) in tetrahydrofuran (13 ml) was added and the solution was stirred for 2 h at −78° C. After this time the mixture was quenched into water (50 ml) and extracted with diethyl ether (3×50 ml). The combined organic layers were dried (MgSO$_4$) and concentrated in vacuo to give an orange oil. The oil was purified by flash chromatography using a Biotage® cartridge (90 g) to give the title compound as a transparent oil (1.05 g, 45%).

Preparation 172: 2-[(1S,2R,4aS,5R,8R,8aR)-2-(acetyloxy)-5-(2,2-dichloro-1-methylethenyl)-8a-hydroxy-3,8-dimethyl-1,2,4a,5,6,7,8,8a-octahydronaphthalen-1-yl]3-(1,1-dimethylethyl)(2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate (2S,9bR)-6-chloro-3-{[(1,1-dimethylethyl)oxy]carbonyl}-9b-({[(1,1-dimethylethyl)oxy]carbonyl}oxy)-5-methyl-1,2,3,3a,5,9b-hexahydropyrrolo[2,3-c][2,1]benzoxazine-2-carboxylic acid (Preparation 153, 1.7 g), 1-methyl imidazole (0.39 g) and 1-(mesitylene-2-sulfonyl)-3-nitro-1,2,4-triazole (1.4 g) were stirred in dichloromethane at room temperature for 20 min. 5-(2,2-dichloro-1-methylethenyl)-1,8a-dihydroxy-3,8-dimethyl-1,2,4a,5,6,7,8,8a-octahydronaphthalen-2-yl acetate (Preparation 173, 0.85 g) was added and the resulting mixture was stirred at room temperature. After 1 h, the reaction mixture was concentrated in vacuo. The crude residue was dissolved in dichloromethane and preabsorbed onto silica gel before purifying by flash chromatography eluting with ethyl acetate:hexane (10:90, and then 30:70, and then 50:50 and then 100:0). The title compound was obtained as a white solid (0.71 g).

Preparation 173: 5-(2,2-dichloro-1-methylethenyl)-1,8a-dihydroxy-3,8-dimethyl-1,2,4a,5,6,7,8,8a-octahydronaphthalen-2-yl acetate To a stirred solution of (3aS,4R,6aR,7R,10R,10aR)-7-(2,2-dichloro-1-methylethenyl)-2,2,5,10-tetramethyl-4,6a,7,8,9,10-hexahydro-3aH-naphtho[1,8a-d][1,3]dioxol-4-yl acetate (Preparation 170, 0.95 g) in ethylene glycol (40 ml) and methanol (10 ml) was added para-toluenesulphonic acid (95 mg). The reaction mixture was heated to 75° C., after 1.5 h the reaction mixture was concentrated in vacuo to remove the methanol. The resultant solution was diluted with diethyl ether (30 ml) and water (30 ml) and the organic layer separated and washed with sodium hydrogen carbonate (3×30 ml). The aqueous layers were back extracted with diethyl ether (2×20 ml) and the combined organic extracts were dried (MgSO$_4$) and concentrated to give the title compound as a white solid.

Preparation 176: 2-{(1S,2R,4aS,5S,8R,8aR)-2-(acetyloxy)-5-[(1R)-2-(cyclopropylamino)-1-methylethyl]-8a-hydroxy-3,8-dimethyl-1,2,4a,5,6,7,8,8a-octahydronaphthalen-1-yl}3-(1,1-dimethylethyl)(2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate To 2-{(1S-2R,4aS,5R,8R,8aR)-2-(acetyloxy)-8a-hydroxy-3,8-dimethyl-5-[1-methyl-2-oxoethyl]-1,2,4a,5,6,7,8,8a-octahydronaphthalen-1-yl}3-(1,1-dimethylethyl) (2S,3aR,9bR)-6-chloro-9b-({[(1,1-dimethylethyl)oxy]carbonyl}oxy)-5-methyl-1, 2,5,9b-tetrahydropyrrolo[2,3-c][2,1]benzoxazine-2,3(3aH)-dicarboxylate (Preparation 160, 0.56 g, 0.73 mmol) in anhydrous dichloromethane (5 ml) was added cyclopropylamine (5.0 □l, 0.73 mmol) and the reaction mixture was stirred at room temperature for 20 min. Sodium triacetoxyborohydride (0.21 g, 1.0 mmol) was added and the reaction mixture was stirred for 18 h. The reaction mixture was diluted with ethyl acetate and washed with sodium hydrogen carbonate solution. The organic extracts were dried (Na$_2$SO$_4$) and concentrated in vacuo to give the title compound as a yellow foam (0.56 g, 96%).

Preparation 177: 2-[(1S,2R,4aS,5S,8R,8aR)-5-{2-[acetyl(cyclopropyl)amino]-1-methylethyl}-2-(acetyloxy)-8a-hydroxy-3,8-dimethyl-1,2,4a,5,6,7,8,8a-octahydronaphthalen-1-yl]3-(1,1-dimethylethyl)(2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate To 2-{(1S,2R,4aS,5S,8R,8aR)-2-(acetyloxy)-5-[(1R)-2-(cyclopropylamino)-1-methylethyl]-8a-hydroxy-3,8-dimethyl-1,2,4a,5,6,7,8,8a-octahydronaphthalen-1-yl}3-(1,1-dimethylethyl)(2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate (Preparation 176, 0.10 g, 0.12 mmol) in anhydrous dichloromethane (3 ml) was added 4-dimethylaminopyridine (0.15 g, 0.12 mmol) and the reaction mixture was cooled to 0° C. Acetic anhydride (2.3 □l, 0.24 mmol) was added dropwise and the reaction mixture was stirred under nitrogen for 1 h. The reaction mixture was diluted with dichloromethane and washed with water and then brine. The organic extracts were dried (Na$_2$SO$_4$) and concentrated in vacuo to give the title compound as a pale yellow solid.

Preparation 178: 2-[(1S,2R,4aS,5S,8R,8aR)-2-(acetyloxy)-5-(2-{ethyl[(methyloxy)carbonyl]amino}-1-methylethyl)-8a-hydroxy-3,8-dimethyl-1,2,4a,5,6,7,8,8a-octahydronaphthalen-1-yl]3-(1,1-dimethylethyl)(2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate 2-{(1S,2R,4aS,5S,8R,8aR)-2-(acetyloxy)-5-[2-(ethylamino)-1-methylethyl]-8a-hydroxy-3,8-dimethyl-1,2,4a,5,6,7,8,8a-octahydronaphthalen-1-yl}3-(1,1-dimethylethyl)(2S,3aR,9bR)-6-chloro-9b-({[(1,1-dimethylethyl)oxy]carbonyl}oxy)-5-methyl-1, 2,5,9b-tetrahydropyrrolo[2,3-c][2,1]benzoxazine-2,3(3aH)-dicarboxylate (Preparation 163, 99 mg, 0.12 mmol) and 4-dimethylaminopyridine (15 mg, 0.12 mmol) were dissolved in anhydrous dichloromethane (3 ml) and pyridine (5.0 □l, 0.61 mmol) was added. The reaction mixture was cooled to 0° C. and methyl chloroformate (28. □l, 0.37 mmol) was added dropwise. After stirring for 18 h, the reaction mixture was diluted with ethyl acetate and washed with water, citric acid (20%, w/v) and then again with water. The organic extracts were dried (Na$_2$SO$_4$) and concentrated in vacuo to give the title compound as a yellow glassy solid (89 mg, 86%).

Preparation 179: 2-[(1S,2R,4aS,5S,8R,8aR)-2-(acetyloxy)-5-(2-{cyclopropyl[(methyloxy)carbonyl]amino}-1-methylethyl)-8a-hydroxy-3,8-dimethyl-1,2,4a,5,6,7,8,8a-octahydronaphthalen-1-yl]3-(1,1-dimethylethyl)(2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate To 2-{(1S,2R,14aS,5S,8R,8aR)-2-(acetyloxy)-5-[(1R)-2-(cyclopropylamino)-1-methylethyl]-8a-hydroxy-3,8-dimethyl-1,2,4a,5,6,7,8,8a-octahydronaphthalen-1-yl}3-(1,1-dimethylethyl)(2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate (Preparation 176, 98 mg, 0.12 mmol) and 4-dimethylaminopyridine (15 mg, 0.12 mmol) in anhydrous dichloromethane (3 ml) was added pyridine (50. □l, 0.60 mmol) and the reaction mixture was cooled to 0° C. Methyl chloroformate was added dropwise and the reaction mixture was stirred for 18 h, before diluting with ethyl acetate and washing with water, citric acid (20% w/v) and water again. The organic extracts were dried (Na$_2$SO$_4$) and concentrated in vacuo to give the title compound as a yellow glassy solid (108 mg, 100%).

Preparation 180: 2-[(1S,2R,4aS,5S,8R,8aR)-2-(acetyloxy)-5-(2-{cyclopropyl[(ethylamino)carbonyl]amino}-1-methylethyl)-8a-hydroxy-3,8-dimethyl-1,2,4a,5,6,7,8,8a-octahydronaphthalen-1-yl]3-(1,1-dimethylethyl)(2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate To 2-{(1S,2R,4aS,5S,8R,8aR)-2-(acetyloxy)-5-[(1R)-2-(cyclopropylamino)-1-methylethyl]-8a-hydroxy-3,8-dimethyl-1,2,4a,5,6,7,8,8a-octahydronaphthalen-1-yl}3-(1,1-dimethylethyl)(2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate (Preparation 176, 0.16 g, 0.2 mmol) in anhydrous dichloromethane (5 ml) cooled to 0° C. was added ethyl isocyanate (0.017 ml, 0.22 mmol) dropwise and the reaction mixture was stirred under nitrogen. The reaction mixture was concentrated in vacuo and the crude yellow residue was purified by flash chromatography on silica gel (8 g) eluting with ethyl acetate:hexane (1:1) to give the desired product as a white solid (114 mg, 61%).

Preparation 181: 2-[(1R,4R,4aS,5R,6R)-5-({[(2S,3aR,9bR)-6-chloro-3-{[(1,1-dimethylethyl)oxy]carbonyl}-9b-({[(1,1-dimethylethyl)oxy]carbonyl}oxy)-5-methyl-1, 2,3,3a,5,9b-hexahydropyrrolo[2,3-c][2,1]benzoxazin-2-yl]carbonyl}oxy)-6-(acetyloxy)-4a-hydroxy-4,7-dimethyl-1,2,3,4,4a,5,6,8a-octahydronaphthalen-1-yl]propanoic acid To a solution of 2-{(1S,2R,4aS,5S,8R,8aR)-2-(acetyloxy)-8a-hydroxy-5-[2-hydroxy-1-methylethyl]-3,8-dimethyl-1,2,4a,5,6,7,8,8a-octahydronaphthalen-1-yl}3-(1,1-dimethylethyl)(2S,3aR,9bR)-6-chloro-9b-({[(1,1-dimethylethyl)oxy]carbonyl}oxy)-5-methyl-1,2,5,9b-tetrahydropyrrolo[2,3-c][2,1]benzoxazine-2,3(3aH)-dicarboxylate (Preparation 157, 500 mg, 0.64 mmol) in anhydrous N,N-dimethylformamide, (5 ml) was added pyridinium dichromate (845 mg, 2.25 mmol) and the resultant mixture stirred at room temperature under nitrogen for 4 hours. The reaction mixture was diluted with water (100 ml) and extracted with diethyl ether (2×100 ml). The organic extracts were washed with water (50 ml), dried (Na$_2$SO$_4$) and concentrated in vacuo. The crude product was purified by column chromatography on a Biotage® silica (8 g) column eluting with ethyl acetate:hexane (2:8) to give the title product as a white foam (240 mg, 45%).

Preparation 182: 1,1-dimethylethyl (3R)-3-(methyloxy)piperidine-1-carboxylate To a solution of 1,1-dimethylethyl (3R)-3-hydroxypiperidine-1-carboxylate (Preparation 128, 1.6 g, 7.95 mmol) in anhydrous tetrahydrofuran (35 ml) was added sodium hydride (60% dispersion in oil, 0.32 g, 7.95 mmol) in portions. The resulting mixture was stirred for 25 min then iodomethane (2.27 g, 16 mmol) was added dropwise and the reaction mixture was stirred for 17 h. The reaction mixture was diluted with ethyl acetate (150 ml) and washed with brine (5% solution, 150 ml). The aqueous layer was extracted with ethyl acetate (2×50 ml) and the combined organic extracts were dried (MgSO$_4$) and concentrated in vacuo. The resulting yellow oil was purified by flash chromatography on silica gel (70 g) eluting with dichloromethane:methanol (100:1 and then 50:1) to give a yellow oil (1.68 g). The trace of iodine was removed by dissolving the product in ethyl acetate (50 ml) and washing with aqueous sodium metabisulphite (5% solution, 2×35 ml), water (35 ml) and aqueous sodium hydrogen carbonate (5% solution, 35 ml). The organic extracts were dried (MgSO$_4$) and concentrated in vacuo to give the desired product as a colourless oil (1.62 g).

Preparation 183 (3R)-3-(methyloxy)piperidine

A solution of 1,1-dimethylethyl (3R)-3-(methyloxy)piperidine-1-carboxylate (Preparation 182, 1.55 g, 7.2 mmol) in anhydrous dichloromethane (60 ml) was cooled to 4° C. and then saturated with hydrogen chloride gas for about 10 min. The reaction mixture was stirred for 1.5 h before concentrating in vacuo and azeotroping with anhydrous diethyl ethyl to produce the hydrochloride salt of the title compound as a white hydroscopic solid (0.90 g).

Preparation 184: 1,1-dimethylethyl (3S)-3-(methyloxy)piperidine-1-carboxylate

To a solution of 1,1-dimethylethyl (3S)-3-hydroxypiperidine-1-carboxylate (Preparation 127, 1.8 g, 9.2 mmol) in anhydrous tetrahydrofuran (40 ml) was added sodium hydride (60% dispersion in oil, 0.39 g, 9.2 mmol) in portions. The resulting mixture was stirred for 25 min then iodomethane (2.83 g, 20 mmol) was added dropwise and the reaction mixture was stirred for 17 h. The reaction mixture was diluted with ethyl acetate (200 ml) and washed with brine (5% solution, 200 ml). The aqueous layer, was extracted with ethyl acetate (2×50 ml) and the combined organic extracts were dried (MgSO$_4$) and concentrated in vacuo. The resulting yellow oil was purified by flash chromatography on silica gel (100 g) eluting with dichloromethane:methanol (100:1 and then 50:1) to give a yellow oil. The trace of iodine was removed by dissolving the product in diethyl ether (60 ml) and washing with aqueous sodium metabisulphite (5% solution, 1×40 ml), water (2×40 ml) and aqueous sodium hydrogen carbonate (5% solution, 40 ml). The organic extracts were dried (MgSO$_4$) and concentrated in vacuo to give the desired product as a colourless oil (1.43 g).

Preparation 186: (3S)-3-(methyloxy)piperidine

A solution of 1,1-dimethylethyl (3S)-3-(methyloxy)piperidine-1-carboxylate (Preparation 184, 1.35 g, 6.27 mmol) in anhydrous dichloromethane (50 ml) was cooled to 4° C. and then saturated with hydrogen chloride gas for about 10 min. The reaction mixture was stirred for 2 h before concentrating in vacuo and azeotroping with anhydrous diethyl ethyl to produce the hydrochloride salt of the title compound as a white hydroscopic solid (0.82 g).

Preparation 185: 4-amino-6-methyl-2-piperazin-1-ylpyrimidine-5-carbonitrile

A solution of 4-amino-2-chloro-2-methylpyrimidine-5-carbonitrile (Maybridge, 100 mg, 0.6 mmol), piperazine (207 mg, 2.4 mmol), and triethylamine (71 mg, 0.7 mmol) in N,N-dimethylacetamide (20 ml) was heated to 108° C. for 6 h. The reaction mixture was stirred at ambient temperature for 18 h before pouring into water (400 ml) and extracting with ethyl acetate (3×30 ml), and then dichloromethane (20 ml). The combined organic extracts were washed with water (3×150 ml), and then dried (MgSO$_4$) and concentrated to give a yellow solid (120 mg). The crude solid was pre-absorbed onto silica gel (250 mg) and then purified by flash chromatography on silica gel (20 g) eluting with ethyl acetate:methanol (90:10 and then 80:20) to give the title compound as a white solid (28 mg).

Preparation 198: 2-piperazin-1-yl-5-(trifluoromethyl)pyrimidine

To a solution of 1-amidino-piperazine sulphate (760 mg, 4.3 mmol) and 1,1,5,5-tetramethyl-1,5-diaza-3-(trifluoromethyl)-1,3-pentadienium chloride (Preparation 199. 720 mg, 3.12 mmol) in acetonitrile (15 ml) was added sodium methoxide (25% in methanol, 1.2 ml). The reaction mixture was heated at 70° C. for 1 h and allowed to cool overnight. The solvents were removed in vacuo and the residue was dissolved in dichloromethane (20 ml) and washed with saturated aqueous sodium hydrogen carbonate (30 ml) and water (10 ml). The reaction mixture was dried (Na$_2$SO$_4$) and the solvent removed in vacuo before the product was purified to give the title compound as a TFA salt (68 mg).

Preparation 200: 4-[(4-chlorophenyl)oxy]piperidine

To a solution of tert-butyl 4-hydroxy-1-piperidinecarboxylate (500 mg, 2.48 mmol), 4-chlorophenol (320 mg, 2.48 mmol) and triphenylphosphine (650 mg, 2.48 mmol) in tetrahydrofuran (15 ml) at 0° C. was added dropwise diisopropylazodicarboxylate (490 µl, 2.48 mmol) in tetrahydrofuran (5 ml). The reaction mixture was allowed to warm to room temperature and stirred overnight in the absence of light. The solution was concentrated to give the Boc protected title compound.

The Boc protected title compound was dissolved in hydrogen chloride (4N in dioxane, 10 ml) and stirred at room temperature for 2 h. The reaction mixture was evaporated to dryness and partitioned between ethyl acetate and water. The layers were separated and to the aqueous layer was added sodium hydroxide solution (2 N) and ethyl acetate. The organic layers were separated, combined and dried (Na$_2$SO$_4$) before being filtered and evaporated to give the title compound.

The invention claimed is:

1. A compound of formula (I):

(I)

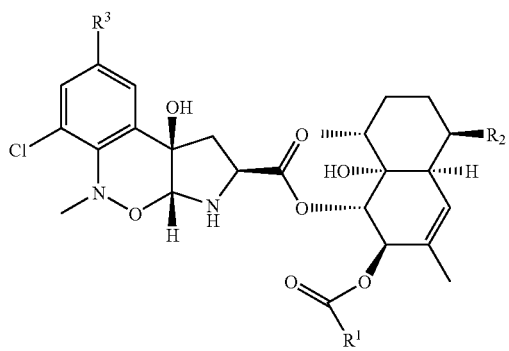

or a pharmaceutically or veterinarily acceptable salt or solvate thereof, wherein $R^1$ is H, $C_1$-$C_6$ alkyl, $C_2$-$C_6$ haloalkyl, $C_3$-$C_8$ cycloalkyl, $C_2$-$C_6$ alkenyl, $C_2$-$C_6$ alkynyl, aryl or —OR$^4$, said $C_1$-$C_6$ alkyl, $C_3$-$C_8$ cycloalkyl and aryl being optionally substituted by one or more substituents selected from $COOR^{13}$, $-OCOR^{12}$, $-OCOOR^{13}$ and $-OCONR^{12}R^{12}$ and said $C_2$-$C_6$ alkenyl and $C_2$-$C_6$ alkynyl being optionally substituted by one or more halo;

$R^2$ is $C_1$-$C_6$ alkyl, $C_2$-$C_6$ alkenyl, or a 5- or 6-membered aromatic or non-aromatic heterocycle containing one or more atoms selected from N, O and S, said $C_1$-$C_6$ alkyl being optionally substituted by one or more substituents selected from $-NR^5R^6$, $-CONR^5R^6$, $-OR^{12}$, $-OCOR^{12}$, $-OCOOR^{12}$, $-OCONR^{12}R^{14}$, $=NOR^7$ and halo, said $C_2$-$C_6$ alkenyl being optionally substituted by one or more substituents selected from halo and $-COOR^{13}$ and said 5- or 6-membered aromatic heterocycle containing one or more atoms selected from N, O and S being optionally substituted by one or more substitutents selected from $C_1$-$C_6$ alkyl and aryl;

$R^3$ is H, halo, aryl, $C_2$-$C_6$ alkenyl, $C_2$-$C_7$ alkanoyl, or a 5- or 6-membered aromatic heterocycle containing one or more atoms selected from N, O and S;

$R^4$ is $C_1$-$C_2$ alkyl, $C_2$-$C_6$ alkenyl or $C_2$-$C_6$ alkynyl, each optionally substituted by one or more halo, or $-OC(O)OR^a$ where $R^a$ is $C_1$-$C_6$ alkyl;

$R^5$ and $R^6$ either, when taken together with the nitrogen atom to which they are attached, represent a saturated, partially unsaturated or aromatic, mono-, bi- or tricyclic heterocycle of up to 16 atoms optionally containing 1 or more additional heteroatoms selected from O, N and S, said heterocycle being optionally fused to a benzene or pyridyl ring and optionally substituted by one or more $R^8$ and optionally substituted on any aromatic ring thereof by $-NR^{15}R^{16}$ and said benzene and pyridyl ring optinally substituted by one or more $R^8$ and said benzene and pyridyl ring optinally substituted on any aromatic ring thereof by $-NR^{15}R^{16}$, with the proviso that the heterocycle may not contain an $-NH-$ group; or $R^5$ and $R^6$ are each independently selected from H, $C_1$-$C_6$ alkyl, $C_3$-$C_8$ cycloalkyl, $-CO-(C_3$-$C_8)$cycloalkyl, $-COR^{10}$, $C_2$-$C_7$ alkanoyl, aryl, $-OR^{13}$, $-COOR^{13}$, $-CONR^{12}R^{12}$ or $-SO_2R^{13}$, said $C_2$-$C_7$ alkanoyl beings optionally substituted by $OR^{13}$ or halo, said $C_1$-$C_6$ alkyl and $C_3$-$C_8$ cycloalkyl being optionally substituted by one or more $R^8$ and said $C_3$-$C_8$ cycloalkyl being optionally fused to a saturated or unsaturated ring of from 5; to 6 atoms, optionally containing one or more O, N or S atoms, said fused ring being optionally substituted by one or more $C_1$-$C_6$ alkyl with the proviso that when $R^5$ is H or $-CH_3$, $R^6$ is not $C_1$-$C_6$ alkyl;

$R^7$ is $C_1$-$C_6$ alkyl, $C_2$-$C_6$ alkenyl, $C_2$-$C_6$ alkynyl or aryl, said alkyl being optionally substituted by aryl;

$R^8$ is $C_1$-$C_6$ alkyl, $C_3$-$C_8$ cycloalkyl, $R^9$, $R^{10}$, $-OR^9$, $-OR^{10}$, $COR^9$, $COR^{10}$, $-O-(C_1$-$C_6$ alkyl)$-R^{10}$, $C_2$-$C_6$ alkenyl, $-OR^{13}$, $-SR^9$, $-SR^{10}$, $-SO_2R^{10}$, $-OCOR^{12}$, $-OCOOR^{12}$, $-OCONR^{12}R^{13}$, $-CONR^{12}OR^{13}$, $-CONR^{12}R^{13}$, $-NR^{12}COR^{12}$, $-NR^{12}COOR^{12}$, $-NR^{12}CONR^{12}R^{12}$, $-COOR^{13}$, $-COR^{12}$, oxo or halo, said $C_3$-$C_8$ cycloalkyl being optionally substituted by aryl, said $C_1$-$C_6$ alkyl being optionally substituted by one or more substituents selected from $C_3$-$C_8$ cycloalkyl, $R^9$, $R^{10}$, $-OR^{10}$, $-OR^{13}$, $-SR^9$, $-SR^{11}-OCOR^{12}$, $-OCOOR^{12}$, $-OCONR^{12}R^{12}$, $-NR^{12}COR^{12}$, $-NR^{12}COOR^{12}$, $-NR^{12}CONR^{12}R^{12}$, $-COR^{12}$ or halo, and said $C_2$-$C_6$ alkenyl being optionally substituted by one or more substituents selected from halo or aryl;

$R^9$ is (a) a 5- or 6-membered aromatic heterocycle containing one or more atom(s) selected from N, O and S and optionally fused to a benzene ring, said aromatic heterocycle being optionally substituted (including on the optional benzene ring) by one or more substituents selected from $C_1$-$C_6$ alkyl, $C_1$-$C_6$ haloalkyl, $C_3$-$C_8$ cycloalkyl, $-OR^{13}$, $-NR^{12}R^{12}$, $-CO_2R^{13}$ cyano and halo, or (b) a 4- to 8-membered saturated heterocycle containing one or more atoms selected from O and S and optionally fused to a benzene ring, said saturated heterocycle being optionally substituted (including on the optional benzene ring) by one or more substituents selected from $C_1$-$C_6$ alkyl and $C_3$-$C_8$ cycloalkyl;

$R^{10}$ is aryl optionally substituted by one or more substitutents selected from $C_1$-$C_6$ alkyl, $C_1$-$C_6$ haloalkyl, $-OR^{13}$, $-NR^{12}R^{12}$, $-CO_2R^{13}$, cyano or halo and optionally fused to a saturated or unsaturated ring of 5 or 6 atoms, optionally containing one or more O, N or S atoms, said fused ring being optionally substituted by one or more $C_1$-$C_6$ alkyl;

$R^{11}$ is H, $C_1$-$C_6$ alkyl or $C_3$-$C_8$ cycloalkyl;

each $R^{12}$ is independently H, $C_1$-$C_6$ alkyl, $C_1$-$C_6$ haloalkyl, $C_3$-$C_8$ cycloalkyl or aryl, said $C_1$-$C_6$ alkyl being optionally substituted by aryl;

each $R^{13}$ is independently $C_1$-$C_6$ alkyl, $C_1$-$C_6$ haloalkyl, $C_3$-$C_8$ cycloalkyl or aryl, said $C_1$-$C_6$ alkyl being optionally substituted by aryl;

$R^{14}$ is $C_1$-$C_6$ alkyl, $C_3$-$C_8$ cycloalkyl or aryl, said $C_1$-$C_6$ alkyl each optionally substituted by aryl or $-NHaryl$;

$R^{15}$ and $R^{16}$ are either each independently selected from H, $C_1$-$C_6$ alkyl and $C_3$-$C_8$ cycloalkyl or, when taken together with the nitrogen atom to which they are attached, represent a 3- to 8- membered ring optionally containing one or more additional heteroatoms selected from O and S; and 'aryl' means phenyl or naphthyl;

with the proviso that when $R^3$ is H and $R^1$ is methyl, $R^2$ is not isopropenyl.

2. A compound as claimed in claim 1, wherein:
$R^1$ is $C_1$-$C_6$ alkyl, $C_1$-$C_4$ alkenyl, $C_1$-$C_4$ alkynyl, $OC_1$-$C_6$ alkyl, $OC_1$-$C_4$ alkenyl or $OC_1$-$C_4$ alkynyl; and
$R^2$ is a thiazole ring optionally substituted with $C_1$ to $C_4$ alkyl; a piperazine ring optionally substituted with $C_1$ to $C_4$ alkyl; an isopropenyl group optionally substituted by halo; or an isopropyl group optionally substituted by one or more halo; $NR^7R^8$ wherein $R^7$ and $R^8$ may be taken together to represent a ring of up to 7 atoms optionally containing oxygen or may be independently selected from H or $C_1$ to $C_4$ cycloalkyl; $=NOR^{17}$ wherein $R^{17}$ may be selected from $C_1$ to $C_6$, $C_1$ to $C_4$ alkynyl or $C_1$ to $C_4$ alkenyl.

3. A compound as claimed in claim 2, wherein:
$R^1$ is $CH_3$, $-O$-allyl or $-O$-propargyl;
$R^2$ is 2-ethylthiazol-4-yl, isopropyl, piperazinyl, 1,2-difluoropropen-2-yl, 1-oxoprop-2-yl methyl oxime, 1-oxoprop-2-yl propargyl oxime, 1-oxoprop-2-yl allyl oxime, 1-N-morpholinoprop-2-yl, 1-fluoroprop-2-yl, 1,1-difluoroprop-2-yl;
$R^3$, $R^4$ and $R^5$ are H.

4. A compound as claimed in claim 1, wherein $R^3$, $R^4$, and $R^5$ all are H, and $R^1$ and $R^2$ are as indicated below:

| R1 = | R2 = |
|---|---|
| $CH_3$ | 2-Ethylthiazol-4-yl, isopropyl |
| $CH_3$ | 1,2-difluoropropen-2-yl |
| $CH_3$ | 1-oxoprop-2-yl methyl oxime |

-continued

| R1 = | R2 = |
| --- | --- |
| CH₃ | 1-oxoprop-2-yl propargyl oxime |
| CH₃ | 1-oxoprop-2-yl allyl oxime |
| CH₃ | isopropyl |
| CH₃ | 1-N-morpholinoprop-2-yl |
| CH₃ | 1-fluoroprop-2-yl |
| CH₃ | 1,1-difluoroprop-2-yl |
| CH₃ | piperazin-1-yl (optionally 4-substituted with C₁-C₆ alkyl, phenyl, benzyl each of which groups may optionally be halo-substituted by up to 3 halo atoms |
| Opropargyl | isopropenyl |
| Opropargyl | isopropyl |
| Oallyl | isopropyl. |

5. A compound as claimed in claim 2, wherein $R^3$, $R^4$, and $R^5$ all are H, and $R^1$ and $R^2$ are as indicated below:

| R1 = | R2 = |
| --- | --- |
| CH₃ | 2-Ethylthiazol-4-yl, isopropyl |
| CH₃ | 1,2-difluoropropen-2-yl |
| CH₃ | 1-oxoprop-2-yl methyl oxime |
| CH₃ | 1-oxoprop-2-yl propargyl oxime |
| CH₃ | 1-oxoprop-2-yl allyl oxime |
| CH₃ | isopropyl |
| CH₃ | 1-N-morpholinoprop-2-yl |
| CH₃ | 1-fluoroprop-2-yl |
| CH₃ | 1,1-difluoroprop-2-yl |
| CH₃ | piperazin-1-yl (optionally 4-substituted with C₁-C₆ alkyl, phenyl, benzyl each of which groups may optionally be halo-substituted by up to 3 halo atoms |
| Opropargyl | isopropenyl |
| Opropargyl | isopropyl |
| Oallyl | isopropyl. |

6. A compound as claimed in claim 1, wherein $R^3$, $R^4$, and $R^5$ all are H, or CH₃ and $R^1$ and $R^2$ are as indicated below:

| R1 = | R2 = |
| --- | --- |
| CH₃ | 2-Ethylthiazol-4-yl, isopropyl |
| CH₃ | 1,2-difluoropropen-2-yl |
| CH₃ | 1-oxoprop-2-yl methyl oxime |
| CH₃ | 1-oxoprop-2-yl propargyl oxime |
| CH₃ | 1-oxoprop-2-yl allyl oxime |
| CH₃ | isopropyl |
| CH₃ | 1-N-morpholinoprop-2-yl |
| CH₃ | 1-fluoroprop-2-yl |
| CH₃ | 1,1-difluoroprop-2-yl |
| CH₃ | piperazin-1-yl (optionally 4-substituted with C₁-C₆ alkyl, phenyl, benzyl each of which groups may optionally be halo-substituted by up to 3 halo atoms |
| Opropargyl | isopropenyl |
| Opropargyl | isopropyl |
| Oallyl | isopropyl. |

7. A pharmaceutical composition comprising a compound of formula (I) as defined in claim 1 or a pharmaceutically acceptable salt thereof, or a pharmaceutically acceptable solvate of the compound or the salt, together with a pharmaceutically acceptable diluent or carrier.

8. A veterinary or agricultural formulation comprising a compound of formula (I) as defined in claim 1, or a veterinarily or agriculturally acceptable salt thereof, or a veterinarily or agriculturally acceptable solvate of the compound or the salt, together with a veterinarily or agriculturally acceptable diluent or carrier.

9. A compound of claim 1 selected from:
  (1S,2R,4aS,5S,8R,8aR)-2-(acetyloxy)-8a-hydroxy-3,8-dimethyl-5-(1-methyl)-1,2,4a,5,6,7,8,8a-octahydronaphthalen-1-yl (2S,3aR,9bR)-6-chloro-9b-hydroxy-5-methyl -1,2,3,3a,5,9b-hexahydropyrrolo[2,3-c][2,1]benzoxazine-2-carboxylate;
  (1S,2R,4aS,5R,8R,8aR)-8a-hydroxy-3,8-dimethyl-5-(1-methylethenyl)-2-[(2-methylpropanoyl)oxy]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;
  (1S,2R,4aS,5R,8R,8aR)-2-(hexanoyloxy)-8a-hydroxy-3,8-dimethyl-5-(1-methylethenyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[-2,3-c][2,1]benzoxazine-2-carboxylate;
  (1S,2R,4aS,5R,8R,8aR)-2-(acetyloxy)-5-[2-(acetyloxy)-1-methylethyl]-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexa hydropyrrolo[2,3-c][2,1]benzoxazine-2-carboxylate;
  (1S,2R,4aS,5R,8R,8aR)-2-(acetyloxy)-8a-hydroxy-3,8-dimethyl-5-{1-methyl-2-[(2-methylpropanoyl)oxy]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[-2,3-c][2,1]benzoxazine-2-carboxylate;
  (1S,2R,4aS,5R,8R,8aR)-2-[(cyclopropylcarbonyl)oxy]-8a-hydroxy-3,8-dimethyl-1-5-(1-methylethenyl)-1,2,4a,5,6,7,8,8a-octahydronaphthalen-1-yl (2S,3aR,9bR)-6-chloro-9b-hydroxy-5-methyl-1,2,3,3a,5,9b-hexahydro pyrrolo[2,3-c][2,1]benzoxazine-2-carboxylate;
  (1S,2R,4aS,5S,8R,8aR)-8a-hydroxy-3,8-dimethyl-5-(1-methylethyl)-2-{[(prop-2-ynyloxy)carbonyl]oxy}-1,2,4a,5,6,7,8,8a-octahydronaphthalen-1-yl (2S,3aR,9bR)-6-chloro-9b-hydroxy-5-methyl-1,2,3,3a,5,9b-hexahydro pyrrolo[2,3-c][2,1]benzoxazine-2-carboxylate;
  (1S,2R,4aS,5S,8R,8aR)-8a-hydroxy-3,8-dimethyl-5-(1-methylethyl)-2-({[(2,2,2-trichloroethyl)oxy]carbonyl}oxy)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;
  (1S,2R,4aS,5S,8R,8aR)-8a-hydroxy-3,8-dimethyl-2-({[(1-methylethenyl)oxy]carbonyl}oxy)-5-(1-methylethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;
  (1S,2R,4aS,5S,8R,8aR)-8a-hydroxy-3,8-dimethyl-5-(1-methylethyl)-2-{[(prop-2-enyloxy)carbonyl]oxy}-1,2,4a,5,6,7,8,8a-octahydronaphthalen-1-yl (2S,3aR,9bR)-6-chloro-9b-hydroxy-5-methyl-1,2,3,3a,5,9b-hexahydro pyrrolo[2,3-c][2,1]benzoxazine-2-carboxylate;
  (1S,2R,4aS,5S,8R,8aR)-1-({[(2S,3aR,9bR)-6-chloro-9b-hydroxy-5-methyl-1,2,3,3a,5,9b-hexahydropyrrolo[2,3-c][2,1]benzoxazin-2-yl]carbonyl}oxy)-8a-hydroxy-3,8-dimethyl-5-(1-methylethenyl)-1,2,4a,5,6,7,8,8a-octahydronaphthalen-2-yl methyl butanedioate;

(1S,2R,4aS,5S,8R,8aR)-8a-hydroxy-3,8-dimethyl-5-(1-methylethenyl)-2-(pent-4-enoyloxy)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[-2,3-c][2,1]benzoxazine-2-carboxylate;

(1S,2R,4aS,5R,8R,8aR)-2-(acetyloxy)-8a-hydroxy-3,8-dimethyl-5-{1-methyl-2-[({[2-(naphthalen-1-ylamino)ethyl]amino}carbonyl)oxy]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5R,8R,8aR)-2-{[(acetyloxy)acetyl]oxy}-8a-hydroxy-3,8-dimethyl-5-(1-methylethenyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5R,8R,8aR)-2-(formyloxy)-8a-hydroxy-3,8-dimethyl-5-(1-methylethenyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5R,8R,8aR)-8a-hydroxy-3,8-dimethyl-5-(1-methylethenyl)-2-[(3,3,3-trifluoropropanoyl)oxy]-1,2,4a,5,6,7,8,8a-octahydronaphthalen-1-yl (2S,3aR,9bR)-6-chloro-9b -hydroxy-5-methyl-1,2,3,3a,5,9b-hexa hydropyrrolo[2,3-c][2,1]benzoxazine-2-carboxylate;

(1S,2R,4aS,5S,8R,8aR)-2-(acetyloxy)-5-[4-(ethyloxy)-1-methyl-4-oxobut-2-enyl]-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5R,8R,8aR)-2-(acetyloxy)-5-(2,2-difluoro-1-methylethenyl)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5R,8R,8aR)-2-(acetyloxy)-5-[2-fluoro-1-methylethyl]-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-[(1-methyl-2-morpholin-4-ylethyl]-1,2,4a,5,6,7,8,8a-octahydronaphthalen-1-yl (2S,3aR,9bR)-6-chloro-9b -hydroxy-5-methyl-1,2,3,3a,5,9b-hexahydropyrrolo[2,3-c][2,1]benzoxazine-2-carboxylate;

(1S,2R,4aS,5R,8R,8aR)-2-(acetyloxy)-5-(2-ethyl-1,3-thiazol-4-yl)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5R,8R,8aR)-2-(acetyloxy)-5-[2,2-difluoro-1-methylethyl]-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5R,8R,8aR)-2-(acetyloxy)-5-[2,2-difluoro-1-methylethyl]-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydro pyrrolo[2,3-c][2,1]benzoxazine-2-carboxylate;

(1S,2R,4aS,5R,8R,8aR)-2-(acetyloxy)-5-(2,2-dichloro-1-methylethenyl)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-{1-methyl-2-[(phenylmethyl)amino]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-(2-{[(2-chlorophenyl)methyl]amino}-1-methylethyl)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[(furan-2-ylmethyl)amino]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-(1-methyl-2-{[(2-methylphenyl)methyl]amino}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-(1-methyl-2-{[(1S)-1-phenylethyl]amino}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-(2-{[(3-chlorophenyl)methyl]amino}-1-methylethyl)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-[1-methyl-2-({[2-(methyloxy)phenyl]methyl}amino)ethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-[1-methyl-2-(4-pyridin-2-ylpiperazin-1-yl)ethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-(2-{bis[2-(methyloxy)ethyl]amino}-1-methylethyl)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-{1-methyl-2-[(2-thien-2-ylethyl)amino]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-[1-methyl-2-({[4-(trifluoromethyl)phenyl]methyl}amino)ethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-{1-methyl-2-[methyl(2-{[2-(methyloxy)phenyl]oxy}ethyl)amino]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-(1-methyl-2-{(1-methylethyl)[2-(phenylsulfonyl)ethyl]amino}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[(2,3-dihydro-1,4-benzodioxin-2-ylmethyl)(methyl)amino]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-[1-methyl-2-(4-{[2-(methyloxy)phenyl]methyl}piperazin-1-yl)ethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[4-(1,1-dimethylethyl)piperidin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-(1-methyl-2-{4-[(phenylmethyl)oxy]piperidin-1-yl}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[7,8-bis(methyloxy)-3,4-dihydroisoquinolin-2(1H)-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-[1-methyl-2-(methyl{[4-(methyloxy)phenyl]methyl}amino)ethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-(2-{4-[(ethyloxy)carbonyl]-1,4-diazepan-1-yl}-1-methylethyl)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-{1-methyl-2-[4-(phenylmethyl)-1,4-diazepan-1-yl]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-5-{2-[acetyl(ethyl)amino]-1-methylethyl}-2-(acetyloxy)-8a-hydroxy-3,8-dimethyl-1,2,4a,5,6,7,8,8a-octahydronaphthalen-1-yl (2S,3aR,9bR)-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-5-{2-[acetyl(cyclopropyl)amino]-1-methylethyl}-2-(acetyloxy)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-(2-{cyclopropyl[(methyloxy)carbonyl]amino}-1-methylethyl)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-(2-{ethyl[(methyloxy)carbonyl]amino}-1-methylethyl)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-(2-{[(2,5-dichlorophenyl)methyl]amino}-1-methylethyl)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-(2-{[(3,5-dichlorophenyl)methyl]amino}-1-methylethyl)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-(2-{cyclopropyl[(ethylamino)carbonyl]amino}-1-methylethyl)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-{1-methyl-2-[methyl(phenylmethyl)amino]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-{1-methyl-2-[4-(phenylmethyl)piperazin-1-yl]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-[1-methyl-2-(3-methylpiperidin-1-yl)ethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-[1-methyl-2-(4-pyrimidin-2-ylpiperazin-1-yl)ethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-(1-methyl-2-{methyl[2-(phenyloxy)ethyl]amino}ethyl)-1,2,4a,5,6,7,8,8a-octahydronaphthalen- 1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-[1-methyl-2-thiomorpholin-4-ylethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[cyclohexyl(methyl)amino]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-{1-methyl-2-[methyl(pyridin-2-ylmethyl)amino]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-[2-(3,6-dihydropyridin-1(2H)-yl)-1-methylethyl]-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-(1-methyl-2-{[phenyl(pyridin-3-yl)methyl]amino}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-{1-methyl-2-[4-(2-phenylethyl)piperazin-1-yl]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[4-(1,3-benzodioxol-5-ylmethyl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-(1-methyl-2-{4-[3-(methyloxy)phenyl]piperazin-1-yl}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-[2-(4-{[(4-chlorophenyl)methyl]oxy}piperidin-1-yl)-1-methylethyl]-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-(1-methyl-2-{4-[2-(methyloxy)phenyl]piperazin-1-yl}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[4-(furan-2-ylmethyl)piperidin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-(1-methyl-2-{4-[(3-methylphenyl)methyl]piperazin-1-yl}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[(2,2-dimethylpropanoyl)(ethyl)amino]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-{1-methyl-2-[methyl(propanoyl)amino]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-{1-methyl-2-[(1-methylethyl)(propanoyl)amino]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[(2,2-dimethylpropanoyl)(1-methylethyl)amino]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5S-(1-methyl-2-{(1-methylethyl)[(methyloxy)acetyl]amino}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[[(2-chlorophenyl)methyl](propanoyl)amino]-11-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-(2-{[(2-chlorophenyl)methyl][(methyloxy)acetyl]amino}-1-methylethyl)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-5-(2-{acetyl[(2-methylphenyl)methyl]amino}-1-methylethyl)-2-(acetyloxy)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-{1-methyl-2-[[(2-methylphenyl)methyl](propanoyl)amino]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-(1-methyl-2-{[(methyloxy)acetyl][(2-methylphenyl)methyl]amino}ethyl)-1,2,4a,5,6,7,8,8a-octahydronaphthalen-1-yl (2S,3aR,9bR)-6-chloro-9b- hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-[2-(4-{[(4-fluorophenyl)methyl]oxy}piperidin-1-yl)-1-methylethyl]-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-(2-{4-[(4-chlorophenyl)methyl]piperazin-1-yl}-1-methylethyl)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-[2-(3,4-dihydroisoquinolin-2(1H)-yl)-1-methylethyl]-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[(2R,6S)-2,6-dimethylmorpholin-4-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-{1-methyl-2-[methyl(3,3,3-trifluoropropanoyl)amino]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-{1-methyl-2-[[(2-methylphenyl)methyl](3,3,3-trifluoropropanoyl)amino]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-(1-methyl-2-{4-[(4-methylphenyl)methyl]piperazin-1-yl}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-(1-methyl-2-{4-[6-(methyloxy)pyridazin-3-yl]piperazin-1-yl}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[4-(6-chloropyrazin-2-yl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[4-(6-chloropyridin-2-yl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-[1-methyl-2-(4-phenylpiperazin-1-yl)ethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[4-(cyclohexylmethyl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-{1-methyl-2-[4-(1,3-thiazol-2-yl)piperazin-1-yl]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[4-(3-chloropyridin-2-yl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5R,8R,8aR)-2-(acetyloxy)-8a-hydroxy-3,8-dimethyl-5-{1-methyl-2-oxo-2-[(phenylmethyl)amino]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5R,8R,8aR)-2-(acetyloxy)-5-{2-[[(2-chlorophenyl)methyl](methyl)amino]-1-methyl-2-oxoethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-8a-hydroxy-3,8-dimethyl-5-(1-methylethyl)-2-{[(phenylamino)carbonyl]oxy}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-[2-(cycloheptylamino)-1-methylethyl]-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[4-(2-chloropyrimidin-4-yl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[4-(5-chloropyridin-2-yl)piperazin-1-yl]-1-methylethyl}-8a-hydroxy-3,8-dimethyl-1,2,4a,5,6,7,8,8a-octahydronaphthalen-1-yl-(2S, 3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[4-(5-chloropyrazin-2-yl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[4-(4-chlorophenyl)piperazin-1-yl]-1-methylethyl}-8a-hydroxy-3,8-dimethyl-1,2,4a,5,6,7,8,8a-octahydronaphthalen-1- yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-{1-methyl-2-[4-(4-methylphenyl)piperazin-1-yl]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[4-(2-chlorophenyl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-(1-methyl-2-{4-[3-(trifluoromethyl)phenyl]piperazin-1-yl}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-(1-methyl-2-{4-[4-(methyloxy)phenyl]piperazin-1-yl}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-(1-methyl-2-{4-[2-(trifluoromethyl)phenyl]piperazin-1-yl}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-(1-methyl-2-{4-[4-(trifluoromethyl)pyrimidin-2-yl]piperazin-1-yl}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[4-(2-fluorophenyl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-{1-methyl-2-[4-(6-methylpyridin-2-yl)piperazin-1-yl]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[4-(4-fluorophenyl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-{1-methyl-2-[4-(1,3-thiazol-2-ylcarbonyl)piperazin-1-yl]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-(1-methyl-2-{4-[(3-phenylpropyl)oxy]piperidin-1-yl}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-(1-methyl-2-{4-[5-(trifluoromethyl)pyridin-2-yl]piperazin-1-yl}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-{1-methyl-2-[4-(phenylmethyl)piperidin-1-yl]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-(1-methyl-2-{4-[3-(trifluoromethyl)pyridin-2-yl]piperazin-1-yl}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-(1-methyl-2-{4-[3-(trifluoromethyl)phenyl]piperidin-1-yl}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-[1-methyl-2-(4-{[3-(trifluoromethyl)phenyl]methyl}piperazin-1-yl)ethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-(2-{4-[({3-[(ethyloxy)carbonyl]phenyl}methyl)oxy]piperidin-1-yl}-1-methylethyl)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[4-(1,3-benzoxazol-2-yl)piperidin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-[2-(4-{[3,5-bis(trifluoromethyl)phenyl]methyl}piperazin-1-yl)-1-methylethyl]-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-(1-methyl-2-{4-[2-(methyloxy)phenyl]piperidin-1-yl}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-(2-{4-[(4-fluorophenyl)methyl]piperazin-1-yl}-1-methylethyl)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[4-(4-cyanophenyl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5- methyl-1,2,3,3a,5,9b-hexahydropyrrolo[2,3-c][2,1]
benzoxazine-2-carboxylate;

(1S,2R,4aS,5S,8R,8aR)-2-(acetyloxy)-5-{2-[4-(2,3-dihydro-1,4-benzodioxin-2-ylcarbonyl)piperazin 1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[4-(4-bromophenyl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-(1-methyl-2-{4-[4-(trifluoromethyl)phenyl]piperazin-1-yl}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[4-(2,4-difluorophenyl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-{1-methyl-2-[4-(pyridin-4-ylmethyl)piperazin-1-yl]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-(2-{4-[5-chloro-2-(methyloxy)phenyl]piperazin-1-yl}-1-methylethyl)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[4-(3,5-dichlorophenyl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-(1-methyl-2-{4-[(2E)-3-phenylprop-2-enyl]piperazin-1-yl}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[4-(diphenylmethyl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[4-(2,3-dimethylphenyl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-[2-(4-cyclopentylpiperazin-1-yl)-1-methylethyl]-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[4-(2-ethylphenyl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-(2-{4-[4-chloro-3-(trifluoromethyl)phenyl]piperazin-1-yl}-1-methylethyl)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-{1-methyl-2-[4-(thien-2-ylcarbonyl)piperazin-1-yl]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-[2-(4-{[(butylamino)carbonyl]oxy}piperidin-1-yl)-1-methylethyl]-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[4-(2,4-dimethylphenyl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[4-(2,5-dimethylphenyl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-[2-(4-cyclopropylpiperazin-1-yl)-1-methylethyl]-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[4-(cyclopentylcarbonyl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-(1-methyl-2-{4-[6-(methyloxy)pyridin-2-yl]piperazin-1-yl}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[4-(3,5-dimethylphenyl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[4-(3,6-dimethylpyrazin-2-yl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b- hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[4-(2,6-dimethylphenyl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-[(1S)-1-methyl-2-pyridin-3-ylethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-[1-methyl-2-(3-oxa-9-azabicyclo[3.3.1]non-9-yl)ethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-{1-methyl-2-[4-(4-methylpentanoyl)piperazin-1-yl]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-[1-methyl-2-(4-oxo-1,3,4,6,7,11b-hexahydro-2H-pyrazino[2,1-a]isoquinolin-2-yl)ethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[3-[(ethyloxy)carbonyl]octahydroisoquinolin-2(1H)-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-(2-{4-[3,5-bis(methyloxy)phenyl]piperazin-1-yl}-1-methylethyl)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[4-(2-cyanophenyl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-[1-methyl-2-(4-phenylpiperidin-1-yl)ethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[4-(3,4-dimethylphenyl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[cyclopropyl(propanoyl)amino]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[(cyclopropylcarbonyl)(phenyl)amino]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[(cyclohexylmethyl)(cyclopropylcarbonyl)amino]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[(cyclohexylmethyl)(propanoyl)amino]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[(cyclopropylcarbonyl)(methyl)amino]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-{1-methyl-2-[methyl(phenylcarbonyl)amino]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-(1-methyl-2-{methyl[(phenyloxy)acetyl]amino}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[4-(4-amino-5-cyano-6-methylpyrimidin-2-yl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[(2S,5R)-2,5-dimethyl-4-prop-2-enylpiperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-[2-(8-azabicyclo[3.2.1]oct-8-yl)-1-methylethyl]-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[(3S,8aR)-3-(phenylmethyl)hexahydropyrrolo[1,2-a]pyrazin-2(1H)-yl]-1-methylethyl}-8a-hydroxy-3, 8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-[2-(3-{[(3,4-difluorophenyl)methyl]oxy}piperidin-1-yl)-1-methylethyl]-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-{1-methyl-2-[(3R)-3-(methyloxy)piperidin-1-yl]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-{1-methyl-2-[1-methyl-6,7-bis(methyloxy)-3,4-dihydroisoquinolin-2(1H)-yl]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-[1-methyl-2-(2-methyl-4-piperidin-1-yl-5,8-dihydropyrido[3,4-d]pyrimidin-7(6H)-yl)ethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[4-(4-chlorophenyl)-6,7-dihydrothieno[3,2-c]pyridin-5(4H)-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-[1-methyl-2-(3-{[4-(methyloxy)phenyl]sulfanyl}-8-azabicyclo[3.2.1]oct-8-yl)ethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-{1-methyl-2-[4-(4-methylpiperazin-1-yl)piperidin-1-yl]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-(2-{3-[(3-chloropyridin-2-yl)oxy]piperidin-1-yl}-1-methylethyl)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-{1-methyl-2-[4-(3-methylquinoxalin-2-yl)piperazin-1-yl]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-5-{2-[7-(hydroxymethyl)-3-azabicyclo[3.3.1]non-3-yl]-1-methylethyl}-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-[2-(3,11-diazatricyclo[7.3.1.0~2,7~]trideca-2,4,6-trien-11-yl)-1-methylethyl]-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-[2-(4,10-diazatricyclo[6.3.1.0~2,7~]dodeca-2,4,6-trien-10-yl)-1-methylethyl]-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-5-{2-[(4aR,9aS)-2,3,4,4a,9,9a-hexahydro-1H-indeno[2,1-b]pyridin-1-yl]-1-methylethyl}-2-(acetyloxy)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-[2-(3-cyclohexyl-3-methylpiperidin-1-yl)-1-methylethyl]-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-5-[2-(4-{[2-(2-hydroxyethyl)oxy]ethyl}piperazin-1-yl)-1-methylethyl]-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-[1-methyl-2-(3-methyl-3-pyridin-2-ylpiperidin-1-yl)ethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[4-(3,5-dichloropyridin-4-yl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-{1-methyl-2-[(3S)-3-methyl-3-phenylpiperidin-1-yl]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-(2-{3-[(4-fluorophenyl)sulfanyl]-8-azabicyclo[3.2.1]oct-8-yl}-1-methylethyl)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-1-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-(1-methyl-2-{4-[(pyridin-2-ylsulfanyl)methyl]piperidin-1-yl}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-(1-methyl-2-{3-[(pyridin-2-ylsulfanyl)methyl]piperidin-1-yl}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-[1-methyl-2-(2-{[methyl(methyloxy)amino]carbonyl}piperidin-1-yl)ethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-(2-{4-[(3,4-dichlorophenyl)methyl]piperazin-1-yl}-1-methylethyl)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-{1-methyl-2-[2-(2-piperidin-1-ylethyl)piperidin-1-yl]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-{1-methyl-2-[(1-methylethyl)(2-{[2-(methyloxy)phenyl]oxy}ethyl)amino]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-{1-methyl-2-[methyl(2-phenylcyclopropyl)amino]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-(1-methyl-2-{methyl[3-(1,2,4,5-tetrahydro-3H-3-benzazepin-3-yl)propyl]amino}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[{2-[(2,6-dichlorophenyl)oxy]ethyl}(methyl)amino]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[[(4-chlorophenyl)methyl](ethyl)amino]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-(1-methyl-2-{methyl[(3-methylthien-2-yl)methyl]amino}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[4-(3-chloro-4-methylphenyl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[(diphenylmethyl)(methyl)amino]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-(1-methyl-2-{4-[5-methyl-2-(methyloxy)phenyl]piperazin-1-yl}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-(2-{4-[2-(ethyloxy)phenyl]piperazin-1-yl}-1-methylethyl)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-(1-methyl-2-{(2S,4R)-4-methyl-2-[(methyloxy)carbonyl]piperidin-1-yl}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]berizoxazine-2-carboxylate;

(1S,2R,4aS,5S,8R,8aR)-2-(acetyloxy)-8a-hydroxy-5-{2-[(2S)-2-(2-hydroxyethyl)piperidin-1-yl]-1-methylethyl}-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-{1-methyl-2-[(3S)-3-(methyloxy)piperidin-1-yl]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-(1-methyl-2-{2-[(methyloxy)carbonyl]octahydro-1H-indol-1-yl}ethyl)-1,2,4a,5,6,7,8,8a-octahydronaphthalen-1-yl (2S,3aS,9bS)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-{1-methyl-2-[(2S)-4-methyl-2-[(methyloxy)carbonyl]-3,6-dihydropyridin-1(2H)-yl]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-5-[2-(3-hydroxy-8-azabicyclo[3.2.1]oct-8-yl)-1-methylethyl]-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-[1-methyl-2-(3-methyl-3-phenylpiperidin-1-yl)ethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-(1-methyl-2-{(phenylmethyl)[2-(phenyloxy)ethyl]amino}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-((1R)-1-methyl-2-{4-[4-(trifluoromethyl)-2-pyrimidinyl]-1-piperazinyl}ethyl)-1,2,4a,5,6,7,8,8a-octahydro-1-naphthalenyl (2S,3aR,9bR)-6-chloro-9b-hydroxy-5-methyl-1,2,3,3a,5,9b-hexahydropyrrolo[2,3-c][2,1]benzoxazine-2-carboxylate-TFA salt;

(1S,2R,4aS,5S,8R,8aR)-2-(acetyloxy)-8a-hydroxy-3,8-dimethyl-5-((1R)-1-methyl-2-{4-[5-(trifluoromethyl)-2-pyridinyl]-1-piperazinyl}ethyl)-1,2,4a,5,6,7,8,8a-octahydro-1-naphthalenyl (2S,3aR,9bR)-6-chloro-9b- hydroxy-5-methyl-1,2,3,3a,5,9b-hexahydropyrrolo[2,3-c][2,1]benzoxazine-2-carboxylate-TFA salt;

(1S,2R,5S,8R,8aR)-2-(acetyloxy)-5-((1R)-2-{4-[bis(4-fluorophenyl)methyl]piperazin-1-yl}-1-methylethyl)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,5S,8R,8aR)-2-(acetyloxy)-5-{(1R)-2-[4-(5-chloropyrimidin-2-yl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{(1R)-2-[4-(5-bromopyrimidin-2-yl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{(1R)-2-[4-(6-chloro-1,3-benzothiazol-2-yl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-((1R)-2-{4-[(3,4-dichlorophenyl)methyl]piperazin-1-yl}-1-methylethyl)-8a-hydroxy-3,8-dimethyl-1, 2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-((1R)-1-methyl-2-{4-[5-(trifluoromethyl)pyrimidin-2-yl]piperazin-1-yl}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate; and (1S,2R,4aS,5S,8R,8aR)-2-(acetyloxy)-5-((1R)-2-{4-[(4-chlorophenyl)oxy]piperidin-1-yl}-1-methylethyl)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate.

10. A compound of claim 1, selected from:

(1S,2R,4aS,5S,8R,8aR)-2-(acetyloxy)-8a-hydroxy-3,8-dimethyl-5-(1-methylethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5R,8R,8aR)-8a-hydroxy-3,8-dimethyl -5-(1-methylethenyl)-2-[(2-methylpropanoyl)oxy]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5R,8R,8aR)-2-(hexanoyloxy)-8a-hydroxy-3,8-dimethyl-5-(1-methylethenyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5R,8R,8aR)-2-(acetyloxy)-5-[2-(acetyloxy)-1-methylethyl]-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5R,8R,8aR)-2-(acetyloxy)-8a-hydroxy -3,8-dimethyl-5-{1-methyl-2-[(2-methylpropanoyl)oxy]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5R,8R,8aR)-2-[(cyclopropylcarbonyl)oxy]-8a-hydroxy-3,8-dimethyl-5-(1-methylethenyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-8a-hydroxy-3,8-dimethyl -5-(1-methylethyl)-2-{[(prop-2-ynyloxy)carbonyl]oxy}-1,2,4a,5,6,7,8,8a-octahydronaphthalen-1-yl (2S,3aR,9bR)-6-chloro-9b-hydroxy-5-methyl-1,2,3,3a,5,9b-hexahydro pyrrolo[2,3-c][2,1]benzoxazine-2-carboxylate;

(1S,2R,4aS,5S,8R,8aR)-8a-hydroxy-3,8-dimethyl -5-(1-methylethyl)-2-({[(2,2,-trichloroethyl)oxy]carbonyl}oxy)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-8a-hydroxy-3,8-dimethyl-2-({[(1-methylethyl)oxy]carbonyl}oxy)-5-(1-methylethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate; and (1S,2R,4aS,5S,8R,8aR)-8a-hydroxy-3,8-dimethyl-5-(1-methylethyl)-2-{[(prop-2-enyloxy)carbonyl]oxy}-1,2,4a,5,6,7,8,8a-octahydronaphthalen-1-yl (2S,3aR,9bR)-6-chloro-9b-hydroxy-5-methyl-1,2,3,3a,5,9b-hexahydro pyrrolo[2,3-c][2,1]benzoxazine-2-carboxylate.

11. A compound of claim 1, selected from:

(1S,2R,4aS,5S,8R,8aR)-1-({[(2S,3aR,9bR)-6-chloro-9b-hydroxy-5-methyl-1,2,3,3a,5,9b-hexahydropyrrolo[2,3-c][2,1]benzoxazin-2-yl]carbonyl}oxy)-8a-hydroxy-3,8-dimethyl-5-(1-methylethenyl)-1,2,4a,5,6,7,8,8a-octahydronaphthalen-2-yl methyl butanedioate;

(1S,2R,4aS,5S,8R,8aR)-8a-hydroxy-3,8-dimethyl -5-(1-methylethenyl)-2-(pent-4-enoyloxy)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5R,8R,8aR)-2-(acetyloxy)-8a-hydroxy -3,8-dimethyl-5-{1-methyl-2-[({[2-(naphthalen-1-ylamino)ethyl]amino}carbonyl)oxy]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5R,8R,8aR)-2-{[(acetyloxy)acetyl]oxy}-8a-hydroxy-3,8-dimethyl-5-(1-methylethenyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5R,8R,8aR)-2-(formyloxy)-8a-hydroxy-3,8-dimethyl-5-(1-methylethenyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5R,8R,8aR)-8a-hydroxy-3,8-dimethyl-5-(1-methylethenyl)-2-[(3,3,3-trifluoropropanoyl)oxy]-1,2,4a,5,6,7,8,8a-octahydronaphthalen-1-yl (2S,3aR,9bR)-

6-chloro-9b-hydroxy-5-methyl-1,2,3,3a,5,9b-hexa hydropyrrolo[2,3-c][2,1]benzoxazine-2-carboxylate;

(1S,2R,4aS,5S,8R,8aR)-2-(acetyloxy)-5-[4-(ethyloxy)-1-methyl-4-oxobut-2-enyl]-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5R,8R,8aR)-2-(acetyloxy)-5-(2,2-difluoro-1-methylethenyl)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5R,8R,8aR)-2-(acetyloxy)-5-[2-fluoro-1-methylethyl]-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-[(1-methyl-2-morpholin-4-ylethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate.

12. A compound of claim 1 selected from:

(1S,2R,4aS,5R,8R,8aR)-2-(acetyloxy)-5-(2-ethyl-1,3-thiazol-4-yl)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5R,8R,8aR)-2-(acetyloxy)-5-[2,2-difluoro-1-methylethyl]-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydro pyrrolo[2,3-c][2,1]benzoxazine-2-carboxylate;

(1S,2R,4aS,5R,8R,8aR)-2-(acetyloxy)-5-[2,2-difluoro-1-methylethyl]-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydro pyrrolo[2,3-c][2,1]benzoxazine-2-carboxylate;

(1S,2R,4aS,5R,8R,8aR)-2-(acetyloxy)-5-(2,2-dichloro-1-methylethenyl)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-{1-methyl-2-[(phenylmethyl)amino]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-(2-{[(2-chlorophenyl)methyl]amino}-1-methylethyl)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[(furan-2-ylmethyl)amino]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-(1-methyl-2-{[(2-methylphenyl)methyl]amino}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-(1-methyl-2-{[(1S)-1-phenylethyl]amino}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate; and (1S,2R,4aS,5S,8R,8aR)-2-(acetyloxy)-5-(2-{[(3-chlorophenyl)methyl]amino}-1-methylethyl)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate.

13. A compound of claim 1 selected from:

(1S,2R,4aS,5S,8R,8aR)-2-(acetyloxy)-8a-hydroxy-3,8-dimethyl-5-[1-methyl-2-({[2-(methyloxy)phenyl]methyl}amino)ethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-[1-methyl-2-(4-pyridin-2-ylpiperazin-1-yl)ethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-(2-{bis[2-(methyloxy)ethyl]amino}-1-methylethyl)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-{1-methyl-2-[(2-thien-2-ylethyl)amino]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-[1-methyl-2-({[4-(trifluoromethyl)phenyl]methyl}amino)ethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-{1-methyl-2-[methyl(2-{[2-(methyloxy)phenyl]oxy}ethyl)amino]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-(1-methyl-2-{(1-methylethyl)[2-(phenylsulfonyl)ethyl]amino}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[(2,3-dihydro-1,4-benzodioxin-2-ylmethyl)(methyl)amino]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-[1-methyl-2-(4-{[2-(methyloxy)phenyl]

methyl}piperazin-1-yl)ethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate; and (1S,2R,4aS,5S,8R,8aR)-2-(acetyloxy)-5-{2-[4-(1,1-dimethylethyl)piperidin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate.

14. A compound of claim 1 selected from:

(1S,2R,4aS,5S,8R,8aR)-2-(acetyloxy)-8a-hydroxy-3,8-dimethyl-5-(1-methyl-2-{4-[(phenylmethyl)oxy]piperidin-1-yl}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[7,8-bis(methyloxy)-3,4-dihydroisoquinolin-2(1H)-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-[1-methyl-2-(methyl{[4-(methyloxy)phenyl]methyl}amino)ethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-(2-{4-[(ethyloxy)carbonyl]-1,4-diazepan-1-yl}-1-methylethyl)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-{1-methyl-2-[4-(phenylmethyl)-1,4-diazepan-1-yl]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-5-{2-[acetyl(ethyl)amino]-1-methylethyl}-2-(acetyloxy)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-5-{2-[acetyl(cyclopropyl)amino]-1-methylethyl}-2-(acetyloxy)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-(2-{cyclopropyl[(methyloxy)carbonyl]amino}-1-methylethyl)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-(2-{ethyl[(methyloxy)carbonyl]amino}-1-methylethyl)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate; and (1S,2R,4aS,5S,8R,8aR)-2-(acetyloxy)-5-(2-{[(2,5-dichlorophenyl)methyl]amino}-1-methylethyl)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate.

15. A compound of claim 1 selected from:

(1S,2R,4aS,5S,8R,8aR)-2-(acetyloxy)-5-(2-{[(3,5-dichlorophenyl)methyl]amino}-1-methylethyl)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-(2-{cyclopropyl[(ethylamino)carbonyl]amino}-1-methylethyl)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-{1-methyl-2-[methyl(phenylmethyl)amino]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-{1-methyl-2-[4-(phenylmethyl)piperazin-1-yl]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-[1-methyl-2-(3-methylpiperidin-1-yl)ethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-[1-methyl-2-(4-pyrimidin-2-ylpiperazin-1-yl)ethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-(1-methyl-2-{methyl[2-(phenyloxy)ethyl]amino}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-[1-methyl-2-thiomorpholin-4-ylethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[cyclohexyl(methyl)amino]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate; and (1S,2R,4aS,5S,8R,8aR)-2-(acetyloxy)-8a-hydroxy-3,8-dimethyl-5-{1-methyl-2-[methyl(pyridin-2-ylmethyl)amino]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate.

16. A compound of claim 1 selected from the group consisting of:

(1S,2R,4aS,5S,8R,8aR)-2-(acetyloxy)-5-[2-(3,6-dihydro-pyridin-1(2H)-yl)-1-methylethyl]-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-(1-methyl-2-{[phenyl(pyridin-3-yl)methyl]amino}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-{1-methyl-2-[4-(2-phenylethyl)piperazin-1-yl]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[4-(1,3-benzodioxol-5-ylmethyl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-(1-methyl-2-{4-[3-(methyloxy)phenyl]piperazin-1-yl}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-[2-(4-{[(4-chlorophenyl)methyl]oxy}piperidin-1-yl)-1-methylethyl]-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-(1-methyl-2-{4-[2-(methyloxy)phenyl]piperazin-1-yl}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[4-(furan-2-ylmethyl)piperidin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-(1-methyl-2-{4-[(3-methylphenyl)methyl]piperazin-1-yl}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate; and (1S,2R,4aS,5S,8R,8aR)-2-(acetyloxy)-5-{2-[(2,2-dimethylpropanoyl)(ethyl)amino]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate.

17. A compound of claim 1 selected from:

(1S,2R,4aS,5S,8R,8aR)-2-(acetyloxy)-8a-hydroxy-3,8-dimethyl-5-{1-methyl-2-[methyl(propanoyl)amino]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-{1-methyl-2-[(1-methylethyl)(propanoyl)amino]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[(2,2-dimethylpropanoyl)(1-methylethyl)amino]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-(1-methyl-2-{(1-methylethyl)[(methyloxy)acetyl]amino}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[[(2-chlorophenyl)methyl](propanoyl)amino]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-(2-{[(2-chlorophenyl)methyl][(methyloxy)acetyl]amino}-1-methylethyl)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-5-(2-{acetyl[(2-methylphenyl)methyl]amino}-1-methylethyl)-2-(acetyloxy)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy -3,8-dimethyl-5-{1-methyl-2-[[(2-methylphenyl)methyl](propanoyl)amino]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-(1 methyl-2-{[(methyloxy)acetyl][(2-methylphenyl)methyl]amino}ethyl)-1,2,4a,5,6,7,8,8a-octahydronaphthalen-1-yl, (2S,3aR,9bR)-6-chloro-9b-hydroxy-5-methyl-1,2,3,3a,5,9b-hexahydropyrrolo[2,3-c][2,1]benzoxazine-2-carboxylate; and (1S,2R,4aS,5S,8R,8aR)-2-(acetyloxy)-5-[2-(4-{[(4-fluorophenyl)methyl]oxy}piperidin-1-yl)-1-methylethyl]-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate.

18. A compound of claim 1 selected from;

(1S,2R,4aS,5S,8R,8aR)-2-(acetyloxy)-5-(2-{4-[(4-chlorophenyl)methyl]piperazin-1-yl}-1-methylethyl)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-[2-(3,4-dihydroisoquinolin-2(1H)-yl)-1-methylethyl]-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[(2R,6S)-2,6-dimethylmorpholin-4-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-{1-methyl-2-[methyl(3,3,3-trifluoropropanoyl)amino]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-{1-methyl-2-[[(2-methylphenyl)methyl](3,3,3-trifluoropropanoyl)amino]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-(1-methyl-2-{4-[(4-methylphenyl)methyl]piperazin-1-yl}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-(1-methyl-2-{4-[6-(methyloxy)pyridazin-3-yl]piperazin-1-yl}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[4-(6-chloropyrazin-2-yl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[4-(6-chloropyridin-2-yl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate; and (1S,2R,4aS,5S,8R,8aR)-2-(acetyloxy)-8a-hydroxy-3,8-dimethyl-5-[1-methyl-2-(4-phenylpiperazin-1-yl)ethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate.

19. A compound of claim 1 selected from:

(1S,2R,4aS,5S,8R,8aR)-2-(acetyloxy)-5-{2-[4-(cyclohexylmethyl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-{1-methyl-2-[4-(1,3-thiazol-2-yl)piperazin-1-yl]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[4-(3-chloropyridin-2-yl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5R,8R,8aR)-2-(acetyloxy)-8a-hydroxy-3,8-dimethyl-5-{1-methyl-2-oxo-2-[(phenylmethyl)amino]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5R,8R,8aR)-2-(acetyloxy)-5-{2-[[(2-chlorophenyl)methyl](methyl)amino]-1-methyl-2-oxoethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-8a-hydroxy-3,8-dimethyl-5-(1-methylethyl)-2-{[(phenylamino)carbonyl]oxy}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-[2-(cycloheptylamino)-1-methylethyl]-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[4-(2-chloropyrimidin-4-yl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[4-(5-chloropyridin-2-yl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate; and (1S,2R,4aS,5S,8R,8aR)-2-(acetyloxy)-5-{2-[4-(5-chloropyrazin-2-yl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate.

20. A compound of claim 1 selected from:

(1S,2R,4aS,5S,8R,8aR)-2-(acetyloxy)-5-{2-[4-(4-chlorophenyl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-{1-methyl-2-[4-(4-methylphenyl)piperazin-1-yl]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[4-(2-chlorophenyl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-(1-methyl-2-{4-[3-(trifluoromethyl)phenyl]piperazin-1-yl}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-(1-methyl-2-{4-[4-(methyloxy)phenyl]piperazin-1-yl}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-(1-methyl-2-{4-[2-(trifluoromethyl)phenyl]piperazin-1-yl}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-(1-methyl-2-{4-[4-(trifluoromethyl)pyrimidin-2-yl]piperazin-1-yl}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[4-(2-fluorophenyl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-{1-methyl-2-[4-(6-methylpyridin-2-yl)piperazin-1-yl]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate; and (1S,2R,4aS,5S,8R,8aR)-2-(acetyloxy)-5-{2-[4-(4-fluorophenyl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate.

21. A compound of claim 1 selected from:

(1S,2R,4aS,5S,8R,8aR)-2-(acetyloxy)-8a-hydroxy-3,8-dimethyl-5-{1-methyl-2-[4-(1,3-thiazol-2-ylcarbonyl)piperazin-1-yl]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-(1-methyl-2-{4-[(3-phenylpropyl)oxy]piperidin-1-yl}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-(1-methyl-2-{4-[5-(trifluoromethyl)pyridin-2-yl]piperazin-1-yl}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-{1-methyl-2-[4-(phenylmethyl)piperidin-1-yl]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-(1-methyl-2-{4-[3-(trifluoromethyl)pyridin-2-yl]piperazin-1-yl}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-(1-methyl-2-{4-[3-(trifluoromethyl)phenyl]piperidin-1-yl}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-[1-methyl-2-(4-{[3-(trifluoromethyl)phenyl]methyl}piperazin-1-yl)ethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-(2-{4-[({3-[(ethyloxy)carbonyl]phenyl}methyl)oxy]piperidin-1-yl}-1-methylethyl)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[4-(1,3-benzoxazol-2-yl)piperidin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate; and (1S,2R,4aS,5S,8R,8aR)-2-(acetyloxy)-5-[2-(4-{[3,5-bis(trifluoromethyl)phenyl]methyl}piperazin-1-yl)-1-methylethyl]-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate.

22. A compound of claim 1 selected from;

(1S,2R,4aS,5S,8R,8aR)-2-(acetyloxy)-8a-hydroxy-3,8-dimethyl-5-(1-methyl-2-{4-[2-(methyloxy)phenyl]piperidin-1-yl}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-(2-{4-[(4-fluorophenyl)methyl]piperazin-1-yl}-1-methylethyl)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[4-(4-cyanophenyl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[4-(2,3-dihydro-1,4-benzodioxin-2-ylcarbonyl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[4-(4-bromophenyl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-(1-methyl-2-{4-[4-(trifluoromethyl)phenyl]piperazin-1-yl}ethyl)-1,2,4a,5,6,7,8,8a-octahydronaphthalen-1-yl, (2S,3aR,9bR)-6-chloro-9b- hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[4-(2,4-difluorophenyl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-{1-methyl-2-[4-(pyridin-4-ylmethyl)piperazin-1-yl]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate; and (1S,2R,4aS,5S,8R,8aR)-2-(acetyloxy)-5-(2-{4-[5-chloro-2-(methyloxy)phenyl]piperazin-1-yl}-1-methylethyl)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate.

23. A compound of claim 1 selected from:
(1S,2R,4aS,5S,8R,8aR)-2-(acetyloxy)-5-{2-[4-(3,5-dichlorophenyl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-(1-methyl-2-{4-[(2E)-3-phenylprop-2-enyl]piperazin-1-yl}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[4-(diphenylmethyl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[4-(2,3-dimethylphenyl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-[2-(4-cyclopentylpiperazin-1-yl)-1-methylethyl]-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[4-(2-ethylphenyl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-(2-{4-[4-chloro-3-(trifluoromethyl)phenyl]piperazin-1-yl}-1-methylethyl)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-{1-methyl-2-[4-(thien-2-ylcarbonyl)piperazin-1-yl]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-[2-(4-{[(butylamino)carbonyl]oxy}piperidin-1-yl)-1-methylethyl]-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate; and (1S,2R,4aS,5S,8R,8aR)-2-(acetyloxy)-5-{2-[4-(2,4-dimethylphenyl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate.

24. A compound of claim 1 selected from:
(1S,2R,4aS,5S,8R,8aR)-2-(acetyloxy)-5-{2-[4-(2,5-dimethylphenyl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-[2-(4-cyclopropylpiperazin-1-yl)-1-methylethyl]-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[4-(cyclopentylcarbonyl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-(1-methyl-2-{4-[6-(methyloxy)pyridin-2-yl]piperazin-1-yl}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[4-(3,5-dimethylphenyl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[4-(3,6-dimethylpyrazin-2-yl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[4-(2,6-dimethylphenyl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-[(1S)-1-methyl-2-pyridin-3-ylethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-[1-methyl-2-(3-oxa-9-azabicyclo[3.3.1]non-9-yl)ethyl]-1,2,4a,5,6,7,8,8a-octahydronaphthalen-1-yl (2S,3aR,9bR)-6-chloro-9b-hydroxy-5-methyl- 1,2,3,3a,5,9b-hexahydropyrrolo[2,3-c][2,1]
benzoxazine-2-carboxylate; and (1S,2R,4aS,5S,8R,8aR)-2-(acetyloxy)-8a-hydroxy-3,8-dimethyl-5-{1-methyl-2-[4-(4-methylpentanoyl)piperazin-1-yl]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate.

25. A compound of claim 1 selected from:

(1S,2R,4aS,5S,8R,8aR)-2-(acetyloxy)-8a-hydroxy-3,8-dimethyl-5-[1-methyl-2-(4-oxo-1,3,4,6,7,11b-hexahydro-2H-pyrazino[2,1-a]isoquinolin-2-yl)ethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[3-[(ethyloxy)carbonyl]octahydroisoquinolin-2(1H)-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-(2-{4-[3,5-bis(methyloxy)phenyl]piperazin-1-yl}-1-methylethyl)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[4-(2-cyanophenyl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-[1-methyl-2-(4-phenylpiperidin-1-yl)ethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[4-(3,4-dimethylphenyl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[cyclopropyl(propanoyl)amino]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[(cyclopropylcarbonyl)(phenyl)amino]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[(cyclohexylmethyl)(cyclopropylcarbonyl)amino]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate; and (1S,2R,4aS,5S,8R,8aR)-2-(acetyloxy)-5-{2-[(cyclohexylmethyl)(propanoyl)amino]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate.

26. A compound of claim 1 selected from:

(1S,2R,4aS,5S,8R,8aR)-2-(acetyloxy)-5-{2-[(cyclopropylcarbonyl)(methyl)amino]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-{1-methyl-2-[methyl(phenylcarbonyl)amino]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-(1-methyl-2-{methyl[(phenyloxy)acetyl]amino}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[4-(4-amino-5-cyano-6-methylpyrimidin-2-yl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[(2S,5R)-2,5-dimethyl-4-prop-2-enylpiperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-[2-(8-azabicyclo[3.2.1]oct-8-yl)-1-methylethyl]-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[(3S,8aR)-3-(phenylmethyl)hexahydropyrrolo[1,2-a]pyrazin-2(1H)-yl]-1-methylethyl}-8a-hydroxy-3, 8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-[2-(3-{[(3,4-difluorophenyl)methyl]oxy}piperidin-1-yl)-1-methylethyl]-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-{1-methyl-2-[(3R)-3-(methyloxy)piperidin-1-yl]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate; and (1S,2R,4aS,5S,8R,8aR)-2-(acetyloxy)-8a-hydroxy-3,8-dimethyl-5-{1-methyl-2-[1-methyl-6,7-bis(methyloxy)-3,4-dihydroisoquinolin-2(1H)-yl]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate.

27. A compound of claim 1 selected from:

(1S,2R,4aS,5S,8R,8aR)-2-(acetyloxy)-8a-hydroxy-3,8-dimethyl-5-[1-methyl-2-(2-methyl-4-piperidin-1-yl-5,8-dihydropyrido[3,4-d]pyrimidin-7(6H)-yl)ethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[4-(4-chlorophenyl)-6,7-dihydrothieno[3,2-c]pyridin-5(4H)-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-[1-methyl-2-(3-{[4-(methyloxy)phenyl]sulfanyl}-8-azabicyclo[3.2.1]oct-8-yl)ethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-{1-methyl-2-[4-(4-methylpiperazin-1-yl)piperidin-1-yl]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-(2-{3-[(3-chloropyridin-2-yl)oxy]piperidin-1-yl}-1-methylethyl)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-{1-methyl-2-[4-(3-methylquinoxalin-2-yl)piperazin-1-yl]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-5-{2-[7-(hydroxymethyl)-3-azabicyclo[3.3.1]non-3-yl]-1-methylethyl}-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-[2-(3,11-diazatricyclo[7.3.1.0~2,7~]trideca-2,4,6-trien-11-yl)-1-methylethyl]-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-[2-(4,10-diazatricyclo[6.3.1.0~2,7~]dodeca-2,4,6-trien-10-yl)-1-methylethyl]-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate; and (1S,2R,4aS,5S,8R,8aR)-5-{2-[(4aR,9aS)-2,3,4,4a,9,9a-hexahydro-1H-indeno[2,1-b]pyridin-1-yl]-1-methylethyl}-2-(acetyloxy)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate.

28. A compound of claim 1 selected from:

(1S,2R,4aS,5S,8R,8aR)-2-(acetyloxy)-5-[2-(3-cyclohexyl-3-methylpiperidin-1-yl)-1-methylethyl]-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-5-[2-(4-{2-[(2-hydroxyethyl)oxy]ethyl}piperazin-1-yl)-1-methylethyl]-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-[1-methyl-2-(3-methyl-3-pyridin-2-ylpiperidin-1-yl)ethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[4-(3,5-dichloropyridin-4-yl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-{1-methyl-2-[(3S)-3-methyl-3-phenylpiperidin-1-yl]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-(2-{3-[(4-fluorophenyl)sulfanyl]-8-azabicyclo[3.2.1]oct-8-yl}-1-methylethyl)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-(1-methyl-2-{4-[(pyridin-2-ylsulfanyl)methyl]piperidin-1-yl}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-(1-methyl-2-{3-[(pyridin-2-ylsulfanyl)methyl]piperidin-1-yl}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-[1-methyl-2-(2-{[methyl(methyloxy)amino]carbonyl}piperidin-1-yl)ethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate; and (1S,2R,4aS,5S,8R,8aR)-2-(acetyloxy)-5-(2-{4-[(3,4-dichlorophenyl)methyl]piperazin-1-yl}-1-methylethyl)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate.

29. A compound of claim 1 selected from:

(1S,2R,4aS,5S,8R,8aR)-2-(acetyloxy)-8a-hydroxy-3,8-dimethyl-5-{1-methyl-2-[2-(2-piperidin-1-ylethyl)piperidin-1-yl]ethyl}-1,2,4a,5,6,7,8,8a-octahydronaphthalen-1-yl (2S,3aR,9bR)-6-chloro-9b-hydroxy-5-methyl- 1,2,3,3a,5,9b-hexahydropyrrolo[2,3-c][2,1]
benzoxazine-2-carboxylate;

(1S,2R,4aS,5S,8R,8aR)-2-(acetyloxy)-8a-hydroxy-3,8-dimethyl-5-{1-methyl-2-[(1-methylethyl)(2-{[2-(methyloxy)phenyl]oxy}ethyl)amino]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-{1-methyl-2-[methyl(2-phenylcyclopropyl)amino]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-(1-methyl-2-{methyl[3-(1,2,4,5-tetrahydro-3H-3-benzazepin-3-yl)propyl]amino}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[{2-[(2,6-dichlorophenyl)oxy]ethyl}(methyl)amino]-1-methylethyl}-8a-hydroxy-3,8-dimethyl-1-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[[(4-chlorophenyl)methyl](ethyl)amino]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-(1-methyl-2-{methyl[(3-methylthien-2-yl)methyl]amino}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[4-(3-chloro-4-methylphenyl)piperazin-1-yl]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-5-{2-[(diphenylmethyl)(methyl)amino]-1-methylethyl}-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate; and (1S,2R,4aS,5S,8R,8aR)-2-(acetyloxy)-8a-hydroxy-3,8-dimethyl-5-(1-methyl-2-{4-[5-methyl-2-(methyloxy)phenyl]piperazin-1-yl}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate.

30. A compound of claim 1 selected from:
(1S,2R,4aS,5S,8R,8aR)-2-(acetyloxy)-5-(2-{4-[2-(ethyloxy)phenyl]piperazin-1-yl}-1-methylethyl)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-(1-methyl-2-{(2S,4R)-4-methyl-2-[(methyloxy)carbonyl]piperidin-1-yl}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-5-{2-[(2S)-2-(2-hydroxyethyl)piperidin-1-yl]-1-methylethyl}-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-{1-methyl-2-[(3S)-3-(methyloxy)piperidin-1-yl]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-(1-methyl-2-{2-[(methyloxy)carbonyl]octahydro-1H-indol-1-yl}ethyl)-1,2,4a,5,6,7,8,8a-octahydronaphthalen-1-yl (2S,3aS,9bS)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-{1-methyl-2-[(2S)-4-methyl-2-[(methyloxy)carbonyl]-3,6-dihydropyridin-1(2H)-yl]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-5-[2-(3-hydroxy-8-azabicyclo[3.2.1]oct-8-yl)-1-methylethyl]-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-[1-methyl-2-(3-methyl-3-phenylpiperidin-1-yl)ethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-carboxylate;

(1S,2R,4aS,5S,8R,8aR)-2-(acetyloxy)-8a-hydroxy-3,8-dimethyl-5-(1-methyl-2-{(phenylmethyl)[2-(phenyloxy)ethyl]amino}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate; and (1S,2R,4aS,5S,8R,8aR)-2-(acetyloxy)-8a-hydroxy-3,8-dimethyl-5-((1R)-1-methyl-2-{4-[4-(trifluoromethyl)-2-pyrimidinyl]-1-piperazinyl}ethyl)-1,2,4a,5,6,7,8,8a-octahydro-1-naphthalenyl (2S,3aR,9bR)-6-chloro-9b-hydroxy-5-methyl-1,2,3,3a,5,9b-hexahydropyrrolo[2,3-c][2,1]benzoxazine-2-carboxylate-TFA salt.

31. A compound of claim 1 selected from:
(1S,2R,4aS,5S,8R,8aR)-2-(acetyloxy)-5-(2-{4-[2-(ethyloxy)phenyl]piperazin-1-yl}-1-methylethyl)-8a-hydroxy-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-(1-methyl-2-{(2S,4R)-4-methyl-2-[(methyloxy)carbonyl]piperidin-1-yl}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-5-{2-[(2S)-2-(2-hydroxyethyl)piperidin-1-yl]-1-methylethyl}-3,8-dimethyl-1,2,4a,5,6,7,8,8a-octahydronaphthalen-1-yl (2S,3aR,9bR)-6-chloro-9b-hydroxy-5-methyl-1,2,3,3a,5-9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-{1-methyl-2-[(3S)-3-(methyloxy)piperidin-1-yl]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-(1-methyl-2-{2-[(methyloxy)carbonyl]octahydro-1H-indol-1-yl}ethyl)-1,2,4a,5,6,7,8,8a-octahydronaphthalen-1-yl (2S,3aS,9bS)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-{1-methyl-2-[(2S)-4-methyl-2-[(methyloxy)carbonyl]-3,6-dihydropyridin-1(2H)-yl]ethyl}-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-5-[2-(3-hydroxy-8-azabicyclo[3.2.1]oct-8-yl)-1-methylethyl]-3,8-dimethyl-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate;

(1S,2R,4aS,5S,8R,8aR)-2-(acetyloxy)-8a-hydroxy-3,8-dimethyl-5-[1-methyl-2-(3-methyl-3-phenylpiperidin-1-yl)ethyl]-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate; and (1S,2R,4aS,5S,8R,8aR)-2-(acetyloxy)-8a-hydroxy-3,8-dimethyl-5-(1-methyl-2-{(phenylmethyl)[2-(phenyloxy)ethyl]amino}ethyl)-1,2,4a,5,6,7,8,8a-octahydronaphthalen-1-yl (2S,3aR,9bR)-6-chloro-9b-hydroxy-5-methyl-1,2,3,3a,5,9b-hexahydropyrrolo[2,3-c][2,1]benzoxazine-2-carboxylate.

* * * * *